United States Patent
Kelly et al.

(10) Patent No.: US 7,312,330 B2
(45) Date of Patent: *Dec. 25, 2007

(54) BICYCLOHETEROARYLAMINE COMPOUNDS AS ION CHANNEL LIGANDS AND USES THEREOF

(75) Inventors: Michael G. Kelly, Thousand Oaks, CA (US); Satyanarayana Janagani, Santa Clara, CA (US); Guoxian Wu, Palo Alto, CA (US); John Kincaid, Foster City, CA (US); David Lonergan, Sunnyvale, CA (US); YunFeng Fang, San Diego, CA (US); Zhi-Liang Wei, San Mateo, CA (US)

(73) Assignee: Renovis, Inc., South San Francisco, CA (US)

( * ) Notice: Subject to any disclaimer, the term of this patent is extended or adjusted under 35 U.S.C. 154(b) by 310 days.

This patent is subject to a terminal disclaimer.

(21) Appl. No.: 11/122,266

(22) Filed: May 4, 2005

(65) Prior Publication Data

US 2005/0277643 A1    Dec. 15, 2005

Related U.S. Application Data

(63) Continuation-in-part of application No. 11/022,324, filed on Dec. 23, 2004, and a continuation-in-part of application No. PCT/US04/43456, filed on Dec. 23, 2004.

(60) Provisional application No. 60/532,371, filed on Dec. 24, 2003.

(51) Int. Cl.
    C07D 471/02    (2006.01)
    C07D 417/14    (2006.01)
    C07D 265/30    (2006.01)
    A61K 31/54     (2006.01)
    A61K 31/535    (2006.01)
    A01N 43/40     (2006.01)

(52) U.S. Cl. .................. 544/279; 544/60; 544/106; 514/227.8; 514/231.5; 514/264.11

(58) Field of Classification Search ............... None
    See application file for complete search history.

(56) References Cited

FOREIGN PATENT DOCUMENTS

WO    WO 2006/062981    6/2006

OTHER PUBLICATIONS

Das et al., caplus AN 2005:409524, (2 Pages).*

* cited by examiner

*Primary Examiner*—Rebecca Anderson
*Assistant Examiner*—Sun Jae Y Loewe
(74) *Attorney, Agent, or Firm*—Klauber & Jackson LLC

(57) ABSTRACT

Amine compounds are disclosed that have a formula represented by the following:

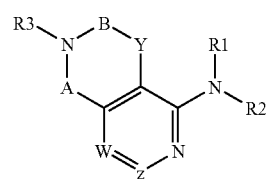

The compounds may be prepared as pharmaceutical compositions, and may be used for the prevention and treatment of a variety of conditions in mammals including humans, including by way of non-limiting example, pain, inflammation, traumatic injury, and others.

38 Claims, 2 Drawing Sheets

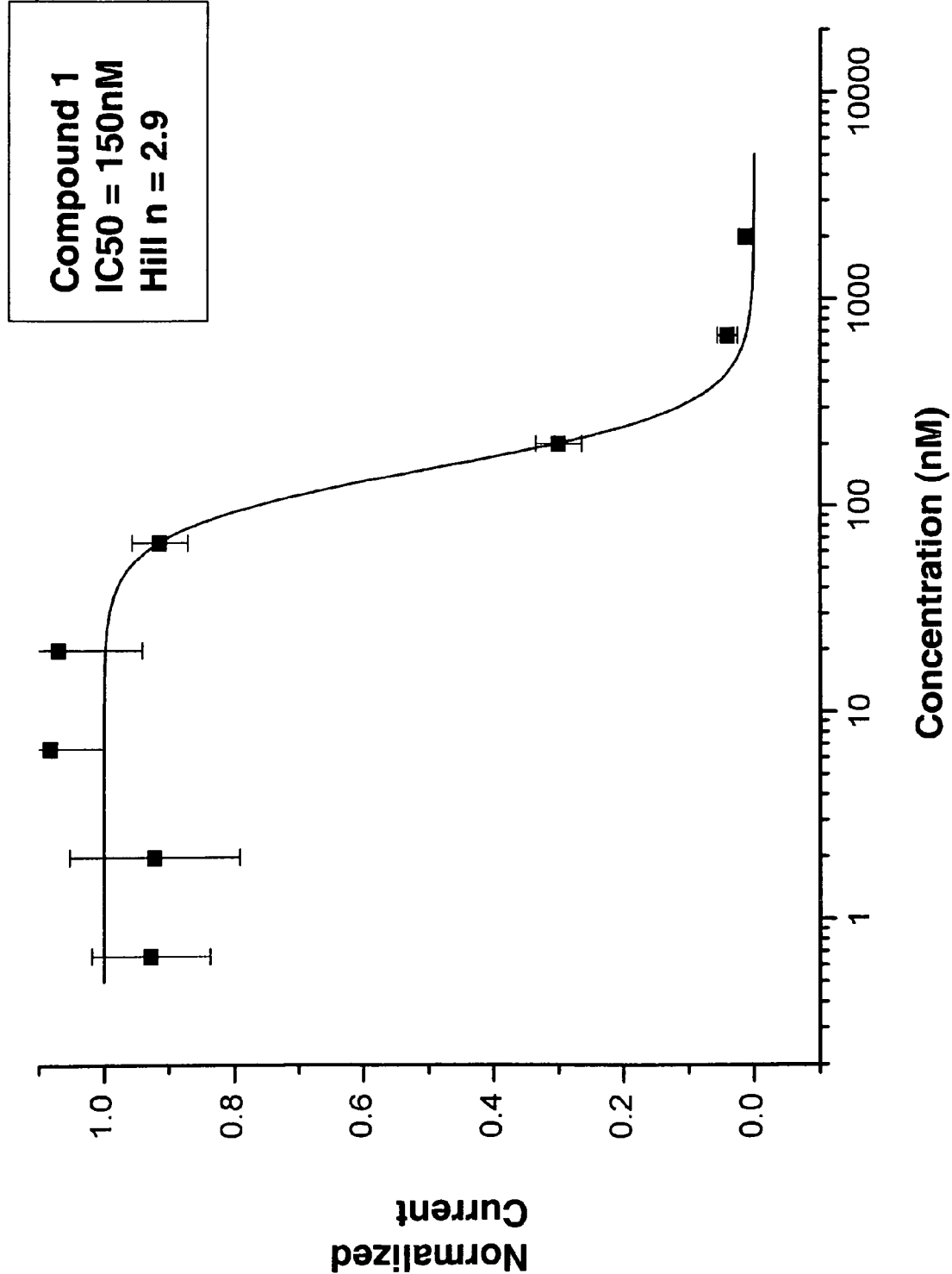

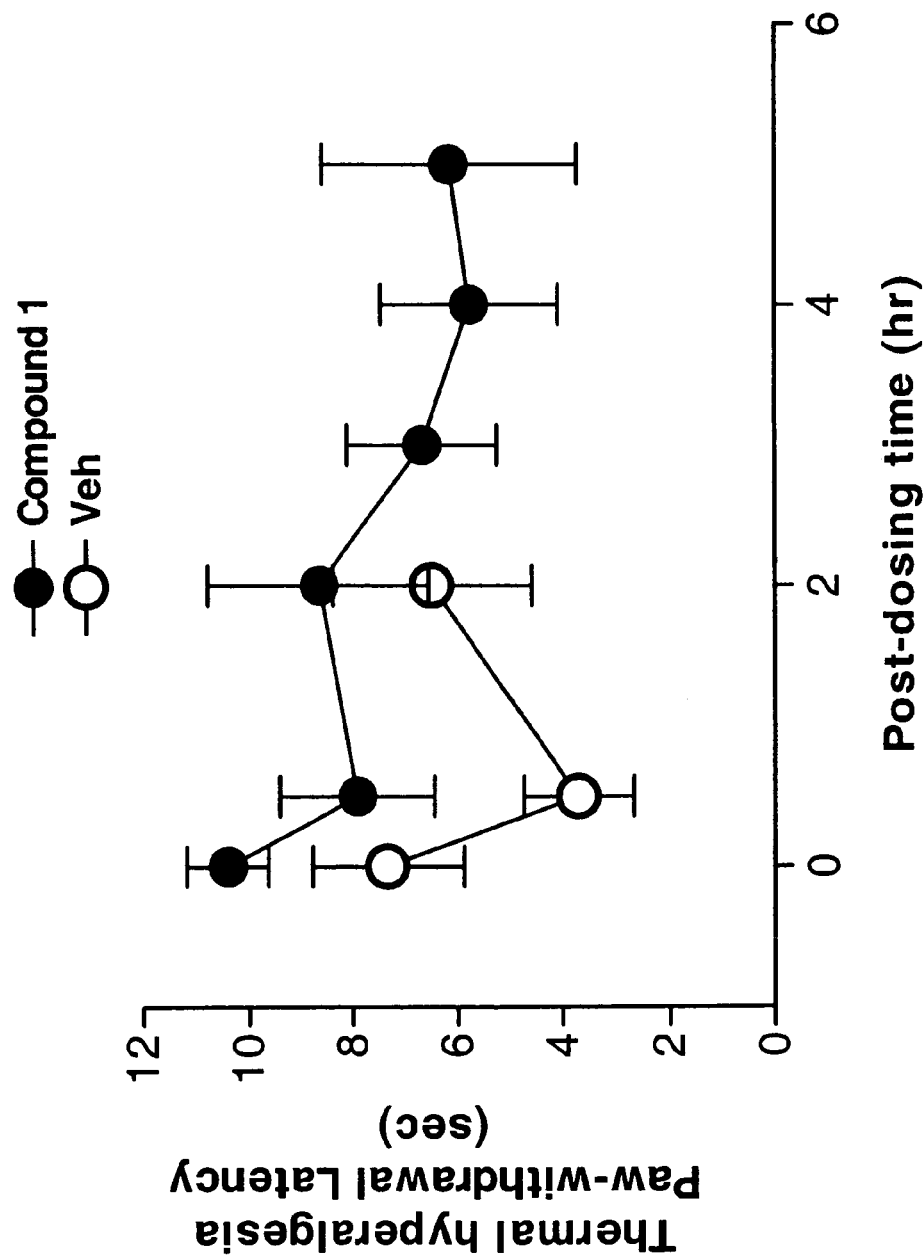

BICYCLOHETEROARYLAMINE COMPOUNDS AS ION CHANNEL LIGANDS AND USES THEREOF

CROSS REFERENCE TO RELATED APPLICATION

The present application is a Continuation-In-Part of U.S. non-provisional application Ser. No. 11/022,324, and International Application No. PCT/US04/043456, both filed Dec. 23, 2004, and claims the priority of now abandoned provisional application U.S. Ser. No. 60/532,371, filed on Dec. 24, 2003. The disclosure of this application is incorporated by reference herein in its entirety. Applicants claim the benefits of this application under 35 U.S.C. §119(e), and the benefits of 35 U.S.C. §120 as to said U.S. non-provisional application and said International application, and the disclosures of all of said applications are incorporated herein by reference in their entireties.

FIELD OF THE INVENTION

This invention relates to novel amine compounds of the class tetrahydronaphthyridines and tetrahydropyrido[3,4-d]pyrimidines and to pharmaceutical compositions containing such compounds. This invention also relates to methods for preventing and/or treating inflammation-related conditions in mammals, such as (but not limited to) arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders, using the amine compounds and pharmaceutical compositions of the invention.

BACKGROUND OF THE INVENTION

Studies of signaling pathways in the body have revealed the existence of ion channels and sought to explain their role. Ion channels are integral membrane proteins with two distinctive characteristics: they are gated (open and closed) by specific signals such as membrane voltage or the direct binding of chemical ligands and, once open, they conduct ions across the cell membrane at very high rates.

There are many types of ion channels. Based on their selectivity to ions, they can be divided into calcium channel, potassium channel, sodium channel, etc. The calcium channel is more permeable to calcium ions than other types of ions, the potassium channel selects potassium ions over other ions, and so forth. Ion channels may also be classified according to their gating mechanisms. In a voltage-gated ion channel, the opening probability depends on the membrane voltage, whereas in a ligand-gated ion channel, the opening probability is regulated by the binding of small molecules (the ligands). Since ligand-gated ion channels receive signals from the ligand, they may also be considered as "receptors" for ligands.

Examples of ligand-gated ion channels include nAChR (nicotinic acetylcholine receptor) channel, GluR (glutamate receptor) channel, ATP-sensitive potassium channel, G-protein activated channel, cyclic-nucleotide-gated channel, etc.

Transient receptor potential (TRP) channel proteins constitute a large and diverse family of proteins that are expressed in many tissues and cell types. This family of channels mediates responses to nerve growth factors, pheromones, olfaction, tone of blood vessels and metabolic stress et al., and the channels are found in a variety of organisms, tissues and cell types including nonexcitable, smooth muscle and neuronal cells. Furthermore, TRP-related channel proteins are implicated in several diseases, such as several tumors and neurodegenerative disorders and the like. See, for example, Minke, et al., *APStracts* 9:0006P (2002).

Nociceptors are specialized primary afferent neurons and the first cells in a series of neurons that lead to the sensation of pain. The receptors in these cells can be activated by different noxious chemical or physical stimuli. The essential functions of nociceptors include the transduction of noxious stimuli into depolarizations that trigger action potentials, conduction of action potentials from primary sensory sites to synapses in the central nervous system, and conversion of action potentials into neurotransmitter release at presynaptic terminals, all of which depend on ion channels.

One TRP channel protein of particular interest is the vanilloid receptor. Also known as VR1, the vanilloid receptor is a non-selective cation channel which is activated or sensitized by a series of different stimuli including capsaicin, heat and acid stimulation and products of lipid bilayer metabolism (anandamide), and lipoxygenase metabolites. See, for example Smith, et al., *Nature,* 418:186-190 (2002). VR1 does not discriminate among monovalent cations, however, it exhibits a notable preference for divalent cations with a permeability sequence of $Ca^{2+}>Mg^{2+}>Na^+=K^+=Cs^+$. $Ca^{2+}$ is especially important to VR1 function, as extracellular $Ca^{2+}$ mediates desensitization, a process which enables a neuron to adapt to specific stimuli by diminishing its overall response to a particular chemical or physical signal. VR1 is highly expressed in primary sensory neurons in rats, mice and humans, and innervates many visceral organs including the dermis, bones, bladder, gastrointestinal tract and lungs. It is also expressed in other neuronal and non-neuronal tissues including the CNS, nuclei, kidney, stomach and T-cells. The VR1 channel is a member of the superfamily of ion channels with six membrane-spanning domains, with highest homology to the TRP family of ion channels.

VR1 gene knockout mice have been shown to have reduced sensory sensitivity to thermal and acid stimuli. See, for example, Caterina, et al. *Science,* 14:306-313 (2000). This supports the concept that VR1 contributes not only to generation of pain responses but also to the maintenance of basal activity of sensory nerves. VR1 agonists and antagonists have use as analgesics for the treatment of pain of various genesis or etiology, for example acute, inflammatory and neuropathic pain, dental pain and headache (such as migraine, cluster headache and tension headache). They are also useful as anti-inflammatory agents for the treatment of arthritis, Parkinson's Disease, Alzheimer's Disease, stroke, uveitis, asthma, myocardial infarction, the treatment and prophylaxis of pain syndromes (acute and chronic [neuropathic]), traumatic brain injury, spinal cord injury, neurodegenerative disorders, alopecia (hair loss), inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

Compounds, such as those of the present invention, which interact with the vanilloid receptor can thus play a role in treating or preventing or ameliorating these conditions.

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant, capsazepine (Tetrahedron, 53, 1997, 4791) and olvanil or —N-(4-hydroxy-3-methoxybenzyl) oleamide (J. Med. Chem., 36, 1993, 2595).

International Patent Application, Publication Number WO 02/08221 discloses diaryl piperazine and related compounds which bind with high selectivity and high affinity to vanilloid receptors, especially Type I Vanilloid receptors, also known as capsaicin or VR1 receptors. The compounds are said to be useful in the treatment of chronic and acute pain conditions, itch and urinary incontinence.

International Patent Application, Publication Numbers WO 02/16317, WO 02/16318 and WO 02/16319 suggest that compounds having a high affinity for the vanilloid receptor are useful for treating stomach-duodenal ulcers.

WO02/053558 describes certain quinazolone derivatives as alpha 1A/B adrenergic receptor antagonists, and WO03/076427 and WO04/041259 both describe compounds of the same class for use in the treatment of female sexual dysfunction. WO04/56774 describe certain substituted biphenyl-4-carboxylic acid arylamide analogues having possible application as receptor modulators. Also, WO03/104230 describes certain bicyclic pyrimidine derivatives, and US Published Application Serial No. 20030092908 and WO02/087513 describe fused heterocyclic PDE7 inhibitors.

U.S. Pat. No. 3,424,760 and U.S. Pat. No. 3,424,761 both describe a series of 3-Ureidopyrrolidines that are said to exhibit analgesic, central nervous system, and pyschopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively. International Patent Applications, Publication Numbers WO 01/62737 and WO 00/69849 disclose a series of pyrazole derivatives which are stated to be useful in the treatment of disorders and diseases associated with the NPY receptor subtype Y5, such as obesity. WO 01/62737 specifically discloses the compound 5-amino-N-isoquinolin-5-yl-1-[3-(trifluoromethyl)phenyl]-1H-pyrazole-3-carboxamide. WO 00/69849 specifically discloses the compounds 5-methyl-N-quinolin-8-yl-1-[3-(trifluoromethyl)phenyl]-1H-pyrazole-3-carboxamide, 5-methyl-N-quinolin-7-yl-1-[3-trifluoromethyl)phenyl]-1H-pyrazole-3-carboxamide, 5-methyl-N-quinolin-3-yl-1-[3-(trifluoromethyl)phenyl]-1H-pyrazole-3-carboxamide, N-isoquinolin-5-yl-5-methyl-1-[3-(trifluoromethyl)phenyl]-1H-pyrazole-3-carboxamide, 5-methyl-N-quinolin-5-yl-1-[3-(trifluoromethyl)phenyl]-1H-pyrazole-3-carboxamide, 1-(3-chlorophenyl)-N-isoquinolin-5-yl-5-methyl-1H-pyrazole-3-carboxamide, N-isoquinolin-5-yl-1-(3-methoxyphenyl)-5-methyl-1H-pyrazole-3-carboxamide, 1-(3-fuorophenyl)-N-isoquinolin-5-yl-5-methyl-1H-pyrazole-3-carboxamide, 1-(2-chloro-5-trifluoromethylphenyl)-N-isoquinolin-5-yl-5-methyl-1N-pyrazole-3-carboxamide, 5-methyl-N-(3-methylisoquinolin-5-yl)-1-[3-(trifluoromethyl)phenyl]-1N-pyrazole-3-carboxamide, 5-methyl-N-(1,2,3,4-tetrahydroisoquinolin-5-yl)-1-[3-(trifluoromethyl)phenyl]-1H-pyrazole-3-carboxamide.

German Patent Application Number 2502588 describes a series of piperazine derivatives. This application specifically discloses the compound N-[3-[2-(diethylamino)ethyl]-1,2-dihydro-4-methyl-2-oxo-7-quinolinyl]-4-phenyl-1-piperazinecarboxamide.

We have now discovered that certain compounds have surprising potency and selectivity as VR1 antagonists. The compounds of the present invention are considered to be particularly beneficial as VR1 antagonists as certain compounds exhibit improved aqueous solubility and metabolic stability.

SUMMARY OF THE INVENTION

It has now been found that tetrahydronaphthyridine compounds are capable of modifying mammalian ion channels such as the VR1 cation channel. This finding leads to novel compounds having therapeutic value. It also leads to pharmaceutical compositions having the amines of the present invetion as active ingredients and to their use to treat, prevent or ameliorate a range of conditions in mammals such as but not limited to pain of various genesis or etiology, for example acute, chronic, inflammatory and neuropathic pain, dental pain and headache (such as migraine, cluster headache and tension headache).

The compounds of the present invention are useful for the treatment of inflammatory pain and associated hyperalgesia and allodynia. They are also useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). The compounds of the present invention are also useful as anti-inflammatory agents for the treatment of arthritis, and as agents to treat Parkinson's Disease, Alzheimer's Disease, stroke, uveitis, asthma, myocardial infarction, traumatic brain injury, spinal cord injury, neurodegenerative disorders, alopecia (hair loss), inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

In one aspect, this invention provides tetrahydronaphthyridine compounds which are capable of modifying ion channels, in vivo. Representative ion channels so modified include voltage-gated channels and ligand-gated channels, including cation channels such as vanilloid channels.

Accordingly, in a first aspect of the invention, amine compounds are disclosed that are capable of modifying ion channels, in vivo, having a formula (1):

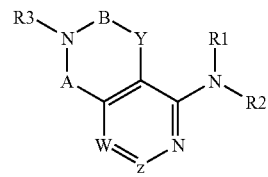

wherein

A and B are independently selected from $CH_2$, $CR^2R^4$, CO, CS, $NR^1$, and $NR^2$;

Y is independently selected from $CH_2$, $CR^2R^4$, $NR^1$, and $NR^2$;

W and Z are independently selected from $CR^4$ and N, provided that W and Z both can not be N;

$R^1$ is selected from substituted and unsubstituted aliphatic, substituted or unsubstituted alkyl, substituted or unsubstituted heteroalkyl, substituted or unsubstituted acyl, substituted or unsubstituted aryl, substituted or unsubstituted heteroaryl, substituted or unsubstituted aralkyl, substituted or unsubstituted heteroalkyl;

$R^2$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl;

$R^3$ is selected from substituted or unsubstituted $C_1$-$C_6$ alkyl, aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, and bicycloheteroaryl ring;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

or a pharmaceutically acceptable salt, solvate or prodrug thereof;

and stereoisomers and tautomers thereof.

More particularly, there is provided an amine compound capable of modifying ion channels, in vivo, having a formula:

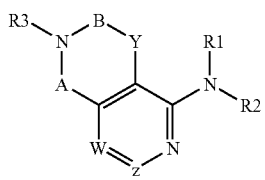

wherein

A and B are independently selected from $CH_2$, $CR^{2'}R^{2'}$, CO, CS and $NR^{2'}$;

Y is independently selected from $CH_2$, $CR^{2'}R^{2'}$ and $NR^{2'}$;

W and Z are independently selected from $CR^4$ and N, provided that W and Z both can not be N;

$R^1$ is selected from substituted and unsubstituted aliphatic, substituted or unsubstituted alkyl, substituted or unsubstituted heteroalkyl, substituted or unsubstituted acyl, substituted or unsubstituted aryl, substituted or unsubstituted heteroaryl, substituted or unsubstituted aralkyl, substituted or unsubstituted heteroalkyl;

Each of $R^2$ and $R^{2'}$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl;

$R^3$ is selected from substituted or unsubstituted $C_1$-$C_6$ alkyl, aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, and bicycloheteroaryl ring;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

or a pharmaceutically acceptable salt, solvate or prodrug thereof;

and stereoisomers and tautomers thereof. In a further embodiment, A, B and Y may all represent $CH_2$.

In a further aspect, the present invention provides pharmaceutical compositions comprising a tetrahydronaphthyridine compound of the invention, and a pharmaceutical carrier, excipient or diluent. In this aspect of the invention, the pharmaceutical composition can comprise one or more of the amine compounds described herein. Moreover, the amine compounds of the present invention useful in the pharmaceutical compositions and treatment methods disclosed herein, are all pharmaceutically acceptable as prepared and used.

In a further aspect of the invention, this invention provides a method of treating a mammal susceptible to or afflicted with a condition from among those listed herein, and particularly, such condition as may be associated with e.g. arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. The amine compounds of the invention have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-mastectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

In additional aspects, this invention provides methods for synthesizing the amine compounds of the invention, with representative synthetic protocols and pathways disclosed later on herein.

Other objects and advantages will become apparent to those skilled in the art from a consideration of the ensuing detailed description which proceeds with reference to the following illustrative drawings.

BRIEF DESCRIPTION OF THE DRAWINGS

FIG. 1: A graph demonstrating the activity of compound 1 in inhibiting a capsaicin induced intracellular calcium current. The graph presents a dose response curve developed using electrophysiology.

FIG. 2: A graph demonstrating the activity of compound 1 in inhibiting thermal hyperalgesia, as measured by increased latency of paw withdrawal. The graph depicts the time interval at which paw withdrawal takes place, measured at baseline and two hours after stimulation.

DETAILED DESCRIPTION OF THE INVENTION

Definitions

When describing the compounds, pharmaceutical compositions containing such compounds and methods of using such compounds and compositions, the following terms have the following meanings unless otherwise indicated. It should also be understood that, consistent with the scope of the present invention, any of the moieties defined herein and/or set forth below may be substituted with a variety of substituents, and that the respective definitions are intended to include such substituted moieties within their scope. By way of non-limiting example, such substituents may include e.g. halo (such as fluoro, chloro, bromo), —CN, —CF$_3$, —OH, —OCF$_3$, C$_{2-6}$ alkenyl, C$_{3-6}$ alkynyl, C$_{1-6}$ alkoxy, aryl and di-C$_{1-6}$ alkylamino.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, cycloheteroalkyl, aryl, arylalkyl, heteroalkyl, heteroaryl, heteroarylalkyl and R is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R where R is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NRC(O)OR' where R is hydrogen, alkyl, aryl or cycloalkyl, and R' is alkyl or cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyl" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" as used herein, which can include "acyl", refers to the group R—C(O)—, where R is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR'—, wherein R' is selected from hydrogen and alkyl.

"Arylamino" refers to the group aryl-NR'—, wherein R' is selected from hydrogen, aryl and heteroaryl.

"Alkoxyamino" refers to a radical —N(H)OR where R represents an alkyl or cycloalkyl group as defined herein.

"Alkoxycarbonyl" refers to a radical —C(O)-alkoxy where alkoxy is as defined herein.

"Alkylarylamino" refers to a radical —NRR' where R represents an alkyl or cycloalkyl group and R' is an aryl as defined herein.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Aminocarbonyl" or "amido" refers to the group —C(O)NRR where each R is independently hydrogen, alkyl, aryl and cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalky, or where the R groups are joined to form an alkylene group.

"Arylalkyloxy" refers to an —O-arylalkyl radical where arylalkyl is as defined herein.

"Arylamino" means a radical —NHR where R represents an aryl group as defined herein.

"Aryloxycarbonyl" refers to a radical —C(O)—O-aryl where aryl is as defined herein.

"Arylsulfonyl" refers to a radical —S(O)$_2$R where R is an aryl or heteroaryl group as defined herein.

"Azido" refers to the radical —N$_3$.

"Carbamoyl" refers to the radical —C(O)N(R)$_2$ where each R group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C=C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{14}$, —O$^-$, =O, —OR$^{14}$, —SR$^{14}$, —S$^-$, =S, —NR$^{14}$R$^{15}$, =NR$^{14}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{14}$, —OS(O$_2$)O$^-$, —OS(O)$_2$R$^{14}$, —P(O)(O$^-$)$_2$, —P(O)(OR$^{14}$)(O$^-$), —OP(O)(OR$^{14}$)(OR$^{15}$), —C(O)OR$^{14}$, —C(S)R$^{14}$, —C(O)OR$^{14}$, —C(O)NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$^{14}$R$^{15}$ and —C(NR$^{16}$)NR$^{14}$R$^{15}$, where each X is independently a halogen; each R$^{14}$, R$^{15}$, R$^{16}$ and R$^{17}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{18}$R$^{19}$, —C(O)R$^{18}$ or —S(O)$_2$R$^{18}$ or optionally R$^{18}$ and R$^{19}$ together with the atom to which they are both attached form a cycloheteroalkyl or substituted cycloheteroalkyl ring; and R$^{18}$ and R$^{19}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

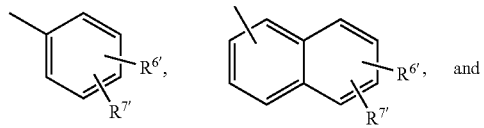

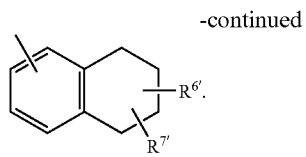

In these formulae one of $R^{6'}$ and $R^{7'}$ may be hydrogen and at least one of $R^{6'}$ and $R^{7'}$ is each independently selected from alkyl, alkenyl, alkynyl, cycloheteroalkyl, alkanoyl, alkoxy, aryloxy, heteroaryloxy, alkylamino, arylamino, heteroarylamino, $NR^{10}COR^{11}$, $NR^{10}SOR^{11}$, $NR^{10}SO_2R^{14}$, COOalkyl, COOaryl, $CONR^{10}R^{11}$, $CONR^{10}OR^{11}$, $NR^{10}R^{11}$, $SO_2NR^{10}R^{11}$, S-alkyl, S-alkyl, SOalkyl, $SO_2$alkyl, Saryl, SOaryl, $SO_2$aryl; or $R^{6'}$ and $R^{2'}$ may be joined to form a cyclic ring (saturated or unsaturated) from 5 to 8 atoms, optionally containing one or more heteroatoms selected from the group N, O or S. $R^{10}$, $R^{11}$, and $R^{12}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, tetrahydroisoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, tetrahydroquinoline, quinolizine, quinoxaline, tetrazole, thiadiazole, thiazole, thiophene, triazole, xanthene, and the like. Particularly, heteroaryl can include other saturated ring systems, and can therefore be derived from indoline, indolizine, tetrahydroquinoline, and tetrahydroisoquinoline. Preferably, the heteroaryl group is between 5-20 membered heteroaryl, with 5-10 membered heteroaryl being particularly preferred. Particular heteroaryl groups are those derived from thiophene, pyrrole, benzothiophene, benzofuran, indole, pyridine, pyrimidine, quinoline, tetrahydroquinoline, isoquinoline, tetrahydroisoquinoline, imidazole, oxazole and pyrazine.

Examples of representative heteroaryls include the following:

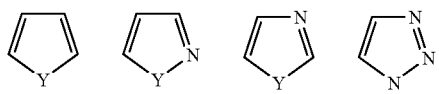

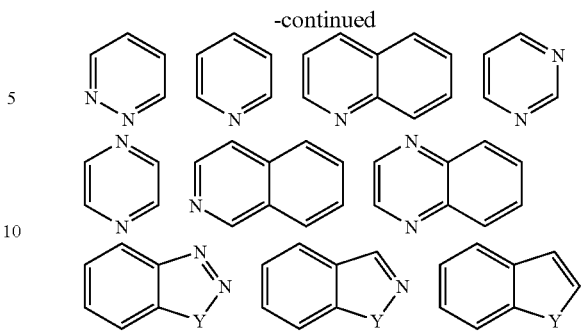

wherein each Y is selected from carbonyl, N, $NR^4$, O, and S, where $R^4$ is as defined herein.

Examples of representative cycloheteroalkyls include the following

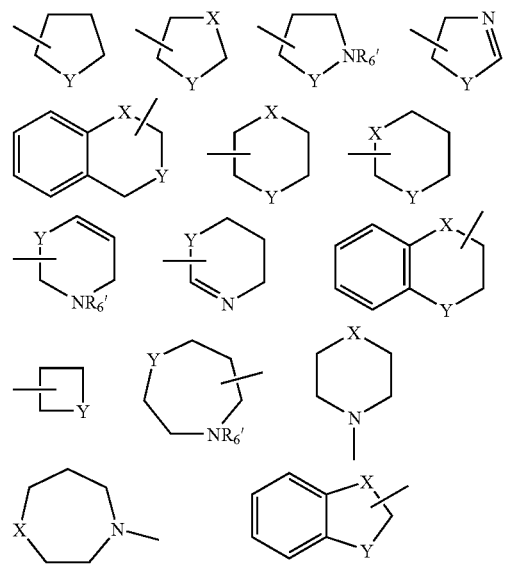

wherein each X is selected from $CR^4_2$, $NR^4$, O and S; and each Y is selected from $NR^4$, O and S, and where $R^{6'}$ is $R^2$, $R^2$ and $R^4$ being as defined herein.

Examples of representative cycloheteroalkenyls include the following:

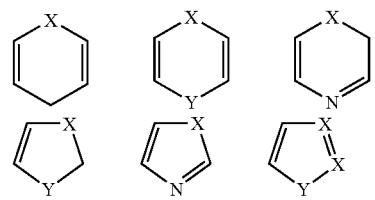

wherein each X is selected from $CR^4$, $NR^4$, O and S; and each Y is selected from carbonyl, N, $NR^4$, O and S, where $R^4$ is as defined herein.

Examples of representative aryl having hetero atoms containing substitution include the following:

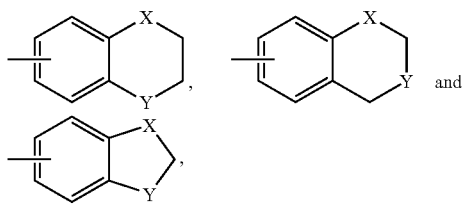

wherein each X is selected from C—R⁴, CR⁴₂, NR⁴, O and S; and each Y is selected from carbonyl, NR⁴, O and S, where R⁴ is as defined herein.

"Hetero substituent" refers to a halo, O, S or N atom-containing functionality that may be present as an R⁴ in a CR⁴ group present as substituents directly on W or Z of the compounds of this invention or may be present as a substituent in the "substituted" aryl, heteroaryl and aliphatic groups present in the compounds.

Examples of hetero substituents include:
-halo,
—NO₂, —NH₂, —NHR, —N(R)₂,
—NRCOR, —NRSOR, —NRSO₂R, OH, CN, CO₂R,
—CO₂H,
—O—R,
—CON(R)₂, —CONROR,
—SO₃H, —S—R, —SO₂N(R)₂,
—S(O)R, and —S(O)₂R, wherein each R is independently an aryl or aliphatic, optionally with substitution. Among hetero substituents containing R groups, preference is given to those materials having aryl and alkyl R groups as defined herein. Where feasible, each R may include hydrogen. Also, where feasible, two R groups when on same atom may join to form a heterocyclic ring of 3-8 atoms. For example, two R groups of NR², SO₂NR², and CONR² may join, together with the N atom, to form a N-morpholino, N-pyrrolo, N-piperidino, and N-pyrazolylo ring. Preferred hetero substituents are those listed above.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

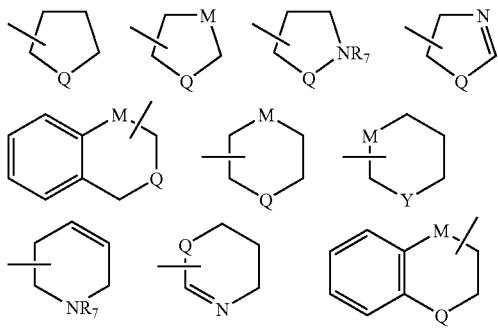

-continued

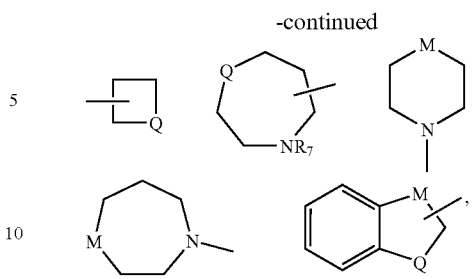

optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)₂— and aryl-S(O)₂—. Substituting groups include carbonyl or thiocarbonyl which provide, for example, lactam and urea derivatives. In the examples, M is CR⁷, NR², O, or S; Q is O, NR² or S, where R² is as defined herein. R⁷ and R⁸ are independently selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)₂— and aryl-S(O)₂—.

"Dihydroxyphosphoryl" refers to the radical —PO(OH)₂.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH₂.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR where R is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)₂— and aryl-S(O)₂—.

"Sulfanyl" refers to the radical HS—. "Substituted sulfanyl" refers to a radical such as RS— wherein R is any substituent described herein.

"Sulfonyl" refers to the divalent radical —S(O₂)—. "Substituted sulfonyl" refers to a radical such as S(O₂)—R wherein R is any substituent described herein. "Aminosulfonyl" or "Sulfonamide" refers to the radical $H_2N(O_2)S$—, and "substituted aminosulfonyl" "substituted sulfonamide" refers to a radical such as $R_2N(O_2)S$— wherein each R is independently any substituent described herein.

"Sulfoxide" refers to the divalent radical —S(O)—. "Substituted sulfoxide" refers to a radical such as S(O)—R, wherein R is any substituent described herein.

"Sulfone" refers to the group —$SO_2R$. In particular embodiments, R is selected from H, lower alkyl, alkyl, aryl and heteroaryl.

"Thioaryloxy" refers to the group —SR where R is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Representative enol-keto structures and equilibrium are illustrated below:

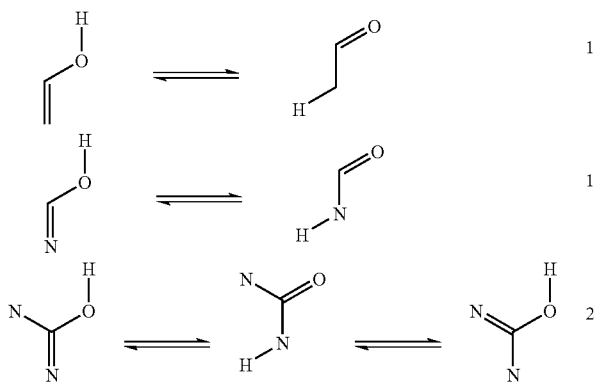

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention provides tetrahydronaphthyridine compounds useful for preventing and/or treating a broad range of conditions, among them, arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders or conditions in mammals.

In a first embodiment, the present invention provides tetrahydronaphthyridine compounds according to formula (1):

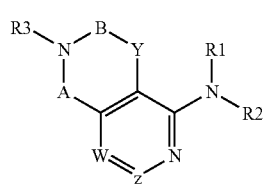

1 wherein

A and B are independently selected from $CH_2$, $CR^2R^4$, CO, CS, $NR^1$, and $NR^2$;

Y is independently selected from $CH_2$, $CR^2R^4$, $NR^1$, and $NR^2$;

W and Z are independently selected from $CR^4$ and N, provided that W and Z both can not be N;

$R^1$ is selected from substituted and unsubstituted aliphatic, substituted or unsubstituted alkyl, substituted or unsubstituted heteroalkyl, substituted or unsubstituted acyl, substituted or unsubstituted aryl, substituted or unsubstituted heteroaryl, substituted or unsubstituted aralkyl, substituted or unsubstituted heteroalkyl;

$R^2$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl;

$R^3$ is selected from substituted or unsubstituted $C_1$-$C_6$ alkyl, aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, and bicycloheteroaryl ring;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

or a pharmaceutically acceptable salt, solvate or prodrug thereof;

and stereoisomers and tautomers thereof.

More particularly there is provided an amine compound capable of modifying ion channels, in vivo, having a formula:

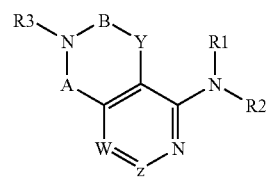

1 wherein

A and B are independently selected from $CH_2$, $CR^{2'}R^{2'}$, CO, CS and $NR^{2'}$;

Y is independently selected from $CH_2$, $CR^{2'}R^{2'}$ and $NR^{2'}$;

W and Z are independently selected from $CR^4$ and N, provided that W and Z both can not be N;

$R^1$ is selected from substituted and unsubstituted aliphatic, substituted or unsubstituted alkyl, substituted or unsubstituted heteroalkyl, substituted or unsubstituted acyl, substituted or unsubstituted aryl, substituted or unsubstituted heteroaryl, substituted or unsubstituted aralkyl, substituted or unsubstituted heteroalkyl;

each of $R^2$ and $R^{2'}$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl;

$R^3$ is selected from substituted or unsubstituted $C_1$-$C_6$ alkyl, aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, and bicycloheteroaryl ring;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

or a pharmaceutically acceptable salt, solvate or prodrug thereof;

and stereoisomers and tautomers thereof.

Compounds according to formula (1) may, for example be further defined as follows:

when A, B and Y all are $CH_2$s then $R^3$ is not alkoxy-4-quinazolinon-2-yl;

when A, B and Y all are $CH_2$s, W is N, Z is $CR^4$, then $R^4$ is not alkylamino, dialkylamino or alkylarylamino; and when A is CO, then $R^3$ is not hydrogen, alkyl or unsubstituted phenyl.

Suitably A, B and Y independently represent $CR^{2'}R^{2'}$.

Suitably $R^1$ is substituted aryl or heteroaryl; $R^2$ is H or lower alkyl, eg. H; and $R^3$ is substituted or unsubstituted aryl, eg. $R^3$ is substituted aryl.

When $R^3$ represents substituted aryl, suitably the substitution on aryl is independently selected from halo, amido, alkyl, alkoxy, sulfonyl, sulfonamidyl, haloalkyl and trihaloalkyl. The substitution on aryl is also suitably independently selected from Cl, F, $CF_3$, Me, OMe, $SO_2R^{2'}$, $NR^{2'}R^{2'}$, and $SO_2NR^{2'}R^{2'}$. The substitution on aryl is also suitably independently selected from 4-halo, 4-amido, 4-alkyl and 4-alkoxy.

Substitution on aryl may, for example, be on the 2- or the 4-position.

Alternatively $R^1$ may represent substituted aryl or heteroaryl; $R^2$ is H or lower alkyl, eg. H; and $R^3$ is substituted or unsubstituted heteroaryl.

For example, $R^3$ may be substituted or unsubstituted pyridyl. For example $R^3$ may be substituted 2-pyridyl. Substitution on 2-pyridyl may be, for example, at the 3-position. Alternatively the substitution on 2-pyridyl may be at the 4-position. Alternatively the substitution on 2-pyridyl may be at the 5-position. Alternatively the substitution on 2-pyridyl may be at the 6-position.

For example, $R^3$ may represent 3,5- or 3,4-disubstituted 2-pyridyl.

Suitably, substitutions on 2-pyridyl are independently selected from halo, amido, alkyl, alkoxy, cyano, sulfonyl, sulfonamidyl, haloalkyl and trihaloalkyl. Substitutions are also independently selected from Cl, F, CN, $CF_3$, Me, OMe, $SO_2R^{2'}$, $NR^{2'}R^{2'}$, and $SO_2NR^{2'}R^{2'}$. Substitutions are also independently selected from Cl, CN, $CF_3$, $NR^1R^2$ and $SO_2NR^1R^2$.

In certain embodiments of the invention W and Z both are $CR^4$. Alternatively W is $CR^4$ and Z is N. Alternatively, W is N and Z is $CR^4$. Suitably $R^4$ is selected from H, cyano, amido, and a group represented by X—$(CR^{2'}R^{2'})_n$—$R^{3''}$; wherein X is a bond, O, S, SO, $SO_2$, or $NR^{2'}$; each $R^{2'}$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl; $R^{3''}$ is selected from a hydrogen, a hetero substituent and aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, and bicycloheteroaryl ring; and n is selected from 0-4; provided when X is other than a bond, $R^{3''}$ is hetero substituent then n is at least 2. In a particular embodiment, $R^4$ may be X—$(CR^{2'}R^{2'})_n$—$R^{3''}$, where X may be a bond, each $R^{2'}$ may be H; and n is 0-4. Alternatively, X may be O, S, SO or $SO_2$; each $R^{2'}$ may be H; and n is 2-4.

In the above embodiment, $R^{3''}$ may be substituted or unsubstituted cycloalkyl, cycloheteroalkyl, aryl or heteroaryl, and in a particular embodiment, $R^{3''}$ is a hetero substituent. In a specific embodiment, $R^{3''}$ is selected from COOH, $SO_2Me$, SMe, OH, OEt, OMe, $NEt_2$, $NHSO_2Me$, $CONH_2$, $CONMe_2$ and $SO_2NMe_2$. For example $R^4$ may represent H.

In further embodiments of the invention, $R^1$ is substituted aryl and $R^2$ is H. Suitably, substitution on aryl is independently selected from alkyl, trihaloalkyl, alkoxy, and dialkylamino, eg. is independently selected from t-Bu, iso-Pr, OMe, $OCF_3$, Br and $NR^1R^2$. For example, the substitution is at the 3-position or the 4-position. For example, $R^1$ is 3,4-disubstituted aryl.

In other embodiments of the invention $R^1$ is substituted heteroaryl and $R^2$ is H. For example, $R^1$ is substituted pyridyl, eg. 2-pyridyl; eg. wherein the substitution on pyridyl is selected from the 3-position, the 4-position and the 5-position. For example, $R^1$ is 3,4- or 3,5-disubstituted 2-pyridyl.

Alternatively $R^1$ is substituted 3-pyridyl; eg. wherein the substitution on pyridyl is at the 4- or 5-position.

Substitutions on pyridyl may, for example, be independently selected from halo, amido, alkyl, alkoxy, cyano, sulfonyl, sulfonamidyl, haloalkyl and trihaloalkyl. Suitably, substitutions may be independently selected from t-Bu, Cl, F, iso-Pr, OMe, $OCF_3$, $OCHF_2$, $SO_2CF_3$, $SO_2R^{2'}$, $SO_2NR^{2'}R^{2'}$, CN, $C(Me)_2CN$ and $NR^1R^2$. Suitably, substitutions may be independently selected from alkyl, trihaloalkyl, alkoxy, and dialkylamino, eg. are independently selected from t-Bu, iso-Pr, OMe, $OCF_3$, Br and $NR^1R^2$.

A, B and Y may, for example, all represent $CH_2$. Alternatively A may represent CO, and B and Y may represent $CH_2$. Alternatively B may represent CO, and A and Y may represent $CH_2$.

Referring further to the compounds of formula (1), in certain embodiments, z is CH or $CX_3$ where X is halo.

Also referring to the compounds of formula (1), in certain embodiments, $R^3$ can be substituted or unsubstituted phenyl, substituted or unsubstituted thiophene, substituted or unsubstituted pyrrole, substituted or unsubstituted di-pyridine, or halo-substituted methyl pyridine.

Also referring the compounds of formula (1), in certain embodiments, one of $R^1$ or $R^2$ is H and the other of $R^1$ and $R^2$ can be aryl, substituted or unsubstituted aryl (especially hetero-substituted aryl), substituted or unsubstituted pyridine, especially t-butyl pyridine.

In a further embodiment, the present invention provides aryl amine compounds according to formula (2):

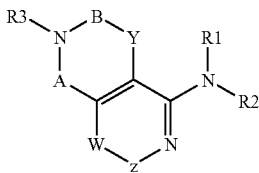

(2)

wherein

A, B and Y are independently selected from $CH_2$, CO, $NR^1$, $NR^2$, and $CR^1R^4$;

W and Z are independently selected from $CR^1R^4$, CO, $NR^1$, $NR^2$, O, S and $SO_2$;

$R^1$ is selected from substituted and unsubstituted aliphatic, substituted or unsubstituted alkyl, substituted or unsubstituted heteroalkyl, substituted or unsubstituted acyl, substituted or unsubstituted aryl, substituted or unsubstituted heteroaryl, substituted or unsubstituted aralkyl, substituted or unsubstituted heteroalkyl;

$R^2$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl;

$R^3$ is selected from substituted or unsubstituted $C_1$-$C_6$ alkyl, aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, and bicycloheteroaryl ring;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

or a pharmaceutically acceptable salt, solvate or prodrug thereof;

and stereoisomers and tautomers thereof.

Suitably, W and Z are independently selected from $CH_2$, CO, $NR^1$, $NR_2$, O, S and $SO_2$.

In a particular embodiment of the compound of formula (2), A, B and Y are independently selected from CO, $NR^{2'}$, and $CR^{2'}R^{2'}$; W and Z are independently selected from $CH_2$, CO, $NR^{2'}$, O, S and $SO_2$; and each of $R^{2'}$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl. For example, A, B and Y each represent $CH_2$.

In a still further embodiment, the present invention provides amine compounds according to formula (3):

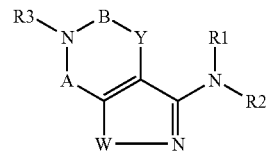

(3)

wherein

A, B and Y are independently selected from $CH_2$, CO, $NR^1$, $NR^2$, and $CR^1R^4$;

W is selected from $CR^1R^4$, CO, $NR^1$, $NR^2$, O, S and $SO_2$;

$R^1$ is selected from substituted and unsubstituted aliphatic, substituted or unsubstituted alkyl, substituted or unsubstituted heteroalkyl, substituted or unsubstituted acyl, substituted or unsubstituted aryl, substituted or unsubstituted heteroaryl, substituted or unsubstituted aralkyl, substituted or unsubstituted heteroalkyl;

$R^2$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl;

$R^3$ is selected from substituted or unsubstituted $C_1$-$C_6$ alkyl, aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, and bicycloheteroaryl ring;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

or a pharmaceutically acceptable salt, solvate or prodrug thereof;

and stereoisomers and tautomers thereof.

Suitably, W is independently selected from $CH_2$, CO, $NR^1$, $NR^2$, O, S and $SO_2$.

In a particular embodiment of the compound of formula (3), A, B and Y are independently selected from CO, $NR^{2'}$, and $CR^{2'}R^{2'}$; W and Z are independently selected from $CH_2$, CO, $NR^{2'}$, O, S and $SO_2$; and each of $R^{2'}$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl.

Referring further to the compound of formula (3), in specific embodiments, W is O, $R^3$ is a pyridine, one of $R^1$ or $R^2$ is H and the other of $R^1$ and $R^2$ is a hetero substituted aryl.

In a further particular embodiment relating to the compounds of formula (2), the invention includes an amine compound capable of modifying ion channels, in vivo, having a formula:

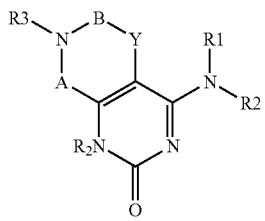

wherein

A and B are independently selected from $CH_2$, $CR^2R^4$, CO, CS, $NR^1$ and $NR^2$;

Y is independently selected from $CH_2$, $CR^2R^4$, $NR^1$ and $NR^2$;

$R^1$ is selected from substituted and unsubstituted aliphatic, substituted or unsubstituted alkyl, substituted or unsubstituted heteroalkyl, substituted or unsubstituted acyl, substituted or unsubstituted aryl, substituted or unsubstituted heteroaryl, substituted or unsubstituted aralkyl, substituted or unsubstituted heteroalkyl;

$R^2$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl;

$R^3$ is selected from substituted or unsubstituted $C_1$-$C_6$ alkyl, aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, and bicycloheteroaryl ring;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio;

or a pharmaceutically acceptable salt, solvate or prodrug thereof;

and stereoisomers and tautomers thereof.

In a particular embodiment of the above compounds, A and B are independently selected from $CR^{2'}R^{2'}$, CO, CS, and $NR^{2'}$; Y is independently selected from $CR^{2'}R^{2'}$, and $NR^{2'}$; and each of $R^2$ and $R^{2'}$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl.

Among the compounds described above by formula (1), there is a general preference for materials wherein $R_3$ is a 6 membered aryl or heteroaryl ring.

In a particular embodiment, the compounds according to Formula (1) can be described by the following formula:

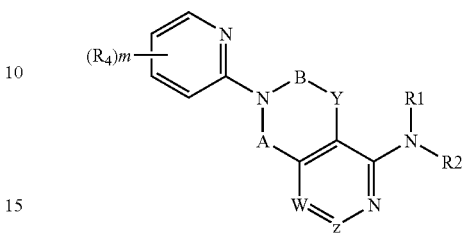

wherein

A and B are independently selected from $CH_2$, $CR^2R^4$, CO, CS, $NR^1$, and $NR^2$;

Y is independently selected from $CH_2$, $CR^2R^4$, $NR^1$, and $NR^2$;

W is selected from $CR^4$ and N;

Z is $CR^4$;

$R^1$ is selected from substituted and unsubstituted aliphatic, substituted or unsubstituted alkyl, substituted or unsubstituted heteroalkyl, substituted or unsubstituted acyl, substituted or unsubstituted aryl, substituted or unsubstituted heteroaryl, substituted or unsubstituted aralkyl, substituted or unsubstituted heteroalkyl;

$R^2$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and m is selected from 0-4;

or a pharmaceutically acceptable salt, solvate or prodrug thereof;

and stereoisomers and tautomers thereof. Suitably m may be selected from 0 to 3.

In a particular embodiment of the compound of the above variant formula, A, B and Y are $CR^{2'}R^{2'}$; W is selected from $CR^4$ and N; Z is $CR^4$; $R^2$ is hydrogen; $R^{2'}$ is hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl. Suitably A, B and Y may all be $CH_2$s, and m is selected from 0-3.

Further variant compounds of this formula may comprise the following:

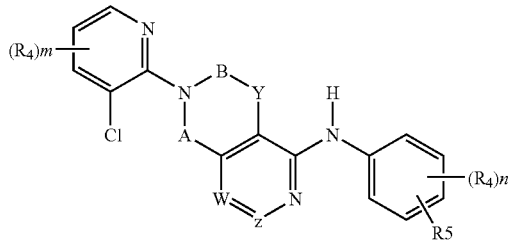

wherein $R^5$ is selected from $R^4$, t-Bu, iso-Pr, $CF_3$, dialkylamino, Br, $OCF_3$, $OCH_2$, and Cl; and m and n are independently selected from 0-3. In this variant, m may, for example represent 0; n may, for example, represent 0; $R_5$ may, for example, be selected from 4-t-Bu, 4-Cl, 4-F, 4-iso-Pr, 4-OMe, 4-$OCF_3$, 4-$OCHF_2$, 4-$SO_2CF_3$, 4-$SO_2R^{2'}$, 4-$SO_2NR^{2'}R^{2'}$, 4-$C(Me)_2CN$, 3,4-diCl and 4-$NR^{2'}R^{2'}$; m may, for example, represent 0; and n may, for example, represent 0;

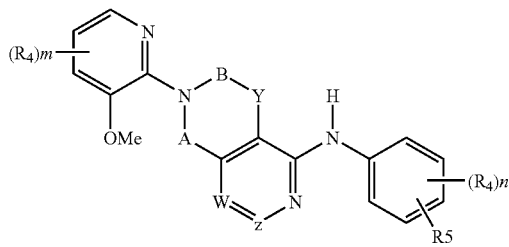

wherein $R^5$ is selected from $R^4$, t-Bu, iso-Pr, $CF_3$, dialkylamino, Br, $OCF_3$, $OCHF_2$, and Cl; and m and n are independently selected from 0-3. Suitably, $R^5$ may be selected from 4-t-Bu, 4-Cl, 4-F, 4-iso-Pr, 4-OMe, 4-$OCF_3$, 4-$OCHF_2$, 4-$SO_2CF_3$, 4-$SO_2R^{2'}$, 4-$SO_2NR^{2'}R^{2'}$, 4-$C(Me)2CN$, 3,4-diCl and 4-$NR^{2'}R^{2'}$; m may, for example, represent 0; and n may, for example, represent 0;

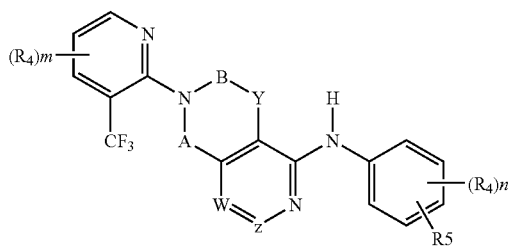

wherein $R^5$ is selected from $R^4$, t-Bu, iso-Pr, $CF_3$, dialkylamino, Br, $OCF_3$, $OCHF_2$, and Cl; and m and n are independently selected from 0-3. Suitably, $R^5$ may be selected from 4-t-Bu, 4-Cl, 4-F, 4-iso-Pr, 4-OMe, 4-$OCF_3$, 4-$OCHF_2$, 4-$SO_2CF_3$, 4-$SO_2R^{2'}$, 4-$SO_2NR^{2'}R^{2'}$, 4-$C(Me)2CN$, 3,4-diCl and 4-$NR^{2'}R^{2'}$; m may, for example, represent 0; and n may, for example, represent 0;

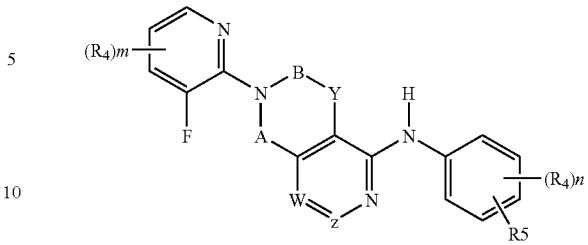

wherein $R^5$ is selected from $R^4$, t-Bu, iso-Pr, $CF_3$, dialkylamino, Br, $OCF_3$, $OCHF_2$, and Cl; and m and n are independently selected from 0-3. Suitably, $R^5$ may be selected from 4-t-Bu, 4-Cl, 4-F, 4-iso-Pr, 4-OMe, 4-$OCF_3$, 4-$OCHF_2$, 4-$SO_2CF_3$, 4-$SO_2R^{2'}$, 4-$SO_2NR^{2'}R^{2'}$, 4-$C(Me)2CN$, 3,4-diCl and 4-$NR^{2'}R^{2'}$; m may, for example, represent 0; and n may, for example, represent 0;

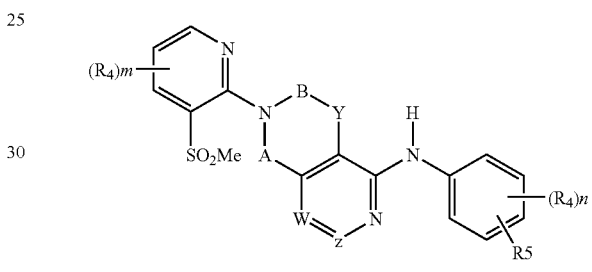

wherein $R^5$ is selected from $R^4$, t-Bu, iso-Pr, $CF_3$, dialkylamino, Br, $OCF_3$, $OCHF_2$, and Cl; and m and n are independently selected from 0-3. Suitably, $R^5$ may be selected from 4-t-Bu, 4-Cl, 4-F, 4-iso-Pr, 4-OMe, 4-$OCF_3$, 4-$OCHF_2$, 4-$SO_2CF_3$, 4-$SO_2R^{2'}$, 4-$SO_2NR^{2'}R^{2'}$, 4-$C(Me)2CN$, 3,4-diCl and 4-$NR^{2'}R^{2'}$; m may, for example, represent 0; and n may, for example, represent 0;

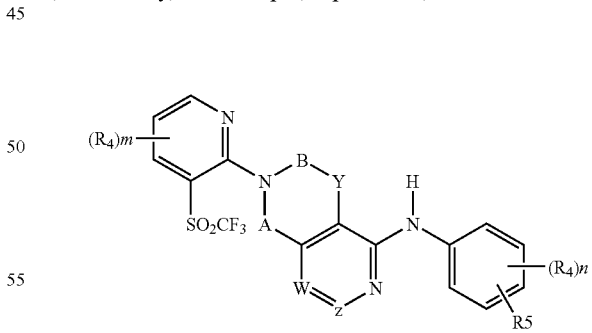

wherein $R^5$ is selected from $R^4$, t-Bu, iso-Pr, $CF_3$, dialkylamino, Br, $OCF_3$, $OCHF_2$, and Cl; and m and n are independently selected from 0-3. Suitably, $R^5$ may be selected from 4-t-Bu, 4-Cl, 4-F, 4-iso-Pr, 4-OMe, 4-$OCF_3$, 4-$OCHF_2$, 4-$SO_2CF_3$, 4-$SO_2R^{2'}$, 4-$SO_2NR^{2'}R^{2'}$, 4-$C(Me)2CN$, 3,4-diCl and 4-$NR^{2'}R^{2'}$; m may, for example, represent 0; and n may, for example, represent 0;

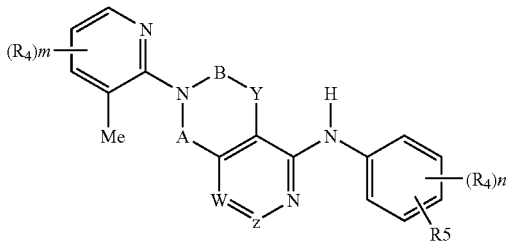

wherein $R^5$ is selected from $R^4$, t-Bu, iso-Pr, $CF_3$, dialkylamino, Br, $OCF_3$, $OCHF_2$, and Cl; and m and n are independently selected from 0-3; and

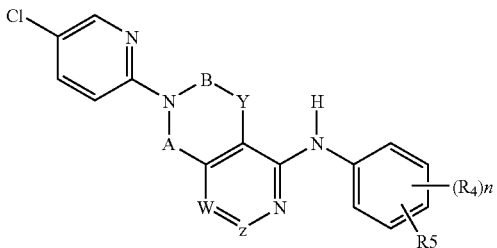

wherein $R^5$ is selected from $R^4$, t-Bu, iso-Pr, $CF_3$, dialkylamino, Br, $OCF_3$, $OCHF_2$, and Cl; and n is from 0-3.

In a particular embodiment, the compounds according to Formula (1) can be described by the following formula:

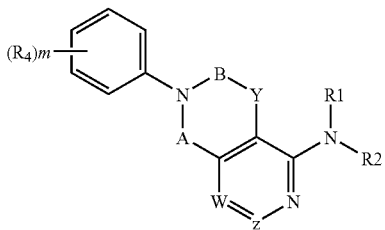

wherein
A and B are independently selected from $CH_2$, $CR^2R^4$, CO, CS, $NR^1$, and $NR^2$;
Y is independently selected from $CH_2$, $CR^2R^4$, $NR^1$, and $NR^2$;
W is selected from $CR^4$ and N;
Z is $CR^4$;
$R^1$ is selected from substituted and unsubstituted aliphatic, substituted or unsubstituted alkyl, substituted or unsubstituted heteroalkyl, substituted or unsubstituted acyl, substituted or unsubstituted aryl, substituted or unsubstituted heteroaryl, substituted or unsubstituted aralkyl, substituted or unsubstituted heteroalkyl;
$R^2$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl;
$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfoxide, substituted or unsubstituted sulfone, substituted or unsubstituted sulfanyl, substituted or unsubstituted aminosulfonyl, substituted or unsubstituted arylsulfonyl, sulfuric acid, sulfuric acid ester, substituted or unsubstituted dihydroxyphosphoryl, substituted or unsubstituted aminodihydroxyphosphoryl, azido, carboxy, substituted or unsubstituted carbamoyl, carboxyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thio; and m is selected from 0-4;
or a pharmaceutically acceptable salt, solvate or prodrug thereof;
and stereoisomers and tautomers thereof. Suitably m may be selected from 0 to 3.

In a particular embodiment of the compound of the above variant formula, A, B and Y are $CR^{2}R^{2'}$; W is selected from $CR^4$ and N; Z is $CR^4$; $R^2$ is hydrogen; $R^{2'}$ is hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl. Suitably A, B and Y may all be $CH_2s$, and m is selected from 0-3.

Further variant compounds of this formula may comprise the following:

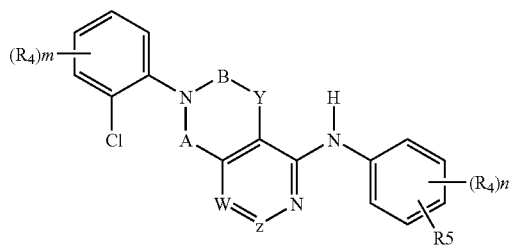

wherein $R^5$ is selected from $R^4$, t-Bu, iso-Pr, $CF_3$, dialkylamino, Br, $OCF_3$, $OCHF_2$, and Cl; and m and n are independently selected from 0-3. In this variant, m may, for example represent 0; n may, for example, represent 0; $R_5$ may, for example, be selected from 4-t-Bu, 4-Cl, 4-F, 4-iso-Pr, 4-OMe, 4-$OCF_3$, 4-$OCHF_2$, 4-$SO_2CF_3$, 4-$SO_2R^{2'}$, 4-$SO_2NR^{2'}R^{2'}$, 4-$C(Me)_2CN$, 3,4-diCl and 4-$NR^{2'}R^{2'}$; m may, for example, represent 0; and n may, for example, represent 0;

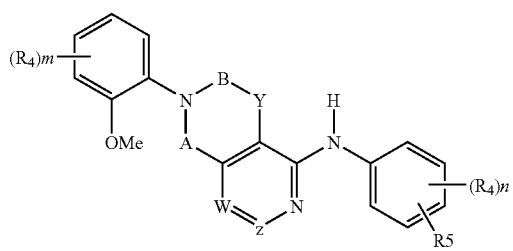

wherein $R^5$ is selected from $R^4$, t-Bu, iso-Pr, $CF_3$, dialkylamino, Br, $OCF_3$, $OCHF_2$, and Cl; and m and n are independently selected from 0-3. Suitably, $R^5$ may be selected from 4-t-Bu, 4-Cl, 4-F, 4-iso-Pr, 4-OMe, 4-$OCF_3$, 4-$OCHF_2$, 4-$SO_2CF_3$, 4-$SO_2R^{2'}$, 4-$SO_2NR^{2'}R^{2'}$, 4-C(Me)2CN, 3,4-diCl and 4-$NR^{2'}R^{2'}$; m may, for example, represent 0; and n may, for example, represent 0;

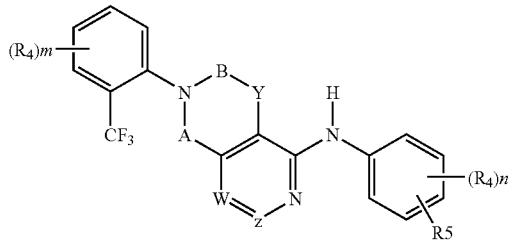

wherein $R^5$ is selected from $R^4$, t-Bu, iso-Pr, $CF_3$, dialkylamino, Br, $OCF_3$, $OCHF_2$, and Cl; and m and n are independently selected from 0-3. Suitably, $R^5$ may be selected from 4-t-Bu, 4-Cl, 4-F, 4-iso-Pr, 4-OMe, 4-$OCF_3$, 4-$OCHF_2$, 4-$SO_2CF_3$, 4-$SO_2R^{2'}$, 4-$SO_2NR^{2'}R^{2'}$, 4-C(Me)2CN, 3,4-diCl and 4-$NR^{2'}R^{2'}$; m may, for example, represent 0; and n may, for example, represent 0;

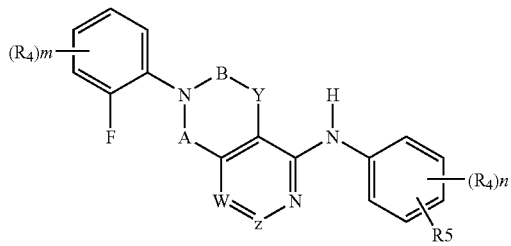

wherein $R^5$ is selected from $R^4$, t-Bu, iso-Pr, $CF_3$, dialkylamino, Br, $OCF_3$, $OCHF_2$, and Cl; and m and n are independently selected from 0-3. Suitably, $R^5$ may be selected from 4-t-Bu, 4-Cl, 4-F, 4-iso-Pr, 4-OMe, 4-$OCF_3$, 4-$OCHF_2$, 4-$SO_2CF_3$, 4-$SO_2R^{2'}$, 4-$SO_2NR^{2'}R^{2'}$, 4-C(Me)2CN, 3,4-diCl and 4-$NR^{2'}R^{2'}$; m may, for example, represent 0; and n may, for example, represent 0;

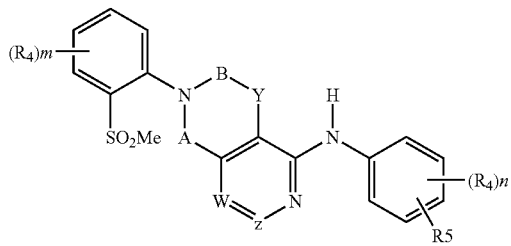

wherein $R^5$ is selected from $R^4$, t-Bu, iso-Pr, $CF_3$, dialkylamino, Br, $OCF_3$, $OCHF_2$, and Cl; and m and n are independently selected from 0-3. Suitably, $R^5$ may be selected from 4-t-Bu, 4-Cl, 4-F, 4-iso-Pr, 4-OMe, 4-$OCF_3$, 4-$OCHF_2$, 4-$SO_2CF_3$, 4-$SO_2R^{2'}$, 4-$SO_2NR^{2'}R^{2'}$, 4-C(Me)2CN, 3,4-diCl and 4-$NR^{2'}R^{2'}$; m may, for example, represent 0; and n may, for example, represent 0;

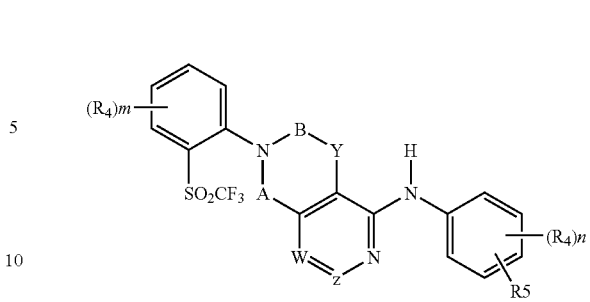

wherein $R^5$ is selected from $R^4$, t-Bu, iso-Pr, $CF_3$, dialkylamino, Br, $OCF_3$, $OCHF_2$, and Cl; and m and n are independently selected from 0-3. Suitably, $R^5$ may be selected from 4-t-Bu, 4-Cl, 4-F, 4-iso-Pr, 4-OMe, 4-$OCF_3$, 4-$OCHF_2$, 4-$SO_2CF_3$, 4-$SO_2R^{2'}$, 4-$SO_2NR^{2'}R^{2'}$, 4-C(Me)2CN, 3,4-diCl and 4-$NR^{2'}R^{2'}$; m may, for example, represent 0; and n may, for example, represent 0;

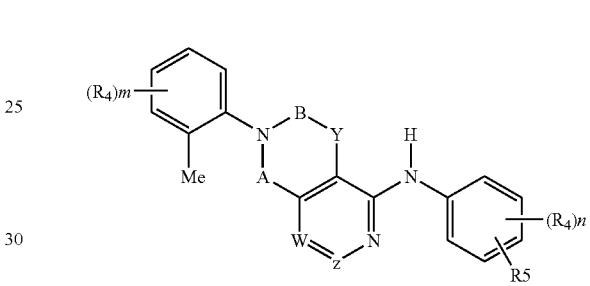

wherein $R^5$ is selected from $R^4$, t-Bu, iso-Pr, $CF_3$, dialkylamino, Br, $OCF_3$, $OCHF_2$, and Cl; and m and n are independently selected from 0-3; and

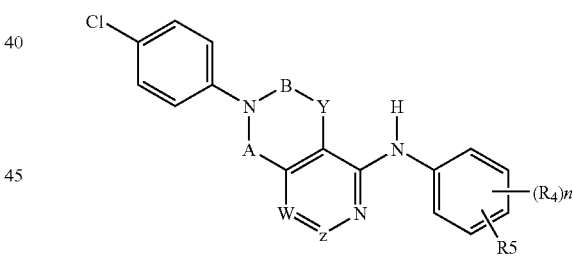

wherein $R^5$ is selected from $R^4$, t-Bu, iso-Pr, $CF_3$, dialkylamino, Br, $OCF_3$, $OCHF_2$, and Cl; and n is from 0-3.

In the aforementioned structures, W and Z may, for example, both represent $CR^4$. Alternatively W may represent N and Z may represent $CR^4$. Suitably $R^4$ is selected from H, cyano, amido, and a group represented by X—$(CR^{2'}R^{2'})_n$—$R^{3''}$; wherein X is a bond, O, S, SO, $SO_2$, or $NR^{2'}$; each $R^2$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl; $R^{3''}$ is selected from a hydrogen, a hetero substituent and aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, and bicycloheteroaryl ring; and n is selected from 0-4; provided when X is other than a bond, $R^{3''}$ is hetero substituent then n is at least 2. In a particular embodiment, $R^4$ may be X—$(CR^{2'}R^{2'})_n$—$R^{3''}$, where X may be a bond, each $R^{2'}$ may be H; and n is 0-4. Alternatively, X may be O, S, SO or $SO_2$; each $R^{2'}$ may be H; and n is 2-4.

In the above embodiment, $R^{3''}$ may be substituted or unsubstituted cycloalkyl, cycloheteroalkyl, aryl or heteroaryl, and in a particular embodiment, $R^{3''}$ is a hetero substituent. In a specific embodiment, $R^{3''}$ is selected from COOH, $SO_2Me$, SMe, OH, OEt, OMe, $NEt_2$, $NHSO_2Me$, $CONH_2$, $CONMe_2$ and $SO_2NMe_2$. For example $R^4$ may represent H. Suitably A, B and Y all are $CH_2$. Alternatively A and B are independently selected from $CH_2$ and $CHCH_3$, and Y is $CH_2$. Alternatively A and B are independently selected from $CH_2$ and CO and Y is $CH_2$. Alternatively A and B are independently selected from CO and CS and Y is $NR^2$.

Further variant compounds are defined by the formula:

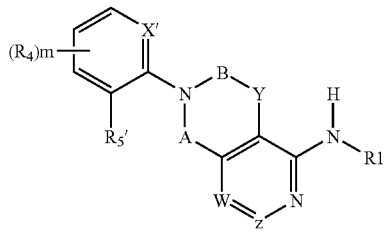

wherein X' is N or CH; and $R^1$ is heteroaryl and $R^{5'}$ is selected from Cl, $CF_3$, F, OMe, $SO_2Me$ and $SO_2CF_3$.

Suitably, $R^1$ is selected from substituted and unsubstituted pyridyl. Suitably the substitution is selected from t-Bu, Cl, F, iso-Pr, OMe, $OCF_3$, $OCHF_2$, $SO_2CF_3$, $SO_2R^{2'}$, $SO_2NR^2R^{2'}$, CN, $C(Me)_2CN$, and $NR^{2'}R^{2'}$.

Alternatively, $R^1$ may be selected from substituted or unsubstituted indolyl, benzimidazolyl, indazolyl, tetrahydroquinoline and tetrahydroisoquinoline. In a particular aspect of the invention, the compound is depicted by the following formula:

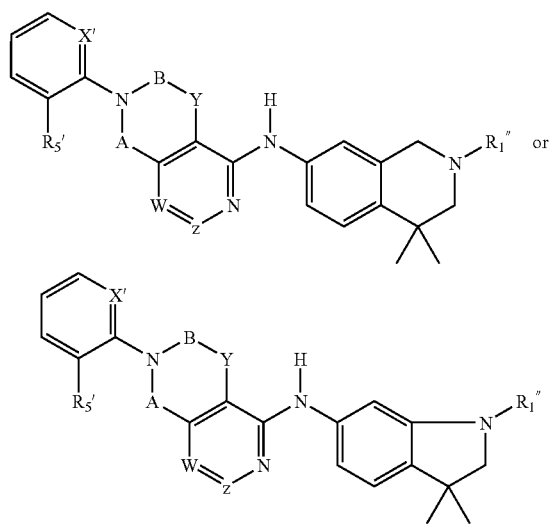

wherein
wherein X' is N or CH; and $R^{1'''}$ is selected from H, alkyl, and a group represented by —$(CR^{2'}R^{2'})_n$—$R^{3''}$;
each $R^{2'}$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl;
$R^{3''}$ is selected from a hydrogen, a hetero substituent and aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, and bicycloheteroaryl ring; and
n is selected from 2-5.

In a particular embodiment, $R^4$ is —$(CR^{2'}R^{2'})_n$—$R^{3''}$ and each $R^{2'}$ may be H, in instance, n may be 2-4. $R^{3''}$ may also be substituted or unsubstituted cycloalkyl, cycloheteroalkyl, aryl or heteroaryl. Particularly, $R^{3''}$ may be substituted or unsubstituted

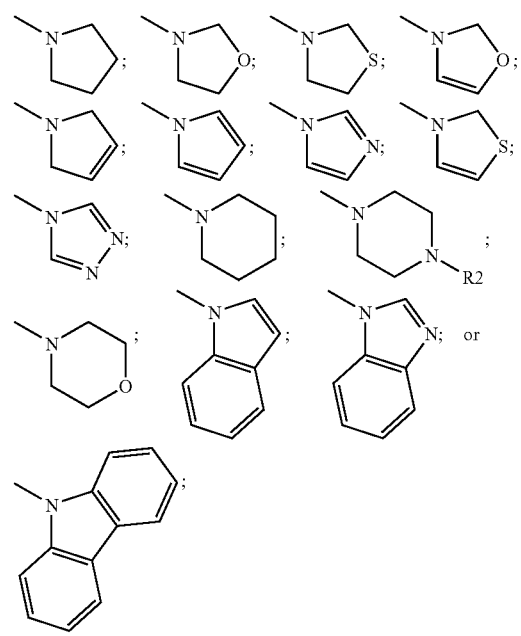

where $R^2$ is as defined herein. In a further particular embodiment, $R^{3''}$ is a hetero substitutent, and more particularly, $R^{3''}$ is selected from COOH, SMe, $SO_2Me$, OH, OEt, OMe, $NEt_2$, halo, $NHSO_2Me$, $CONH_2$, $CONMe_2$, $SO_2NH_2$, and $SO_2NMe_2$.

In one embodiment, W and Z are both $CR^4$. Alternatively W is N and Z is $CR^4$.

Suitably $R^4$ is selected from H, cyano, amido, and a group represented by X—$(CR^{2'}R^{2'})_n$—$R^{3''}$; wherein X is a bond, O, S, SO, $SO_2$, or $NR^{2'}$; each $R^{2'}$ is selected from hydrogen, substituted or unsubstituted $C_1$-$C_6$ alkyl, substituted or unsubstituted $C_1$-$C_6$ cycloalkyl, substituted or unsubstituted aryl and substituted or unsubstituted aralkyl; $R^{3''}$ is selected from a hydrogen, a hetero substituent and aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, and bicycloheteroaryl ring; and n is selected from 0-4; provided when X is other than a bond, $R^{3''}$ is hetero substituent then n is at least 2. In a particular embodiment, $R^4$ may be X—$(CR^{2'}R^{2'})_n$—$R^{3''}$, where X may be a bond, each $R^{2'}$ may be H; and n is 0-4. Alternatively, X may be O, S, SO or $SO_2$; each $R^{2'}$ may be H; and n is 2-4.

In the above embodiment, $R^{3''}$ may be substituted or unsubstituted cycloalkyl, cycloheteroalkyl, aryl or heteroaryl, and in a particular embodiment, $R^{3''}$ is a hetero substituent. In a specific embodiment, R³'' is selected from COOH, SO₂Me, SMe, OH, OEt, OMe, NEt₂, NHSO₂Me, CONH₂, CONMe₂ and SO₂NMe₂. For example R⁴ may represent H.

Suitably A, B and Y are all CH₂. Alternatively A and B are independently selected from CH₂ and CHCH₃, and Y is CH₂.

Particular non-limiting examples of compounds corresponding to the structural variant just described, are as follows:

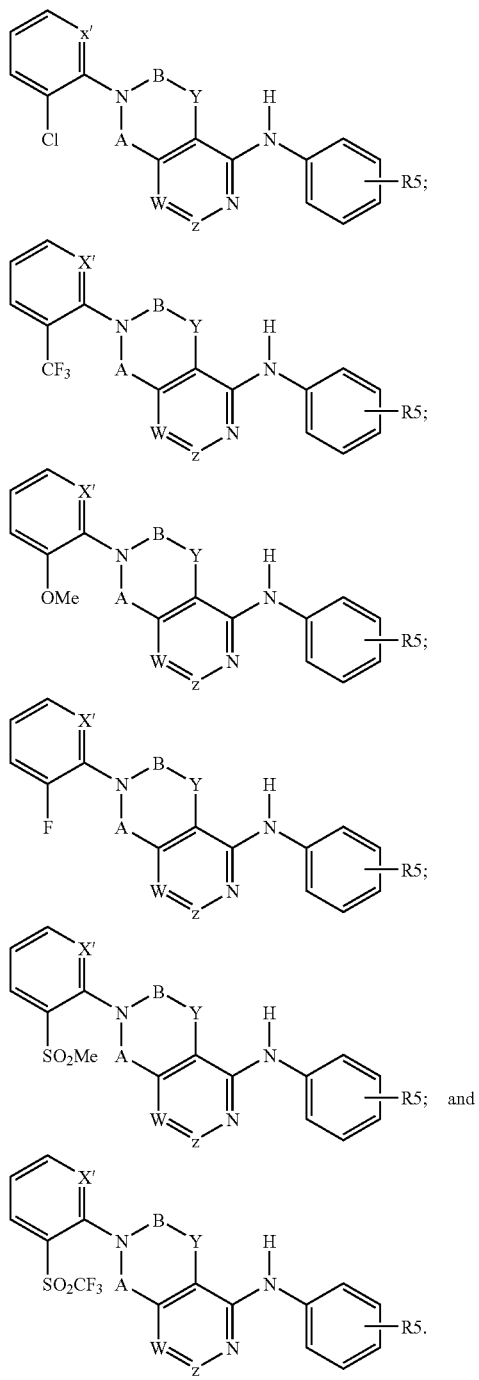

In the instance of all of the above compounds, X' is N or CH; and R⁵ may be selected from 4-t-Bu, 4-Cl, 4-F, 4-iso-Pr, 4-OMe, 4-OCF₃, 4-OCHF₂, 4-SO₂CF₃, 4-SO₂R²', 4-SO₂NR²'R²', 4-C(Me)2CN, 3,4-diCl and 4-NR²'R²'. In the instance of all of the above compounds W and Z may, for example, both represent CR⁴. Alternatively W may represent N and Z may represent CR⁴. Suitably R⁴ is selected from H, cyano, amido, and a group represented by X—(CR²'R²')ₙ—R³''; wherein X is a bond, O, S, SO, SO₂, or NR²'; each R²' is selected from hydrogen, substituted or unsubstituted C₁-C₆ alkyl, substituted or unsubstituted C₁-C₆ cycloalkyl, substituted or unsubstituted aryl and substituted or unsubstituted aralkyl; R³'' is selected from a hydrogen, a hetero substituent and aryl, heteroaryl, heteroalkyl, cycloalkyl, cycloheteroalkyl, cycloalkenyl, cycloheteroalkenyl, bicycloalkyl, bicycloheteroalkyl, bicycloalkenyl, bicycloheteroalkenyl, bicycloaryl, and bicycloheteroaryl ring; and n is selected from 0-4; provided when X is other than a bond, R³'' is hetero substituent then n is at least 2. In a particular embodiment, R⁴ may be X—(CR²'R²')ₙ—R³'', where X may be a bond, each R²' may be H; and n is 0-4. Alternatively, X may be O, S, SO or SO₂; each R²' may be H; and n is 2-4.

In the above embodiment, R³'' may be substituted or unsubstituted cycloalkyl, cycloheteroalkyl, aryl or heteroaryl, and in a particular embodiment, R³'' is a hetero substituent. In a specific embodiment, R³'' is selected from COOH, SO₂Me, SMe, OH, OEt, OMe, NEt₂, NHSO₂Me, CONH₂ and CONMe₂. For example R⁴ may represent H. Suitably A, B and Y are all CH₂. Alternatively A and B are independently selected from CH₂ and CHCH₃, and Y is CH₂. Alternatively A and B are independently selected from CH₂ and CO and Y is CH₂. Alternatively A and B are independently selected from CO and CS and Y is NR².

Additional variant compounds within the scope of the present invention are set forth in non-limiting fashion later on herein and in the examples. It should be understood that these examples are for illustrative purposes only and are not to be construed as limiting this invention in any manner.

Further compounds related to Formula 3 of the invention are set forth below.

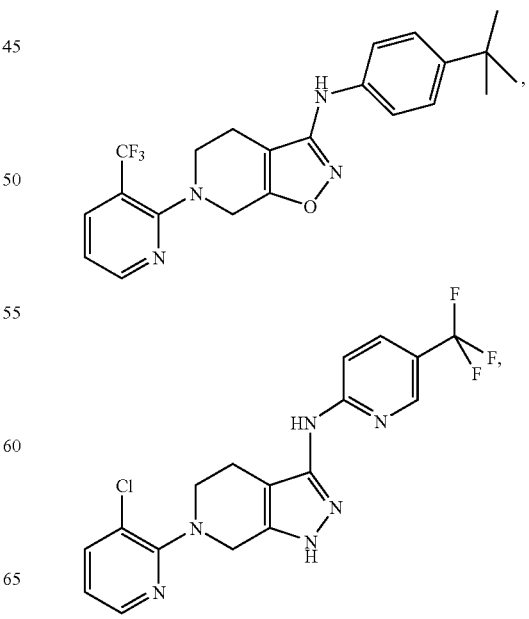

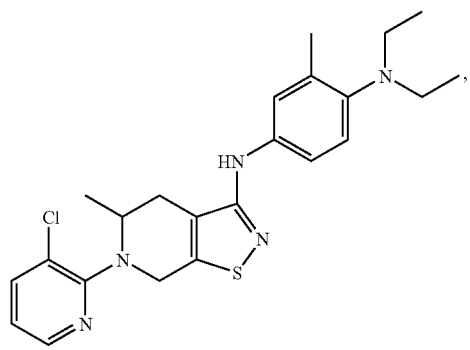

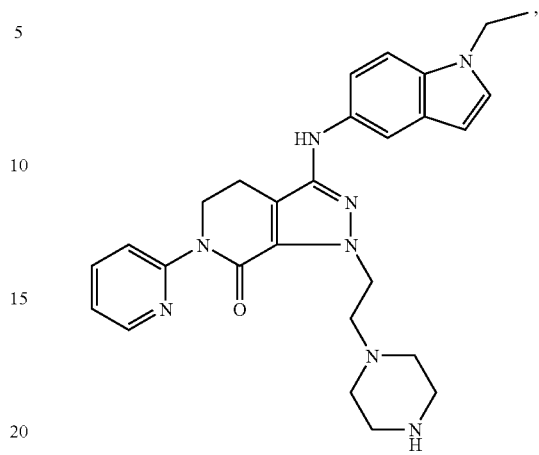

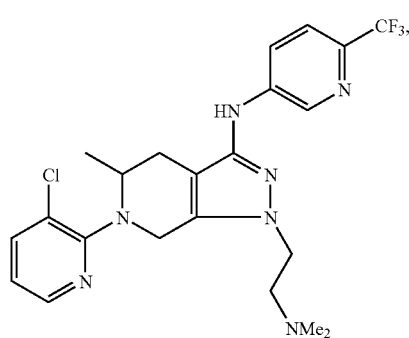

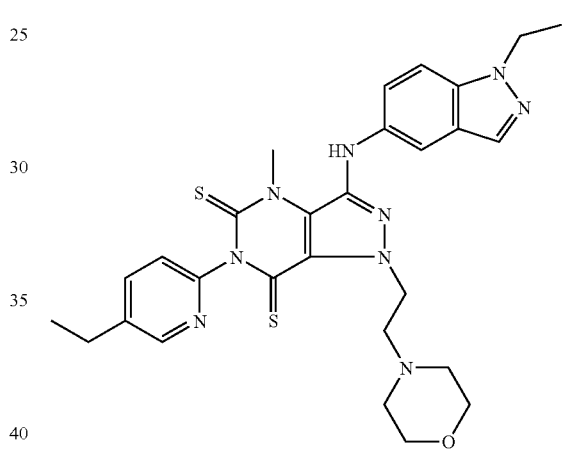

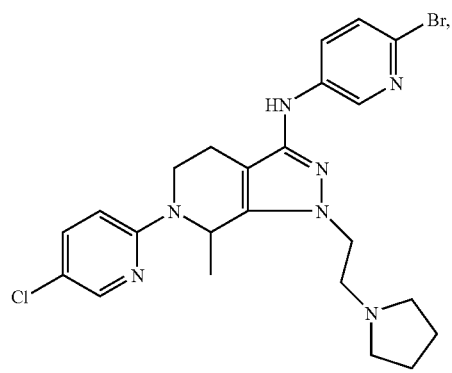

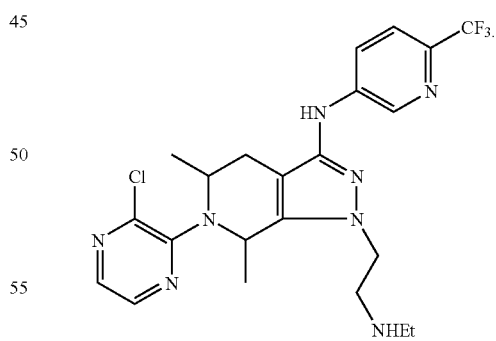

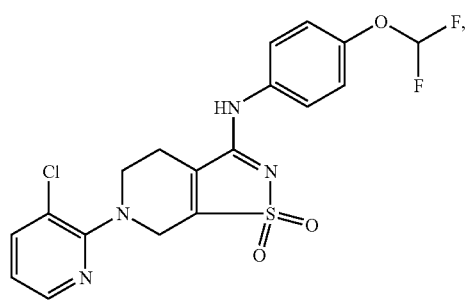

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the amine compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of formula I is admixed as a dry powder with a starch diluent in an approximate 1:1 weight ratio. The mixture is filled into 250 mg capsules (125 mg of active compound per capsule).

Formulation 3—Liquid

A compound of formula I (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

The compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

The compound of formula I is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of formula I (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present amine compounds are used as therapeutic agents for the treatment of conditions in mammals. Accordingly, the compounds and pharmaceutical compositions of this invention find use as therapeutics for preventing and/or treating neurodegenerative, autoimmune and inflammatory conditions in mammals including humans.

In a method of treatment aspect, this invention provides a method of treating a mammal susceptible to or afflicted with a condition associated with arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. The present amines have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

As a further aspect of the invention there is provided the present amine compounds for use as a pharmaceutical especially in the treatment or prevention of the aforementioned conditions and diseases. We also provide the use of a present amine compound in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of a compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the amine compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other active amines or derivatives.

General Synthetic Procedures

The tetrahydronaphthyridine compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, N.Y., 1991, and references cited therein.

The compounds of this invention, for example, may be prepared by the reaction of a chloro derivative with an appropriately substituted amine and the product isolated and purified by known standard procedures. Such procedures include (but are not limited to) recrystallization, column chromatography or HPLC. The following schemes are presented with details as to the preparation of representative tetrahydronaphthyridines and tetrahydropyrido[3,4-d]pyrimidines that have been listed hereinabove. The compounds of the invention may be prepared from known or commercially available starting materials and reagents by one skilled in the art of organic synthesis.

Synthetic Scheme 1

Various N-substituted-7-(pyridin-2-yl)-5,6,7,8-tetrahydropyrido[3,4-d]pyrimidin-4-amine derivatives are prepared using a general procedure described below. Accordingly, ethyl 1-benzyl-3-oxopiperidine-4-carboxylate hydrochloride is reacted with formamidine acetate to yield 7-benzyl-5,6,7,8-tetrahydropyrido[3,4-d]pyrimidin-4(4aH)-one, which, in turn, is reacted with POCl₃ to afford the 4-chloro derivative. The intermediate chloro derivative is then condensed with substituted aniline or amine to give the desired N-substituted-7-benzyl-5,6,7,8-tetrahydropyrido[3,4-d]pyrimidin-4-amine. Debenzylation using standard procedures known in the art followed by nucleophilic displacement of an appropriate 2-halo-pyridine yields the appropriate N-substituted-7-(pyridin-2-yl)-5,6,7,8-tetrahydropyrido[3,4-d]pyrimidin-4-amine. As a representative example, synthesis of N-(4-tert-butylphenyl)-7-(3-chloropyridin-2-yl)-5,6,7,8-tetrahydropyrido[3,4-d]pyrimidin-4-amine is depicted in Scheme 1.

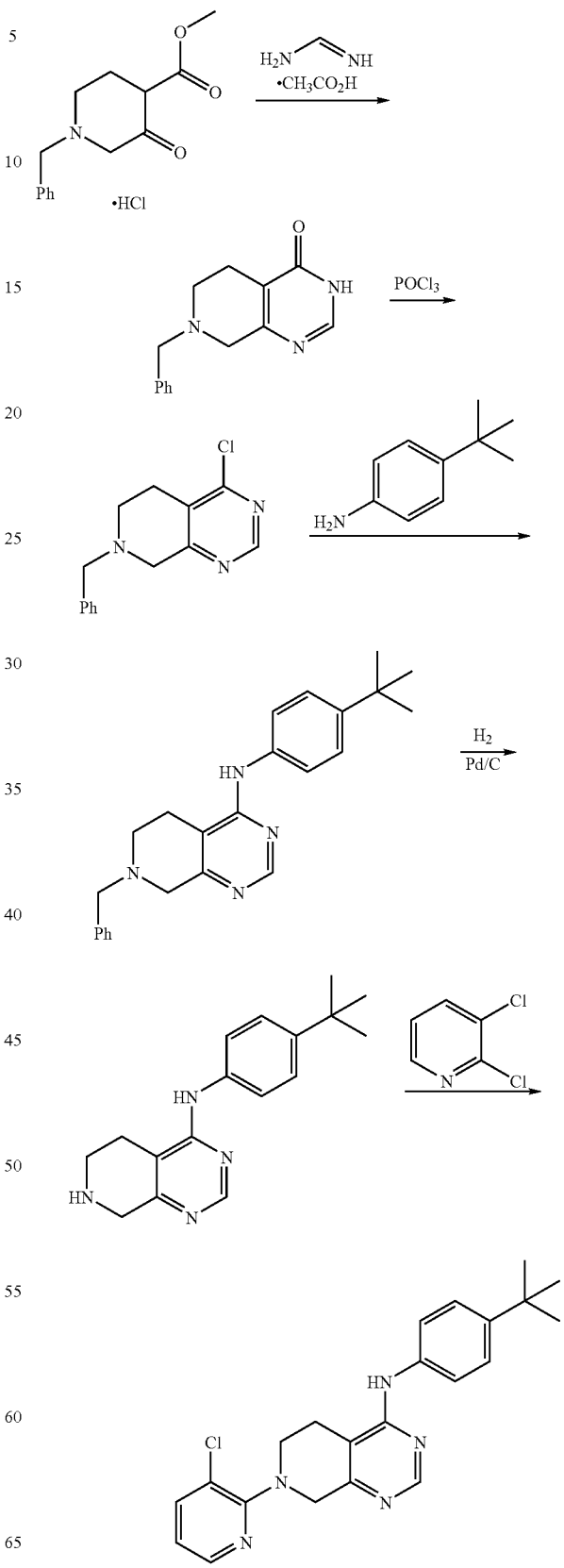

Conversly, N-substituted-7-(pyridin-2-yl)-5,6,7,8-tetrahydropyrido[3,4-d]pyrimidin-4-amine derivatives are prepared by first deprotecting the 7-benzyl-5,6,7,8-tetrahydropyrido[3,4-d]pyrimidin-4(4aH)-one and reacting the product with an appropriate 2-halo-pyridine to give the 7-(pyridin-2-yl)-5,6,7,8-tetrahydropyrido[3,4-d]pyrimidin-4(4aH)-one which is reacted with POCl₃ followed by condensation with an appropriate aniline or amine to yield the appropriate the appropriate N-substituted-7-(pyridin-2-yl)-5,6,7,8-tetrahydropyrido[3,4-d]pyrimidin-4-amine. As a representative example, synthesis of N-(4-tert-butylphenyl)-7-(3-chloropyridin-2-yl)-5,6,7,8-tetrahydropyrido[3,4-d]pyrimidin-4-amine is depicted in Scheme 2.

chloride with thiourea. This intermediate methylthio derivative is then subjected to synthetic sequence outlined above (Scheme 2) to give the appropriate N-substituted-7-(pyridin-2-yl)-5,6,7,8-tetrahydro-2-(methylthio)pyrido[3,4-d]pyrimidin-4-amine derivative, which is oxidized to the corresponding sulfone derivative and in turn reacted with an appropriate nucleophile to give the analogous 2-substituted-N-substituted-7-(pyridin-2-yl)-5,6,7,8-tetrahydropyrido[3,4-d]pyrimidin-4-amine derivative. As a representative example, synthesis of N-(4-tert-butylphenyl)-7-(3-chloropyridin-2-yl)-5,6,7,8-tetrahydro-2-methoxypyrido[3,4-d]pyrimidin-4-amine is depicted in Scheme 3.

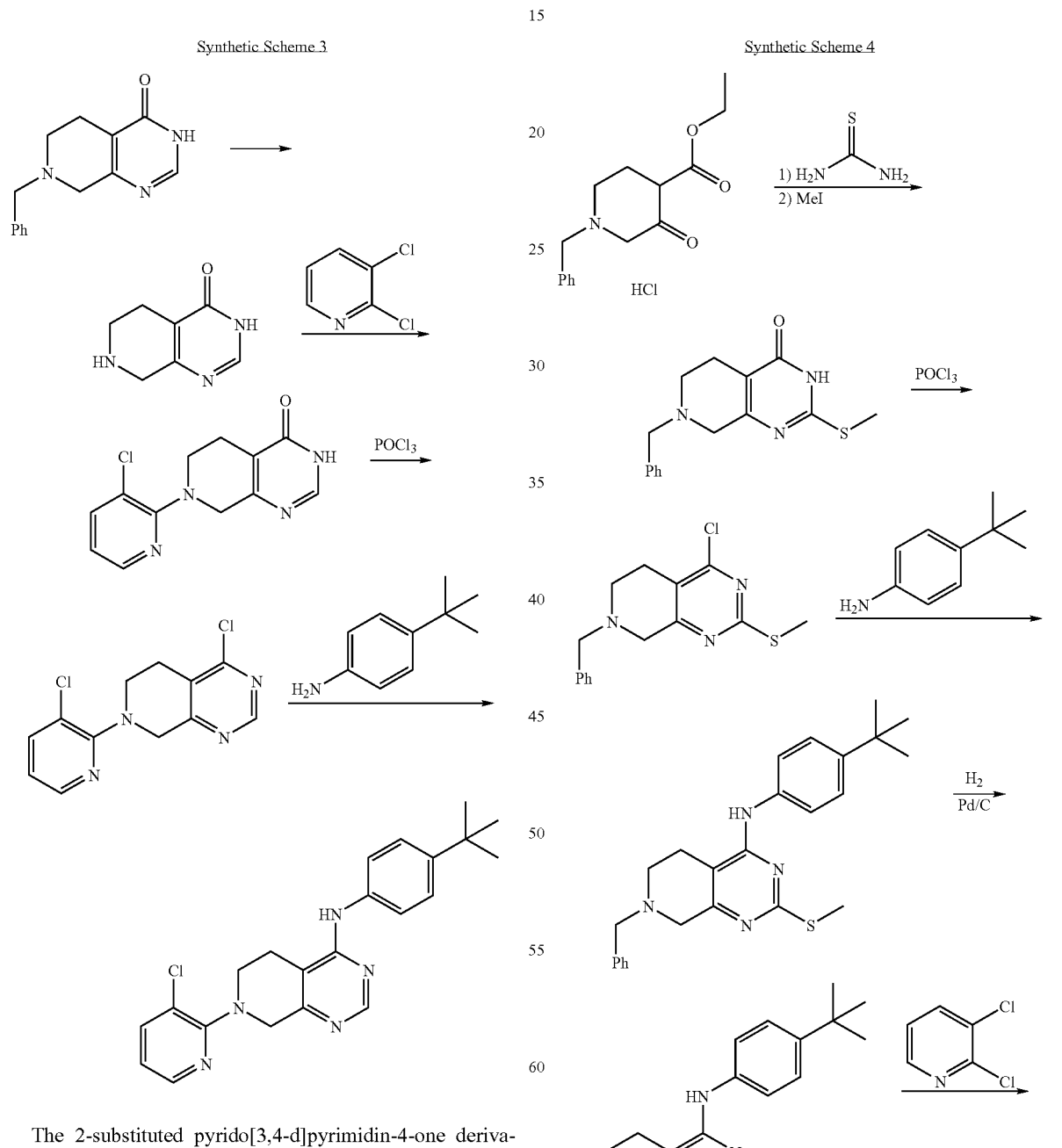

The 2-substituted pyrido[3,4-d]pyrimidin-4-one derivatives are prepared using the synthetic sequence given below. The intermediate 7-benzyl-5,6,7,8-tetrahydro-2-(methylthio)pyrido[3,4-d]pyrimidin-4)3H)-one is formed by reaction of ethyl 1-benzyl-3-oxopiperidine-4-carboxylate hydro- -continued

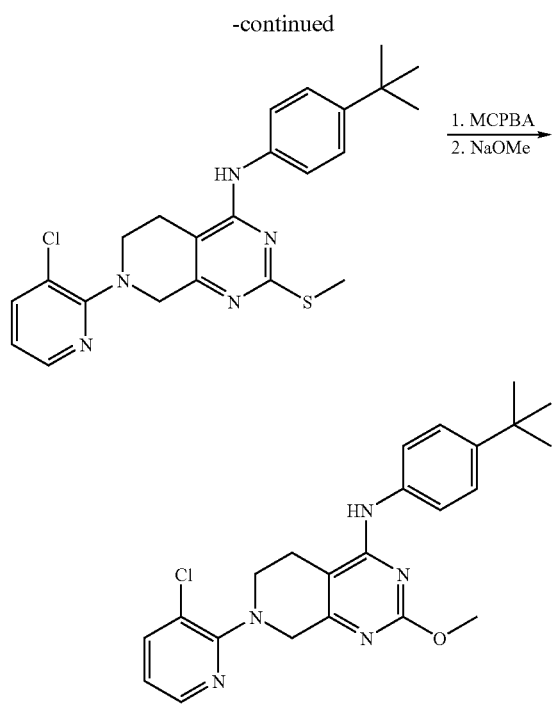

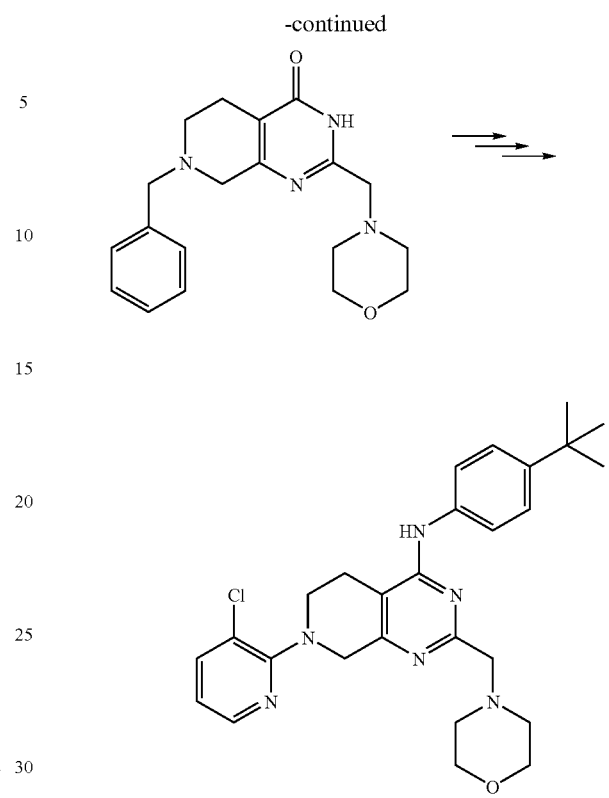

Conversely, 2-chloroacetamidine hydrochloride is reacted with an appropriate nucleophile to form an appropriate amidine derivative. The amidine is reacted with ethyl 1-benzyl-3-oxopiperidine-4-carboxylate hydrochloride to afford the intermediate 2-substituted-N-substituted-7-(pyridin-2-yl)-5,6,7,8-tetrahydropyrido[3,4-d]pyrimidin-4-amine derivative. This intermediate pyrido[3,4-d]pyrimidin-4-amine is then subjected to the reaction sequence described in Scheme 2 to yield appropriately 2-substituted N-substituted-7-(pyridin-2-yl)-5,6,7,8-tetrahydropyrido[3,4-d]pyrimidin-4-amine derivative. As a representative example, synthesis of N-(4-tert-butylphenyl)-7-(3-chloropyridin-2-yl)-5,6,7,8-tetrahydro-2-(morpholinomethyl)pyrido[3,4-d]pyrimidin-4-amine is depicted in Scheme 4.

Appropriate N-aryl substituted-5,6,7,8-tetrahydro-7-arylpyrido[3,4-d]pyrimidin-4-amine, obtained by following synthetic scheme 2, are prepared by the reaction of the corresponding N-substituted-5,6,7,8-tetrahydropyrido[3,4-d]pyrimidin-4-amine with an appropriate aryl boronic acid in the presence of copper acetate and triethylamine. As a representative example, preparation of N-(4-(trifluoromethyl)phenyl)-5,6,7,8-tetrahydro-7-m-tolylpyrido[3,4-d]pyrimidin-4-amine is depicted in Scheme 5. Conversly, N-aryl substituted-5,6,7,8-tetrahydro-7-arylpyrido[3,4-d]pyrimidin-4-amines can be prepared by the reaction of the corresponding N-substituted-5,6,7,8-tetrahydropyrido[3,4-d]pyrimidin-4-amine with an appropriate aryl bromide in the presence of palladium acetate and BINAP.

Synthetic Scheme 5

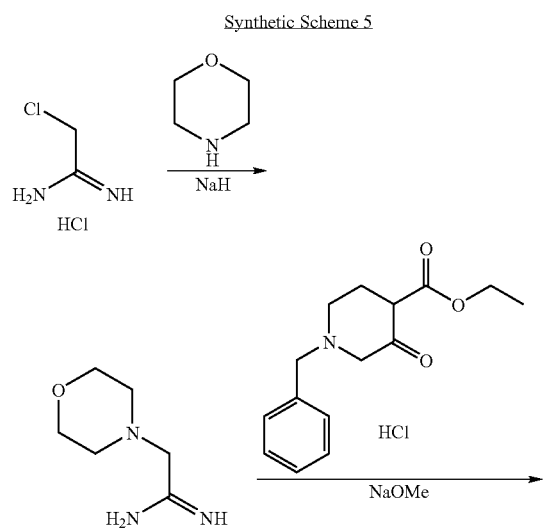

Synthetic Scheme 6

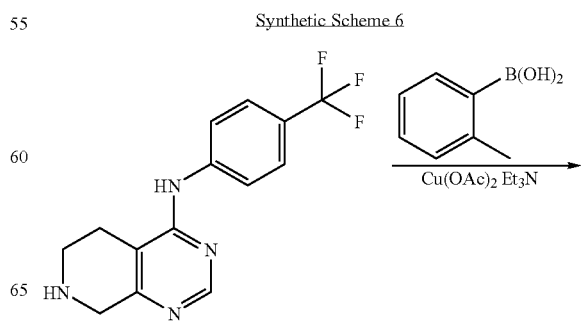

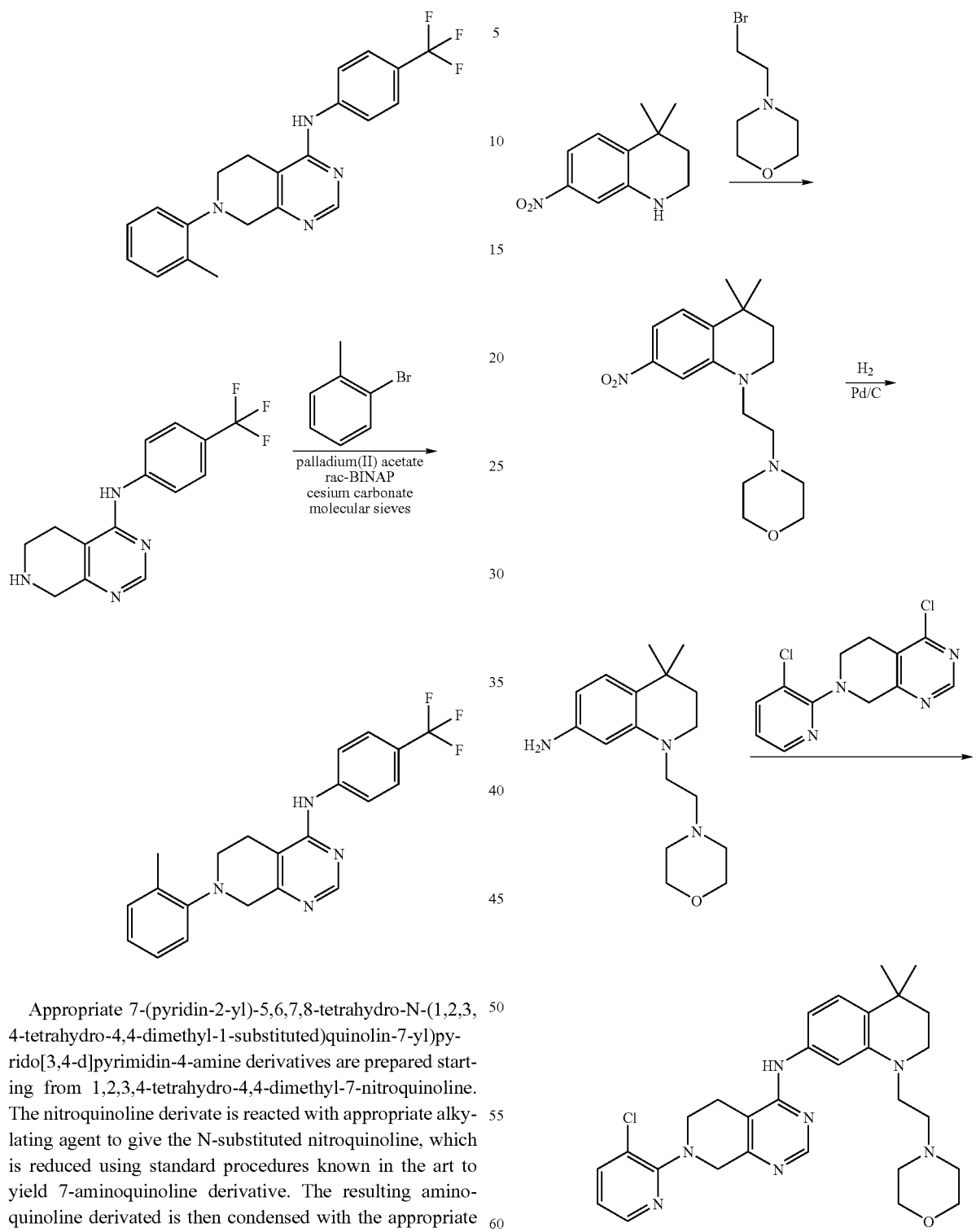

Appropriate 7-(pyridin-2-yl)-5,6,7,8-tetrahydro-N-(1,2,3,4-tetrahydro-4,4-dimethyl-1-substituted)quinolin-7-yl)pyrido[3,4-d]pyrimidin-4-amine derivatives are prepared starting from 1,2,3,4-tetrahydro-4,4-dimethyl-7-nitroquinoline. The nitroquinoline derivate is reacted with appropriate alkylating agent to give the N-substituted nitroquinoline, which is reduced using standard procedures known in the art to yield 7-aminoquinoline derivative. The resulting aminoquinoline derivated is then condensed with the appropriate 4-chloro-7-(pyridin-2-yl)-5,6,7,8-tetrahydropyrido[3,4-d]pyrimidine to give the desired 7-(pyridin-2-yl)-5,6,7,8-tetrahydro-N-(1,2,3,4-tetrahydro-4,4-dimethyl-1-substituted) quinolin-7-yl)pyrido[3,4-d]pyrimidin-4-amine derivative. As a representative example, preparation of the N-morpholionethyl derivative is depicted in Scheme 6.

A similar sequence of reactions using substituted amidines, and set forth in the scheme presented below, gives rise to 2-substituted products. For example, trifluoromethyl amidine can be employed in the similar sequence of reactions to afford 2-trifluoromethyl substituted products.

Synthetic Scheme 8

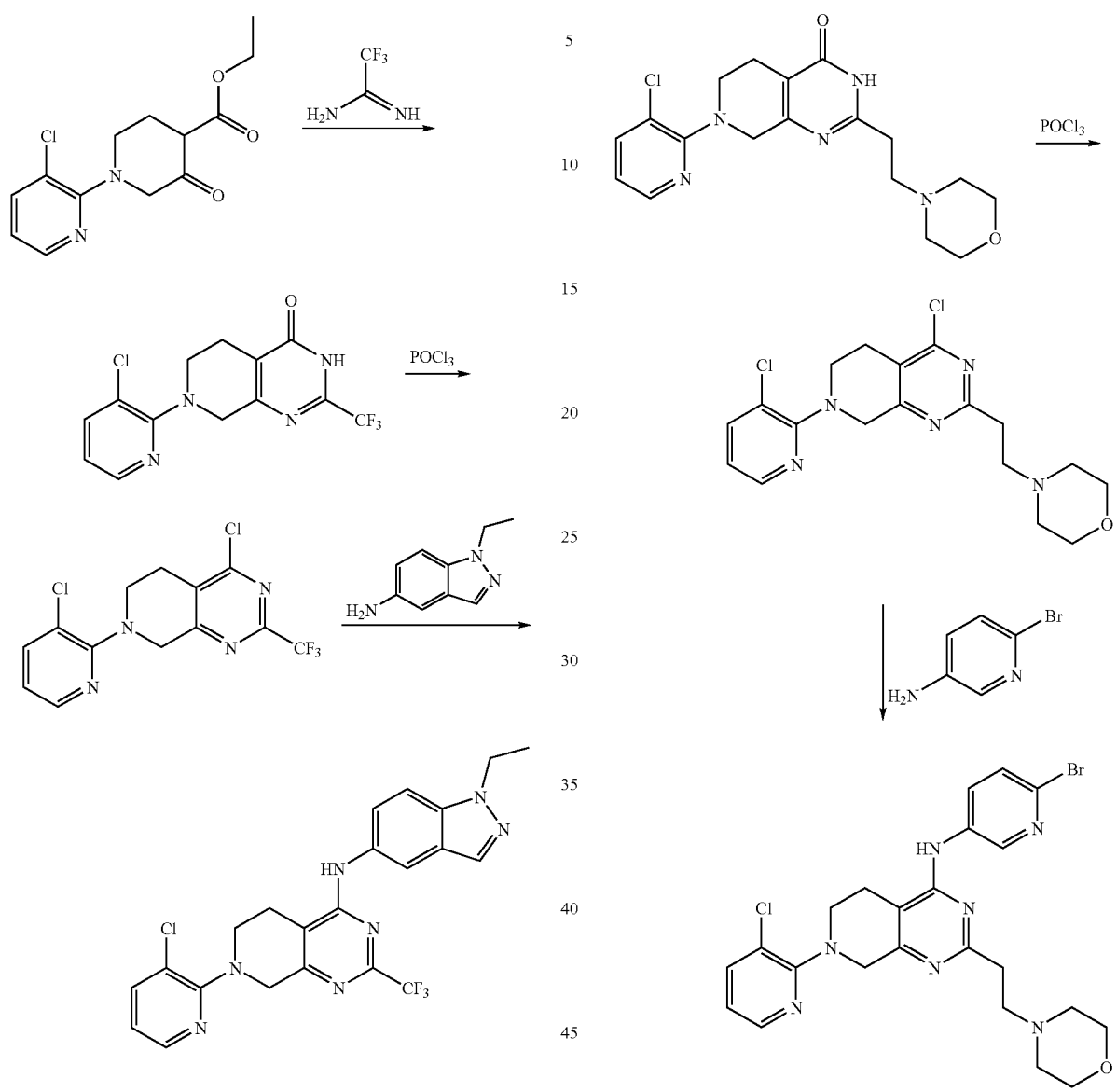

Similarly, another sequence of reactions, as depicted in Scheme 8, using substituted amidines can be employed to prepare 2-substituted derivatives.

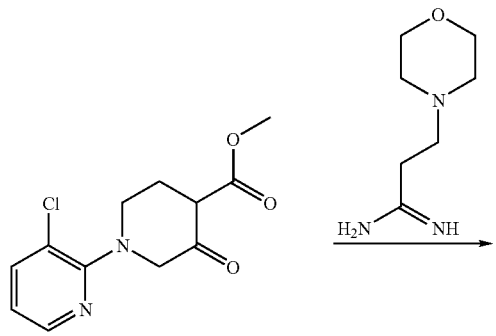

The following synthetic and biological examples are offered to illustrate this invention and are not to be construed in any way as limiting the scope of this invention. In the examples below, all temperatures are in degrees Celsius (unless otherwise indicated). The syntheses of these representative compounds were carried out in accordance with the methods set forth above and using the appropriate reagents, starting materials and purification methods known to those skilled in the art.

Exemplary Compounds of the Invention

The following compounds have been prepared according to the methods of the invention. Corresponding compounds have been recited hereinabove and in the claims. Unless otherwise indicated, reactions in microwave were carried out in Emrys Optimizer or Smith Creator microwave models manufactured by Personal Chemistry, Inc.

EXAMPLES

Example 1

7-(3-Chloropyridin-2-yl)-N-(4-(trifluoromethyl)phenyl)-5,6,7,8-tetrahydropyrido[3,4-d]pyrimidin-4-amine

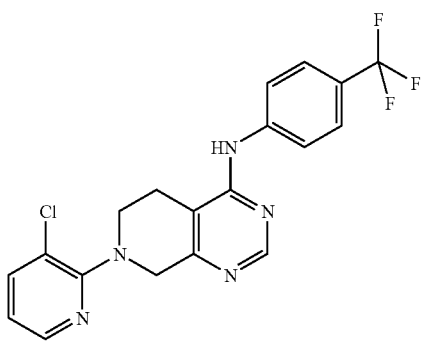

A. 7-Benzyl-5,6,7,8-tetrahydropyrido[3,4-d]pyrimidin-4) 3H)-one

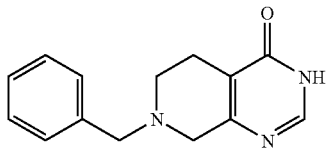

Ethyl 1-benzyl-3-oxopiperidine-4-carboxylate hydrochloride (50 g, 168 mmol) was suspended in 25% sodium methoxide in methanol (200 ml; 839 mmol) and formamidine acetate (20.9 g, 201 mmol) was added to the mixture. The reaction mixture was refluxed until all of the starting material was consumed (8 hours). The methanol was removed under vacuum, and the resulting white solid was dissolved in a 3:1 mixture of chloroform:isopropanol. The mixture was washed with water and brine, dried over $Na_2SO_4$, filtered and evaporated to give the desired product as a white solid which was used without further purification.

MS: M+H=242. $^1$H NMR (DMSO-d6): δ 2.32(t, J=5.8 Hz, 2H); 2.56(t, J=5.8 Hz, 2H); 3.11(s, 2H); 3.57(s, 2H); 7.22-7.35(m, 5H); 7.81(s, 1H); 8.5(s, 0.2H).

B. 7-Benzyl-4-chloro-5,6,7,8-tetrahydropyrido[3,4-d]pyrimidine

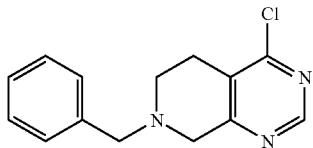

7-Benzyl-5,6,7,8-tetrahydropyrido[3,4-d]pyrimidin-4) 3H)-one (31 g, 128 mmol) was dissolved in anhydrous 1,2-dichloroethane and stirred under $N_2$(g) atmosphere. The mixture was cooled to 0° C. and $POCl_3$ (95 mL, 1024 mmol) was added dropwise, followed by N,N-dimethylaniline (16.2 mL, 128 mmol). The mixture was warmed to room temperature and brought to reflux for 2 hrs. After stirring at room temperature overnight the solvents were removed under vacuum and evaporated 3 times with xylenes to give a red residue. The residue was dissolved in ethyl acetate, poured over a crushed ice/water slurry and neutralized using solid $NaHCO_3$. After neutralization, ethyl acetate was added and the organic layer was washed with water and brine. The organic layer was dried over $Na_2SO_4$ and the solvents were removed under vacuum. The resulting red residue was purified using a gradient of ethyl acetate:hexane (0-100%) to give the desired compound as a brown oil (19.9 g).

MS: M+H=260.

C. 7-Benzyl-N-(4-(trifluoromethyl)phenyl)-5,6,7,8-tetrahydropyrido[3,4-d]pyrimidin-4-amine

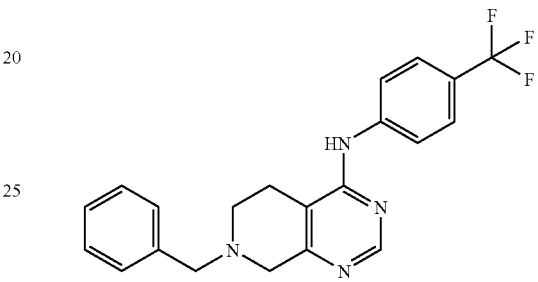

7-Benzyl-4-chloro-5,6,7,8-tetrahydropyrido[3,4-d]pyrimidine (12.0 g, 46.3 mmol) was dissolved in 20 mL of anhydrous acetonitrile and 4-(trifluoromethyl)aniline was added (7.0 mL, 55.6 mmol), followed by 47% $HI/H_2O$ (2.0 L) and sodium iodide (10.3 g, 69.5 mmol). The mixture was heated at refluxed overnight and solvents were removed under vacuum. The residue was dissolved in ethyl acetate and washed with sat. $NaHCO_3$ and brine. The organic layer was dried over $Na_2SO_4$, filtered and evaporated to a yellow solid which was purified by silica gel flash chromatography using a gradient of ethyl acetate:hexane (0-100%) to give the desired compound as a brown oil (15 g).

MS: M+H=385.

D. N-(4-(Trifluoromethyl)phenyl)-5,6,7,8-tetrahydropyrido[3,4-d]pyrimidin-4-amine

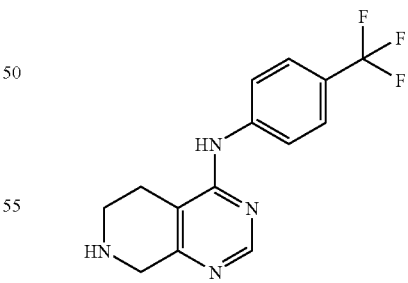

7-Benzyl-N-(4-(trifluoromethyl)phenyl)-5,6,7,8-tetrahydropyrido[3,4-d]pyrimidin-4-amine (13 g, 33.8 mmol) was dissolved in methanol (50 mL) and palladium hydroxide (20% wt. % (dry basis) on carbon) was added (5.0 g). The mixture was shaken on a Parr Shaker under $H_2$(g) atmosphere (60 PSI) for 20 hours. The mixture was filtered through celite and evaporated to give 9.0 g of material as a grey solid (91%). 1.5 g of this material was purified on alumina in 10% MeOH-DCM to give 600 mg of the pure compound as an off white solid.

MS: M+H=295. ¹H NMR (DMSO-d6): δ 2.98(t, J=6.0 Hz, 2H); 3.46(brs, 2H); 4.18(s, 2H); 7.70(d, J=8.6 Hz, 2H) 7.98(d, J=8.6 Hz, 2H); 8.57(s, 1H); 9.23(s, 1H); 9.87(s, 1H)

E. 7-(3-Chloropyridin-2-yl)-N-(4-(trifluoromethyl)phenyl)-5,6,7,8-tetrahydropyrido[3,4-d]pyrimidin-4-amine

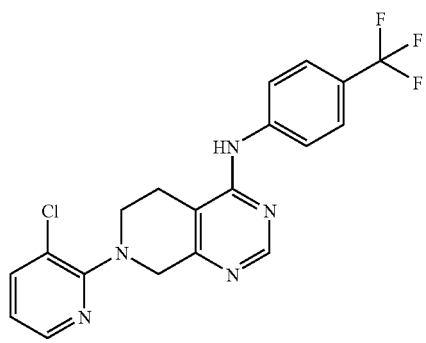

A mixture of N-(4-(trifluoromethyl)phenyl)-5,6,7,8-tetrahydropyrido[3,4-d]pyrimidin-4-amine (0.250 g, 0.85 mmol), 2,3-dichloropyridine (0.251 g, 1.69 mmol) and N,N-diisopropylethylamine (0.22 mL, 1.27 mmol) in a mixture of 1,4-dioxane (2 mL) and N,N-dimethylacetamide (0.2 mL) was heated in a sealed tube via microwave (Emerys Optimizer model, Personal Chemistry) for 10 hr at 170° C. The mixture was allowed to cool to room temperature and poured into water (60 mL). The mixture was extracted with ethyl acetate (2×30 mL) and the combined organic layers were washed with brine, dried over sodium sulfate and concentrated to leave an oil. The residue was purified by flash chromatography over silica gel (ethyl acetate/hexane gradient 0 to 100%) to obtain 198 mg of a white solid.

MS: M+H=406. ¹H NMR (DMSO-d6): δ 2.87(t, J=5.6 Hz, 2H); 3.69(t, J=5.6 Hz, 2H); 4.39(s, 2H); 704(dd, J=4.9 Hz, 7.9 Hz, 1H); 7.68(d, J=8.8 Hz, 2H); 7.86(dd, J=1.6 Hz, 7.9 Hz, 1H); 7.99(d, J=8.8 Hz, 2H); 8.25(dd, J=1.6 Hz, 4.9 Hz, 1H); 8.52(s, 1H); 8.81(s, 1H).

Example 2

N-(4-tert-Butylphenyl)-7-benzyl-5,6,7,8-tetrahydropyrido[3,4-d]pyrimidin-4-amine

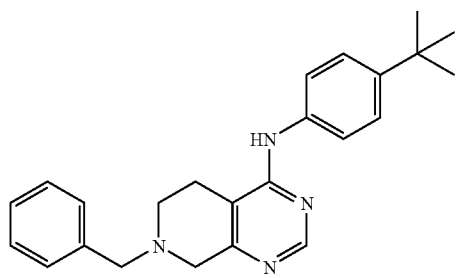

A mixture of 4-tert-butylbenzenamine (0.312 mL, 1.98 mmol) and 7-benzyl-4-chloro-5,6,7,8-tetrahydropyrido[3,4-d]pyrimidine (0.467 g, 1.80 mmol), prepared as described in Example 1.B. in acetonitile (2 mL) was heated in a sealed tube at 170° C. in a microwave (Emrys Optimizer model, Personal Chemistry) for five min. Upon cooling to room temperature, a precipitate formed. The mixture was diluted with hexane (5 mL) and the precipitate was collected by filtration to give 0.576 g of the title compound as a tan solid.

MS: M+H=373.

Example 3

N-(4-tert-Butylphenyl)-7-(3-chloropyridin-2-yl)-5,6,7,8-tetrahydropyrido[3,4-d]pyrimidin-4-amine hydrochloride

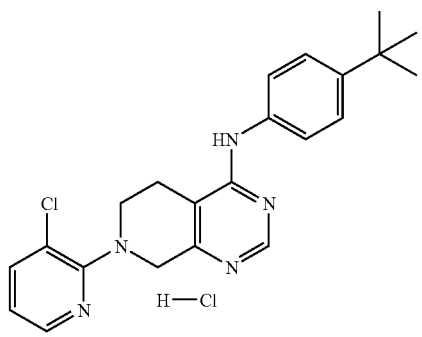

A. N-(4-tert-Butylphenyl)-5,6,7,8-tetrahydropyrido[3,4-d]pyrimidin-4-amine

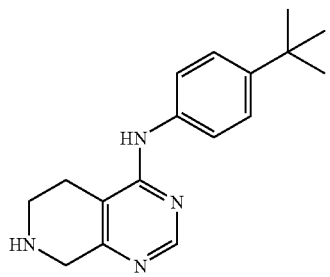

A mixture of N-(4-tert-butylphenyl)-7-benzyl-5,6,7,8-tetrahydropyrido[3,4-d]pyrimidin-4-amine (0.359 g, 0.96 mmol), prepared as described in Example 2, ammonium formate (0.304 g, 4.82 mmol) and palladium (10% wt. on activated carbon, 40 mg) in MeOH (5 mL) was stirred at r.t. for 1 h and then at 60° C. for 2 h. The mixture was cooled to r.t. and filtered over celite. The filtrate was concentrated under reduced pressure to give a white solid which was dissolved in water. The mixture was extracted twice with a 3:1 mixture of chloroform:isopropanol. The combined organic extracts were dried over sodium sulfate and concentrated to dryness to give 0.26 g of the title compound which was used directly without further purification.

MS: M+H=283.

B. N-(4-tert-Butylphenyl)-7-(3-chloropyridin-2-yl)-5,6,7,8-tetrahydropyrido[3,4-d]pyrimidin-4-amine hydrochloride

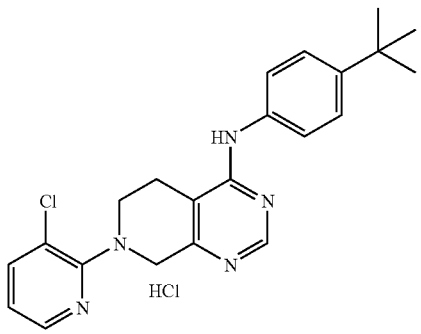

A mixture of N-(4-tert-butylphenyl)-5,6,7,8-tetrahydropyrido[3,4-d]pyrimidin-4-amine 0.173 g, 0.61 mmol), 2,3-dichloropyridine (0.91 g, 0.61 mmol) and potassium carbonate (0.234 g, 1.84 mmol) in DMF was heated in a sealed tube in a microwave oven (Emrys Optimizer model, Personal Chemistry) at 200° C. for 2 h. The mixture was cooled to r.t. and diluted with water (30 mL). The mixture was extracted with ethyl acetate (3×30 mL). The combined organic extracts were washed with brine, dried over sodium sulfate and concentrated to leave an oil. The product was purified by silica gel chromatography (ethyl acetate/hexane gradient) to obtain 0.035 g of the title compound as a light yellow oil. The oil was dissolved in 1 mL ethyl acetate and treated with 1.0 M HCl in diethyl ether (0.09 mL). The resulting solid was collected by filtration, washed with diethyl ether and dried to give 0.030 g light yellow solid.

MS: M+H=394. $^1$H NMR (DMSO-d6): δ 1.30 (s, 9H), 2.83 (t, J=5.6 Hz, 2H), 3.74 (t, J=5.6 Hz, 2H), 4.55 (s, 2H), 7.10 (dd, J=7.9 Hz, 4.7 Hz, 1H), 7.42-7.50 (m, 4H), 7.92 (dd, J=7.6 Hz, 1.6 Hz, 1H), 8.26 (dd, J=4.7 Hz, 1.6 Hz, 1H), 8.75 (s, 1H), 10.04 (brs, 1H).

Example 4

N-(4-tert-Butylphenyl)-7-(3-(trifluoromethyl)pyridin-2-yl)-5,6,7,8-tetrahydropyrido[3,4-d]pyrimidin-4-amine hydrochloride

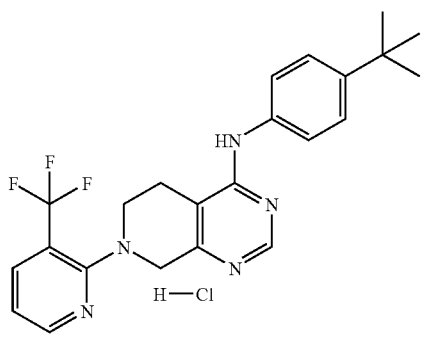

The title compound was prepared using the general procedure set forth in Example 3, above, by heating a mixture of 2-chloro-3-(trifluoromethyl)pyridine (0.108 g, 0.59 mmol), N-(4-tert-butylphenyl)-5,6,7,8-tetrahydropyrido[3,4-d]pyrimidin-4-amine (0.112 g, 0.40 mmol) and potassium carbonate (0.16 g, 1.19 mmol) in DMF (2 mL) for 1 h.

MS: M+H=428. $^1$H NMR (DMSO-d6): δ 1.30 (s, 9H), 2.81 (t, J=5.2 Hz, 2H), 3.62 (t, J=5.6 Hz, 2H), 4.46 (s, 2H), 7.28 (dd, J=7.6 Hz, 4.9 Hz, 1H), 7.43 (d, J=8.8 Hz, 2H), 7.49 (d, J=8.8 Hz, 2H), 8.17 (dd, J=7.6 Hz, 1.7 Hz, 1H), 8.57 (dd, J=4.9 Hz, 1.7 Hz, 1H), 8.69 (s, 1H), 9.72 (brs, 0.7H).

Example 5

N-(4-tert-Butylphenyl)-7-(3-chloropyridin-2-yl)-5,6,7,8-tetrahydro-2-(methoxymethyl)pyrido[3,4-d]pyrimidin-4-amine hydrochloride

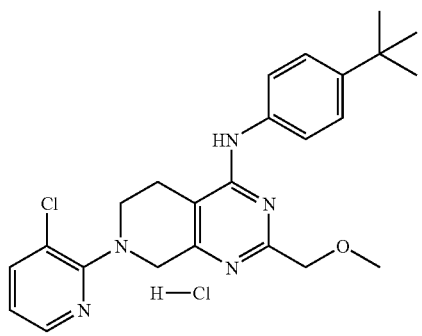

A. 7-Benzyl-5,6,7,8-tetrahydro-2-(methoxymethyl)pyrido[3,4-d]pyrimidin-4)3H)-one

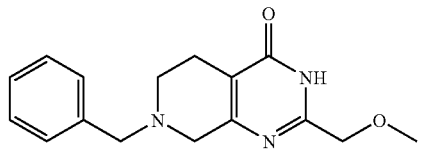

A mixture of 1-benzyl-3-ethoxycarbonyl-4-piperidone hydrochloride (0.285 g, 0.96 mmol), 2-chloroacetamidine hydrochloride (0.149 g, 1.16 mmol) and sodium methoxide (1.9 ml of a 25% wt/wt solution in methanol) and methanol (0.5 mL) was heated in a sealed tube via microwave (Emrys Optimizer model, Personal Chemistry) at 100° C. for 15 min. The mixture was allowed to cool to r.t. and concentrated under reduced pressure to leave a brown solid. The solid was taken up in water (30 mL) and extracted with a 3:1 mixture of chloroform:isopropanol (3×30 mL). The combined organic extracts were dried over sodium sulfate and concentrated to dryness to leave the title compound (0.196 g) which was used directly without further purification.

MS: M+H=286.

B. 7-Benzyl-4-chloro-5,6,7,8-tetrahydro-2-(methoxymethyl)pyrido[3,4-d]pyrimidine

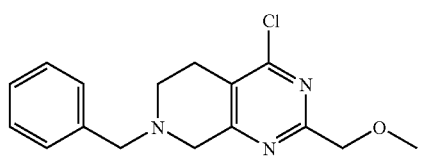

A mixture of 7-benzyl-5,6,7,8-tetrahydro-2-(methoxymethyl)pyrido[3,4-d]pyrimidin-4)3H)-one (2.01 g, 7.04 mmol), phosphorus oxychloride (5.16 mL, 56.35 mmol) and N,N-dimethylaniline (0.89 mL, 7.04 mmol) in 1,2-dichloroethane was heated to 80° C. for 2 h. The mixture was allowed to cool to r.t. and poured over crushed ice (100 mL). The mixture was made basic (pH=~8) by the addition of saturated aqueous sodium bicarbonate and extracted with ethyl acetate (200 mL). The organic layer was dried over magnesium sulfate and concentrated to leave a dark oil which was purified by silica gel chromatography (ethyl acetate/hexane gradient) to yield 1.76 g of the title compound as a brown oil.

MS: M+H=304.

C. N-(4-tert-Butylphenyl)-7-benzyl-5,6,7,8-tetrahydro-2-(methoxymethyl)pyrido[3,4-d]pyrimidin-4-amine

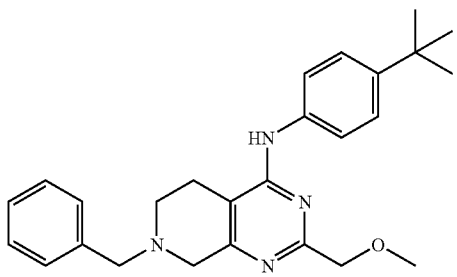

The title compound was prepared using the general procedure set forth in Example 2, above, using 7-benzyl-4-chloro-5,6,7,8-tetrahydro-2-(methoxymethyl)pyrido[3,4-d]pyrimidine (0.583 g, 1.92 mmol), 4-tert-butylbenzenamine (0.33 mL, 2.11 mmol) and acetonitrile (3 mL) to give 0.524 g (66%) of the title compound as an off-white powder.

MS: M+H=417.

D. N-(4-tert-butylphenyl)-5,6,7,8-tetrahydro-2-(methoxymethyl)pyrido[3,4-d]pyrimidin-4-amine

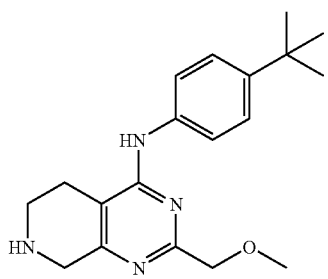

The title compound was prepared using the general procedure set forth in Example 3.A. using N-(4-tert-butylphenyl)-7-benzyl-5,6,7,8-tetrahydro-2-(methoxymethyl)pyrido[3,4-d]pyrimidin-4-amine (0.453 g, 1.09 mmol), ammonium formate (0.69 g, 10.87 mmol), palladium, 10% wt. on activated carbon (100 mg) and MeOH (15 mL). 0.334 g (94%) Of the title compound was obtained as a white foam.

MS: M+H=327.

D. (4-tert-Butyl-phenyl)-[7-(3-chloro-pyridin-2-yl)-2-methoxymethyl-5,6,7,8-tetrahydro-pyrido[3,4-d]pyrimidin-4-yl]-amine hydrochloride The title compound was prepared using the general procedure set forth in Example 3.B. using N-(4-tert-butylphenyl)-5,6,7,8-tetrahydro-2-(methoxymethyl)pyrido[3,4-d]pyrimidin-4-amine (0.105 g, 0.32 mmol), 2,3-dichloropyridine (0.071 g, 0.48 mmol), potassium carbonate (0.13 g, 0.96 mmol) and DMF (2 mL) and heating the reaction mixture for 1 h. The title compound was obtained as a light yellow solid after formation and isolation of its hydrochloride salt (15 mg)

MS: M+H=438. $^1$H NMR (DMSO-d6): δ 1.30 (s, 9H), 2.80 (t, J=4.8 Hz, 2H), 3.41 (s, 3H), 3.62 (t, J=4.8 Hz, 2H), 4.50 (s, 2H), 4.51 (s, 2H), 7.28 (dd, J=7.6 Hz, 4.9 Hz, 1H), 7.42 (d, J=8.8 Hz, 2H), 7.56 (d, J=8.8 Hz, 2H), 8.17 (dd, J=7.6 Hz, 1.7 Hz, 1H), 8.57 (dd, J=4.9 Hz, 1.7 Hz, 1H), 9.8 (brs, 0.6H).

Example 6

(4-tert-Butyl-phenyl)-[2-methoxymethyl-7-(3-trifluoromethyl-pyridin-2-yl)-5,6,7,8-tetrahydro-pyrido[3,4-d]pyrimidin-4-yl]-amine hydrochloride

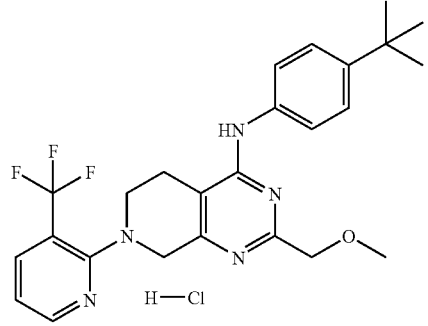

The title compound was prepared using the general procedure set forth in Example 5 using 2-chloro-3-(trifluoromethyl)pyridine (0.084 g, 0.46 mmol), N-(4-tert-butylphenyl)-5,6,7,8-tetrahydro-2-(methoxymethyl)pyrido[3,4-d]pyrimidin-4-amine (0.101 g, 0.31 mmol), potassium carbonate (0.128 g, 0.93 mmol) in DMF (2 mL). The title compound was obtained as a light yellow solid after formation and isolation of its hydrochloride salt.

MS: M+H=472. $^1$H NMR (DMSO-d6): δ 1.30 (s, 9H), 2.81 (t, J=5.6 Hz, 2H), 3.42 (s, 3H), 3.74 (t, J=5.6 Hz, 2H), 4.53 (s, 2H), 4.56 (s, 2H), 7.09 (dd, J=7.8 Hz, 4.7 Hz, 1H), 7.43 (d, J=8.8 Hz, 2H), 7.54 (d, J=8.8 Hz, 2H), 7.91 (dd, J=7.8 Hz, 1.6 Hz, 1H), 8.25 (dd, J=4.7 Hz, 1.6 Hz, 1H), 9.83 (brs, 0.5H).

Example 7

(2,3-Dihydro-benzo[1,4]dioxin-6-yl)-[7-(3,3,3-trifluoro-propyl)-5,6,7,8-tetrahydro-pyrido[3,4-d]pyrimidin-4-yl]-amine hydrochloride

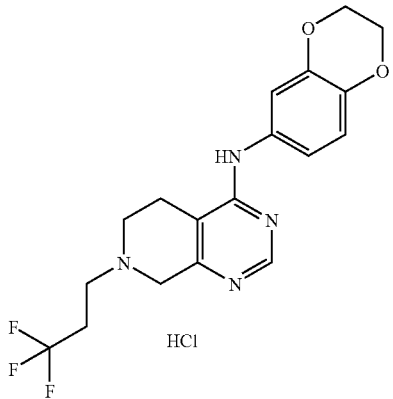

A. 7-Benzyl-5,6,7,8-tetrahydro-N-(2,3-dihydrobenzo[b][1,4]dioxin-6-yl)pyrido[3,4-d]pyrimidin-4-amine

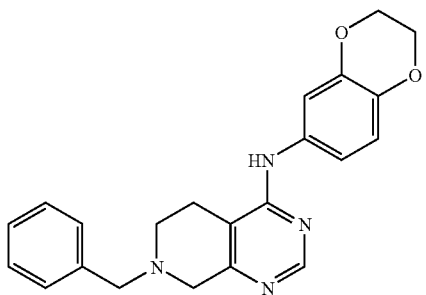

The title compound was prepared using the general procedure set forth in Example 2, above, using 2,3-dihydrobenzo[b][1,4]dioxin-6-amine (0.32 mL, 2.63 mmol) and 7-benzyl-4-chloro-5,6,7,8-tetrahydropyrido[3,4-d]pyrimidine (0.621 g, 2.39 mmol) in acetonitrile (3 mL).

The title compound was obtained as a brown solid (0.756 g).

MS: M+H=375.

B. 1-(4-(2,3-Dhydrobenzo[b][1,4]dioxin-6-ylamino)-5,6-dihydropyrido[3,4-d]pyrimidin-7(8H)-yl)-3,3,3-trifluoropropan-1-one

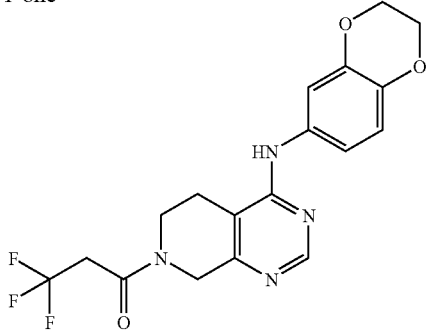

A mixture of 7-benzyl-5,6,7,8-tetrahydro-N-(2,3-dihydrobenzo[b][1,4]dioxin-6-yl)pyrido[3,4-d]pyrimidin-4-amine (0.742 g, 1.98 mmol), ammonium formate (1.25 g, 19.83 mmol) and palladium, 10% wt. on activated carbon (75 mg) in methanol (10 mL was heated to 60° C. for 2 h. The mixture was cooled to r.t. and filtered over celite. The filtrate was concentrated under reduced pressure to give a white solid which was dissolved in water. The mixture was extracted twice with a 3:1 mixture of chloroform:isopranol. The combined organic extracts were dried over sodium sulfate and concentrated to dryness to give 0.55 g (98%) of a white solid. The solid (0.240 g, 0.84 mmol) was dissolved in DMF (5 mL). To the solution was added 3,3,3-trifluoropropanoic acid (0.10 mL 1.10 mmol), 1-(3-dimethylaminopropyl)-3-ethylcarbodiimide hydrochloride (0.21 g, 1.10 mmol), 1-hydroxybenzotriazole (0.148 g, 1.10 mmol) and N,N-diisopropylethylamine (0.37 mL, 2.11 mmol). The mixture was stirred at r.t. for 16 h and poured into water (50 mL). The mixture was extracted with ethyl acetate (50 mL). The organic layer was washed with saturated aqueous sodium bicarbonate, water and brine and dried over magnesium sulfate. The solvent was concentrated to leave an oil which was purified by silica gel chromatography (ethyl acetate/hexane gradient) to give 0.180 g of the title compound as a white solid.

MS: M+H=395.

C. 7-(3,3,3-Trifluoropropyl)-5,6,7,8-tetrahydro-N-(2,3-dihydrobenzo[b][1,4] dioxin-6-yl)pyrido[3,4-d]pyrimidin-4-amine hydrochloride

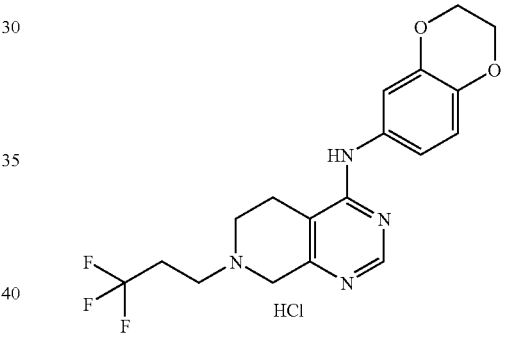

A solution of 1-(4-(2,3-dihydrobenzo[b][1,4]dioxin-6-ylamino)-5,6-dihydropyrido[3,4-d]pyrimidin-7)8H)-yl)-3,3,3-trifluoropropan-1-one (0.069 g, 0.17 mmol) in THF (5 mL) was cooled to 0° C. under nitrogen. Lithium aluminum hydride was added (0.85 mL of a 1.0M solution in THF, 0.85 mmol) and the mixture was stirred at 0° C. for 1 h. The mixture was allowed to gradually warm to r.t. with overnight stirring and then cooled again to 0° C. Water (1 mL) was added dropwise. After five min, 10N NaOH (1 mL) was added and the mixture was allowed to warm to r.t. Water (3 mL) was added. The mixture was then extracted with ethyl acetate (2×15 mL). The combined organic extracts were washed with water and brine and dried over sodium sulfate. The solvent was concentrated to leave an oil which was purified by silica gel chromatography (ethyl acetate/hexane gradient). The colorless oil so obtained (0.020 g) was dissolved in diethyl ether and treated with 1.0 M HCl in diethyl ether (0.05 mL) to produce a solid which was triturated with diethyl ether and dried to yield the product (17 mg).

MS: M+H=381. $^1$H NMR (DMSO-d6): δ 2.90-3.10 (m, 4H), 3.42-3.48 (m, 2H), 4.20-4.90 (m, 8H), 6.58 (d, J=8.4 Hz, 1H), 7.04 (dd, J=8.4 Hz, 2.5 Hz, 1H), 7.19 (d, J=2.5 Hz, 1H), 8.52 (s, 1H), 9.08 (brs, 0.8H).

Example 8

(4-tert-Butyl-phenyl)-[7-(3-methanesulfonyl-pyridin-2-yl)-5,6,7,8-tetrahydro-pyrido[3,4-d]pyrimidin-4-yl]-amine

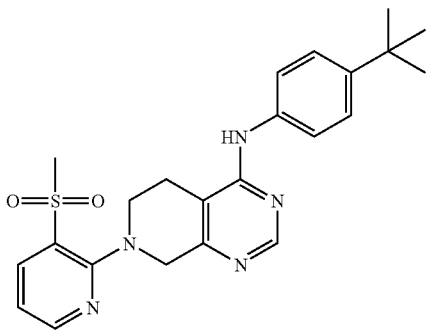

A mixture of N-(4-tert-butylphenyl)-5,6,7,8-tetrahydropyrido[3,4-d]pyrimidin-4-amine (0.066 g, 0.23 mmol), 2-chloro-3-(methylsulfonyl)pyridine (Ponticello et al, *J. Org. Chem.*, 44(17), 1979), (0.088 g, 0.47 mmol) and N,N-diisopropylethlamine (0.041 mL, 0.23 mmol) was heated in a sealed tube via microwave (Emrys Optimizer model, Personal Chemistry) for 30 min at 150° C. The reaction mixture was cooled to r.t. and poured into water (20 mL). The mixture was extracted with ethyl acetate (2×20 mL). The combined organic layers were washed with brine, dried over magnesium sulfate and concentrated to leave an oil which was purified by silica gel chromatography (ethyl acetate/hexane gradient) to give the title compound as a white solid (0.049 g).

MS: M+H=438. $^1$H NMR (DMSO-d6): δ 1.29 (s, 9H), 2.82 (t, J=5.7 Hz, 2H), 3.32 (s, 3H), 3.57 (t, J=5.7 Hz, 2H), 4.31 (s, 2H), 7.34 (d, J=8.7 Hz, 2H), 7.43 (dd, J=7.9 Hz, 4.7 Hz, 1H), 7.59 (d, J=8.7 Hz, 2H), 8.34 (dd, J=7.9 Hz, 1.8 Hz, 1H), 8.37 (s, 1H), 8.48 (s, 1H), 8.66 (dd, J=4.7 Hz, 1.8 Hz, 1H).

Example 9

[7-(3-Methanesulfonyl-pyridin-2-yl)-5,6,7,8-tetrahydro-pyrido[3,4-d]pyrimidin-4-yl]-(4-trifluoromethyl-phenyl)-amine

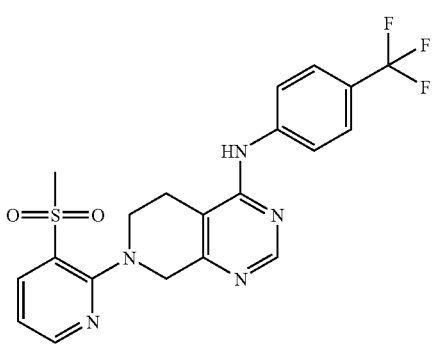

N-(4-(Trifluoromethyl)phenyl)-5,6,7,8-tetrahydropyrido[3,4-d]pyrimidin-4-amine (0.100 g, 0.34 mmol) was dissolved in a mixture of dioxane/N,N-dimethylacetamide (10:1) (1.1 mL). To the solution was added 2-chloro-3-(methylsulfonyl)pyridine (Ponticello et al, *J. Org. Chem.*, 44(17), 1979) (0.128 mg, 0.67 mmol) and N,N-diisopropylethylamine (0.09 mL, 0.51 mmol). The mixture was heated via microwave (Emrys Optimizer model, Personal Chemistry) at 150° C. for 20 min. The reaction mixture was poured into water (20 mL) and extracted with ethyl acetate (2×20 mL). The combined organic layers were washed with brine, dried over magnesium sulfate, and concentrated to leave a solid. The solid was purified by silica gel chromatography using a gradient of ethyl acetate:hexane (0-100%) to give the desired compound as an white solid (75 mg).

MS: M+H=450. $^1$H NMR (DMSO-d6): δ 2.90 (t, J=5.6 Hz, 2H), 3.32 (s, 3H), 3.58 (t, J=5.6 Hz, 2H), 4.36 (s, 2H), 4.44 (dd, J=7.9 Hz, 4.7 Hz, 1H), 7.68 (d, J=8.7 Hz, 2H), 8.02 (d, J=8.7 Hz, 2H), 8.35 (dd, J=7.9 Hz, 1.9 Hz, 1H), 8.52 (s, 1H), 8.67 (dd, J=4.7 Hz, 1.9 Hz, 1H), 8.86 (s, 1H).

Example 10

7-(3-(Ethylsulfonyl)pyridin-2-yl)-N-(4-(trifluoromethyl)phenyl)-5,6,7,8-tetrahydropyrido[3,4-d]pyrimidin-4-amine

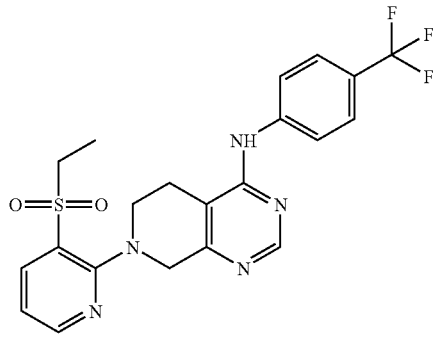

A. 2-Chloro-3-(ethylsulfonyl)pyridine

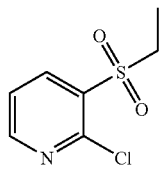

2-Chloropyridin-3-amine (6.1 g, 48 mmol) was dissolved in ethanol (40 mL) and HBF$_4$ (20 mL, 50%) was added at 0° C. After stirring for 5 min, a solution of NaNO$_2$ (3.5 g) in water (20 mL) was added dropwise mantaining a temperature of <5° C. Ether was then added and the salts were precipitated, filtered and rinsed with ether to give pink crystals (8.6 g). The crystals were dissolved in acetonitrile at 0° C. and sodium ethanthiolate was added (50 mmol, 4.2 g) and stirred for 24 h. The solvent was evaporated after filtration and the residue was purified by HPLC to give the material as an orange solid (0.8 g). The material was then dissolved in chloroform (30 mL) and m-CPBA (3.2 g, 9.3 mmol) was added and the mixture was stirred overnight. The solution was neutralized with NaHCO$_3$ and the organic layer was dried over Na$_2$SO$_4$, filtered and evaporated to give the product as an off-white powder (0.5 g).

MS: M+H=206.

B. 7-(3-(Ethylsulfonyl)pyridin-2-yl)-N-(4-(trifluoromethyl)phenyl)-5,6,7,8-tetrahydropyrido[3,4-d]pyrimidin-4-amine

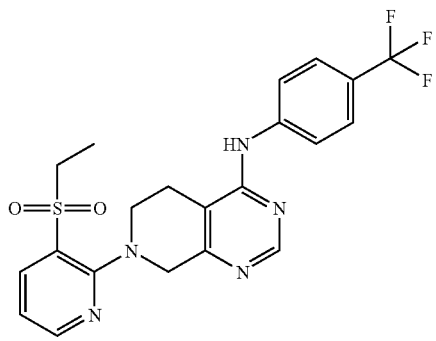

The title compound was prepared according to the procedure given for Example 9 using N-(4-(trifluoromethyl)phenyl)-5,6,7,8-tetrahydropyrido[3,4-d]pyrimidin-4-amine prepared as described in Example 1.D. (0.100 g, 0.34 mmol), 2-chloro-3-(ethylsulfonyl)pyridine (0.140 g, 0.68 mmol) and N,N-diisopropylethylamine (0.09 mL, 0.51 mmol) to obtain 0.062 g of a white solid.

MS: M+H=464. $^1$H NMR (DMSO-d6): δ 0.98 (t, J=7.4 Hz, 3H), 2.89 (t, J=5.6 Hz, 2H), 3.50 (q, 7.4 Hz, 2H), 3.59 (t, J=5.6 Hz, 2H), 4.36 (s, 2H), 7.44 (dd, J=7.8 Hz, 4.7 Hz, 1H), 7.68 (d, J=8.7 Hz, 2H), 8.02 (d, J=8.7 Hz, 2H), 8.33 (dd, J=7.8 Hz, 1.8 Hz, 1H), 8.52 (s, 1H), 8.67 (dd, J=4.7 Hz, 1.8 Hz, 1H), 8.87 (s, 1H).

Example 11

[7-(3-Fluoro-pyridin-2-yl)-5,6,7,8-tetrahydro-pyrido[3,4-d]pyrimidin-4-yl]-(4-trifluoromethyl-phenyl)-amine

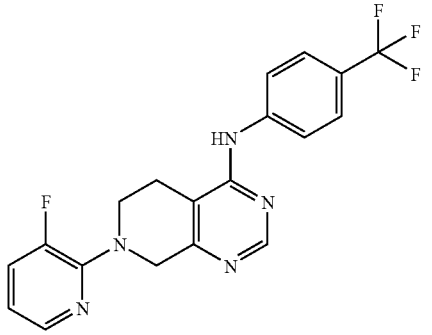

The title compound was prepared according to the procedure given for Example 9 using N-(4-(trifluoromethyl)phenyl)-5,6,7,8-tetrahydropyrido[3,4-d]pyrimidin-4-amine (0.15 g, 0.51 mmol), 2-chloro-3-fluoropyridine (0.134 g, 0.10 mmol), N,N-diisopropylethylamine (0.133 mL, 0.76 mmol) and heating the reaction mixture 9 h at 170° C. to obtain 0.062 g of a white solid.

MS: M+H=390.

Example 12

(4-Trifluoromethyl-phenyl)-[7-(3-trifluoromethyl-pyridin-2-yl)-5,6,7,8-tetrahydro-pyrido[3,4-d]pyrimidin-4-yl]-amine

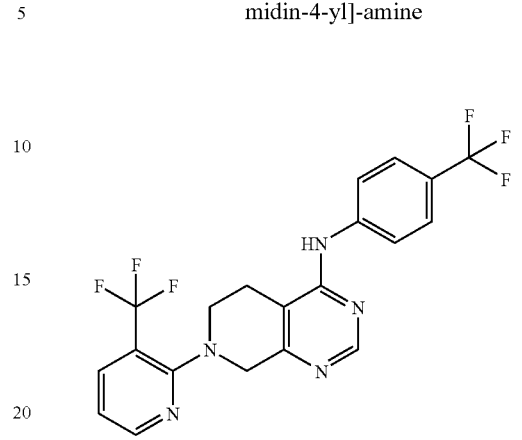

The title compound was prepared according to the procedure given for Example 9 using N-(4-(trifluoromethyl)phenyl)-5,6,7,8-tetrahydropyrido[3,4-d]pyrimidin-4-amine (0.150 g, 0.51 mmol), 2-chloro-3-(trifluoromethyl)pyridine (0.185 g, 0.10 mmol), N,N-diisopropylethylamine (0.133 mL, 0.76 mmol) and heating the reaction mixture 6 h at 180° C. to obtain 0.130 g of a light yellow solid.

MS: M+H=440. $^1$H NMR (DMSO-d6): δ 2.85 (t, J=5.8 Hz, 2H), 3.61 (t, J=5.8 Hz, 2H), 4.36 (s, 2H), 7.22 (dd, J=7.8 Hz, 4.9 Hz, 1H), 7.68 (d, J=8.7 Hz, 2H), 7.99 (d, J=8.7 Hz, 2H), 8.12 (dd, J=7.8 Hz, 1.7 Hz, 1H), 8.51 (s, 1H), 8.55 (dd, J=4.9 Hz, 1.7 Hz, 1H), 8.82 (s, 1H).

Example 13

(4-tert-Butyl-phenyl)-[7-(3-chloro-pyridin-2-yl)-2-morpholin-4-ylmethyl-5,6,7,8-tetrahydro-pyrido[3,4-d]pyrimidin-4-yl]-amine

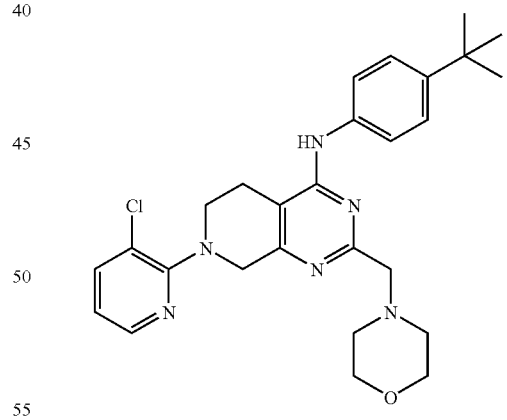

A. 2-morpholinoacetamidine

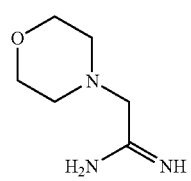

Sodium hydride (2.4 g, 60 mmol, 60%) was added to a solution of morpholine (5.2 g, 60 mmol) in THF (40 mL, anhydrous) and stirred for 30 min at room temperature under nitrogen. Chloroacetamidine hydrochloride (2.58 g, 20 mmol) was added to this solution in one portion and stirred at 50° C. overnight. Solvent was removed under reduced pressure and the dark brown oily residue was directly used in the next step.

B. 7-Benzyl-5,6,7,8-tetrahydro-2-(morpholinomethyl)pyrido[3,4-d]pyrimidin-4(4aH)-one

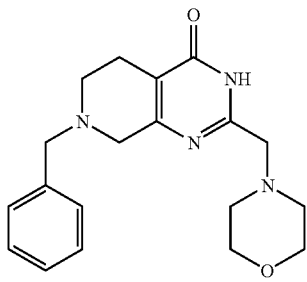

Ethyl N-benzyl-3-oxo-4-piperidinecarboxylate hydrochloride (2.98 g, 10 mmol) and 2-Morpholinoethane-1,1-diamine (~20 mmol) were dissolved in a solution of sodium methoxide in methanol (12 mL, 25% wt) and stirred at 100° C. in a sealed tube for 4 h. Solvent was removed in vacuo, residue was dissolved in water (100 mL) and was extracted by CHCl₃ and i-PrOH (3:1, 5×80 mL), dried over sodium sulfate. Solvent was removed in vacuo, and the remaining brown solid residue was used directly in the next step.

MS: M+H=341.4

C. 7-Benzyl-4-chloro-5,6,7,8-tetrahydro-2-(morpholinomethyl)pyrido[3,4-d]pyrimidine

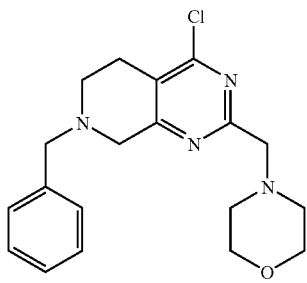

N,N-Dimethylaniline (1.2 g, 10 mmol) and phosphorus oxychloride (12.2 g, 80 mmol) were added to the solution of 7-benzyl-5,6,7,8-tetrahydro-2-(morpholinomethyl)pyrido[3,4-d]pyrimidin-4(4aH)-one (~10 mmol) in 1,2-dichloroethane (30 mL, anhydrous) and were stirred in a preheated oil bath at 90° C. for 30 min. Reaction mixture was poured into ice, neutralized by solid sodium bicarbonate, extracted by ethyl acetate and dried over sodium sulfate. Solvent was removed in vacuo and the resulting brown oil was used directly in the next step.

MS: M+H=359.2.

D. N-(4-tert-Butylphenyl)-7-benzyl-5,6,7,8-tetrahydro-2-(morpholinomethyl)pyrido[3,4-d]pyrimidin-4-amine

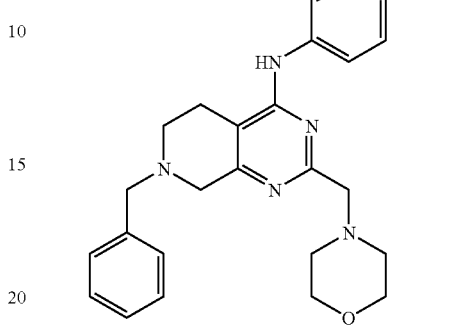

A mixture of 7-Benzyl-4-chloro-5,6,7,8-tetrahydro-2-(morpholinomethyl)pyrido[3,4-d]pyrimidine (358 mg, 1 mmol) and 4-tert-butylaniline (179 mg, 1.2 mmol) in acetonitrile (2 mL) was heated via microwave in a sealed tube at 180° C. for 5 min. Solvent was removed and the residue was dissolved in water, extracted by ethyl acetate, dried over sodium sulfate and purified by column chromatography. The desired product was obtained as a white foam (120 mg).

MS: M+H=372.1.

E. N-(4-tert-Butylphenyl)-5,6,7,8-tetrahydro-2-(morpholinomethyl)pyrido[3,4-d]pyrimidin-4-amine

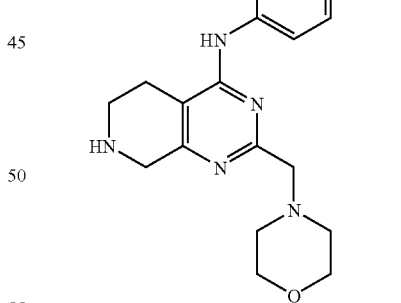

A catalytic amount palladium hydroxide on carbon powder (20% Pd moisture ea. 60%) was added to a solution of N-(4-tert-butylphenyl)-7-benzyl-5,6,7,8-tetrahydro-2-(morpholinomethyl)pyrido[3,4-d]pyrimidin-4-amine (240 mg, 0.51 mmol) in methanol and was stirred under a hydrogen filled balloon over night at room temperature. Reaction solution was filtered through celite and filtrate was concentrated to yield the product as a white powder (150 mg).

MS: M+H=382.3.

F. N-(4-tert-Butylphenyl)-7-(3-chloropyridin-2-yl)-5,6,7,8-tetrahydro-2-(morpholinomethyl)pyrido[3,4-d]pyrimidin-4-amine

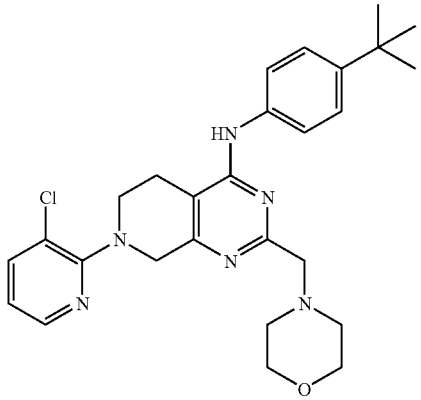

A mixture of diisopropylethylamine (35 mg, 0.27 mmol), N-(4-tert-butylphenyl)-5,6,7,8-tetrahydro-2-(morpholinomethyl)pyrido[3,4-d]pyrimidin-4-amine (70 mg, 0.18 mmol) and 2,3-dichloropyridine (54 mg, 0.36 mmol) in dioxane (2 mL) and N,N-diethylacetamide (0.2 mL) was heated via microwave in a sealed tube at 180° C. for 10 hr. Solvent was removed in vacuo and residue was purified by column chromatography, product was obtained as a light yellow foam (27 mg).

MS: M+H=493.5. $^1$H NMR CDCl$_3$ δ: 1.33 (s, 9H), 2.67-2.69 (m, 4H), 2.76-2.79 (m, 2H), 3.69 (s, 2H), 3.76-3.80 (m, 6H), 4.54 (s, 2H), 6.35 (br s, 1H), 6.84-6.88 (m, 1H), 7.36-7.38 (m, 2H), 7.57-7.63 (m, 3H), 8.18-8.20 (m, 1H).

Example 14

N-(4-(Difluoromethoxy)phenyl)-5,6,7,8-tetrahydro-7-(3-(methylsulfonyl)pyridin-2-yl)pyrido[3,4-d]pyrimidin-4-amine

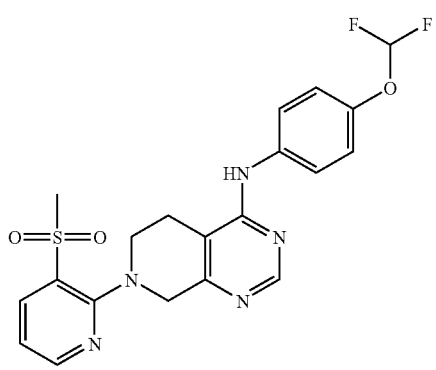

A. 7-Benzyl-N-(4-(difluoromethoxy)phenyl)-5,6,7,8-tetrahydropyrido[3,4-d]pyrimidin-4-amine

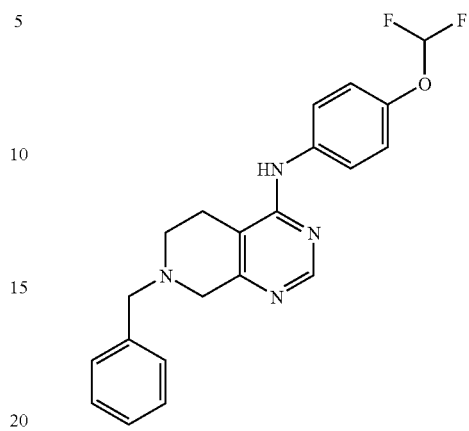

A mixture of 7-benzyl-4-chloro-5,6,7,8-tetrahydropyrido[3,4-d]pyrimidine prepared as described in Example 1.B. (1.09 g, 4.21 mmol) and 4-(difluoromethoxy)benzenamine (1.34 g, 8.42 mmol) in 1,4-dioxane (15 mL) was heated in a sealed tube at 100° C. for 16 h. The dark slurry was cooled to r.t. and diluted with diethyl ether. The solid was collected by flitration and triturated with ethyl acetate:hexane (1:9) and dried to give a tan solid (1.3 g, 81%) which was used directly.

MS: M+H=383

B. N-(4-(Difluoromethoxy)phenyl)-5,6,7,8-tetrahydropyrido[3,4-d]pyrimidin-4-amine

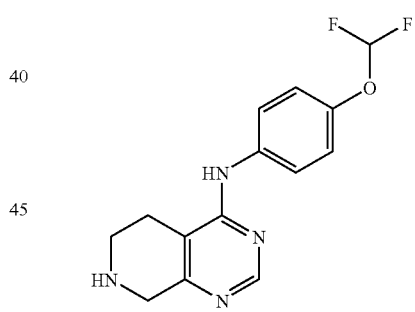

7-Benzyl-N-(4-(difluoromethoxy)phenyl)-5,6,7,8-tetrahydropyrido[3,4-d]pyrimidin-4-amine (1.01 g, 2.65 mmol), ammonium formate (1.67 g, 26.46 mmol) and palladium, 10% wt. on activated carbon (100 mg) in methanol (20 mL) was heated to 60° C. for 1 h. The mixture was cooled to r.t. and filtered over celite. The filtrate was concentrated under reduced pressure to give a white solid which was taken up in saturated aqueous sodium bicarbonate. The mixture was extracted three times with ethyl acetate. The combined organic extracts were washed with brine, dried over sodium sulfate and concentrated to dryness to give 0.82 g of a tan solid. The compound was further purified by silica gel chromatography using a gradient of methanol:chloroform (0-20%) to give the desired compound as an white solid.

MS: M+H=293.

C. N-(4-(Difluoromethoxy)phenyl)-5,6,7,8-tetrahydro-7-(3-(methylsulfonyl)pyridin-2-yl)pyrido[3,4-d]pyrimidin-4-amine

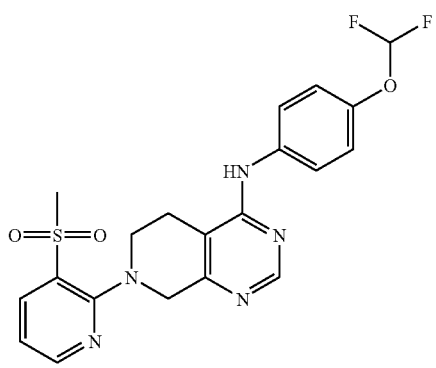

The title compound was prepared according to the procedure given for Example 9 using N-(4-(difluoromethoxy)phenyl)-5,6,7,8-tetrahydropyrido[3,4-d]pyrimidin-4-amine (0.088 g, 0.30 mmol), 2-chloro-3-(methylsulfonyl)pyridine (Ponticello et al, *J. Org. Chem.*, 44(17), 1979) (0.115 mg, 0.60 mmol) and N,N-diisopropylethylamine (0.079 mL, 0.45 mmol) to obtain 0.085 g of title compound as a light yellow solid.

MS: M+H=448. $^1$H NMR (DMSO-d6): δ 2.93 (t, J=5.8 Hz, 2H), 3.33 (s, 3H), 3.51 (t, J=5.8 Hz, 2H), 4.31 (s, 2H), 7.12 (d, J=8.9 Hz, 2H), 7.15 (t, J=75 Hz, 1H), 7.51 (dd, J=7.9 Hz, 4.9 Hz, 1H), 7.68 (d, J=8.9 Hz, 2H), 8.36 (dd, J=7.9 Hz, 1.8 Hz, 1H), 8.42 (s, 1H), 8.56 (s, 1H), 8.74 (dd, J=4.9 Hz, 1.8 Hz, 1H).

Example 15

7-(3-Chloropyridin-2-yl)-N-(4-(difluoromethoxy)phenyl)-5,6,7,8-tetrahydropyrido[3,4-d]pyrimidin-4-amine

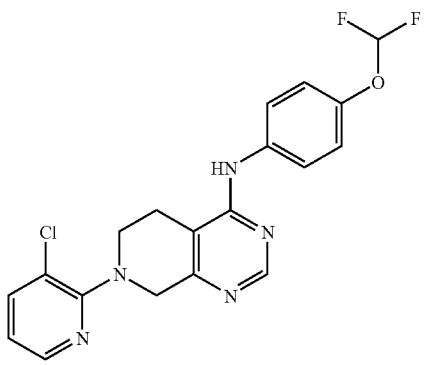

A. 5,6,7,8-Tetrahydro-3H-pyrido[3,4-d]pyrimidin-4-one

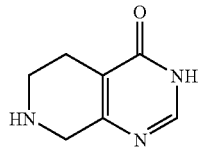

7-Benzyl-5,6,7,8-tetrahydropyrido[3,4-d]pyrimidin-4) 3H)-one (12.5 g; 52 mmol) was dissolved in methanol (100 mL) and palladium hydroxide was added (3.0, 20% wt). The mixture was shaken on a Parr Shaker under H$_2$(g) atmosphere (60 PSI) for 48 hours. The mixture was filtered through celite and evaporated to give 7.0 g of material as a white solid (89%), which was used as such for the next step.

MS: M+H=152.

B. 7-(3-Chloro-pyridin-2-yl)-5,6,7,8-tetrahydro-3H-pyrido[3,4-d]pyrimidin-4-one

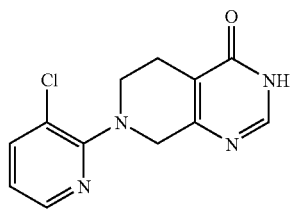

5,6,7,8-Tetrahydro-3H-pyrido[3,4-d]pyrimidin-4-one (1.5 g, 10 mmol) was dissolved in a mixture of dioxane-dimethylacetamide (2 ml, 3:1) and 2,3-dichloropyridine was added (1.5 g, 10 mmol), followed by DIEA (1.7 ml; 10 mmol). The mixture was heated at 150° C. for 2 hours in a microwave (Personal Chemistry, Smith Creator). The solvents were evaporated and the residue was dissolved in a 3:1 mixture of chloroform-isopropanol and washed with water. The organic layer washed with brine, dried over soldium sulphate, filtered and evaporated to give a yellow solid (3 g). The crude material was used for the subsequent step.

MS: M+H=263.

C. 4-Chloro-7-(3-chloro-pyridin-2-yl)-5,6,7,8-tetrahydro-pyrido[3,4-d]pyrimidine

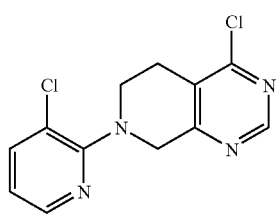

7-(3-Chloro-pyridin-2-yl)-5,6,7,8-tetrahydro-3H-pyrido[3,4-d]pyrimidin-4-one (1 g crude, 3.8 mmol) was dissolved in anhydrous 1,2-dichloroethane (60 ml) and stirred under N₂(g) atmosphere. The mixture was cooled to 0° C. and POCl₃ (2.8 ml, 31 mmole) was added dropwise, followed by N,N-dimethylaniline (0.49 ml, 3.8 mole). The mixture was warmed to room temperature and brought to reflux for 2 hrs. After stirring at room temperature overnight, J=the solvents were removed under vacuum and evaporated 3× with xylenes to give a red residue. The residue was dissolved in ethyl acetate and water and neutralized using with ice and solid NaHCO₃. After neutralization, ethyl acetate was added and the organic layer was washed with water and brine. The organic layer was dried over Na₂SO₄ and the solvents were removed under vacuum. The resulting red residue was purified using a gradient of ethyl acetate:hexane (0-100%) to give the desired compound as a brown oil (780 mg; 73%).

MS: MH+=281.

D. 7-(3-Chloropyridin-2-yl)-N-(4-(difluoromethoxy)phenyl)-5,6,7,8-tetrahydropyrido[3,4-d]pyrimidin-4-amine A mixture of 4-chloro-7-(3-chloropyridin-2-yl)-5,6,7,8-tetrahydropyrido[3,4-d]pyrimidine (0.103 g, 0.000366 mol) and 4-(difluoromethoxy)aniline (0.091 mL, 0.00073 mol) in acetonitrile (3 mL, 0.06 mol) was heated via microwave in a sealed tube at 160° C. for 10 minutes. After cooling to room temperature, the mixture was added to saturated sodium bicarbonate and extracted with ethyl acetate. The organic layer was washed with brine and dried over sodium sulfate. Concentrated to leave an oil. The residue was purified by flash chromatography over silica gel (ethyl acetate/hexane gradient 0 to 100%) to give 0.113 g of a light yellow solid.

MS: M+H=404 ¹H NMR (DMSO-d6): δ 2.80(t, J=5.6 Hz, 2H); 3.68(t, J=5.6 Hz, 2H); 4.35(s, 2H); 7.04(dd, J=7.6 Hz, 4.7 Hz, 1H); 7.15(d, J=9.0 Hz, 2H); 7.17(t, J=75.0 Hz, 1H); 7.69-7.74(m, 2H); 7.86 (dd, J=7.9 Hz, 1.6 Hz, 1H); 8.24(dd, J=4.7 Hz, 1.6 Hz, 1H); 8.40(s, 1H); 8.57(s, 1H).

Example 16

N-(4-(Trifluoromethyl)phenyl)-5,6,7,8-tetrahydro-7-(3-(isopropylsulfonyl)pyridin-2-yl)pyrido[3,4-d]pyrimidin-4-amine A. 2-Chloro-3-(isopropylsulfonyl)pyridine

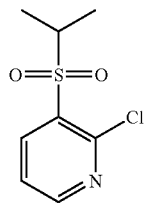

2-Chloropyridin-3-amine (6.1 g, 48 mmol) was dissolved in ethanol (40 mL) and HBF₄ (20 mL, 50%) was added at 0° C. After stirring for 5 min, a solution of NaNO₂ (3.5 g) in water (20 mL) was added dropwise maintaining a temperature of <5° C. Ether was then added and the salts were precipitated, J=filtered and rinsed with ether to give pink crystals (8.6 g). The crystals were dissolved in acetonitrile at 0° C. and sodium 2-propanethiolate (4.9 g, 50 mmol) was added and stirred for 24 h. The solvent was evaporated after filtration and the residue was purified by HPLC to give the material as an orange solid (0.98 g). The material was then dissolved in chloroform (30 mL) and mCPBA (3.7 g, 10.6 mmol) was added and the mixture was stirred overninght. The solution was neutralized with NaHCO₃ and the organic layer was dried over Na₂SO₄, filtered and evaporated to give the product as an off-white powder (0.7 g).

MS: M+H=220.

B. N-(4-(Trifluoromethyl)phenyl)-5,6,7,8-tetrahydro-7-(3-(isopropylsulfonyl)pyridin-2-yl)pyrido[3,4-d]pyrimidin-4-amine The title compound was prepared according to the procedure given for Example 9 using N-(4-(trifluoromethyl)phenyl)-5,6,7,8-tetrahydropyrido[3,4-d]pyrimidin-4-amine (0.073 g, 0.25 mmol), 2-chloro-3-(isopropylsulfonyl)pyridine (0.070 g, 0.32 mmol) and N,N-diisopropylethylamine (0.082 mL, 0.47 mmol) to obtain 0.073 g of a white solid.

MS: M+H=478. ¹H NMR (DMSO-d6): δ 1.06 (d, J=6.9 Hz, 6H), 2.88 (t, J=5.8 Hz, 2H), 3.58 (t, J=5.8 Hz, 2H), 3.94 (heptet, J=6.9 Hz, 1H), 4.36 (s, 2H), 7.44 (dd, J=7.8 Hz, 4.7 Hz, 1H), 7.68 (d, J=8.6 Hz, 2H), 8.03 (d, J=8.6 Hz, 2H), 8.33 (dd, J=7.8 Hz, 1.8 Hz, 1H), 8.52 (s, 1H), 8.67 (dd, J=4.7 Hz, 1.8 Hz, 1H), 8.87 (s, 1H).

Example 17

7-(3-Chloro-pyridin-2-yl)-N⁴-(4-trifluoromethylphenyl)-5,6,7,8-tetrahydro-pyrido[3,4-d]pyrimidine-2,4-diamine

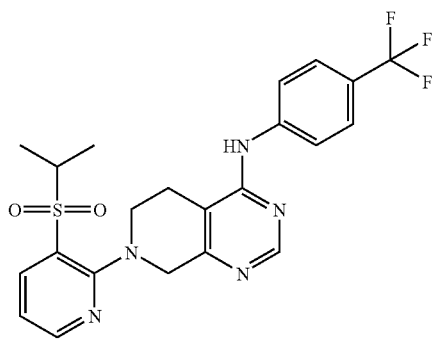

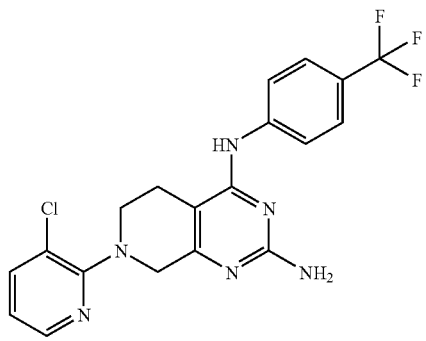

A. 2-Amino-7-benzyl-5,6,7,8-tetrahydropyrido[3,4-d]pyrimidin-4(4aH)-one

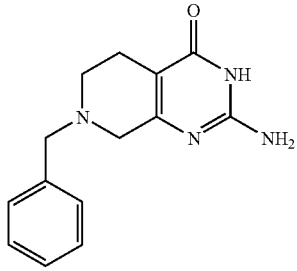

A suspension of ethyl N-benzyl-3-oxo-4-piperidine-carboxylate hydrochloride (2.98 g, 10 mmol) and guanidine hydrochloride (1.15 g, 12 mmol) in a solution of sodium methoxide in methanol (11.5 mL, 25% wt) was stirred at 100° C. in a sealed tube overnight before solvent was removed in vacuo. Residue was dissolved in water (10 mL) and was extracted by CHCl$_3$ and i-PrOH (3:1, 5×80 mL), dried over sodium sulfate. Solvent was removed in vacuo, and the product was obtained as a light yellow powder (2.45 g).

MS: M+H=257.2

B. 2-Benzyl-5-chloro-1,2,3,4-tetrahydroisoquinolin-7-amine

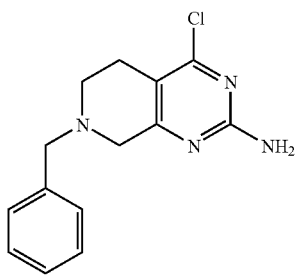

N,N-Dimethylaniline (1.4 g, 11.4 mmol) and phosphorus oxychloride (14 g, 91.2 mmol) were added to a solution of 2-amino-7-benzyl-5,6,7,8-tetrahydropyrido[3,4-d]pyrimidin-4(4aH)-one (2.9 g, 11.4 mmol) in 1,2-dichloroethane (23 mL, anhydrous) and were stirred in a preheated oil bath at 90° C. for 45 min. The reaction mixture was poured into ice, neutralized by solid sodium carbonate, extracted by ethyl acetate, and the dark brown semi solid was dissolved in methanol. The combined ethyl acetate and methanol solution was dried over sodium sulfate. Solvent was removed in vacuo and product was obtained as a light brown solid (2.6 g).

MS: M+H=275.2.

C. 2-Benzyl-N$^5$-(4-(trifluoromethyl)phenyl)-1,2,3,4-tetrahydroisoquinoline-5,7-diamine

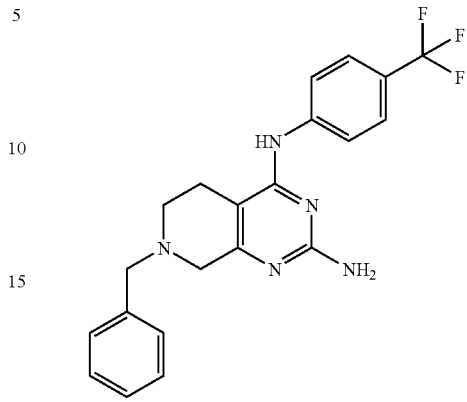

Sodium iodide (252 mg, 1.68 mmol) and hydriodic acid (1 mL, 47% aqueous solution) were added to the solution of 2-benzyl-5-chloro-1,2,3,4-tetrahydroisoquinolin-7-amine (380 mg, 1.4 mmol) and 4-aminobenzotrifluoride (446 mg, 2.8 mmol) in dioxane (10 mL) and the reaction solution was stirred at 100° C. over night before solvent was removed in vacuo. Residue was dissolved in ethyl acetate, washed by water, brine, dried over sodium sulfate and was purified by column chromatography. Product was obtained as brown oil (440 mg, 79%).

MS: M+H=400.2.

D. N$^5$-(4-(Trifluoromethyl)phenyl)-1,2,3,4-tetrahydroisoquinoline-5,7-diamine

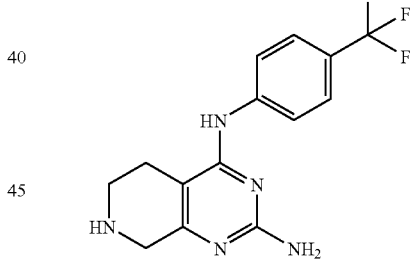

1-Chloroethyl chloroformate (864 mg, 6 mmol) was added dropwise to the solution of 2-benzyl-N-5-(4-(trifluoromethyl)phenyl)-1,2,3,4-tetrahydroisoquinoline-5,7-diamine (1.2 g, 3 mmol) and diisopropylethyl amine (774 mg, 6 mmol) in 1,2-dichloroethane (30 mL, anhydrous) at 0° C. After addition, the reaction mixture was stirred at room temperature for 1 hr. Solvent was removed in vacuo, residue was dissolved in methanol (10 mL) and was stirred at room temperature for 10 h. Solvent was removed in vacuo and solid residue was washed by diethyl ether. Product was obtained as a light brown solid (834 mg, 90%).

MS: M+H=310.2.

E. 7-(3-Chloropyridin-2-yl)-N-4-(4-(trifluoromethyl)phenyl)-5,6,7,8-tetrahydropyrido[3,4-d]pyrimidine-2,4-diamine The solution of diisopropylethylamine (97 mg, 0.75 mmol), N$^5$-(4-(trifluoromethyl)phenyl)-1,2,3,4-tetrahydroisoquinoline-5,7-diamine (155 mg, 0.5 mmol) and 2,3-dichloropyridine (148 mg, 1.0 mmol) in dioxane (2 mL) and N,N-diethylacetamide (0.2 mL) was irradiated in microwave at 180° C. for 10 hr. Solvent was removed in vacuo and the residue was purified by column chromatography over silica gel. The product was obtained as a light orange solid (10 mg).

MS: M+H=421.4. $^1$H NMR CDCl$_3$ δ: 2.72 (t, J=6.0 Hz, 2H), 3.77 (t, J=6.0 Hz, 2H), 4.39 (s, 2H), 4.77 (br s,2H), 6.45 (br s, 1H), 6.84-6.88 (m, 1H), 7.56-7.63 (m, 3H), 7.74-7.76 (m, 2H), 8.18-8.20(m, 1H).

Example 18

7-(3-Chloropyridin-2-yl)-N-(phenyl)-5,6,7,8-tetrahydropyrido[3,4-d]pyrimidin-4-amine

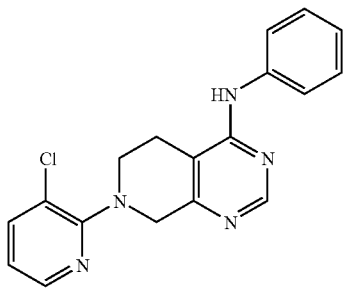

4-Chloro-7-(3-chloro-pyridin-2-yl)-5,6,7,8-tetrahydropyrido[3,4-d]pyrimidine (150 mg, 0.54 mmol) was dissolved in acetonitrile (2 mL). To the mixture was added aniline (60 mg). The mixture was heated in a sealed tube at 180° C. for 30 minutes in a Personal Chemistry Microwave (Smith Creator). The solvent was removed under vacuum and the resulting orange residue was purified by flash chromatography over silica gel using a 0-100% ethyl acetate-hexane gradient to give the product as an off white solid (60 mg).

MS: MH+=338. $^1$H NMR (DMSO-d6): δ 2.81 (t, J=5.6 Hz, 2H); 3.68 (t, J=5.7 Hz, 2H); 4.35 (s, 2H); 7.01-7.08 (m, 2H); 7.29-7.36 (m, 2H); 7.67-7.71 (m, 2H); 7.86 (dd, J=1.6 Hz, 7.9 Hz, 1H); 8.24 (dd, J=1.6 Hz, 4.9 Hz, 1H); 8.41 (s, 1H); 8.49 (s, 1H).

Example 19

7-(3-Chloropyridin-2-yl)-N-(4-fluorophenyl)-5,6,7,8-tetrahydropyrido[3,4-d]pyrimidin-4-amine

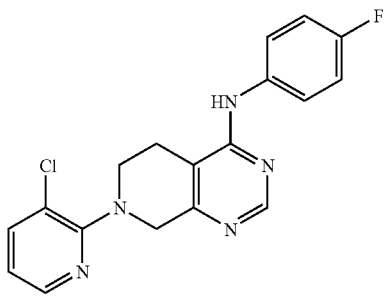

4-Chloro-7-(3-chloro-pyridin-2-yl)-5,6,7,8-tetrahydropyrido[3,4-d]pyrimidine (100 mg, 0.35 mmol) was dissolved in acetonitrile (2 mL). To the mixture was added 4-flouroaniline (0.067 mL, 0.71 mmol), sodium iodide (80 mg, 0.53 mmol) and HI (47%, 0.2 mL). The mixture was heated in a sealed tube at 130° C. for 10 minutes in a Personal Chemistry Microwave (Smith Creator). The solvent was removed under vacuum and the resulting orange residue dissolved in ethyl acetate and washed with saturated sodium bicarbonate and brine. The organic layer was dried over sodium sulphate, filtered and evaporated. The residue was purified by flash chromatography over silica gel using a 0-100% ethyl acetate-hexane gradient to give the product as an off white solid (53 mg).

MS: MH+=356. $^1$H NMR (DMSO-d6): δ 2.80(t, J=5.8 Hz, 2H); 3.68(t, J=5.8 Hz, 2H); 4.35(s, 2H); 7.03(dd, J=4.7 Hz, 7.7 Hz, 1H); 7.14-7.20(m, 2H); 7.66-7.71(m, 2H); 7.86(dd, J=1.6 Hz, 7.9 Hz, 1H); 8.24(dd, J=1.6 Hz, 4.7 Hz, 1H); 8.39(s, 1H); 8.54(s, 1H).

Example 20

7-(3-Chloropyridin-2-yl)-N-(5-(trifluoromethyl)pyridin-2-yl)-5,6,7,8-tetrahydropyrido[3,4-d]pyrimidin-4-amine

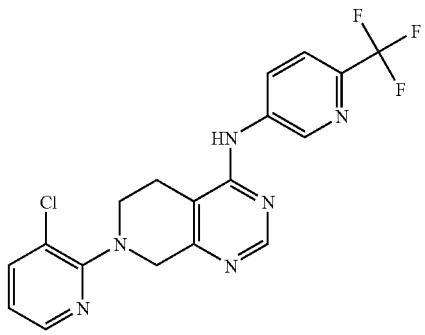

4-Chloro-7-(3-chloro-pyridin-2-yl)-5,6,7,8-tetrahydropyrido[3,4-d]pyrimidine (250 mg, 0.89 mmol) was dissolved in acetonitrile (2 mL). To the mixture was 5-amino-2-(trifluoromethyl)pyridine (288 mg, 1.8 mmol), sodium iodide (200 mg, 1.34 mmol) and HI (47%, 0.2 mL). The mixture was heated in a sealed tube at 130° C. for 10 minutes in a Personal Chemistry Microwave (Smith Creator). The solvent was removed under vacuum and the resulting orange residue dissolved in ethyl acetate and washed with saturated sodium bicarbonate and brine. The organic layer was dried over sodium sulphate, filtered and evaporated. The residue was purified using a 0-100% ethyl acetate-hexane gradient to give the product as an off white solid (70 mg).

MS: MH+=407. $^1$H NMR (DMSO-d6): δ 2.89(t, J=5.6 Hz, 2H); 3.71(t, J=5.6 Hz, 2H); 4.41(s, 2H); 7.05(dd, J=4.8 Hz, 7.9 Hz, 1H); 7.85-7.89(m, 2H); 8.25(dd, J=1.5 Hz, 4.6 Hz, 1H); 8.50(dd, J=2.1 Hz, 8.6 Hz, 1H); 8.55(s, 1H); 9.06-9.09(m, 2H).

Example 21

7-(3-Methanesulphonylpyridin-2-yl)-N-(5-(trifluoromethyl)pyridine-2-yl)-5,6,7,8-tetrahydropyrido[3,4-d]pyrimidin-4-amine

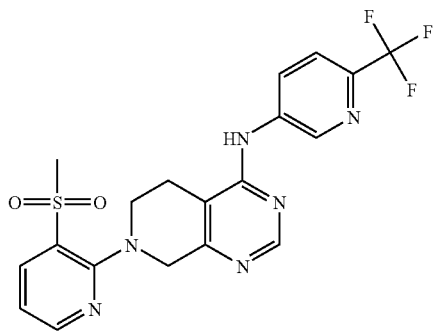

A. 7-Benzyl-N-(4-(5-(trifluoromethyl)pyridine-2-yl)-5,6,7,8-tetrahydropyrido[3,4-d]pyrimidin-4-amine

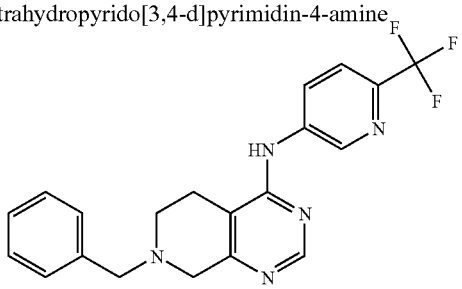

7-Benzyl-4-chloro-5,6,7,8-tetrahydro-pyrido[3,4-d]pyrimidine (1.0 g, 3.9 mmol), was dissolved in anhydrous dioxane (2 mL) and 5-amino-2-(trifluoromethyl)pyridine was added (1.0 g, 4.6 mmol), followed by HI/H$_2$O (0.2 mL, 47%) and sodium iodide (750 mg, 4.7 mmol). The mixture was heated at 130° C. in a sealed tube for 10 min in a microwave (Smith creator model, Personal Chemistry). The solvents were removed under vacuum and the residue was dissolved in ethyl acetate and washed with sat. NaHCO$_3$ and brine. The organic layer was dried over Na$_2$SO$_4$, filtered and evaporated to give the desired compound as a brown solid (800 mg) which was purified by flash chromatography over silca gel using a 0-100% gradient of ethyl acetate/hexanes to give the desired product as a white solid (500 mg).

M+H=386.

B. N-(5-(Trifluoromethyl)pyridine-2-yl)-5,6,7,8-tetrahydropyrido[3,4-d]pyrimidin-4-amine

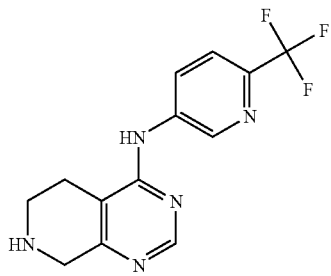

7-Benzyl-N-(4-(5-(trifluoromethyl)pyridin-2-yl)-5,6,7,8-tetrahydropyrido[3,4-d]pyrimidin-4-amine (500 mg, 1.3 mmol) was dissolved in methanol (25 mL) and palladium hydroxide was added (150 mg, 20% wt). The mixture was shaken on a Parr Shaker under H$_2$ (g) atmosphere (60 PSI) for 24 hours. The mixture was filtered through celite and evaporated to give 280 mg of material as a white solid which was used directly in the next step.

MS: M+H=296.

C. 7-(3-Methanesulphonylpyridin-2-yl)-N-(5-(trifluoromethyl)pyridin-2-yl)-5,6,7,8-tetrahydropyrido[3,4-d]pyrimidin-4-amine

N-(5-(Trifluoromethyl)pyridine-2-yl)-5,6,7,8-tetrahydropyrido[3,4-d]pyrimidin-4-amine (100 mg, 0.34 mmol) was dissolved in a mixture of acetonitrile (2 mL). To the mixture was added 2-chloro-3-methanesulphonylpyridine (122 mg, 0.68 mmol) and N,N-diisopropylethylamine (0.23 mL, 0.68 mmol). The mixture was heated in a sealed tube at 150° C. in microwave (Model, Personal Chemistry) for 16 h. The solvents were removed under vacuum and the residue was dissolved in ethyl acetate and washed with sat. NaHCO$_3$ and brine. The organic layer was dried over Na$_2$SO$_4$, filtered and evaporated to give a brown residue. The residue was purified by flash chromatography over silica gel using a gradient of ethyl acetate:hexane (0-100%) to give the desired compound as an off-white powder (66 mg).

MS: M+H=451 $^1$H NMR (DMSO-d6): δ 2.92 (t, J=5.6 Hz, 2H); 3.32 (s, 3H); 3.59 (t, J=5.6 Hz, 2H); 4.38 (s, 2H); 7.44 (dd, J=4.9 Hz, 7.8 Hz, 1H); 7.88 (d, J=8.6 Hz, 1H); 8.35 (dd, J=1.6 Hz, 7.7 Hz, 1H); 8.53 (dd, J=2.1 Hz, 8.6 Hz, 1H); 8.55 (s, 1H); 8.67 (dd, J=1.9 Hz, 4.8 Hz, 1H); 9.01 (d, J=2.3 Hz, 1H); 9.11 (s, 1H).

Example 22

7-(3-Chloropyridin-2-yl)-N-(4-(trifluoromethylsulphonyl)phenyl)-5,6,7,8-tetrahydropyrido[3,4-d]pyrimidin-4-amine

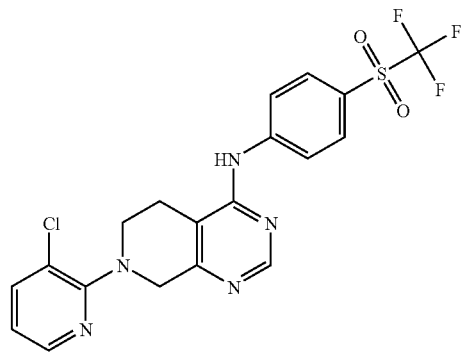

4-Chloro-7-(3-chloro-pyridin-2-yl)-5,6,7,8-tetrahydropyrido[3,4-d]pyrimidine (250 mg, 0.89 mmol) was dissolved in acetonitrile (2 mL). To the mixture was added 4-(trifluoromethyanesulphonyl)aniline (400 mg, 1.8 mmol), sodium iodide (200 mg, 1.34 mmol) and HI (47%, 0.2 mL). The mixture was heated in a sealed tube at 130° C. for 10 minutes in a Personal Chemistry Microwave (Smith Creator). The solvent was removed under vacuum and the resulting orange residue dissolved in ethyl acetate and washed with saturated sodium bicarbonate and brine. The organic layer was dried over sodium sulphate, filtered and evaporated. The residue was purified by flash chromatography over silica gel using a 0-100% ethyl acetate-hexane gradient to give the product as an off white solid (44 mg).

MS: M+H=470. $^1$H NMR (DMSO-d6): δ 2.92 (t, J=5.6 Hz, 2H); 3.70(t, J=5.7 Hz, 2H); 4.43(s, 2H); 7.05(dd, J=4.8 Hz, 7.8 Hz, 1H); 7.87(dd, J=1.6 Hz, 7.9 Hz, 1H); 8.05(d, J=9.0 Hz, 2H); 8.22-8.26(m, 3H); 8.63(s, 1H); 9.26(s, 1H).

Example 23

7-(3-Methanesulphonylpyridin-2-yl)-N-(4-(trifluoromethylsulphonyl)phenyl)-5,6,7,8-tetrahydropyrido[3,4-d]pyrimidin-4-amine

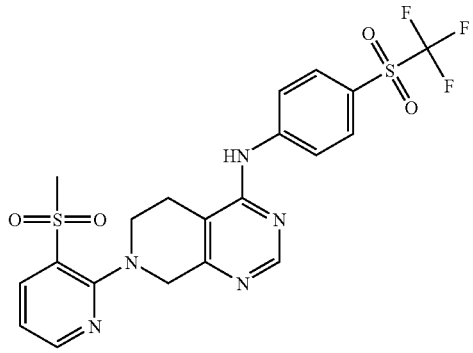

A. 7-Benzyl-N-(4-(trifluoromethanesulphonyl)phenyl)-5,6,7,8-tetrahydropyrido[3,4-d]pyrimidin-4-amine

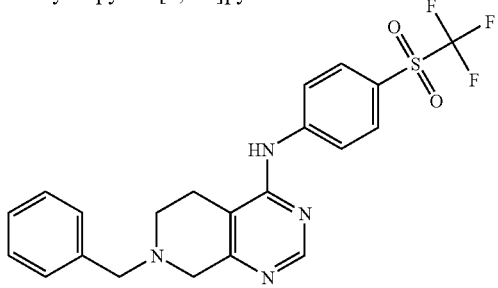

7-Benzyl-4-chloro-5,6,7,8-tetrahydro-pyrido[3,4-d]pyrimidine (1.0 g, 3.9 mmol) was dissolved in anhydrous dioxane (2 mL) and 4-(trifluoromethyanesulphonyl)aniline was added (1.0 g, 4.6 mmol), followed by HI/H$_2$O (0.2 mL, 47%) and sodium iodide (0.87 g, 5.8 mmol). The mixture was heated at 130° C. in a sealed tube for 10 min in a microwave (Smith creator model, Personal Chemistry). The solvents were removed under vacuum and the residue was dissolved in ethyl acetate and washed with sat. NaHCO$_3$ and brine. The organic layer was dried over Na$_2$SO$_4$, filtered and evaporated to give the desired compound as a brown solid (800 mg, 91%) which was purified by flash chromatography over silica gel using a 0-100% gradient of ethyl acetate/hexanes to give the desired product as a white solid (0.15 g).

MS: M+H=449.

B. N-(4-(Trifluoromethanesulphonyl)phenyl)-5,6,7,8-tetrahydropyrido[3,4-d]pyrimidin-4-amine

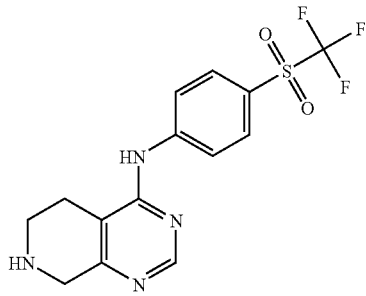

7-Benzyl-N-(4-(trifluoromethanesulphonyl)phenyl)-5,6,7,8-tetrahydropyrido[3,4-d]pyrimidin-4-amine (0.15 g, 0.33 mmol) was dissolved in methanol (25 mL) and palladium hydroxide was added (0.15 g, 20% wt). The mixture was shaken on a Parr Shaker under H$_2$ (g) atmosphere (60 PSI) for 24 hours. The mixture was filtered through celite and evaporated to give 91 mg of material as a white solid (77%), which was used directly in the next step.

MS: M+H=359.

E. 7-(3-Methanesulphonylpyridin-2-yl)-N-(4-(trifluoromethanesulphonyl)phenyl)-5,6,7,8-tetrahydropyrido[3,4-d]pyrimidin-4-amine N-(4-(Trifluoromethyanesulphonyl)phenyl)-5,6,7,8-tetrahydropyrido[3,4-d]pyrimidin-4-amine (80 mg, 0.22 mmol) was dissolved in a mixture of acetonitrile (2 mL). To the mixture was added 2-chloro-3-methanesulphonylpyridine (86 mg, 0.45 mmol) and N,N-diisopropylethylamine (0.15 mL, 0.45 mmol). The mixture was heated in a sealed tube at 150° C. in microwave (Model, Personal Chemistry) for 16 h. The solvents were removed under vacuum and the residue was dissolved in ethyl acetate and washed with sat. NaHCO$_3$ and brine. The organic layer was dried over Na$_2$SO$_4$, filtered and evaporated to give a brown residue. The residue was purified by flash chromatography over silica gel using a gradient of ethyl acetate:hexane (0-100%) to give the desired compound as an off-white powder (43 mg).

MS: M+H=514. $^1$H NMR (DMSO-d6): δ 2.92 (t, J=5.6 Hz, 2H), 3.63 (t, J=5.6 Hz, 2H), 4.44 (s, 2H), 7.08 (dd, J=7.6 Hz, 4.7 Hz, 1H), 7.67 (d, J=8.4 Hz, 2H), 7.89 (dd, J=7.7 Hz, 1.6 Hz, 1H), 7.94 (d, J=8.4 Hz, 2H), 8.28 (dd, J=4.7 Hz, 1.6 Hz, 1H), 8.50 (s, 1H), 8.91 (brs, 1H).

Example 24

[7-(3-Chloro-pyridin-2-yl)-2-methylsulfanyl-5,6,7,8-tetrahydro-pyrido[3,4-d]pyrimidin-4-yl]-(4-trifluoromethyl-phenyl)-amine

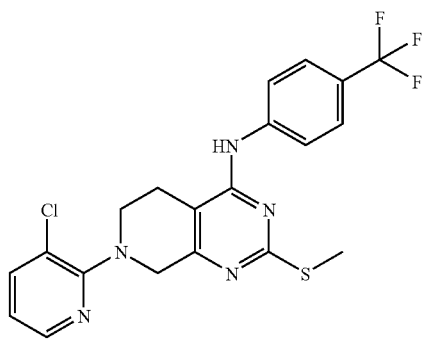

A. 7-Benzyl-5,6,7,8-tetrahydro-2-(methylthio)pyrido[3,4-d]pyrimidin-4(4aH)-one

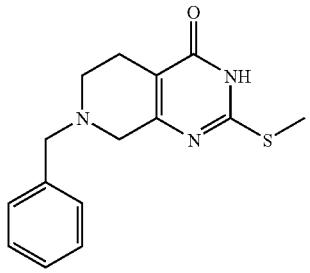

A suspension of ethyl N-benzyl-3-oxo-4-piperidine-carboxylate hydrochloride (8.9 g, 30 mmol) and thiourea (4.56 g, 60 mmol) in a solution of sodium methoxide in methanol (34 mL, 25% wt/wt) was stirred at 100° C. in a sealed tube overnight. Iodomethane (5.1 g, 42 mmol) was added dropwise to the reaction mixture after cooling to room temperature and stirred at room temperature for 1 hr. Solvent was removed in vacuo and the residue was dissolved in water (100 mL), extracted by CHCl$_3$ and i-PrOH (3:1, 10×40 mL) and dried over sodium sulfate. Solvent was removed in vacuo, product was obtained as a beige powder (7.6 g).

MS: M+H=287.9.

B. 7-Benzyl-4-chloro-5,6,7,8-tetrahydro-2-(methylthio)pyrido[3,4-d]pyrimidine

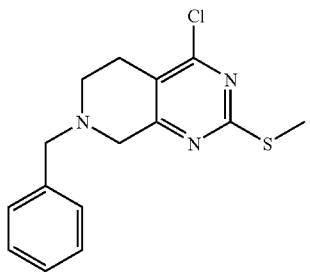

N,N-Dimethylaniline (3.2 g, 26.6 mmol) and phosphorus oxychloride (32.6 g, 213 mmol) were added to the solution of 7-benzyl-5,6,7,8-tetrahydro-2-(methylthio)pyrido[3,4-d]pyrimidin-4(4aH)-one (7.6 g, 26.6 mmol) in 1,2-dichloroethane (20 mL, anhydrous) and were stirred in a preheated oil bath at 90° C. for 1 hr. Reaction mixture was poured into ice, neutralized by solid sodium carbonate, extracted by ethyl acetate and dried over sodium sulfate. Solvent was removed in vacuo and light brown oil residue was used directly in the next step.

MS: M+H=307.1.

C. 7-Benzyl-N-(4-(trifluoromethyl)phenyl)-5,6,7,8-tetrahydro-2-(methylthio)pyrido[3,4-d]pyrimidin-4-amine

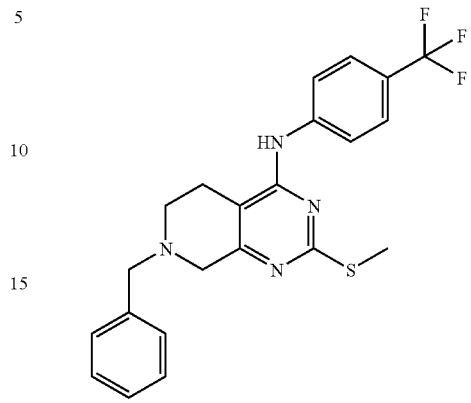

Sodium iodide (3.9 g, 26 mmol) and hydriodic acid (10 mL, 47% aqueous solution) were added to a mixture of 7-benzyl-4-chloro-5,6,7,8-tetrahydro-2-(methylthio)pyrido [3,4-d]pyrimidine (8.0 g, 26 mmol) and 4-aminobenzotrifluoride (5.06 g, 0.031 mol) in dioxane (100 mL) and the reaction mixture was stirred at 100° C. overnight. Solid thus formed was filtered out, washed with ethyl acetate and diethyl ether and dried in vacuo. Product was obtained as white needle solid (8.2 g).

MS: M+H=431.7.

D. N-(4-(Trifluoromethyl)phenyl)-5,6,7,8-tetrahydro-2-(methylthio)pyrido[3,4-d]pyrimidin-4-amine

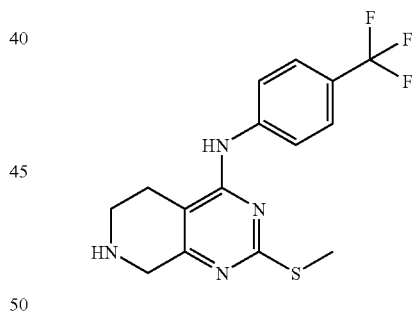

1-Chloroethyl chloroformate (572 mg, 4 mmol) was added dropwise to a mixture of 7-benzyl-N-(4-(trifluoromethyl)phenyl)-5,6,7,8-tetrahydro-2-(methylthio)pyrido[3,4-d]pyrimidin-4-amine (860 mg, 2 mmol) and diisopropylethyl amine (516 mg, 4 mmol) in 1,2-dichloroethane (5 mL, anhydrous) at 0° C. After addition, the reaction mixture was stirred at room temperature for 1 hr. Solvent was removed in vacuo, residue was dissolved in methanol (10 mL) and was stirred at room temperature overnight. Solvent was removed in vacuo, residue was dissolved in ethyl acetate and was washed with saturated aqueous sodium bicarbonate, brine and dried over sodium sulfate. Solvent was removed in vacuo and residue was triturated with diethyl ether to yield the product as a beige solid (454 mg).

MS: M+H=340.7.

E. 7-(3-Chloropyridin-2-yl)-N-(4-(trifluoromethyl)phenyl)-5,6,7,8-tetrahydro-2-(methylthio)pyrido[3,4-d]pyrimidin-4-amine A mixture of diisopropylethylamine (252 mg, 1.95 mmol), N-(4-(trifluoromethyl)phenyl)-5,6,7,8-tetrahydro-2-(methylthio)pyrido[3,4-d]pyrimidin-4-amine (443 mg, 1.3 mmol) and 2,3-dichloropyridine (386 mg, 2.6 mmol) in dioxane (5 mL) and N,N-diethylacetamide (0.5 mL) was heated via microwave in a sealed tube at 180° C. for 10 h. Solvent was removed in vacuo and residue was purified by column chromatography. The product was obtained as a beige solid (100 mg).

MS: M+H=452.0. $^1$H NMR DMSO-d$_6$ δ: 2.45 (s, 3H), 2.78 (t, J=5.6 Hz, 2H), 3.68 (t, J=5.6 Hz, 2H), 4.34 (s, 2H), 7.02-7.05 (m, 1H), 7.68-7.70 (m, 2H), 7.85-7.87 (m, 1H), 7.94-7.96 (m, 2H), 8.23-8.24 (m, 1H), 8.85 (s, 1H).

Example 25

[7-(3-Chloro-pyridin-2-yl)-2-methanesulfonyl-5,6,7,8-tetrahydro-pyrido[3,4-d]pyrimidin-4-yl]-(4-trifluoromethyl-phenyl)-amine

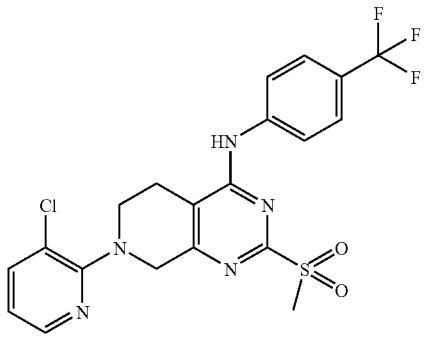

m-CPBA (148 mg, 0.6 mmol, 70%) was added to a solution of 7-(3-chloropyridin-2-yl)-N-(4-(trifluoromethyl)phenyl)-5,6,7,8-tetrahydro-2-(methylthio)pyrido[3,4-d]pyrimidin-4-amine from (92 mg, 0.2 mmol) in ethanol (5 mL) and stirred at room temperature for 3 h. Solvent was removed in vacuo, residue was dissolved in ethyl acetate and washed with saturated aqueous sodium bicarbonate, saturated aqueous sodium hydrosulfite and brine, dried over sodium sulfate. After purification by column chromatography, the product was obtained as a white powder (16 mg).

MS: M+H=484.0. $^1$H NMR DMSO-d$_6$ δ: 2.90 (t, J=5.6 Hz, 2H), 3.30 (s, 3H), 3.75 (t, J=5.6 Hz, 2H), 4.50 (s, 2H), 7.04-7.08 (m, 1H), 7.73-7.76 (m, 2H), 7.88-7.90 (m, 1H), 7.95-7.97 (m, 2H), 8.24-8.26 (m, 1H), 9.36 (s, 1H).

Example 26

6-(3-Chloropyridin-2-yl)-N-(4-(trifluoromethyl)phenyl)-5,6,7,8-tetrahydro-2,6-naphthyridin-1-amine

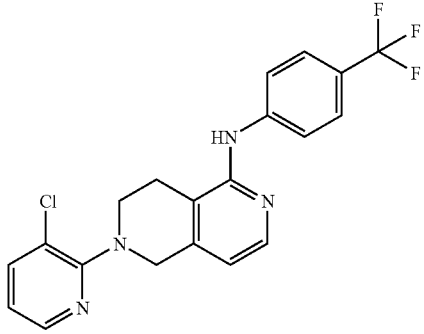

A. 7-Benzyl-N-(4-(trifluoromethyl)phenyl)-5,6,7,8-tetrahydro-2,6-naphthyridin-1-amine

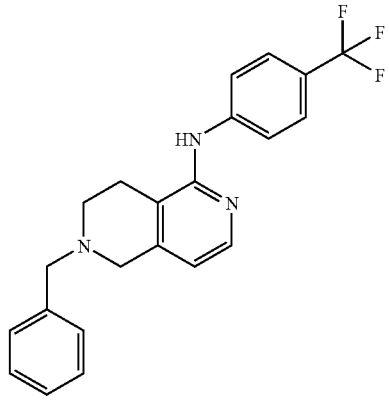

Benzyl-5-bromo-1,2,3,4-tetrahydro-2,6-naphthyridine (see WO03/076427) (250 mg, 0.82 mmol) was dissolved in 1 mL of anhydrous toluene. To the mixture was added Pd$_2$(dba)$_3$ (10 mol %, 85 mg) and PdCl$_2$(DPPF) (33 mg, 5 mol %), followed by NaOtBu (118 mg, 1.23 mmol). After mixing for 5 min, 4-(trifluoromethyl)aniline (0.153 mL, 1.23 mmol) was added and the mixture was heated at 160° C. for 1200s in a Personal Chemistry microwave. The reaction mixture was filtered and the solvent was evaporated and the residue was dissolved in ethyl acetate and washed with saturated aqueous sodium bicarbonate and brine. The organic layer was dried over Na$_2$SO$_4$, filtered and evaporated to give a brown-purple residue. The residue was purified by flash chromatography over silica gel using a gradient of ethyl acetate:hexane (0-100%) to give the desired compound as an off-white powder (288 mg, 92%).

MS: M+H=384.

B. N-(4-(Trifluoromethyl)phenyl)-5,6,7,8-tetrahydro-2,6-naphthyridin-1-amine

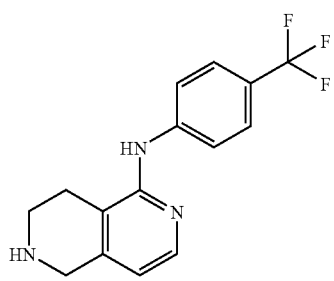

6-Benzyl-N-(4-(trifluoromethyl)phenyl)-5,6,7,8-tetrahydro-2,6-naphthyridin-1-amine (280 mg, 0.73 mmol) was dissolved in methanol (25 mL) and palladium hydroxide was added (0.2 g, 20% wt). The mixture was shaken on a Parr Shaker under H$_2$ (g) atmosphere (60 PSI) for 1 day. The mixture was filtered through celite and evaporated to give 0.21 g of material as grey crystals (quant.), which was used directly in the next step.

MS: M+H=294.

C. 6-(3-Chloropyridin-2-yl)-N-(4-(trifluoromethyl)phenyl)-5,6,7,8-tetrahydro-2,6-naphthyridin-1-amine N-(4-(Trifluoromethyl)phenyl)-5,6,7,8-tetrahydro-2,6-naphthyridin-1-amine (200 mg, 0.68 mmol) was dissolved in a mixture of dioxane/N,N-dimethylacetamide (4:1) (3 mL). To the mixture was added 2,3-dichloropyridine (200 mg, 1.36 mmol) and N,N-diisopropylethylamine (0.24 mL, 1.36 mmol). The mixture was heated at 150° C. in a Personal Chemistry microwave for 16 h. The solvents were removed under vacuum and the residue was dissolved in ethyl acetate and washed with sat. NaHCO$_3$ and brine. The organic layer was dried over Na$_2$SO$_4$, filtered and evaporated to give a brown residue. The residue was purified by flash chromatography over silica gel using a gradient of ethyl acetate: hexane (0-100%) to give the desired compound as an off-white powder (76 mg).

MS: M+H=405.

Example 27

7-(3-Chloropyridin-2-yl)-N-(4-(trifluoromethyl)phenyl)-5,6,7,8-tetrahydro-2-methoxypyrido[3,4-d]pyrimidin-4-amine

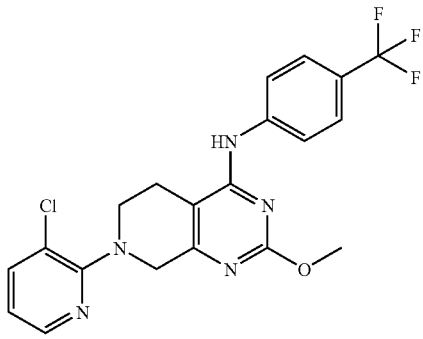

Sodium methoxide (16 mg, 0.3 mmol) was added to a suspension of 7-(3-chloropyridin-2-yl)-N-(4-(trifluoromethyl)phenyl)-5,6,7,8-tetrahydro-2-(methylsulfonyl)pyrido[3,4-d]pyrimidin-4-amine from Example 25 (100 mg, 0.2 mmol) in methanol (5 mL, anhydrous) and stirred at 60° C. overnight. Solvent was removed in vacuo, residue was dissolved in ethyl acetate and washed with water and brine and dried over sodium sulfate. After concentration, solid residue was triturated by diethyl ether to yield the product as a white powder (70 mg).

MS: M+H=435.8. $^1$H NMR DMSO-d$_6$ δ: 2.78 (t, J=5.6 Hz, 2H), 3.68 (t, J=5.6 Hz, 2H), 3.84 (s, 3H), 4.32 (s, 2H), 7.01-7.04 (m, 1H), 7.67-7.69 (m, 2H), 7.84-7.87 (m, 1H), 8.00-8.02 (m, 2H), 8.22-8.23 (m, 1H), 8.83 (s, 1H).

Example 28

N-(4-tert-Butylphenyl)-7-(3-chloropyridin-2-yl)-5,6,7,8-tetrahydro-2-(methylthio)pyrido[3,4-d]pyrimidin-4-amine

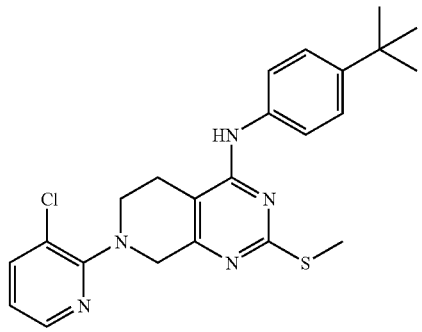

A. N-(4-tert-Butylphenyl)-7-benzyl-5,6,7,8-tetrahydro-2-(methylthio)pyrido[3,4-d]pyrimidin-4-amine

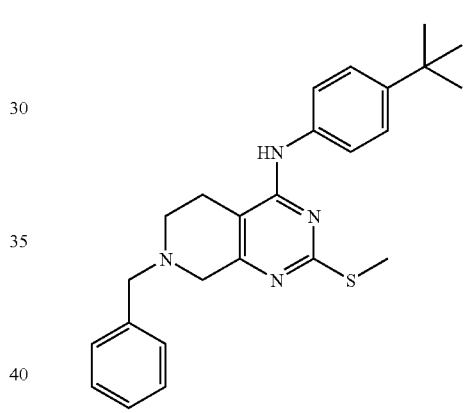

The solution of 7-benzyl-4-chloro-5,6,7,8-tetrahydro-2-(methylthio)pyrido[3,4-d]pyrimidine (915 mg, 3 mmol) from Example 24. B. and 4-tert-butylaniline (537 mg, 3.6 mmol) in acetonitrile (5 mL) was heated in a sealed tube via microwave at 180° C. for 10 min. Solid thus formed was filtered out and washed with hexanes. Product was obtained as a light brown solid (750 mg).

MS: M+H=418.9.

B. N-(4-tert-Butylphenyl)-5,6,7,8-tetrahydro-2-(methylthio)pyrido[3,4-d]pyrimidin-4-amine

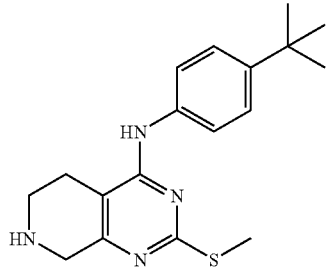

1-Chloroethyl chloroformate (732 mg, 5.12 mmol) was added dropwise to a mixture of N-(4-tert-butylphenyl)-7-benzyl-5,6,7,8-tetrahydro-2-(methylthio)pyrido[3,4-d]pyrimidin-4-amine (1.07 g, 2.56 mmol) and diisopropylethyl amine (660 mg, 5.12 mmol) in 1,2-dichloroethane (10 mL, anhydrous) at 0° C. After addition, the reaction mixture was stirred at room temperature for 1 hr. Solvent was removed in vacuo, residue was dissolved in methanol (10 mL) and was stirred at room temperature overnight. Solvent was removed in vacuo, residue was dissolved in ethyl acetate and was washed with saturated aqueous sodium bicarbonate, brine and dried over sodium sulfate. Solvent was removed in vacuo and residue was triturated by diethyl ether to yield the product as a light brown solid (303 mg, 36%).

MS: M+H=329.4.

C. N-(4-tert-Butylphenyl)-7-(3-chloropyridin-2-yl)-5,6,7,8-tetrahydro-2-(methylthio)pyrido[3,4-d]pyrimidin-4-amine The solution of diisopropylethylamine (235 mg, 1.82 mmol), N-(4-tert-butylphenyl)-5,6,7,8-tetrahydro-2-(methylthio)pyrido[3,4-d]pyrimidin-4-amine (300 mg, 0.91 mmol) and 2,3-dichloropyridine (270 mg, 1.82 mmol) in dioxane (5 mL) and N,N-diethylacetamide (0.5 mL) was irradiated in microwave at 180° C. for 10 hr. Solvent was removed in vacuo and residue was dissolved in ethyl acetate, washed with water and brine and dried over sodium sulfate and purified by column chromatography, product was obtained as a beige solid (100 mg).

MS: M+H=439.9. $^1$H NMR DMSO-d$_6$ δ: 1.28 (s, 9H), 2.43 (s, 3H), 2.73 (t, J=5.6 Hz, 2H), 3.67 (t, J=5.6 Hz, 2H), 4.30 (s, 2H), 7.01-7.04 (m, 1H), 7.33-7.35 (m, 2H), 7.60-7.62 (m, 2H), 7.84-7.86 (m, 1H), 8.22-8.24 (m, 1H), 8.46 (s, 1H).

Example 29

N-(4-tert-Butylphenyl)-7-(3-chloropyridin-2-yl)-5,6,7,8-tetrahydro-2-methoxypyrido[3,4-d]pyrimidin-4-amine

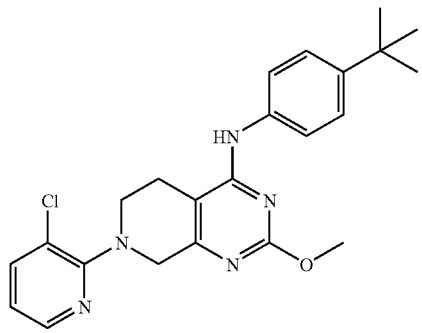

m-CPBA (148 mg, 0.6 mmol) was added to a solution of N-(4-tert-butylphenyl)-7-(3-chloropyridin-2-yl)-5,6,7,8-tetrahydro-2-(methylthio)pyrido[3,4-d]pyrimidin-4-amine from Example 28.C. (88 mg, 0.2 mmol) in ethanol (7 mL) and stirred at room temperature for 1 hr. Solid thus formed was filtered out and dried in vacuo (50 mg). The solid was suspended in methanol (5 mL) and sodium methoxide (9 mg, 0.165 mmol) was added and stirred at 60° C. overnight. Solvent was removed in vacuo and residue was dissolved in ethyl acetate, washed with water, sodium hydrosulfite aqueous solution, brine and dried over sodium sulfate. Purified by flash chromatography to yield the product as a white solid (33 mg).

MS: M+H=424.1. $^1$H NMR DMSO-d$_6$ δ: 1.28 (s, 9H), 2.72 (t, J=5.6 Hz, 2H), 3.67 (t, J=5.6 Hz, 2H), 3.79 (s, 3H), 4.28 (s, 2H), 7.01-7.02 (m, 1H), 7.33-7.35 (m, 2H), 7.62-7.64 (m, 2H), 7.84-7.86 (m, 1H), 8.22-8.24 (m, 1H), 8.44 (s, 1H).

Example 30

(7-Benzyl-5,6,7,8-tetrahydro-pyrido[3,4-d]pyrimidin-4-yl)-(2,3-dihydro-benzo[1,4]dioxin-6-yl)-amine

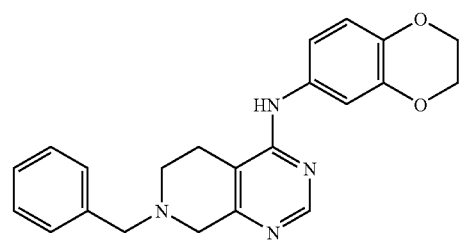

The title compound was prepared as described in Example 7A.

$^1$H NMR (DMSO-d6): δ 2.90 (brs, 2H); 3.3-3.60 (m, 4H); 4.01 (brs, 2H); 4.20 (brs, 2H); 4.40 (brs, 2H); 6.82 (d, J=8.8 Hz, 1H); 7.06 (dd, J=8.8 Hz, 2.5 Hz, 1H); 7.22 (d, J=2.5 Hz, 1H); 7.46-7.51 (m, 3H); 7.66-7.71 (m, 2H); 8.40 (s, 1H); 8.72 (s, 1H).

Example 31

7-Benzyl-N-(4-(trifluoromethyl)phenyl)-5,6,7,8-tetrahydro-2-(methoxymethyl)pyrido[3,4-d]pyrimidin-4-amine

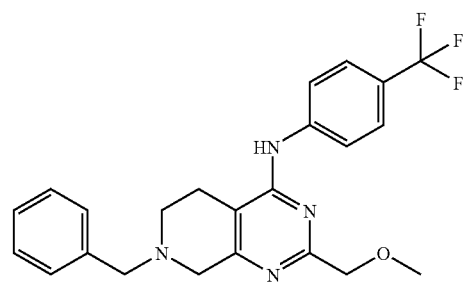

Sodium iodide (720 mg, 4.8 mmol) and hydriodic acid (2.0 mL, 47% aqueous solution) were added to a mixture of 7-benzyl-4-chloro-5,6,7,8-tetrahydro-2-(methoxymethyl) pyrido[3,4-d]pyrimidine as prepared for Example 5.B. (1.2 g, 4.0 mmol) and 4-aminobenzotrifluoride (1.3 g, 8 mmol) in dioxane (20 mL) and the reaction solution was stirred at 100° C. overnight. Solvent was removed in vacuo and the residue was dissolved in water. Solid sodium carbonate was added to the solution to a pH>7 and the mixture was extracted with ethyl acetate. The ethyl acetate phase was washed with brine, and dried over sodium sulfate. Solvent was removed and the residue was purified by column chromatography to yield the product as a beige solid (910 mg).

MS: M+H=428.8. $^1$H NMR DMSO-$d_6$ δ: 2.71-2.72 (m, 2H), 2.78-2.79 (m, 2H), 3.33 (s, 3H), 3.42 (s, 2H), 3.69 (s, 2H), 4.33 (s, 2H), 7.29-7.30 (m, 1H), 7.34-7.37 (m, 4H), 7.65-7.67 (m, 2H), 8.03-8.05 (m, 2H), 8.73 (s, 1H).

Example 32

7-(3-Chloropyridin-2-yl)-N-2-(2-(dimethylamino)ethyl)-N-4-(4-(trifluoromethyl)phenyl)-5,6,7,8-tetrahydropyrido[3,4-d]pyrimidine-2,4-diamine

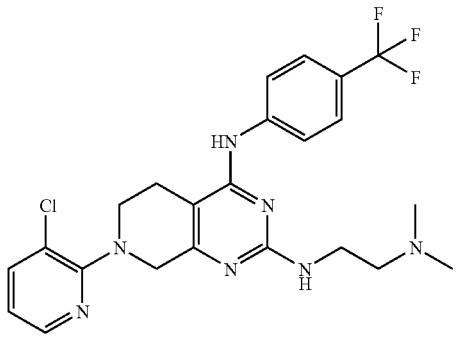

A mixture of 7-(3-chloropyridin-2-yl)-N-(4-(trifluoromethyl)phenyl)-5,6,7,8-tetrahydro-2-(methylsulfonyl)pyrido[3,4-d]pyrimidin-4-amine from Example 25 (50 mg, 0.1 mmol) and unsym-dimethylethylenediamine (100 mg, 1.1 mmol) in DMSO was heated in a sealed tube via microwave at 150° C. for 10 min. The reaction mixture was partioned between water and ethyl acetate. Solid material between the two phases was filtered out and this solid was dissolved in methanol. The methanol was filtered and the filtrate was concentrated to yield the product as beige powder (20 mg).

MS: M+H=492.1. $^1$H NMR DMSO-$d_6$ δ: 2.32 (s, 6H), 2.58-2.59 (m, 2H), 2.72 (t, J=5.2 Hz, 2H), 3.35-3.41 (m, 2H), 3.63 (t, J=5.6 Hz, 2H), 4.20 (s, 2H), 6.56 (br s, 1H), 7.00-7.03 (m, 1H), 7.60-7.62 (m, 2H), 7.83-7.85 (m, 1H), 8.02-8.04 (m, 2H), 8.22-8.23 (m, 1H), 8.45 (s, 1H).

Example 33

7-(3-Chloropyridin-2-yl)-N$^4$-(4-(trifluoromethyl)phenyl)-5,6,7,8-tetrahydro-N$^2$-(2-morpholinoethyl)pyrido[3,4-d]pyrimidine-2,4-diamine

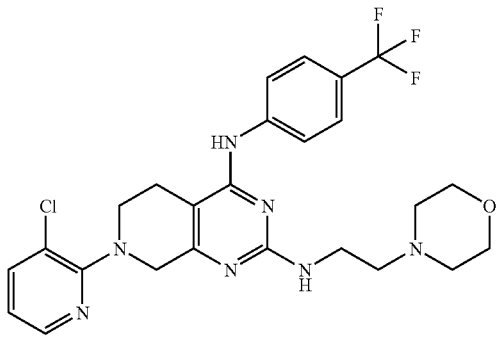

The title compound was prepared in a manner similar to the procedure given for Example 32 using the appropriate reagents and starting materials.

MS: M+H=533.7. $^1$H NMR DMSO-$d_6$ δ: 2.32-2.38 (m, 4H), 2.45-2.47 (m, 2H), 2.70-2.73 (m, 2H), 3.34-3.38 (m, 2H), 3.53-3.55 (m, 4H), 3.62-3.64 (m, 2H), 4.20 (s, 2H), 6.56 (br s, 1H), 7.00-7.03 (m, 1H), 7.60-7.62 (m, 2H), 7.83-7.85 (m, 1H), 8.02-8.04 (m, 2H), 8.22-8.24 (m, 1H), 8.45 (s, 1H).

Example 34

7-(3-Chloropyridin-2-yl)-N$^4$-(4-(trifluoromethyl)phenyl)-5,6,7,8-tetrahydro-N$^2$N$^2$-dimethylpyrido[3,4-d]pyrimidine-2,4-diamine

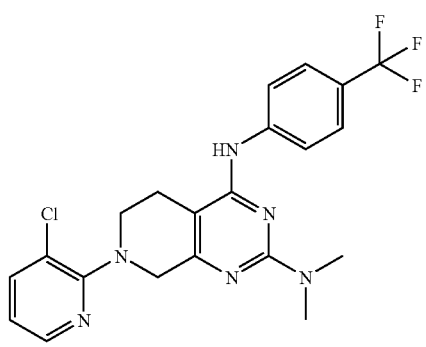

The title compound was prepared in a manner similar to the procedure given for Example 32 using the appropriate reagents and starting materials.

MS: M+H=448.7. $^1$H NMR DMSO-$d_6$ δ: 2.71 (t, J=5.6 Hz, 2H), 3.07 (s, 6H), 3.65 (t, J=5.6 Hz, 2H), 4.23 (s, 2H), 6.99-7.02 (m, 1H), 7.63-7.65 (m, 2H), 7.82-7.84 (m, 1H), 8.00-8.03 (m, 2H), 8.20-8.22 (m, 1H), 8.49 (s, 1H).

Example 35

7-(3-Chloropyridin-2-yl)-N-(4-(trifluoromethyl)phenyl)-5,6,7,8-tetrahydro-2-(methoxymethyl)pyrido[3,4-d]pyrimidin-4-amine

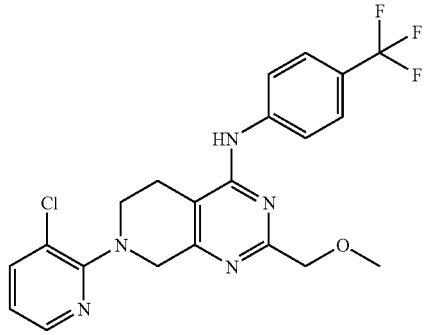

A. N-(4-(Trifluoromethyl)phenyl)-5,6,7,8-tetrahydro-2-(methoxymethyl)pyrido[3,4-d]pyrimidin-4-amine

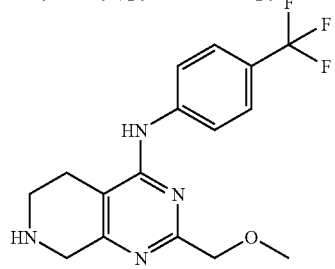

1-Chloroethyl chloroformate (543 mg, 3.8 mmol) was added dropwise to a mixture of 7-benzyl-N-(4-(trifluoromethyl)phenyl)-5,6,7,8-tetrahydro-2-(methoxymethyl)pyrido[3,4-d]pyrimidin-4-amine from Example 31 (820 mg, 1.9 mmol) and diisopropylethyl amine (490 mg, 3.8 mmol) in 1,2-dichloroethane (5 mL, anhydrous) at room temperature. After addition, the reaction mixture was stirred at 60° C. for 2 h under nitrogen. Solvent was removed in vacuo, residue was dissolved in methanol (10 mL) and was stirred at 60° C. for 1 hr. Solvent was removed in vacuo, residue was dissolved in ethyl acetate and was washed with saturated aqueous sodium bicarbonate, brine and dried over sodium sulfate. Solvent was removed in vacuo and light orange oily residue which was usd directly in the next step.

MS: M+H=339.0

B. 7-(3-Chloropyridin-2-yl)-N-(4-(trifluoromethyl)phenyl)-5,6,7,8-tetrahydro-2-(methoxymethyl)pyrido[3,4-d]pyrimidin-4-amine.

A mixture of diisopropylethylamine (490 mg, 3.8 mmol), N-(4-(trifluoromethyl)phenyl)-5,6,7,8-tetrahydro-2-(methoxymethyl)pyrido[3,4-d]pyrimidin-4-amine (~1.9 mmol) and 2,3-dichloropyridine (562 mg, 3.8 mmol) in dioxane (5 mL) and N,N-diethylacetamide (1.0 mL) was irradiated in microwave at 180° C. for 10 h. Solvent was removed in vacuo and the residue was purified by column chromatography. The product was obtained as a beige solid (102 mg).

MS: M+H=450.4. $^1$H NMR DMSO-$d_6$ δ: 2.85 (t, J=5.6 Hz, 2H), 3.38 (s, 3H), 3.70 (t, J=5.6 Hz, 2H), 4.37 (s, 2H), 4.39 (s, 2H), 7.02-7.05 (m, 1H), 7.66-7.68 (m, 2H), 7.85-7.87 (m, 1H), 8.02-8.07 (m, 2H), 8.23-8.24 (m, 1H), 8.82 (s, 1H).

Example 36

(2,3-Dihydro-benzo[1,4]dioxin-6-yl)-(7-m-tolyl-5,6,7,8-tetrahydro-pyrido[3,4-d]pyrimidin-4-yl)-amine

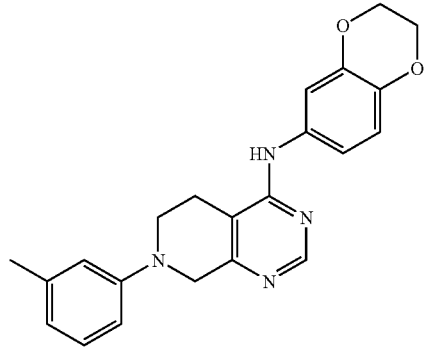

A. (2,3-Dihydro-benzo[1,4]dioxin-6-yl)-(5,6,7,8-tetrahydro-pyrido[3,4-d]pyrimidin-4-yl)-amine

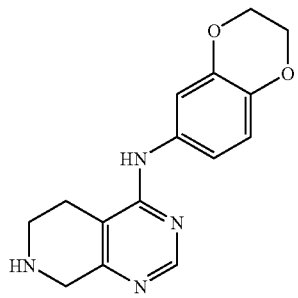

7-Benzyl-(2,3-Dihydro-benzo[1,4]dioxin-6-yl)-(5,6,7,8-tetrahydro-pyrido[3,4-d]pyrimidin-4-yl)-amine(700 mg, 1.8 mmol) was dissolved in methanol (25 mL) and palladium hydroxide was added (150 mg, 20% wt). The mixture was shaken on a Parr Shaker under H$_2$(g) atmosphere (60 PSI) for 24 hours. The mixture was filtered through celite and evaporated to give 480 mg of material as a white solid, which was used as such for the next step.

MS: M+H=285.

B. (2,3-Dihydro-benzo[1,4]dioxin-6-yl)-(7-m-tolyl-5,6,7,8-tetrahydro-pyrido[3,4-d]pyrimidin-4-yl)-amine To 2 ml of Dioxane was added 10 mol % of palladium (II)acetate (12 mg) and 20 mol % rac-BINAP (58 mg). After stirring for 3 hours, 3-bromotoluene was added (0.064 ml, 0.53 mmol), cesium carbonate (682 mg, 2.12 mmol), (2,3-Dihydro-benzo[1,4]dioxin-6-yl)-(5,6,7,8-tetrahydro-pyrido[3,4-d]pyrimidin-4-yl)-amine (150 mg, 0.53 mmol) and activated molecular sieves (340 mg). The mixture was sonicated for 10 minutes and heated at 160° C. for 3 hours in a sealed tube via microwave (Personal Chemistry Microwave (Smith Creator)). After completion, the mixture was filtered through celite, evaporated and purified by flash chromatography using a 0-100% gradient of ethyl acetate/hexanes to give the desired product as a white solid (15 mg).

M+H=375. $^1$H NMR DMSO-$d_6$ δ: 2.27(s, 3H); 2.70(t, J=5.7 Hz, 2H); 3.60(t, J=5.7 Hz, 2H); 4.19-4.25(m, 4H); 6.61(d, J=7.4 Hz, 1H); 6.79(d, J=8.8 Hz, 1H); 6.82-6.89(m, 2H); 7.05-7.15(m, 2H); 7.25(d, J=2.5 Hz, 1H); 8.35(s, 1H); 8.36(s, 1H).

Example 37

4-(4-(Trifluoromethyl)phenylamino)-7-(3-chloropyridin-2-yl)-5,6,7,8-tetrahydropyrido[3,4-d]pyrimidine-2-carbonitrile

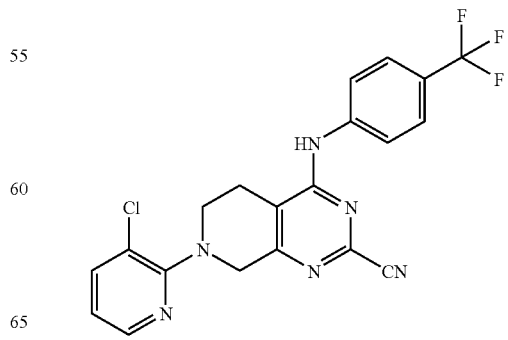

The title compound was prepared in a manner similar to the procedure given for Example 32 using the appropriate reagents and starting materials.

MS: M+H=430.5. $^1$H NMR DMSO-$d_6$ δ: 2.50 (t, J=5.2 Hz, 2H), 3.71 (t, J=5.2 Hz, 2H), 4.44 (s, 2H), 7.05-7.08 (m, 1H), 7.75-7.77 (m, 2H), 7.87-7.90 (m, 3H), 8.24-8.26 (m, 1H), 9.29 (s, 1H).

Example 38

7-Benzyl-5,6,7,8-tetrahydro-N-(quinolin-3-yl)pyrido[3,4-d]pyrimidin-4-amine

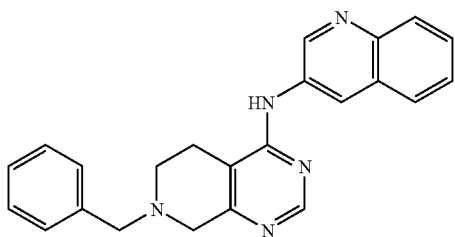

Sodium iodide (434 mg, 2.9 mmol) and hydriodic acid (0.4 mL, 47% aqueous solution) were added to a mixture of 7-benzyl-4-chloro-5,6,7,8-tetrahydropyrido[3,4-d]pyrimidine (500 mg, 1.93 mmol) and 3-aminoquinoline (418 mg, 2.9 mmol) in dioxane (4 mL) and the reaction solution was heated in a sealed tube via microwave at 150° C. for 20 min. The solvent was removed under reduced pressure. The residue was suspended in water, solid sodium carbonate was added to a pH>8, and the mixture was extracted with ethyl acetate. The organic layer was removed in vacuo and the residue was purified by column chromatography to yield the product as a beige solid (405 mg).

MS: M+H=368.0. $^1$H NMR DMSO-$d_6$ δ: 2.75-2.77 (m, 2H), 2.80-2.83 (m, 2H), 3.45 (s, 2H), 3.71 (s, 2H), 7.29-7.31 (m, 1H), 7.34-7.40 (m, 4H), 7.54-7.65 (m, 2H), 7.90-7.97 (m, 2H), 8.44 (s, 1H), 8.70 (d, J=2.0 Hz, 1H), 8.86 (s, 1H), 9.13 (d, J=2.0 Hz, 1H).

Example 39

7-(3-Chloropyridin-2-yl)-5,6,7,8-tetrahydro-N-phenethylpyrido[3,4-d]pyrimidin-4-amine

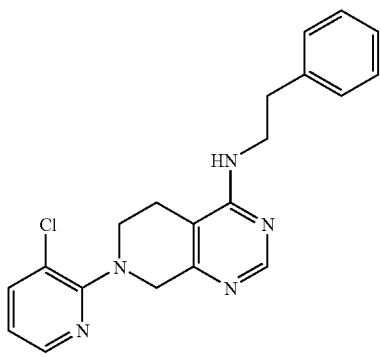

A mixture of 4-chloro-7-(3-chloropyridin-2-yl)-5,6,7,8-tetrahydropyrido[3,4-d]pyrimidine (0.025 g, 0.09 mmol) and 2-phenylethanamine (0.065 mL, 0.51 mmol)) in acetonitrile (1 mL) was heated in a sealed tube via microwave (Emrys Optimizer model, Personal Chemistry) to 180° C. for 10 min. The reaction mixture was cooled to r.t. and concentrated to dryness. The residue was purified by silica gel chromatography using a gradient of ethyl acetate:hexane (0-100%) to give the desired compound as a white solid (19 mg).

MS: M+H=366.

Example 40

N-(4-Chlorophenethyl)-7-(3-chloropyridin-2-yl)-5,6,7,8-tetrahydropyrido[3,4-d]pyrimidin-4-amine

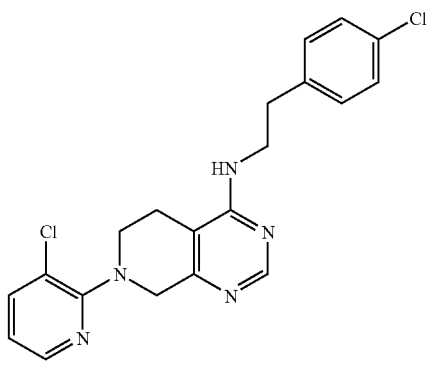

The title compound was prepared following the procedure described above for Example 39 and using the appropriate reagents and starting materials and heating the reaction mixture for 25 min.

MS: M+H=400.

Example 41

N-(4-Chlorobenzyl)-7-(3-chloropyridin-2-yl)-5,6,7,8-tetrahydropyrido[3,4-d]pyrimidin-4-amine

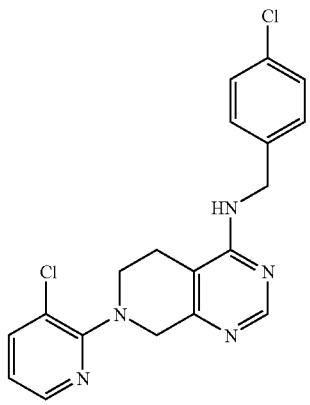

The title compound was prepared following the procedure described above for Example 39 and using the appropriate reagents and starting materials.

MS: M+H=386.

Example 42

N-(3,4-Dichlorophenyl)-7-(3-chloropyridin-2-yl)-5,6,7,8-tetrahydropyrido[3,4-d]pyrimidin-4-amine

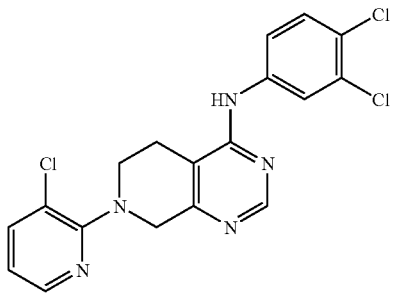

Method—The title compound was prepared following the procedure described above for Example 39 and adding hydroiodic acid (0.1 mL) and NaI (0.013 g, 0.09 mmol) to the reaction mixture and heating for 30 min.
MS: M+H=406.

Example 43

7-(3-Chloropyridin-2-yl)-N-(3-(trifluoromethyl)phenyl)-5,6,7,8-tetrahydropyrido[3,4-d]pyrimidin-4-amine

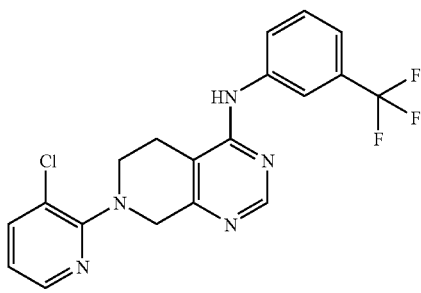

The title compound was prepared following the procedure described above for Example 39 and using the appropriate reagents and starting materials and heating the reaction mixture for 60 min.
MS: M+H=406.

Example 44

7-(Phenyl)-N-(4-(trifluoromethyl)phenyl)-5,6,7,8-tetrahydropyrido[3,4-d]pyrimidin-4-amine

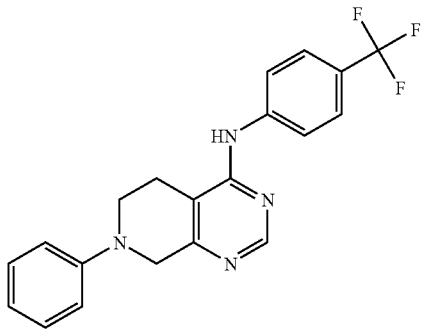

To 2 mL of Dioxane was added 10 mol % of palladium (II)acetate (12 mg) and 20 mol % rac-BINAP (58 mg). After stirring for 3 hours, bromobenzene was added (0.054 ml, 0.53 mmol), cesium carbonate (682 mg, 2.12 mmol), N-(4-(Trifluoromethyl)phenyl)-5,6,7,8-tetrahydropyrido[3,4-d]pyrimidin-4-amine (150 mg, 0.51 mmol) and activated molecular sieves (340 mg). The mixture was sonicated for 10 minutes and heated in a sealed tube via microwave at 160° C. for 3 hours in a Personal Chemistry Microwave (Smith Creator). After completion, the mixture was filtered through celite, evaporated and purified by flash chromatography over silica gel using a 0-100% gradient of ethyl acetate/hexanes to give the desired product as a white solid (36 mg).

M+H=371. $^1$H NMR (DMSO-d6): δ 2.82 (t, J=5.6 Hz, 2H); 3.64 (t, J=5.6 Hz, 2H); 4.27 (s, 2H); 6.76-6.84 (m, 1H); 7.04-7.11 (m, 2H); 7.21-7.29 (m, 2H); 7.67 (d, J=8.3 Hz, 2H); 7.98 (d, J=8.3 Hz, 2H); 8.52 (s, 1H); 8.85 (s, 1H).

Example 45

7-(o-Tolyl)-N-(4-(trifluoromethyl)phenyl)-5,6,7,8-tetrahydropyrido[3,4-d]pyrimidin-4-amine

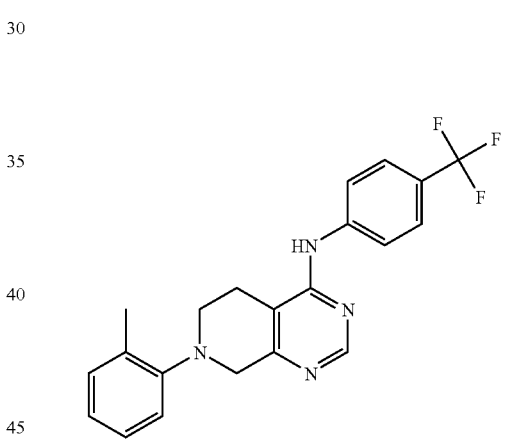

To 2 mL of dioxane was added 10 mol % of palladium (II)acetate (12 mg) and 20 mol % rac-BINAP (58 mg). After stirring for 3 hours, 2-bromotoluene (0.064 ml, 0.53 mmol), cesium carbonate (682 mg, 2.12 mmol), N-(4-(Trifluoromethyl)phenyl)-5,6,7,8-tetrahydropyrido[3,4-d]pyrimidin-4-amine (150 mg, 0.51 mmol) and activated molecular sieves (340 mg) were added. The mixture was sonicated for 10 minutes and heated in a sealed tube via microwave at 160° C. for 3 h in a Personal Chemistry Microwave (Smith Creator). After completion, the mixture was filtered through celite, evaporated and purified by flash chromatography over silica gel using a 0-100% gradient of ethyl acetate/hexanes to give the desired product as a white solid (16 mg).

M+H=385. $^1$H NMR (DMSO-d6): 2.30 (s, 3H); 2.84 (t, J=5.6 Hz, 2H); 3.24 (t, J=5.6 Hz, 2H); 3.99 (s, 2H); 6.98-7.04 (m, 1H); 7.11-7.24 (m, 3H); 7.68 (d, J=8.6 Hz, 2H); 8.00 (d, J=8.6 Hz, 2H); 8.51 (s, 1H); 8.83 (s, 1H).

Example 46

7-(m-Tolyl)-N-(4-(trifluoromethyl)phenyl)-5,6,7,8-tetrahydropyrido[3,4-d]pyrimidin-4-amine

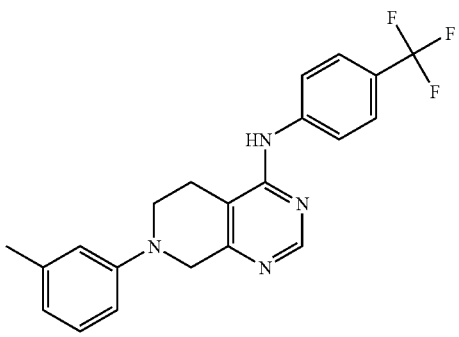

To 2 mL of dioxane was added 10 mol % of palladium (II)acetate (12 mg) and 20 mol % rac-BINAP (58 mg). After stirring for 3 hours, 3-bromotoluene (0.064 ml, 0.53 mmol), cesium carbonate (682 mg, 2.12 mmol), N-(4-(Trifluoromethyl)phenyl)-5,6,7,8-tetrahydropyrido[3,4-d]pyrimidin-4-amine (150 mg, 0.51 mmol) and activated molecular sieves (340 mg) were added. The mixture was sonicated for 10 minutes and heated in a sealed tube via microwave at 160° C. for 3 hours in a Personal Chemistry Microwave (Smith Creator). After completion, the mixture was filtered through celite, evaporated and purified by flash chromatography over silica gel using a 0-100% gradient of ethyl acetate/hexanes to give the desired product as a white solid (34 mg).

M+H=385. $^1$H NMR (DMSO-d6): δ 2.27 (s, 3H); 2.80 (t, J=5.6 Hz, 2H); 3.58 (t, J=5.8 Hz, 2H); 4.21 (s, 2H); 6.97 (d, J=8.6 Hz, 2H); 7.07 (d, J=8.6 Hz, 2H); 7.67 (d, J=8.7 Hz, 2H); 7.98 (d, J=8.7 Hz, 2H); 8.51 (s, 1H); 8.83 (s, 1H).

Example 47

7-(p-Tolyl)-N-(4-(trifluoromethyl)phenyl)-5,6,7,8-tetrahydropyrido[3,4-d]pyrimidin-4-amine

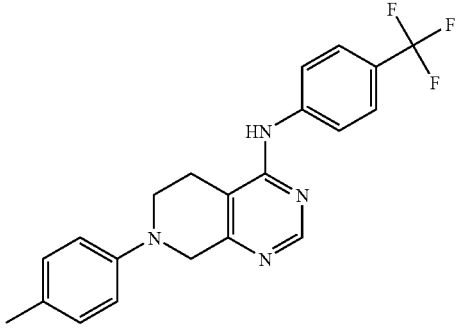

To 2 mL of dioxane was added 10 mol % of palladium (II)acetate (12 mg) and 20 mol % rac-BINAP (58 mg). After stirring for 3 hours, 4-bromotoluene (90 mg, 0.53 mmol), cesium carbonate (682 mg, 2.12 mmol), N-(4-(Trifluoromethyl)phenyl)-5,6,7,8-tetrahydropyrido[3,4-d]pyrimidin-4-amine (150 mg, 0.51 mmol) and activated molecular sieves (340 mg) were added. The mixture was sonicated for 10 minutes and heated in a sealed tube via microwave at 160° C. for 3 hours in a Personal Chemistry Microwave (Smith Creator). After completion, the mixture was filtered through celite, evaporated and purified by flash chromatography over silica gel using a 0-100% gradient of ethyl acetate/hexanes to give the desired product as a white solid (34 mg).

M+H=385. $^1$H NMR (DMSO-d6): δ 2.21 (s, 3H); 2.80 (t, J=5.6 Hz, 2H); 3.58 (t, J=5.8 Hz, 2H); 4.21 (s, 2H); 6.97 (d, J=8.6 Hz, 2H); 7.07 (d, J=8.6 Hz, 2H); 7.67 (d, J=8.7 Hz, 2H); 7.98 (d, J=8.7 Hz, 2H); 8.51 (s, 1H); 8.83 (s, 1H).

Example 48

7-(3-Chloropyridin-2-yl)-2-ethoxy-N-(4-(trifluoromethyl)phenyl)-5,6,7,8-tetrahydropyrido[3,4-d]pyrimidin-4-amine

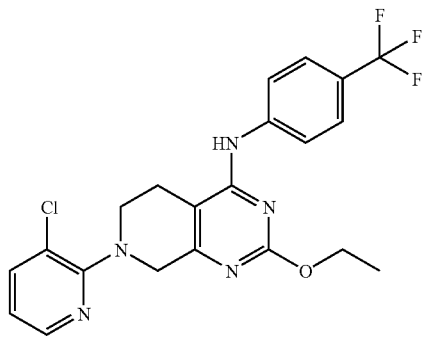

The title compound was prepared according to the procedure given for Example 27.

MS: M+H=450. $^1$H NMR DMSO-d$_6$ δ: 1.28-1.32 (m, 3H), 2.77 (t, J=5.6 Hz, 2H), 3.67 (t, J=5.6 Hz, 2H), 4.24-2.32 (m, 4H), 7.01-7.05 (m, 1H), 7.68-7.70 (m, 2H), 7.85-7.87 (m, 1H), 7.98-7.80 (m, 2H), 8.23-8.24 (m, 1H), 8.80 (s, 1H).

Example 49

N-(6-tert-Butylpyridin-3-yl)-7-(3-chloropyridin-2-yl)-5,6,7,8-tetrahydropyrido[3,4-d]pyrimidin-4-amine

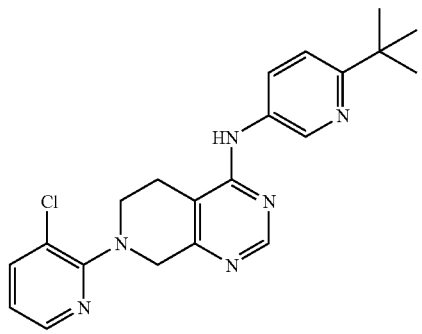

The title compound was prepared following the procedure described above for Example 39 and using the appropriate reagents and starting materials and heating the reaction mixture for 60 min.

MS: M+H=395. $^1$H NMR DMSO-d$_6$ δ 1.31 (s, 9H); 2.81 (t, J=5.5 Hz, 2H); 3.69 (t, J=5.8 Hz, 2H); 4.36 (s, 2H); 7.04

(dd, J=4.6 Hz, 7.6 Hz, 1H); 7.39 (dd, J=0.7 Hz, 8.6 Hz, 1H); 7.86 (dd, J=1.6 Hz, 7.6 Hz, 1H); 7.98 (dd, J=2.8 Hz, 8.8 Hz, 1H); 8.25 (dd, J=1.6 Hz, 4.6 Hz, 1H); 8.40 (s, 1H); 8.64 (s, 1H); 8.73 (dd, J=0.6 Hz, 2.5 Hz, 1H).

Example 50

N-(3-(Trifluoromethyl)phenethyl)-7-(3-chloropyridin-2-yl)-5,6,7,8-tetrahydropyrido[3,4-d]pyrimidin-4-amine

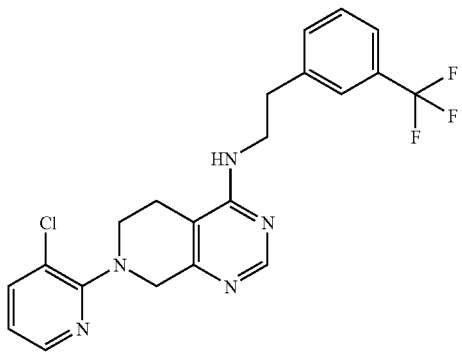

The title compound was prepared following the procedure described above for Example 39 and using the appropriate reagents and starting materials and heating the reaction mixture for 60 min.

MS: M+H=434.

Example 51

7-(3-Chloropyridin-2-yl)-5,6,7,8-tetrahydro-N-(3-phenylpropyl)pyrido[3,4-d]pyrimidin-4-amine

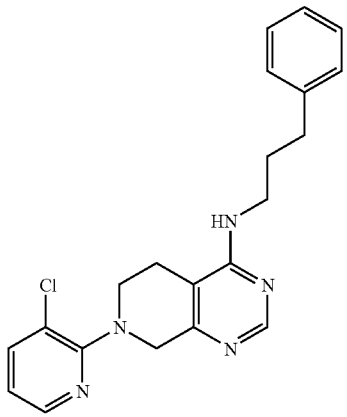

The title compound was prepared following the procedure described above for Example 39 and using the appropriate reagents and starting materials and heating the reaction mixture for 60 min.

MS: M+H=380.

Example 52

7-(3-Chloropyridin-2-yl)-5,6,7,8-tetrahydro-N-(2-phenoxyethyl)pyrido[3,4-d]pyrimidin-4-amine

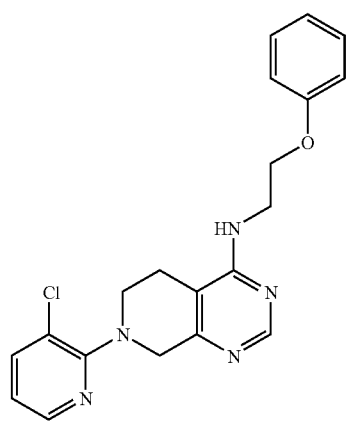

The title compound was prepared following the procedure described above for Example 39 and using the appropriate reagents and starting materials and heating the reaction mixture for 60 min.

MS: M+H=382.

Example 53

7-(Cyclohexylmethyl)-5,6,7,8-tetrahydro-N-(quinolin-3-yl)pyrido[3,4-d]pyrimidin-4-amine

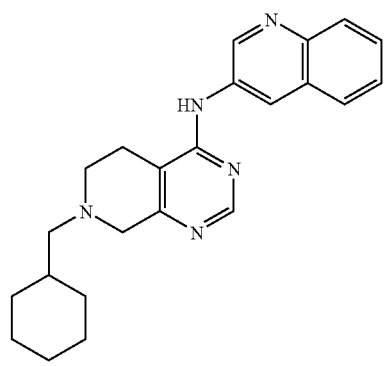

Diisopropylethyl amine (258 mg, 2 mmol) was added to a mixture of 5,6,7,8-tetrahydro-N-(quinolin-3-yl)pyrido[3,4-d]pyrimidin-4-amine (55 mg, 0.2 mmol) and (bromomethyl)cyclohexane (177 mg, 1 mmol) in ethanol (2 mL) and stirred at 80° C. for 48 h. Solvent was removed in vacuo, and the residue was purified by column chromatography to yield the product as a light orange powder (7 mg).

MS: M+H=374.1. $^1$H NMR DMSO-$d_6$ δ: 0.84-0.99 (m, 2H), 1.07-1.29 (m, 6H), 1.58-1.69 (m, 5H), 1.75-1.78 (m, 2H), 2.29-2.31 (m, 2H), 3.43 (s, 2H), 7.54-7.65 (m, 2H), 7.91-7.97 (m, 2H), 8.46 (s, 1H), 8.69 (d, J=2.4 Hz, 1H), 8.85 (s, 1H), 9.12 (d, J=2.4 Hz, 1H).

Example 54

5,6,7,8-Tetrahydro-7-phenethyl-N-(quinolin-3-yl)pyrido[3,4-d]pyrimidin-4-amine

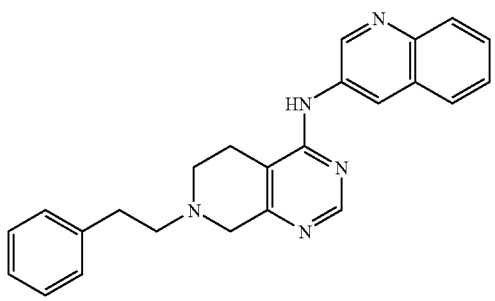

The title compound was prepared following the procedure described above for Example 53 and using the appropriate reagents and starting materials.

MS: M+H=382.2. $^1$H NMR DMSO-$d_6$ δ: 2.73-2.78 (m, 4H), 2.85-2.88 (m, 4H), 3.57 (s, 2H), 7.19-7.21 (m, 1H), 7.27-7.30 (m, 4H), 7.55-7.58 (m, 1H), 7.61-7.66 (m, 1H), 7.90-7.97 (m, 2H), 8.47 (s, 1H), 8.71 (d, J=2.2 Hz, 1H), 8.87 (s, 1H), 9.13 (d, J=2.2 Hz, 1H).

Example 55

5,6,7,8-tetrahydro-7-(3-phenylpropyl)-N-(quinolin-3-yl)pyrido[3,4-d]pyrimidin-4-amine

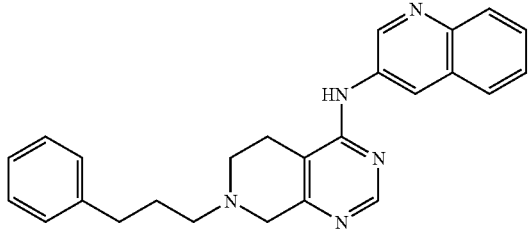

The title compound was prepared following the procedure described above for Example 53 and using the appropriate reagents and starting materials.

MS: M+H=396.2. $^1$H NMR DMSO-$d_6$ δ: 1.83-1.88 (m, 2H), 2.49-2.53 (m, 2H), 2.62-2.66 (m, 2H), 2.76-2.77 (m, 4H), 3.48 (s, 2H), 7.16-7.31 (m, 5H), 7.54-7.65 (m, 2H), 7.90-7.97 (m, 2H), 8.46 (s, 1H), 8.71 (d, J=2.4 Hz, 1H), 8.87 (s, 1H), 9.13 (d, J=2.4 Hz, 1H).

Example 56

2-(4-(7-(3-Chloropyridin-2-yl)-5,6,7,8-tetrahydropyrido[3,4-d]pyrimidin-4-ylamino)phenyl)-2-methylpropanenitrile

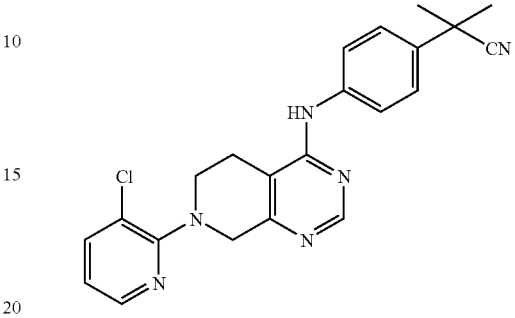

A mixture of 4-chloro-7-(3-chloropyridin-2-yl)-5,6,7,8-tetrahydropyrido[3,4-d]pyrimidine (40 mg, 0.14 mmol), 2-(4-aminophenyl)-2-methylpropanenitrile (100 mg, 0.63 mmol) (prepared according to the reference: Axton, C. A. et al, *J. Chem. Soc. Perkin Trans.* 1, 1992, 2203.), and acetonitrile (0.5 mL) was heated in a sealed tube via microwave at 180° C. for 60 min. The solvent was removed in vacuo and the residue was purified by chromatography to give a light yellow solid (50 mg).

MS: M+H=405. $^1$H NMR (DMSO-d6) δ 8.59 (s, 1H), 8.42 (s, 1H), 8.24 (dd, J=1H, J=4.8, 1.6 Hz), 7.86 (dd, J=1H, J=8.0, 1.6 Hz), 7.74 (dd, J=2H, J=6.8, 2.0 Hz), 7.46 (dd, J=2H, J=6.8, 2.0 Hz), 7.04 (dd, J=1H, J=8.0, 4.4 Hz), 4.36 (s, 2H), 3.68 (t, J=2H, J=5.6 Hz), 2.81 (t, J=2H, J=5.6 Hz), 1.68 (s, 6H).

Example 57

4-(4-(Trifluoromethyl)phenylamino)-7-(3-chloropyridin-2-yl)-5,6,7,8-tetrahydropyrido[3,4-d]pyrimidin-2-ol

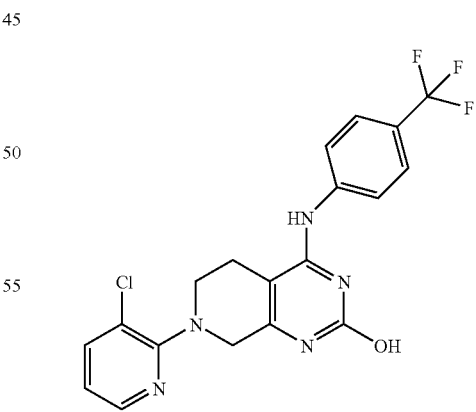

Sodium hydride (40 mg, 1 mmol, 60%) was added to a solution of 2-(methansulphonyl)ethanol (124 mg, 1 mmol) in DMF (5 mL, anhydrous) and stirred at room temperature for 10 min. This mixture (0.6 mL) was added to a solution of 7-(3-chloropyridin-2-yl)-N-(4-(trifluoromethyl)phenyl)-5,6,7,8-tetrahydro-2-(methylsulfonyl)pyrido[3,4-d]pyrimidin-4-amine (50 mg, 0.1 mmol) in DMF (1 mL) and was heated in a sealed tube via microwave at 150° C. for 20 min. Solvent was removed in vacuo and the residue was purified by column chromatography to yield the product as a light brown solid (5 mg).

MS: M+H=422.4. ¹H NMR DMSO-$d_6$ δ: 2.62 (t, J=5.6 Hz, 2H), 3.62 (t, J=5.6 Hz, 2H), 4.19 (s, 2H), 7.04-7.07 (m, 1H), 7.67-7.71 (m, 2H), 7.86-7.88 (m, 1H), 8.03-8.05 (m, 2H), 8.23-8.25 (m, 1H), 8.71 (s, 1H), 11.01 (s, 1H).

Example 58

7-(7-(3-Chloropyridin-2-yl)-5,6,7,8-tetrahydropyrido [3,4-d]pyrimidin-4-ylamino)-4,4-dimethylisoquinoline-1,3(2H,4H)-dione

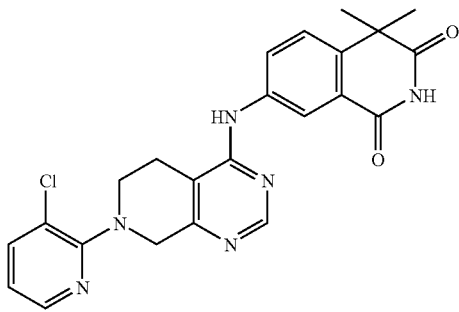

A mixture of 4-chloro-7-(3-chloropyridin-2-yl)-5,6,7,8-tetrahydropyrido[3,4-d]pyrimidine (7.5 mg), 7-amino-4,4-dimethylisoquinoline-1,3)2H,4H)-dione (30 mg) (prepared according to the reference: Snow, R. J. et al, *J. Med. Chem.* 2002, 45, 3394), and acetonitrile (0.5 mL) was heated in a sealed tube via microwave at 180° C. for 60 min. The solvent was removed and the residue was purified by chromatography to give an off-white solid (6 mg).

MS: M+H=449 ¹H NMR (DMSO-d6) δ 11.31 (s, 1H), 8.77 (s, 1H), 8.46 (s, 1H), 8.39 (s, 1H), 8.25 (d, J=1H, J=4.8 Hz), 8.10 (d, J=8.0 Hz, 1H), 7.87 (d, J=8.0 Hz, 1H), 7.64 (d, J=8.0 Hz, 1H), 7.04 (dd, J=8.0, 4.8 Hz, 1H), 4.37 (s, 2H), 3.70 (s, 2H), 2.84 (s, 2H), 1.52 (s, 6H).

Example 59

7-(3-chloropyridin-2-yl)-5,6,7,8-tetrahydro-N-(1,2,3, 4-tetrahydro-4,4-dimethylquinolin-7-yl)pyrido[3,4-d]pyrimidin-4-amine

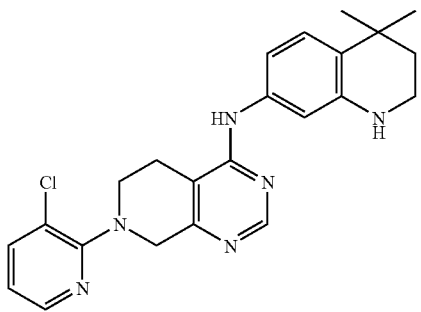

A. 1-(3,4-Dihydro-4,4-dimethyl-7-nitroquinolin-1)2H)-yl) ethanone:

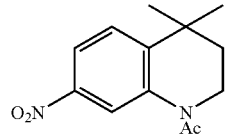

To a stirred solution of 1,2,3,4-tetrahydro-4,4-dimethyl-7-nitroquinoline (Rami et al, WO 03/068749) (500 mg, 2.42 mmol), DMAP (5 mg) in pyridine (2 µL) was added acetic anhydride (0.46 mL, 4.9 mmol). The mixture was stirred at room temperature for 10 h, and then heated at 60° C. for 5 h. After cooling, the mixture was treated with water and extracted with EtOAc. The combined organic layers were washed with saturated aqueous. NaHCO₃, 1N HCl, brine, dried, and evaporated. The residue was purified by flash chromatography over silica gel to give a light yellow solid (550 mg).

MS: M+H=249.

B. 1-(7-Amino-3,4-dihydro-4,4-dimethylquinolin-1(2H)-yl) ethanone:

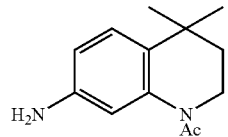

A mixture of the nitro compound (530 mg, 2.14 mmol), 10% Pd—C (30 mg), MeOH (10 mL) was stirred at H₂ atmosphere (1 atm) for 2 h. The mixture was filtered and the filtrate was evaporated under reduced pressure. The residue was purified by flash chromatography over silica gel to give a light yellow solid (380 mg).

MS: M+H=219.

C. 1-(7-(7-(3-Chloropyridin-2-yl)-5,6,7,8-tetrahydropyrido [3,4-d]pyrimidin-4-ylamino)-3,4-dihydro-4,4-dimethylquinolin-1(2H)-yl)ethanone:

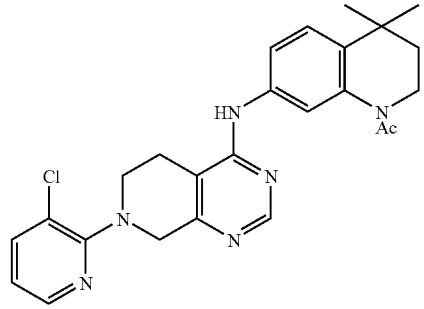

A mixture of 4-chloro-7-(3-chloropyridin-2-yl)-5,6,7,8-tetrahydropyrido[3,4-d]pyrimidine (20 mg, 0.071 mmol), 1-(7-amino-3,4-dihydro-4,4-dimethylquinolin-[(2H)-yl) ethanone (40 mg, 0.18 mmol), and acetonitrile (0.5 mL) was heated in a sealed tube via microwave at 180° C. for 60 min. The mixture was diluted with EtOAc (50 mL), washed with aqueous sodium bicarbonate, brine, dried, and concentrated.

The residue was purified by flash chromatography over silica gel to give the product (15 mg).

MS: M+H=463.

D. 7-(3-Chloropyridin-2-yl)-5,6,7,8-tetrahydro-N-(1,2,3,4-tetrahydro-4,4-dimethylquinolin-7-yl)pyrido[3,4-d]pyrimidin-4-amine A mixture of 1-(7-(7-(3-chloropyridin-2-yl)-5,6,7,8-tetrahydropyrido[3,4-d]pyrimidin-4-ylamino)-3,4-dihydro-4,4-dimethylquinolin-1(2H)-yl)ethanone (10 mg), acetonitrile (2 mL), and 5 N HCl (0.5 mL) was heated at 90° C. for 3 h. The cooled solution was treated with saturated aqueous sodium bicarbonate and extracted with EtOAc (15 mL×3). The combined organic layers were washed with brine, dried, and evaporated. The residue was purified by peparative TLC to give an off-white solid (7 mg).

MS: M+H=421. $^1$H NMR (DMSO-d6) δ 8.33 (s, 1H), 8.24 (dd, J=4.8, 1.6 Hz, 1H), 8.14 (s, 1H), 7.85 (dd, J=8.0, 1.6 Hz, 1H), 7.03 (dd, J=7.6, 4.8 Hz, 1H), 7.01 (d, J=8.0 Hz, 1H), 6.78 (d, J=1.6 Hz, 1H), 6.68 (dd, J=8.4, 2.0 Hz, 1H), 5.70 (s, 1H), 4.32 (s, 2H), 3.66 (t, J=5.6 Hz, 2H), 3.17 (m, 2H), 2.75 (t, J=5.6 Hz, 2H), 1.60 (t, J=5.6 Hz, 2H), 1.19 (s, 6H).

Example 60

7-(3-Chloropyridin-2-yl)-5,6,7,8-tetrahydro-N-(1,2,3,4-tetrahydro-1,4,4-trimethylquinolin-7-yl)pyrido[3,4-d]pyrimidin-4-amine

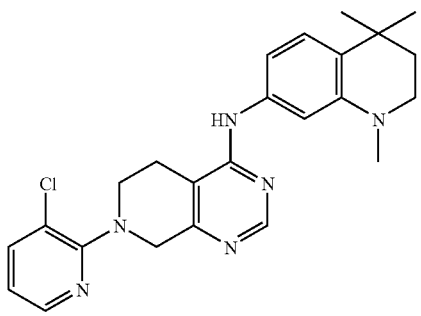

A mixture of the chloride (15 mg, 0.053 mmol), 1,2,3,4-tetrahydro-1,4,4-trimethylquinolin-7-amine (30 mg, 0.16 mmol), and acetonitrile (0.5 mL) was heated with microwave at 180° C. for 60 min. The mixture was diluted with EtOAc (50 mL), washed with aq. NaHCO$_3$, brine, dried, and concentrated. The residue was purified by peparative TLC to give the product as an off-white foam.

MS: M+H=435. $^1$H NMR (DMSO-d6) δ 8.35 (s, 1H), 8.24 (dd, J=4.8, 1.6 Hz, 1H), 8.21 (s, 1H), 7.85 (dd, J=7.6, 1.6 Hz, 1H), 7.07 (d, J=8.4 Hz, 1H), 7.03 (dd, J=7.6, 4.8 Hz, 1H), 6.99 (dd, J=8.4, 2.4 Hz, 1H), 6.84 (d, J=1.6 Hz, 1H), 4.33 (s, 2H), 3.67 (t, J=5.6 Hz, 2H), 3.18 (t, J=6.0 Hz, 2H), 2.82 (s, 3H), 2.77 (t, J=5.6 Hz, 2H), 1.70 (t, J=5.6 Hz, 2H), 1.22 (s, 6H).

Example 61

1-(7-(7-(3-chloropyridin-2-yl)-5,6,7,8-tetrahydropyrido[3,4-d]pyrimidin-4-ylamino)-3,4-dihydro-4,4-dimethylisoquinolin-2)1H)-yl)ethanone

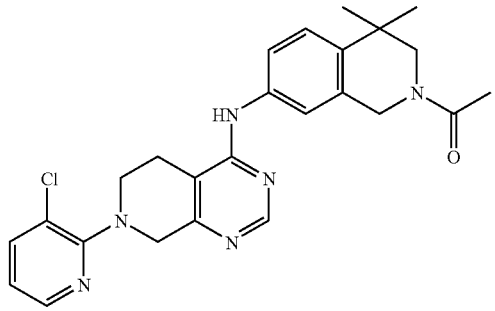

A. 1,2,3,4-Tetrahydro-4,4-dimethylisoquinolin-7-amine:

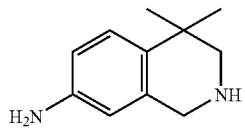

To a stirred mixture of LiAlH$_4$ (800 mg, 21 mmol) and anhydrous THF (30 mL) was added at 0° C. a solution of 7-amino-4,4-dimethylisoquinoline-1,3)2H,4H)-dione (500 mg, 2.5 mmol) in THF (5 mL). The mixture was stirred at room temperature under N$_2$ for 24 h, and then carefully treated with wet THF, 10% aq. NaOH, and filtered through Celite. The filtrate was concentrated and the residue was dissolved in EtOAc (150 mL). The organic phase was washed with brine, dried (Na$_2$SO$_4$), and evaporated. The residue was purified by flash chromatography over silica gel to give the title compound (270 mg).

MS: M+H=177.

B. 1-(7-Amino-3,4-dihydro-4,4-dimethylisoquinolin-2)1H)-yl)ethanone:

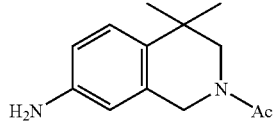

To a stirred solution of 1,2,3,4-tetrahydro-4,4-dimethylisoquinolin-7-amine (200 mg, 1.14 mmol) and Et$_3$N (0.12 mL) in CH$_2$Cl$_2$ (10 mL) at −15° C. was added a solution of acetic anhydride (70 μL) in CH$_2$Cl$_2$ (1 mL). The mixture was stirred at −15° C. for 30 min, and then slowly warmed to room temperature and stirred overnight. The mixture was diluted with CH$_2$Cl$_2$ (50 mL), washed with sat. aq. NaHCO$_3$, brine, dried, and concentrated. The residue was purified by chromatography to give the product as a foam.

MS: M+H=219. ¹H NMR (DMSO-d6) δ 7.00 (m, 1H), 6.43 (m, 1H), 6.26 (s, 1H), 4.88 and 4.90 (s, 2H), 4.51 and 4.45 (s, 2H), 3.38 and 3.37 (s, 2H), 2.09 and 2.05 (s, 3H), 1.16 and 1.10 (s, 6H).

C. 1-(7-(7-(3-Chloropyridin-2-yl)-5,6,7,8-tetrahydropyrido[3,4-d]pyrimidin-4-ylamino)-3,4-dihydro-4,4-dimethylisoquinolin-2)1H)-yl)ethanone A mixture of the chloride (35 mg, 0.12 mmol), 1-(7-amino-3,4-dihydro-4,4-dimethylisoquinolin-2)1H)-yl)ethanone (80 mg, 0.37 mmol), and acetonitrile (1.5 mL) was heated with microwave at 180° C. for 60 min. The mixture was treated with aq. Na₂CO₃ solution, and extracted with EtOAc (30 mL×3). The combined organic layers were washed with brine, dried, and evaporated. The residue was purified by TLC to give the product as a light yellow solid (18 mg).

MS: M+H=463. ¹H NMR (DMSO-d6) δ 8.45 and 8.44 (s, 1H), 8.40 and 8.39 (s, 1H), 8.24 (m, 1H), 7.88-7.84 (m, 1H), 7.53-7.43 (m, 2H), 7.33 (m, 1H), 7.04 (m, 1H), 4.67 and 4.61 (s, 2H), 4.34 (s, 2H), 3.68 (t, J=5.6 Hz, 2H), 3.47 (s, 2H), 2.79 (m, 2H), 2.13 and 2.09 (s, 3H), 1.25 and 1.19 (s, 6H).

Example 62

7-(3-chloropyridin-2-yl)-5,6,7,8-tetrahydro-N-(1,2,3,4-tetrahydro-4,4-dimethylisoquinolin-7-yl)pyrido[3,4-d]pyrimidin-4-amine

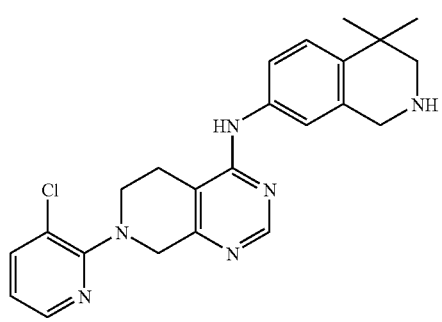

A mixture of 1-(7-(7-(3-chloropyridin-2-yl)-5,6,7,8-tetrahydropyrido[3,4-d]pyrimidin-4-ylamino)-3,4-dihydro-4,4-dimethylisoquinolin-2)1H)-yl)ethanone (10 mg), acetonitrile (2 mL), and 5 N HCl (0.5 mL) was heated overnight at 90° C. The cooled solution was treated with aq. Na₂CO₃, extracted with EtOAc (15 mL×3). The combined organic layers were washed with brine, dried, and evaporated. The residue was purified by preparative TLC to give a light yellow solid (5 mg).

MS: M+H=421. ¹H NMR (DMSO-d6) δ 8.42-8.36 (m, 2H), 8.24 (dd, J=4.4, 1.6 Hz, 1H), 7.86 (dd, J=8.0, 1.6 Hz, 1H), 7.45 (m, 1H), 7.32 (m, 2H), 7.03 (m, 1H), 4.34 (s, 2H), 3.92 and 3.63 (s, 2H), 3.67 (t, J=5.6 Hz, 2H), 2.82 and 2.57 (s, 2H), 2.78 (t, J=5.6 Hz, 2H), 1.26 and 1.24 (s, 6H).

Example 63

N-(4-(Trifluoromethyl)phenyl)-5,6,7,8-tetrahydro-7-(3-(methylsulfonyl)pyridin-2-yl)-2-(methylthio)pyrido[3,4-d]pyrimidin-4-amine

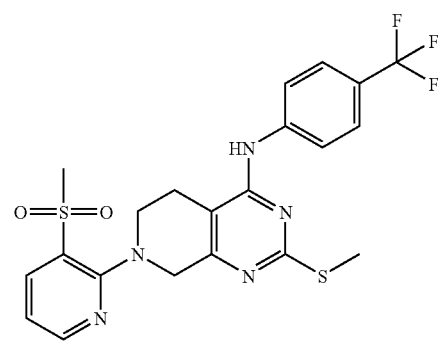

N-(4-(Trifluoromethyl)phenyl)-5,6,7,8-tetrahydro-2-(methylthio)pyrido[3,4-d]pyrimidin-4-amine (320 mg, 0.00089 mol) and 2-chloro-3-(methylsulfonyl)pyridine (200.0 mg, 0.0009915 mol) were dissolved in dioxane (5 mL) and DMA (0.5 mL), N,N-diisopropylethylamine (0.17 g, 0.0013 mol) was added and the mixture was heated in a sealed tube via microwave at 150° C. for 30 min. Solvent was removed and the residue was purified by flash chromatography over silica gel to obtain the product as a white solid (230 mg).

MS: M+H=496.4 ¹H NMR DMSO-d₆ δ: 2.46 (s, 3H), 2.50 (s, 3H), 2.82 (t, J=5.2 Hz, 2H), 3.56 (t, J=5.6 Hz, 2H), 4.30 (s, 2H), 7.42-7.44 (m, 1H), 7.69 (d, J=8.4 Hz, 2H), 7.98 (d, J=8.4 Hz, 2H), 8.33-8.35 (m, 1H), 8.65-8.67 (m, 1H), 8.91 (s, 1H).

Example 64

2-Ethoxy-N-(4-(trifluoromethyl)phenyl)-5,6,7,8-tetrahydro-7-(3-(methylsulfonyl)pyridin-2-yl)pyrido[3,4-d]pyrimidin-4-amine

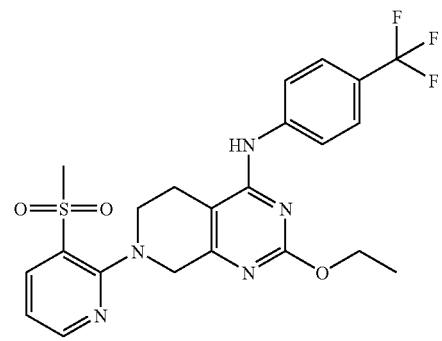

A. N-(4-(Trifluoromethyl)phenyl)-5,6,7,8-tetrahydro-2-(methylsulfonyl)-7-(3-(methylsulfonyl)pyridin-2-yl)pyrido[3,4-d]pyrimidin-4-amine

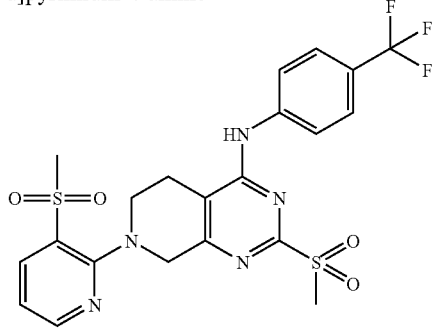

N-(4-(Trifluoromethyl)phenyl)-5,6,7,8-tetrahydro-7-(3-(methylsulfonyl)pyridin-2-yl)-2-(methylthio)pyrido[3,4-d]pyrimidin-4-amine (210 mg, 0.4 mmol) was dissolved in EtOH (8 mL) and MeOH (5 mL), m-CPBA (300 mg, 1.2 mmol) was added and stirred at room temperature overnight. Solid thus formed was filtered and dried under vacuum to give the as a white solid (102 mg).
MS: M+H=528.6

B. 2-Ethoxy-N-(4-(trifluoromethyl)phenyl)-5,6,7,8-tetrahydro-7-(3-(methylsulfonyl)pyridin-2-yl)pyrido[3,4-d]pyrimidin-4-amine N-(4-(Trifluoromethyl)phenyl)-5,6,7,8-tetrahydro-2-(methylsulfonyl)-7-(3-(methylsulfonyl)pyridin-2-yl)pyrido[3,4-d]pyrimidin-4-amine (150 mg, 0.27 mmol) was suspended in dioxane (5.0 mL) and ethanol (2.0 mL), sodium ethoxide (20 mg, 0.28 mmol) was added and the mixture was stirred at at 80° C. for 2 hrs. Solvent was removed and the residue was purified by flash chromatography over silica gel and then by preparative TLC to obtain the product as a white solid (102 mg).
MS: M+H=494.4 $^1$H NMR DMSO-d$_6$ δ: 1.30 (t, J=7.2 Hz, 3H), 2.50 (s, 3H), 2.81 (t, J=5.6 Hz, 2H), 3.56 (t, J=5.6 Hz, 2H), 4.24-4.29 (m, 4H), 7.41-7.44 (m, 1H), 7.69 (d, J=8.4 Hz, 2H), 8.01 (d, J=8.4 Hz, 2H), 8.33-8.35 (m, 1H), 8.65-8.66 (m, 1H), 8.85 (s, 1H).

Example 65

7-(3-Chloropyridin-2-yl)-5,6,7,8-tetrahydro-N-(3,4-dihydro-4-methyl-2H-benzo[b][1,4]oxazin-7-yl)pyrido[3,4-d]pyrimidin-4-amine

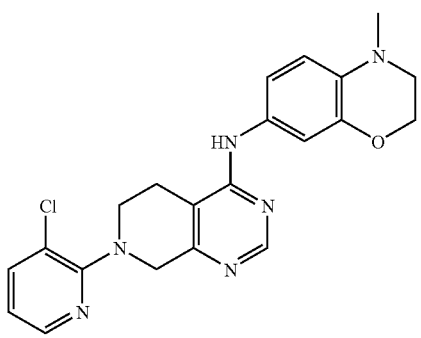

4-Chloro-7-(3-chloropyridin-2-yl)-5,6,7,8-tetrahydropyrido[3,4-d]pyrimidine (112 mg, 0.36 mmol) and 3,4-dihydro-4-methyl-2H-benzo[b][1,4]oxazin-7-amine (130 mg, 0.72 mmol) were dissolved in CH$_3$CN (3 mL), Sodium iodide (10 mg, 0.06 mmol) was added and the reaction was heated via microwave at 180° C. for 40 minutes. Solvent was removed and the residue was purified by preparative TLC to obtain the product as a beige foam (24 mg).
MS: M+H=409.4 $^1$H NMR DMSO-d$_6$ δ: 2.73 (t, J=5.6 Hz, 2H), 2.80 (s, 3H), 3.18 (t, J=4.8 Hz, 2H), 3.66 (t, J=6.0 Hz, 2H), 4.24 (t, J=4.8 Hz, 2H), 4.31 (s, 2H), 6.66 (d, J=8.4 Hz, 1H), 7.00-7.06 (m, 3H), 7.84-7.86 (m, 1H), 8.22-8.25 (m, 2H), 8.32 (s, 1H).

Example 66

Methyl 2-(4-(4-(trifluoromethyl)phenylamino)-7-(3-chloropyridin-2-yl)-5,6,7,8-tetrahydropyrido[3,4-d]pyrimidin-2-yloxy)acetate

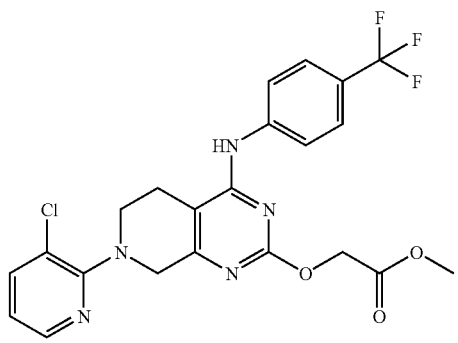

Methyl glycolate (31 mg, 0.33 mmol) was dissolved in DMF (dry), NaH (8 mg, 0.31 mmol) was added and stirred at room temperature under an atmosphere of Nitrogen for 30 min. 7-(3-Chloropyridin-2-yl)-N-(4-(trifluoromethyl)phenyl)-5,6,7,8-tetrahydro-2-(methylsulfonyl)pyrido[3,4-d]pyrimidin-4-amine (120.0 mg, 0.22 mol) (in 4 mL DMF, dry) was added to the above mixture. The reaction was heated via microwave at 180° C. for 15 minutes. Solvent was removed and the residue was purified by flash chromatography over silica gel to obtain the product as a white solid (25 mg).
MS: M+H=494.4 $^1$H NMR (DMSO-d$_6$) δ: 2.78 (t, J=5.6 Hz, 2H), 3.59 (s, 3H), 3.37 (t, J=5.6 Hz, 2H), 4.29 (s, 2H), 4.84 (s, 2H), 7.02-7.05 (m, 1H), 7.66 (d, J=8.4 Hz, 2H), 7.85-7.90 (m, 3H), 8.23-8.25 (m, 1H), 8.90 (s, 1H).

Example 67

6-(7-(3-Chloropyridin-2-yl)-5,6,7,8-tetrahydropyrido[3,4-d]pyrimidin-4-ylamino)-3,3-dimethylindolin-2-one

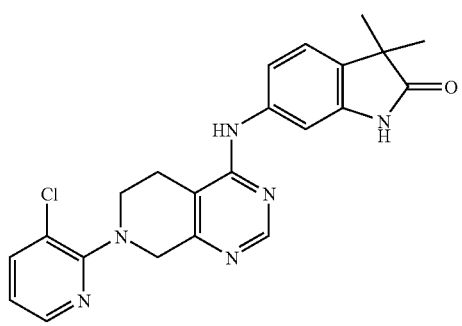

113

A. 3,3-Dimethyl-6-nitroindolin-2-one

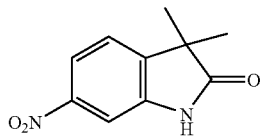

To a stirred solution of NaOH (8.4 g, 225 mmol) in water (70 mL) at 0° C. was added bromine (2.1 mL, 45 mmol) followed by 3.6 g (15.4 mmol) of 4,4-dimethyl-7-nitroisoquinoline-1,3)2H,4H)-dione (prepared according to the reference: Snow, R. J. et al, *J. Med. Chem.* 2002, 45, 3394). The mixture was stirred at room temperature for 1 h, and then was heated at 80° C. for another 1 h. After cooling, the mixture was acidified with acetic acid. The crude product was obtained by filtration, washed with water, and recrystallized from EtOH to give brown crystals (2.7 g).

MS: M+H=207

B. 6-Amino-3,3-dimethylindolin-2-one

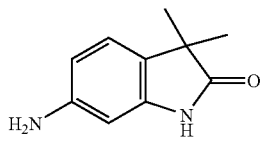

A mixture of 3,3-dimethyl-6-nitroindolin-2-one (500 mg, 2.4 mmol), 10% Pd—C (100 mg), and MeOH (100 mL) was stirred under $H_2$ (1 atm) for 3 h. After that the catalyst was filtered off and the filtrate was concentrated to give an off-white solid (420 mg).

MS: M+H=177.3

C. 6-(7-(3-Chloropyridin-2-yl)-5,6,7,8-tetrahydropyrido[3,4-d]pyrimidin-4-ylamino)-3,3-dimethylindolin-2-one A mixture of the 4-chloro-7-(3-chloropyridin-2-yl)-5,6,7,8-tetrahydropyrido[3,4-d]pyrimidine (50 mg, 0.18 mmol), 6-amino-3,3-dimethylindolin-2-one (63 mg, 0.36 mmol), and acetonitrile (3 mL) was heated in a sealed tube via at 180° C. for 60 min. The mixture was treated with EtOAc (50 mL) and sat. aq. solution of $NaHCO_3$. The organic layer was separated and washed with brine, dried ($Na_2SO_4$), and evaporated. The residue was purified by flash chromatography over silica gel to give a light yellow solid (50 mg).

MS: M+H=421.6 & 423.5 (M+1) $^1$H NMR (DMSO-d6) δ 10.33 (s, 1H), 8.44 (s, 1H), 8.41 (s, 1H), 8.24 (dd, J=4.8, 1.6 Hz, 1H), 7.86 (dd, J=8.0, 1.6 Hz, 1H), 7.38 (d, J=1.6 Hz, 1H), 7.24-7.18 (m, 2H), 7.03 (dd, J=8.0, 4.8 Hz, 1H), 4.35 (s, 2H), 3.67 (t, J=5.6 Hz, 2H), 2.81 (t, J=5.6 Hz, 2H), 1.24 (s, 6H).

114

Example 68

1-(6-(7-(3-Chloropyridin-2-yl)-5,6,7,8-tetrahydropyrido[3,4-d]pyrimidin-4-ylamino)-3,3-dimethylindolin-1-yl)ethanone

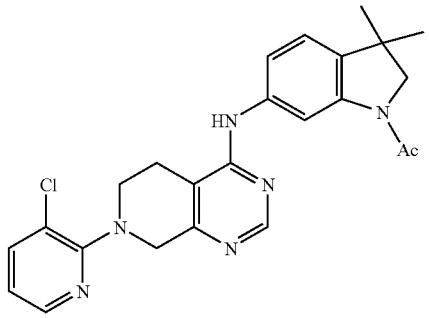

A. 3,3-Dimethyl-6-nitroindoline

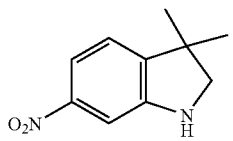

To a stirred solution of 3-dimethyl-6-nitroindolin-2-one (350 mg, 1.7 mmol) in THF (20 mL) at 0° C. under $N_2$ was added 2 M solution of $BH_3.Me_2S$ complex in THF (4.0 mL, 8.0 mmol). The mixture was stirred at room temperature for 2 h, and then 40° C. overnight. After cooling, the reaction was quenched with water and aq. $Na_2CO_3$ solution, and extracted with EtOAc. The organic layer was separated, washed with brine, dried ($Na_2SO_4$), and evaporated. The residue was purified by flash chromatography over silica gel to give an orange oil which became solid when kept at low temperature (220 mg).

MS: M+H=193 (M+1);

B. 1-(3,3-Dimethyl-6-nitroindolin-1-yl)ethanone

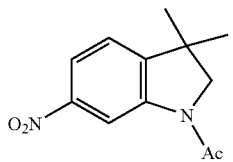

To a stirred solution of 3,3-dimethyl-6-nitroindoline (450 mg, 2.3 mmol) in $CH_2Cl_2$ (15 mL) and $Et_3N$ (0.6 mL) at −10° C. was added acetyl chloride (180 μL, 2.5 mmol). The mixture was stirred at room temperature overnight, quenched by adding saturated aqueous sodium bicarbonate, and extracted with EtOAc. The organic layer was separated, washed with brine, dried ($MgSO_4$), and evaporated. The residue was purified by flash chromatography over silica gel to give a light yellow solid (390 mg).

MS: M+H=235 (M+1);

C. 1-(6-Amino-3,3-dimethylindolin-1-yl)ethanone

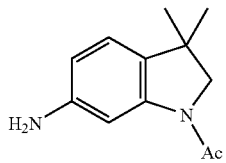

A mixture of 1-(3,3-dimethyl-6-nitroindolin-1-yl)ethanone (300 mg, 1.3 mmol), 10% Pd—C (50 mg), and EtOH (50 mL) was stirred under H$_2$ (1 atm) for 3 h. After that the catalyst was filtered off and the filtrate was concentrated to give a light yellow solid (260 mg).

MS: M+H=205 (M+1);

D. 1-(6-(7-(3-Chloropyridin-2-yl)-5,6,7,8-tetrahydropyrido[3,4-d]pyrimidin-4-ylamino)-3,3-dimethylindolin-1-yl)ethanone A mixture of 4-chloro-7-(3-chloropyridin-2-yl)-5,6,7,8-tetrahydropyrido[3,4-d]pyrimidine (40 mg, 0.14 mmol), 1-(6-amino-3,3-dimethylindolin-1-yl)ethanone (60 mg, 0.29 mmol), and acetonitrile (3 mL) was heated in a sealed tube via microwave at 180° C. for 60 min. The mixture was treated with EtOAc (50 mL) and saturated aqueous sodium bicarbonate. The organic layer was separated and washed with brine, dried (Na$_2$SO$_4$), and evaporated. The residue was purified by flash chromatography over silica gel to give an off-white solid (50 mg).

MS: M+H=449.5 & 451.3 (M+1); $^1$H NMR (DMSO-d6) δ 8.53 (s, 1H), 8.34 (s, 1H), 8.24 (dd, J=4.4, 1.6 Hz, 1H), 8.23 (d, J=1.6 Hz, 1H), 7.86 (dd, J=8.0, 1.6 Hz, 1H), 7.38 (dd, J=8.0, 1.6 Hz, 1H), 7.16 (d, J=8.0 Hz, 1H), 7.03 (dd, J=8.0, 4.8 Hz, 1H), 4.34 (s, 2H), 3.86 (s, 2H), 3.67 (t, J=5.6 Hz, 2H), 2.79 (t, J=5.6 Hz, 2H), 2.16 (s, 3H), 1.30 (s, 6H).

Example 69

7-(3-Chloropyridin-2-yl)-5,6,7,8-tetrahydro-N-(3,3-dimethylindolin-6-yl)pyrido[3,4-d]pyrimidin-4-amine

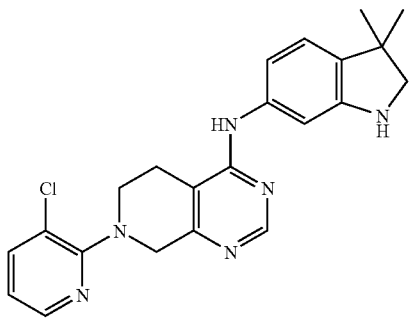

A mixture of compound of Example 68 (40 mg), EtOH (5 mL), and 5 N HCl (1.0 mL) was stirred at 55° C. overnight. After cooling, the solvent was removed in vacuo to give a yellow solid (45 mg).

MS: M+H=407.3 & 409.3 (M+1); $^1$H NMR (DMSO-d6) δ 10.12 (s, 1H), 8.79 (s, 1H), 8.26 (dd, J=4.8, 1.6 Hz, 1H), 7.92 (dd, J=8.0, 1.6 Hz, 1H), 7.50 (br s, 2H), 7.42 (d, J=8.0 Hz, 1H), 7.10 (dd, J=8.0, 4.8 Hz, 1H), 4.56 (s, 2H), 3.74 (t, J=5.6 Hz, 2H), 3.46 (s, 2H), 2.86 (t, J=5.2 Hz, 2H), 1.36 (s, 6H).

Example 70

7-(3-Chloropyridin-2-yl)-5,6,7,8-tetrahydro-N-(1,3,3-trimethylindolin-6-yl)pyrido[3,4-d]pyrimidin-4-amine

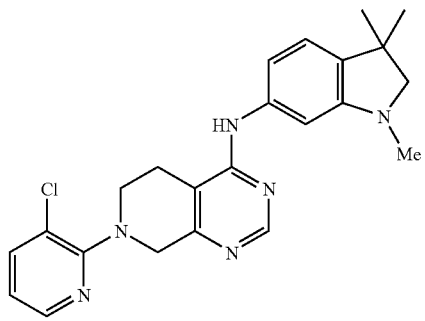

To a stirred solution of compound of Example 69 hydrogen chloride (20 mg) in DMF (5 mL) was added K$_2$CO$_3$ (50 mg), followed by MeI (50 μL). The mixture was stirred at room temperature for 2 h, and then treated with water, extracted with EtOAc (50 mL). The organic layer was separated, washed with brine, dried (Na$_2$SO$_4$), and evaporated. The residue was purified by flash chromatography over silica ghel to give a light yellow solid (10 mg).

MS: M+H=421.5 & 423.4 (M+1); $^1$H NMR (DMSO-d6) δ 8.35 (s, 1H), 8.30-8.20 (m, 2H), 7.86 (d, J=7.6 Hz, 1H), 7.03 (dd, J=7.6, 4.8 Hz, 1H), 6.93 (m, 2H), 6.77 (s, 1H), 4.33 (s, 2H), 3.67 (t, J=5.6 Hz, 2H), 3.03 (s, 2H), 2.77 (t, J=4.8 Hz, 2H), 2.67 (s, 3H), 1.23 (s, 6H).

Example 71

7-(4-(Trifluoromethyl)pyridin-2-yl)-5,6,7,8-tetrahydro-N-(2,3-dihydrobenzo[b][1,4]dioxin-7-yl)pyrido[3,4-d]pyrimidin-4-amine

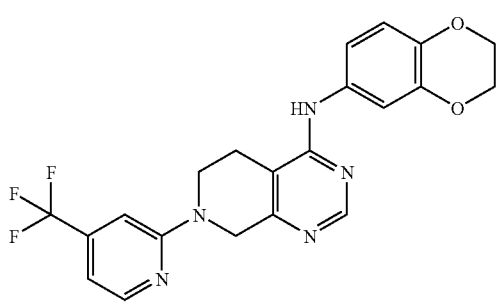

A. 7-(4-(Trifluoromethyl)pyridin-2-yl)-5,6,7,8-tetrahydropyrido[3,4-d]pyrimidin-4)3H)-one

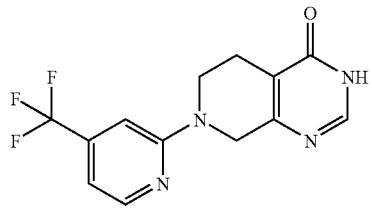

A mixture of 5,6,7,8-tetrahydropyrido[3,4-d]pyrimidin-4)3H)-one (0.514 g, 0.00340 mol), 2-chloro-4-(trifluoromethyl)pyridine (0.93 g, 0.0051 mol) and N,N-Diisopropylethylamine (0.89 mL, 0.0051 mol) in N-Methylpyrrolidinone (3 mL) was heated in a sealed tube via microwave at 150° C. for 110 minutes. After cooling to room temperature, mixture poured into water (25 mL) and extracted with ethyl acetate (3×25 ml). The combined organic layers were dried over magnesium sulfate. Concentrated to leave an oil which solidified to leave a brown solid (0.284 g) upon drying under vaccum and used without further purification.

MS: M+H=297

B. 4-chloro-7-(4-(trifluoromethyl)pyridin-2-yl)-5,6,7,8-tetrahydropyrido[3,4-d]pyrimidine

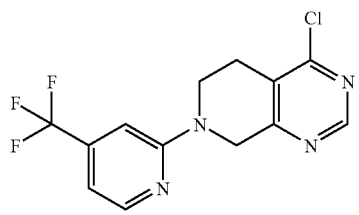

A mixture of 7-(4-(trifluoromethyl)pyridin-2-yl)-5,6,7,8-tetrahydropyrido[3,4-d]pyrimidin-4)3H)-one (0.263 g, 0.000888 mol), Phosphoryl chloride (0.662 mL, 0.00710 mol) and N,N-Dimethylaniline (0.112 mL, 0.000888 mol) in 1,2-Dichloroethane (20 mL) was heated to reflux for 4 hours. The mixture was cooled to r.t. Mixture was concentrated under reduced pressure to leave a black oil. Residue was taken up in dichloromethane (20 mL) and poured over crushed ice. Mixture slowly neutralized by addition of solid sodium bicarbonate. Layers separated and organic layer dried over magnesium sulfate. Concentrated to leave a dark brown oil Purified by flash chromatography over silica gel (ethyl acetate/hexane gradient 0 to 100%) to obtain 0.279 g of a white solid.

MS: M+H=315 $^1$H NMR (DMSO-d$_6$): δ 2.89(t, J=5.8 Hz, 2H); 4.03(t, J=5.8 Hz, 2H); 4.86(s, 2H); 6.95(d, J=5.1 Hz, 1H); 7.31(s, 1H); 8.37(d, J=5.1 Hz, 1H); 8.87(s, 1H).

C. 7-(4-(trifluoromethyl)pyridin-2-yl)-5,6,7,8-tetrahydro-N-(2,3-dihydrobenzo[b][1,4]dioxin-7-yl)pyrido[3,4-d]pyrimidin-4-amine A mixture of 4-chloro-7-(4-(trifluoromethyl)pyridin-2-yl)-5,6,7,8-tetrahydropyrido[3,4-d]pyrimidine (0.041 g, 0.00013 mol) and 2,3-dihydrobenzo[b][1,4]dioxin-6-amine (0.041 g, 0.00026 mol) in Acetonitrile (1.00 mL, 0.0191 mol) and 47% Hydrogen iodide (0.1 mL, 0.001 mol) was heated at 160° C. for 10 minutes in a sealed tube via microwave. After cooling to r.t., the mixture was poured into saturated aqueous sodium bicarbonate (5 mL) and extracted with ethyl acetate (10 mL). The organic layer was washed with brine and dried over magnesium sulfate. Concentrated to leave a brown solid. The residue was purified by flash chromatography over silica gel (ethyl acetate/hexane gradient 0 to 100%) to give a light yellow solid (0.032 g).

MS: M+H=430 $^1$H NMR (DMSO-d$_6$): δ 2.71(t, J=5.5 Hz, 2H); 4.01(t, J=5.8 Hz, 2H); 4.19-4.25(m, 4H); 4.63(s, 2H); 6.80(d, J=8.6 Hz, 1H); 6.93(dd, J=5.2 Hz, 0.9 Hz, 1H); 7.06(dd, J=8.8 Hz, 2.6 Hz, 1H); 7.24(d, J=2.3 Hz, 1H); 7.27(brs, 1H); 8.36-8.39(m, 3H).

Example 72

7-(4-(Trifluoromethyl)pyridin-2-yl)-5,6,7,8-tetrahydro-N-(3-methoxyphenyl)pyrido[3,4-d]pyrimidin-4-amine

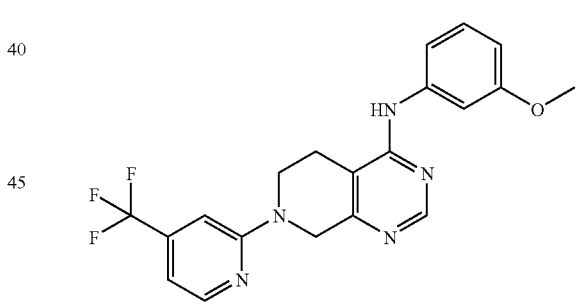

A mixture of 4-chloro-7-(4-(trifluoromethyl)pyridin-2-yl)-5,6,7,8-tetrahydropyrido[3,4-d]pyrimidine (0.041 g, 0.00013 mol), 3-methoxyaniline (0.018 mL, 0.00016 mol) in acetonitrile (1.00 mL, 0.0191 mol) and 47% HI (0.11 mL, 0.001 mol) was heated at 160° C. for 10 minutes in in a sealed tube via microwave. After cooling to r.t., the mixture was poured into saturated aqueous sodium bicarbonate (5 mL) and extracted with ethyl acetate (10 mL). The organic layer was washed with brine and dried over magnesium sulfate. Concentrated to leave a brown solid. Residue was purified by flash chromatography over silica gel (ethyl acetate/hexane gradient 0 to 100%) to give a white foam (0.013 g)

MS: M+H=402

Example 73

7-(5-(Trifluoromethyl)pyridin-2-yl)-5,6,7,8-tetrahydro-N-(3-methoxyphenyl)pyrido[3,4-d]pyrimidin-4-amine

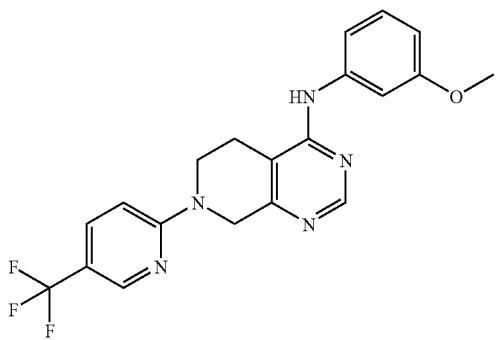

A. 7-(5-(trifluoromethyl)pyridin-2-yl)-5,6,7,8-tetrahydropyrido[3,4-d]pyrimidin-4)3H)-one.

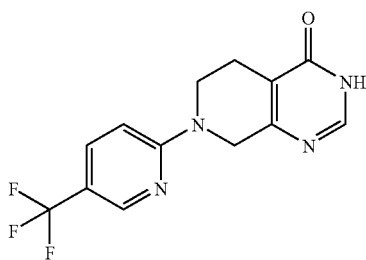

A mixture of 5,6,7,8-tetrahydropyrido[3,4-d]pyrimidin-4)3H)-one (0.511 g, 0.00338 mol), 2-chloro-5-(trifluoromethyl)pyridine (0.92 g, 0.0051 mol) and N,N-Diisopropylethylamine (0.88 mL, 0.0051 mol) in N-Methylpyrrolidinone (3 mL, 0.03 mol) was heated in a sealed vessel via microwave at 150° C. for 2 hours. After cooling to rt, a solid precipitated which was collected by filtration and washed with diethyl ether. The filtrate was concentrated and triturated with diethyl ether. The solid was collected by filtration and washed with diethyl ether and hexane. The solids were combined to give the product as a light brown solid.

MS: M+H=297

B. 4-chloro-7-(5-(trifluoromethyl)pyridin-2-yl)-5,6,7,8-tetrahydropyrido[3,4-d]pyrimidine

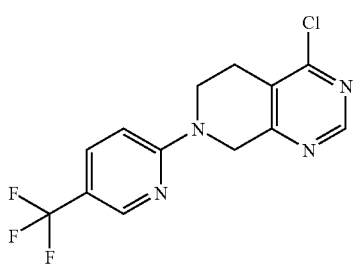

A mixture of 7-(5-(trifluoromethyl)pyridin-2-yl)-5,6,7,8-tetrahydropyrido[3,4-d]pyrimidin-4)3H)-one (0.472 g, 0.00159 mol), Phosphoryl chloride (1.19 mL, 0.0127 mol) and N,N-Dimethylaniline (0.202 mL, 0.00159 mol) in 1,2-Dichloroethane (20 mL, 0.2 mol) was heated to reflux for 4 hours. The mixture was cooled to r.t. Mixture was concentrated under reduced pressure to leave a black oil. Residue was taken up in dichloromethane (50 ml) and poured over crushed ice. Mixture slowly neutralized by addition of solid sodium bicarbonate. Layers separated and organic layer dried over magnesium sulfate. Concentrated to leave a dark brown oil which purified by flash chromatography over silica gel (ethyl acetate/hexane gradient 0 to 100%) to obtain 0.080 g of a white solid.

MS: M+H=315

C. 7-(5-(trifluoromethyl)pyridin-2-yl)-5,6,7,8-tetrahydro-N-(3-methoxyphenyl)pyrido[3,4-d]pyrimidin-4-amine A mixture of 4-chloro-7-(5-(trifluoromethyl)pyridin-2-yl)-5,6,7,8-tetrahydropyrido[3,4-d]pyrimidine (0.035 g, 0.00011 mol), 3-methoxyaniline (0.018 mL, 0.00016 mol) in acetonitrile (0.5 mL, 0.01 mol) and 47% HI (0.05 mL, 0.0007 mol) was heated at 160° C. for 20 minutes in in a sealed tube via microwave. After cooling to r.t., the mixture was poured into saturated aqueous sodium bicarbonate (5 mL) and extracted with ethyl acetate (10 mL). The organic layer was washed with brine and dried over magnesium sulfate. Concentrated to leave a brown solid. Residue was purified by flash chromatography over silica gel (ethyl acetate/hexane gradient 0 to 100%) to give 0.196 g of a white foam.

MS: M+H=402

Example 74

7-(3-Chloropyridin-2-yl)-5,6,7,8-tetrahydro-N-(2,3-dihydrobenzo[b][1,4]dioxin-6-yl)pyrido[3,4-d]pyrimidin-4-amine

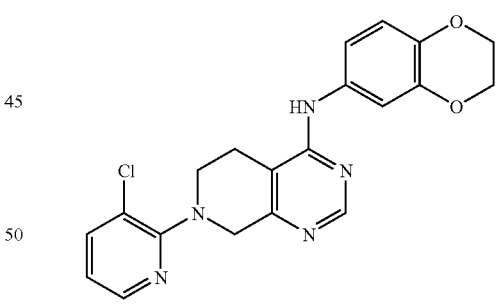

A mixture of 4-chloro-7-(3-chloropyridin-2-yl)-5,6,7,8-tetrahydropyrido[3,4-d]pyrimidine (0.095 g, 0.00034 mol), 2,3-dihydrobenzo[b][1,4]dioxin-6-amine (0.10 g, 0.00068 mol) and sodium iodide (0.02 g, 0.0001 mol) in acetonitrile was heated at 150° C. by microwave in a sealed tube for 10 minutes. After cooling to r.t., the mixture was poured into saturated sodium bicarbonate and extracted with ethyl acetate. The organic layer was washed with brine and dried over magnesium sulfate and concentrated to leave an oil. Residue purified by flash chromatography over silica gel (ethyl acetate/hexane gradient 0 to 100%) to give 0.110 g of a white solid.

MS: M+H=396

Example 75

2-(4-(4-(Trifluoromethyl)phenylamino)-7-(3-chloropyridin-2-yl)-5,6,7,8-tetrahydropyrido[3,4-d]pyrimidin-2-yloxy)acetic acid

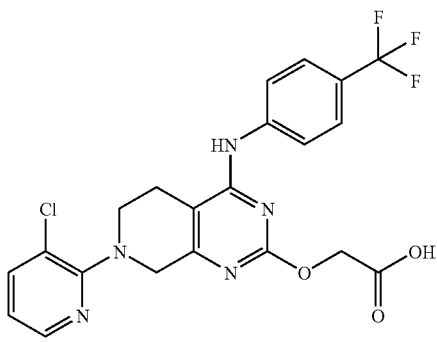

Methyl 2-(4-(4-(trifluoromethyl)phenylamino)-7-(3-chloropyridin-2-yl)-5,6,7,8-tetrahydropyrido[3,4-d]pyrimidin-2-yloxy)acetate (52.0 mg, 0.1 mmol) was suspended in MeOH (10 mL). NaOH (100 mg) and H$_2$O (3 mL) were added and the mixture was stirred at 60° C. for 10 min. Solvent was removed, residue was dissolved in water, dilute HCl aqueous solution was added until a pH of 7 was obtained. Extracted by EtOAc, dried over Na$_2$SO$_4$ and the solvent was removed in vacuo, product was obtained as a white solid (47 mg).

MS: M+H=480.3 $^1$H NMR (DMSO-d$_6$) δ: 2.76 (t, J=5.6 Hz, 2H), 3.66 (t, J=5.6 Hz, 2H), 4.27 (s, 2H), 4.56 (s, 2H), 7.01-7.04 (m, 1H), 7.63 (d, J=8.8 Hz, 2H), 7.84-7.86 (m, 1H), 7.96 (d, J=8.8 Hz, 2H), 8.22-8.24 (m, 1H), 8.80 (s, 1H).

Example 76

7-(3-(trifluoromethyl)pyridin-2-yl)-5,6,7,8-tetrahydro-N-(4-(trifluoromethylsulfonyl)-phenyl)pyrido[3,4-d]pyrimidin-4-amine

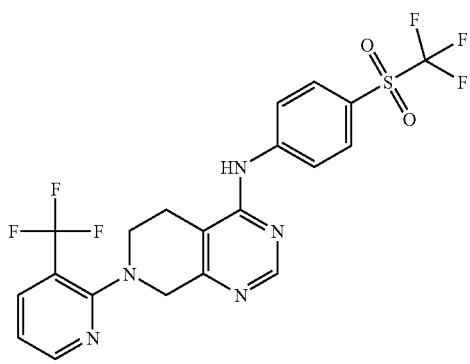

A. 4-Chloro-7-(3-(trifluoromethyl)pyridin-2-yl)-5,6,7,8-tetrahydropyrido[3,4-d]pyrimidine

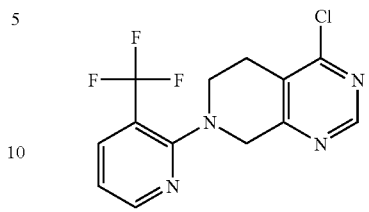

A mixture of 5,6,7,8-tetrahydropyrido[3,4-d]pyrimidin-4(3H)-one (1.5 g, 0.0099 mol), 2-chloro-3-(trifluoromethyl)pyridine (2.7 g, 0.015 mol) and N,N-diisopropylethylamine (2.6 mL, 0.015 mol) in N-methylpyrrolidinone (9 mL, 0.09 mol) was heated in a sealed vessel via microwave at 150° C. for 2 hours. After cooling to rt, the reaction mixture was poured into water (30 mL) and extracted with ethyl acetate (4×30 mL). The combined extracts were washed with brine and dried over magnesium sulfate and concentrated to dryness to leave a yellow solid which was taken on without futher purification. The solid (1.00 g, 0.00338 mol), Phosphoryl chloride (1.19 mL, 0.0127 mol) and N,N-Dimethylaniline (0.202 mL, 0.00159 mol) in 1,2-Dichloroethane (20 mL) was heated to reflux for 3 hours. The mixture was concentrated under reduced pressure to leave a black oil. Residue was taken up in dichloromethane (50 mL) and poured over crushed ice. Mixture slowly neutralized by addition of solid sodium bicarbonate. The layers were separated and organic layer dried over magnesium sulfate and concentrated to leave a dark brown oil Purified by flash chromatography over silica gel (ethyl acetate/hexane gradient 0 to 100%) to yield the desired product as a yellow solid (0.716 g).

MS: M+H=315 $^1$H NMR (DMSO-d6): δ 2.88(t, J=5.6 Hz, 2H); 3.60(t, J=5.6 Hz, 2H); 4.48(s, 2H); 7.25(dd, J=7.8 Hz, 4.8 Hz, 1H); 8.14(dd, J=7.8 Hz, 1.6 Hz, 1H); 8.54(dd, J=4.7 Hz, 1.2 Hz, 1H); 8.85(s, 1H).

B. 7-(3-(trifluoromethyl)pyridin-2-yl)-5,6,7,8-tetrahydro-N-(4-(trifluoromethylsulfonyl)phenyl)pyrido[3,4-d]pyrimidin-4-amine A mixture of 4-chloro-7-(3-(trifluoromethyl)pyridin-2-yl)-5,6,7,8-tetrahydropyrido[3,4-d]pyrimidine (0.100 g, 0.000314 mol) tris(dibenzylideneacetone)dipalladium(0) (0.058 g, 0.000063 mol), Cesium Carbonate (0.311 g, 0.000944 mol) and Xantphos (0.018 g, 0.000031 mol) in 1,4-Dioxane (3 mL, 0.04 mol) was stirred at room temperature for 10 minutes in a 5 mL microwave vial. 4-(trifluoromethylsulfonyl)benzenamine (0.15 g, 0.00063 mol) was then added as a solution in dioxane (0.5 mL) and the mixture was stirred for an additional 5 minutes. The mixture was heated via microwave in a sealed tube at 140° C. for 30 minutes, allowed to cool, and reduced in vacuo. The resulting black solid was taken up in ethyl acetate (50 mL) and washed with brine and water (2×50 mL), dried over magnesium sulfate, and reduced in vacuo. The mixture was purified by flash chromatography using an ethyl acetate: hexanes (0-100%) gradient. The combined pure fractions were reduced in vacuo to yield the desired product as a tan solid (0.087 g).

MS: M+H=504 $^1$H NMR (DMSO-d6): δ 2.91(t, J=5.6 Hz, 2H); 3.61(t, J=5.6 Hz, 2H); 4.40(s, 2H); 7.23(dd, J=7.4 Hz, 4.5 Hz, 1H); 8.05(d, J=9.1 Hz, 2H); 8.13(dd, J=7.9 Hz, 1.9 Hz, 1H); 8.22-8.27(m, 2H); 8.55(dd, J=4.5 Hz, 1.4 Hz, 1H); 8.63(s, 1H); 9.27(s, 1H).

Example 77

N-(4-(difluoromethoxy)phenyl)-7-(3-(trifluoromethyl)pyridin-2-yl)-5,6,7,8-tetrahydropyrido[3,4-d]pyrimidin-4-amine

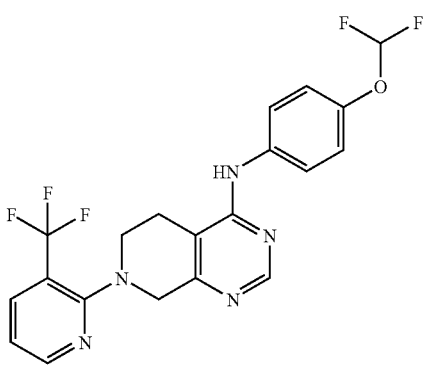

In a 5 mL microwave vial was combined 4-chloro-7-(3-(trifluoromethyl)pyridin-2-yl)-5,6,7,8-tetrahydropyrido[3,4-d]pyrimidine (0.113 g, 0.000356 mol), 4-(trifluoromethoxy)aniline (0.0964 mL, 0.000711 mol), acetonitrile (2 mL, 0.04 mol), and sodium iodide (0.00533 g, 0.0000356 mol). The mixture was heated at at 150° C. for 10 minutes and reduced in vacuo. The remaining solid was taken up in ethyl acetate (10 mL) and washed with saturated sodium bicarbonate (2×10 mL) and water (1×10 mL). The organic layer was dried over magnesium sulfate and reduced in vacuo to yield an off white solid. The mixture was purified by flash chromatography using an ethyl acetate:hexanes (0-50%) gradient to yield the desired product as an off white solid (0.052 g).

MS: M+H=438 $^1$H NMR (DMSO-d6): δ 2.79(t, J=5.6 Hz, 2H); 3.61(t, J=5.6 Hz, 2H); 4.32(s, 2H); 7.15(d, J=9.0 Hz, 2H); 7.17(t, J=74.5 Hz, 1H); 7.21(dd, J=7.6 Hz, 4.9 Hz, 1H); 7.67-7.74(m, 2H); 8.12 (dd, J=7.8 Hz, 1.9 Hz, 1H); 8.40(s, 1H); 8.55(dd, J=4.9 Hz, 1.4 Hz, 1H); 8.59(s, 1H).

Example 78

7-(3-Chloropyridin-2-yl)-5,6,7,8-tetrahydro-N-(4-(trifluoromethoxy)-phenyl)pyrido[3,4-d]pyrimidin-4-amine

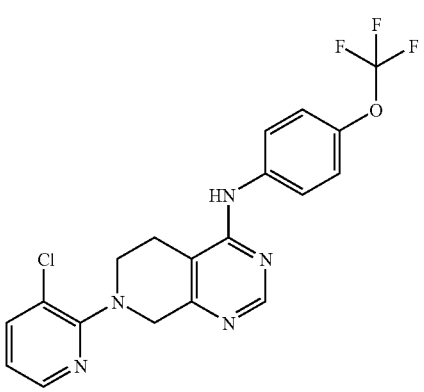

A mixture of 4-chloro-7-(3-chloropyridin-2-yl)-5,6,7,8-tetrahydropyrido[3,4-d]pyrimidine (0.103 g, 0.000366 mol), 4-(trifluoromethoxy)aniline (0.0983 mL, 0.000733 mol) and sodium iodide (0.020 g, 0.00013 mol) in Acetonitrile (3 mL, 0.06 mol) was heated via microwave in a sealed tube at 180° C. for 15 minutes. After cooling to room temperature, the mixture was added to saturated aqueous sodium bicarbonate and extracted with ethyl acetate. The organic layer was washed with brine and dried over sodium sulfate. Concentrated to leave an oil. The residue was purified by flash chromatography over silica gel (ethyl acetate/hexane gradient 0 to 100%) to give 0.092 g of an off-white solid.

MS: M+H=422 $^1$H NMR (DMSO-d6): δ 2.82(t, J=5.6 Hz, 2H); 3.68(t, J=5.6 Hz, 2H); 4.37(s, 2H); 7.04(dd, J=7.9 Hz, 4.6 Hz, 1H); 7.33(d, J=8.6 Hz, 2H); 7.80-7.84(m, 2H); 7.86 (dd, J=7.9 Hz, 1.6 Hz, 1H); 8.24(dd, J=4.6 Hz, 1.6 Hz, 1H); 8.44(s, 1H); 8.66(s, 1H).

Example 79

7-(3-(trifluoromethyl)pyridin-2-yl)-5,6,7,8-tetrahydro-N-(4-(trifluoromethoxy)-phenyl)pyrido[3,4-d]pyrimidin-4-amine

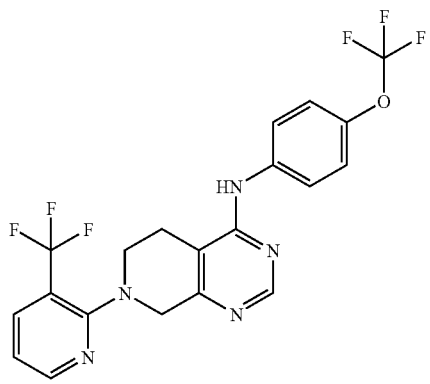

In a 5 ml microwave vial was combined 4-chloro-7-(3-(trifluoromethyl)pyridin-2-yl)-5,6,7,8-tetrahydropyrido[3,4-d]pyrimidine (0.113 g, 0.000356 mol), 4-(trifluoromethoxy)aniline (0.0964 mL, 0.000711 mol), acetonitrile (2 mL, 0.04 mol), and sodium iodide (0.00533 g, 0.0000356 mol). The mixture was heated at at 150° C. for 10 minutes and reduced in vacuo. The remaining solid was taken up in ethyl acetate (10 mL) and washed with saturated sodium bicarbonate (2×10 mL) and water (1×10 mL). The organic layer was dried over magnesium sulfate and reduced in vacuo to yield an off white solid. The mixture was purified by flash chromatography using an ethyl acetate:hexanes (0-50%) gradient to yield the desired product as an off white solid (0.105 g).

MS: M+H=456 $^1$H NMR (DMSO-d6): δ 2.81(t, J=5.5 Hz, 2H); 3.61(t, J=5.5 Hz, 2H); 4.33(s, 2H); 7.21(dd, J=7.2 Hz, 4.8 Hz, 1H); 7.33(d, J=8.4 Hz, 2H); 7.79-7.85(m, 2H); 8.12(dd, J=7.9 Hz, 1.6 Hz, 1H); 8.44(s, 1H); 8.55(dd, J=4.8 Hz, 1.4 Hz, 1H); 8.68(s, 1H).

In addition to the amine compounds exemplified above, the following compounds recited below, which comprise various substituted amines of this invention, can be prepared using the procedure and synthetic schemes described above, or some modification their of, and the corresponding starting materials, appropriate reagents, and purification methods known to those skilled in the art.

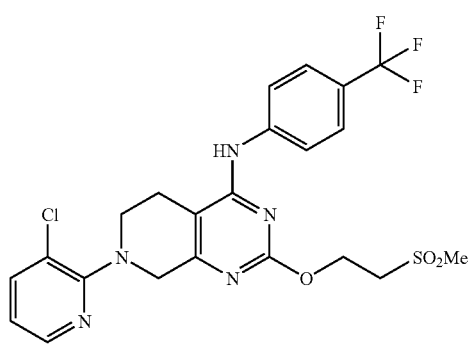

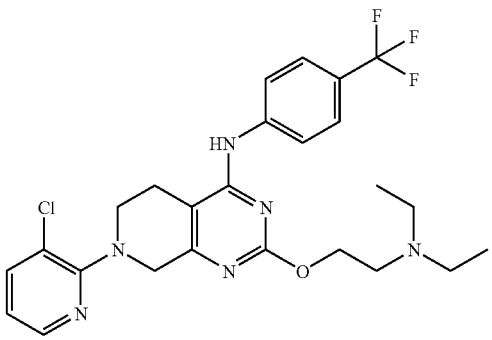

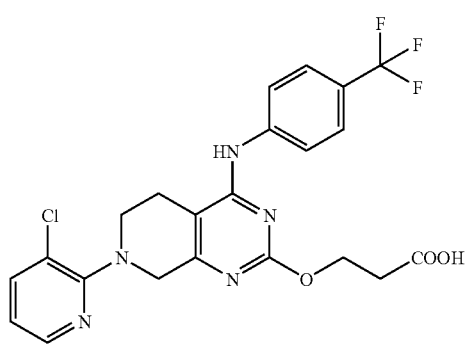

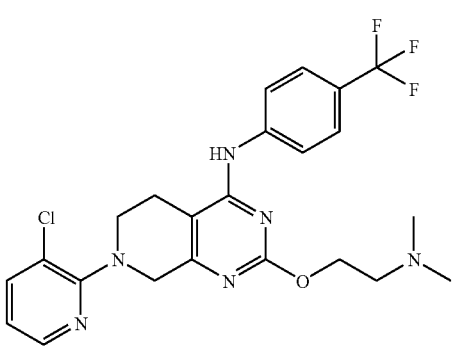

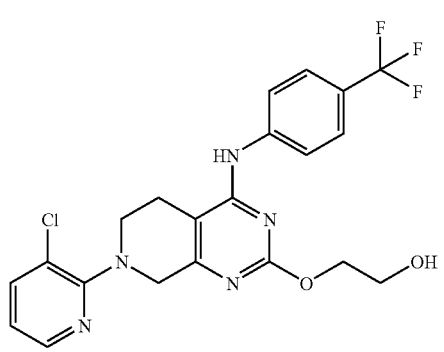

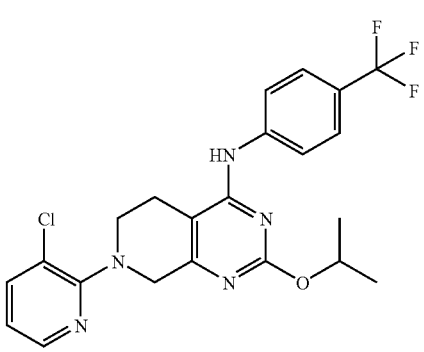

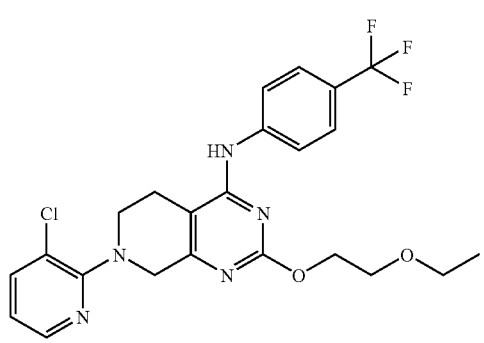

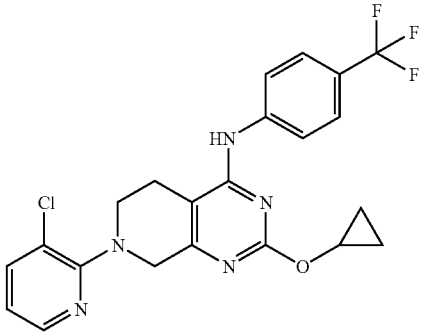

127
-continued
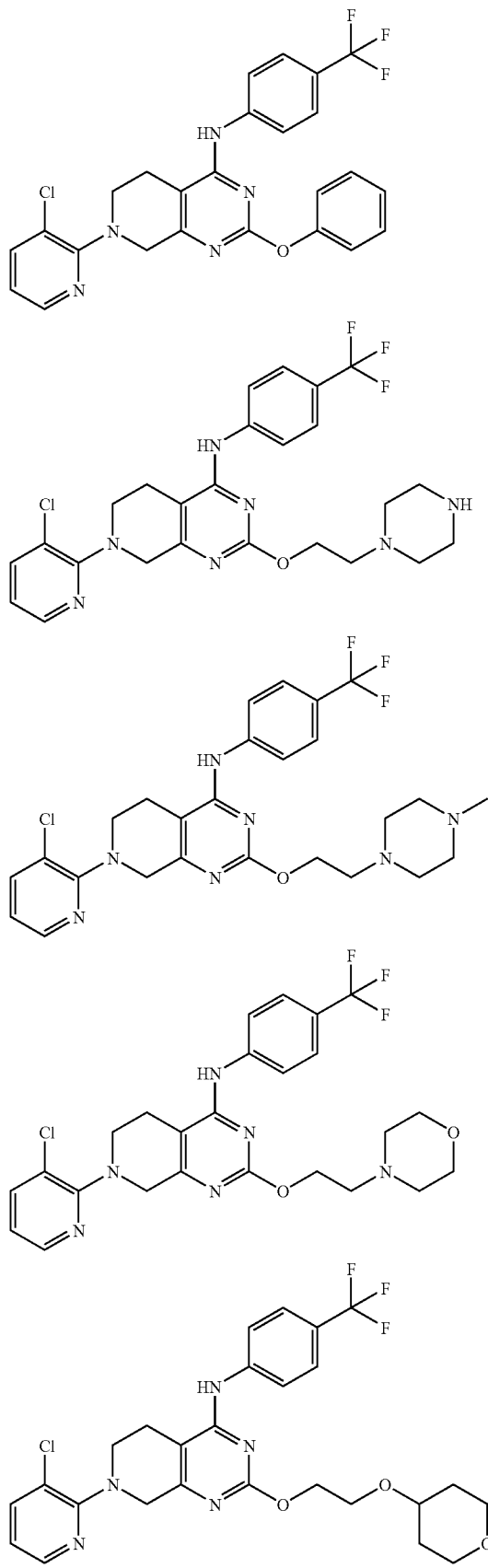
128
-continued
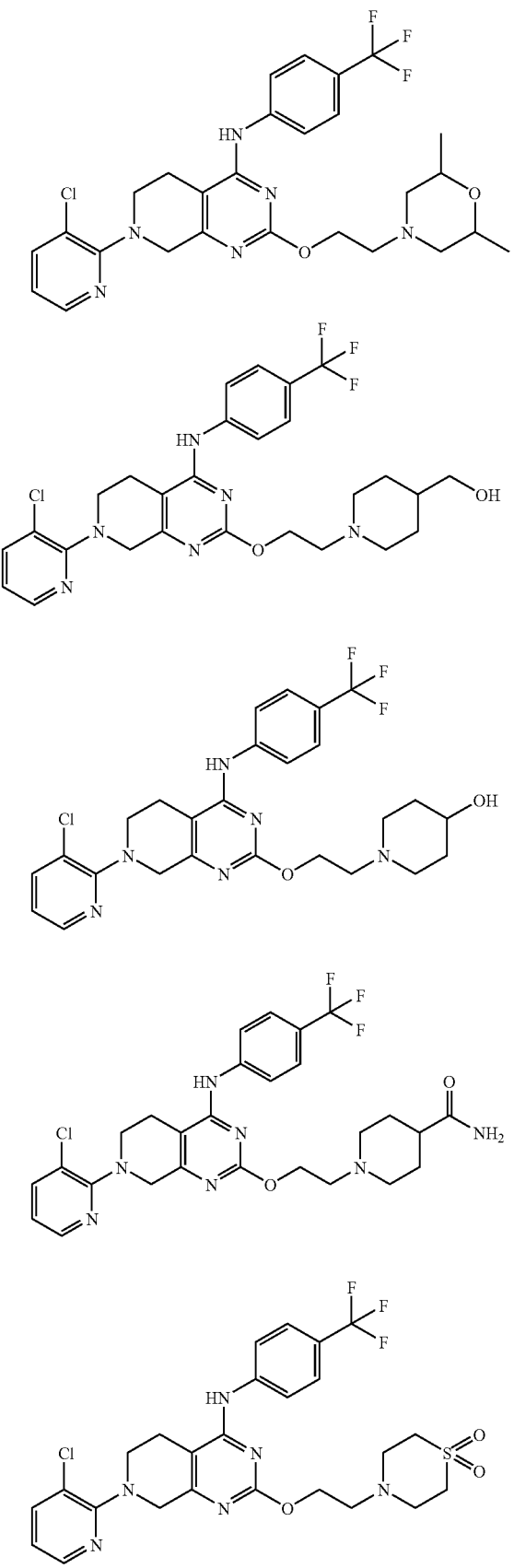

-continued
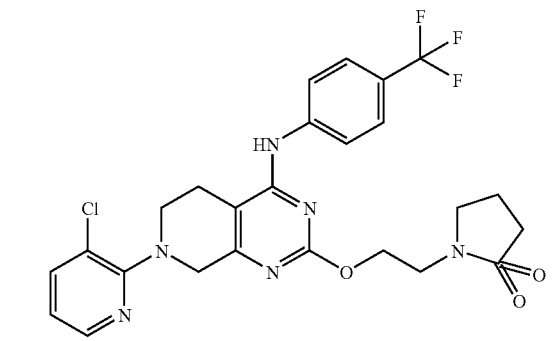
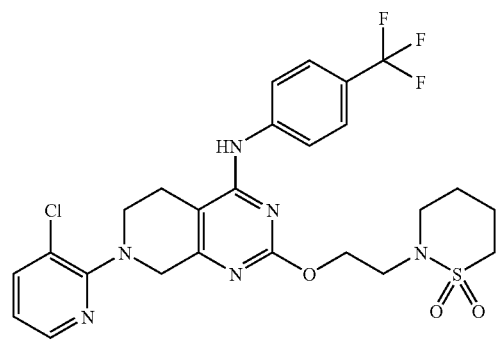
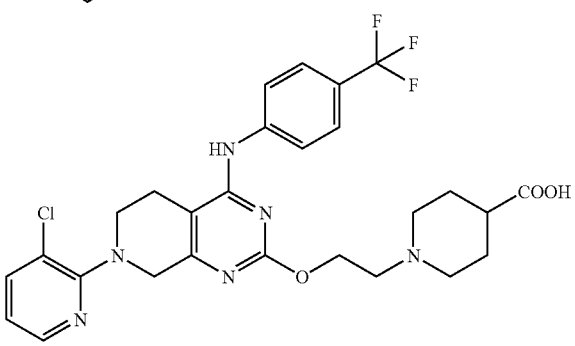
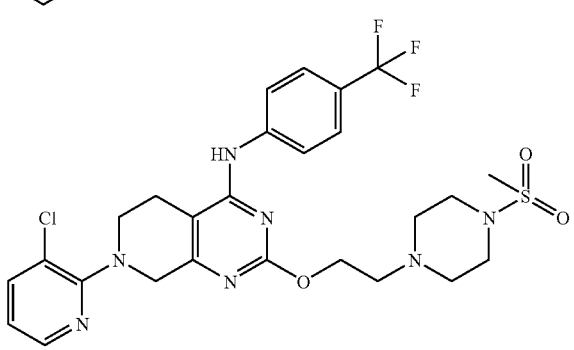
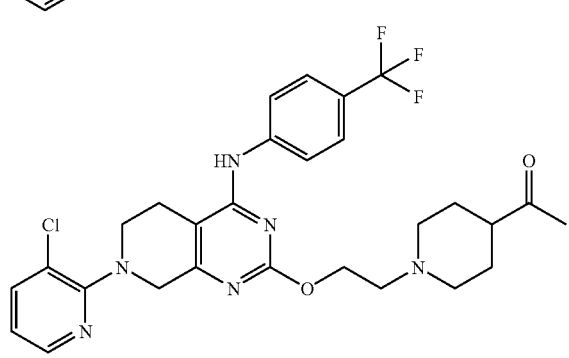
-continued
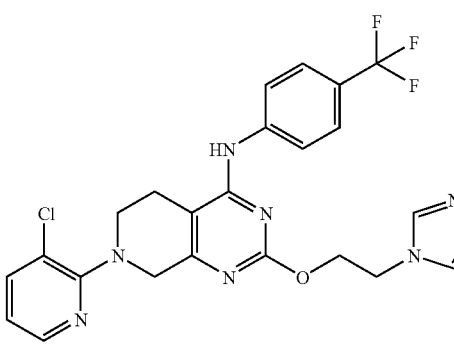
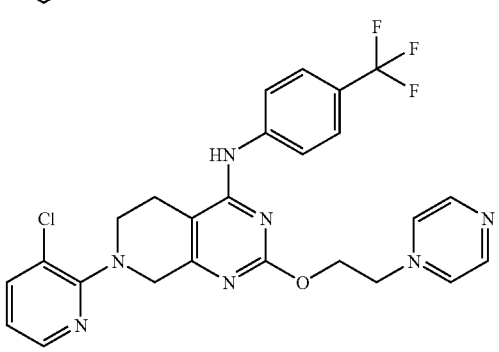
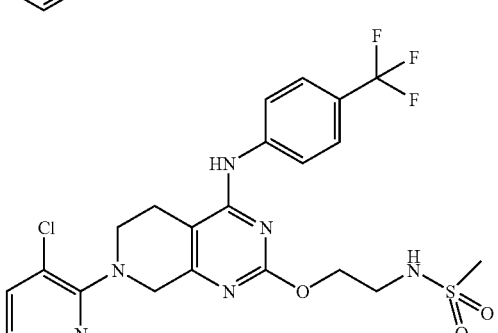
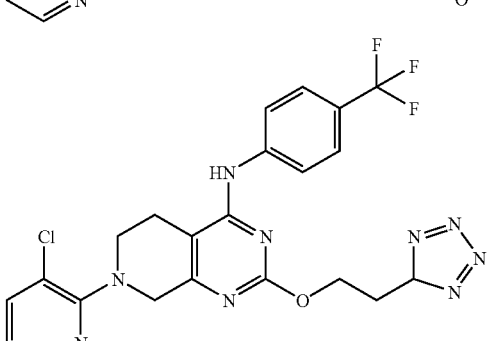
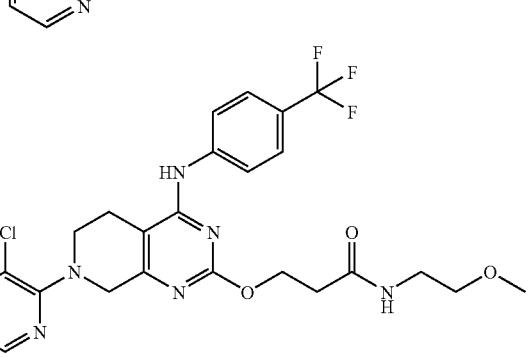

-continued
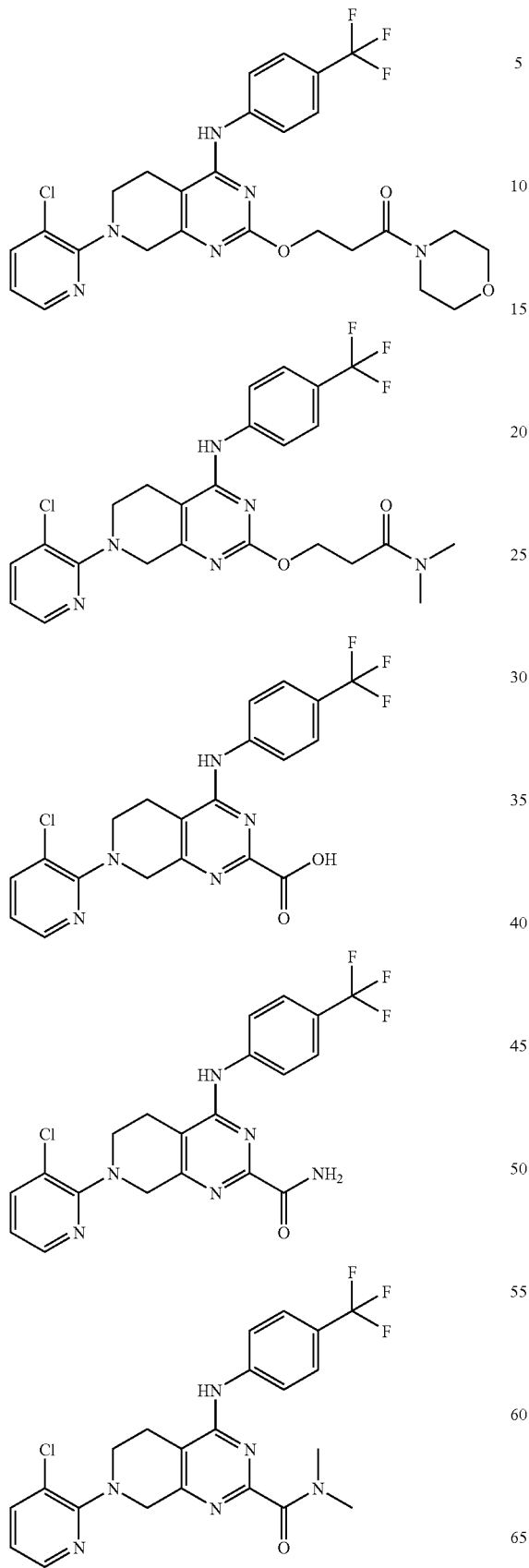
-continued
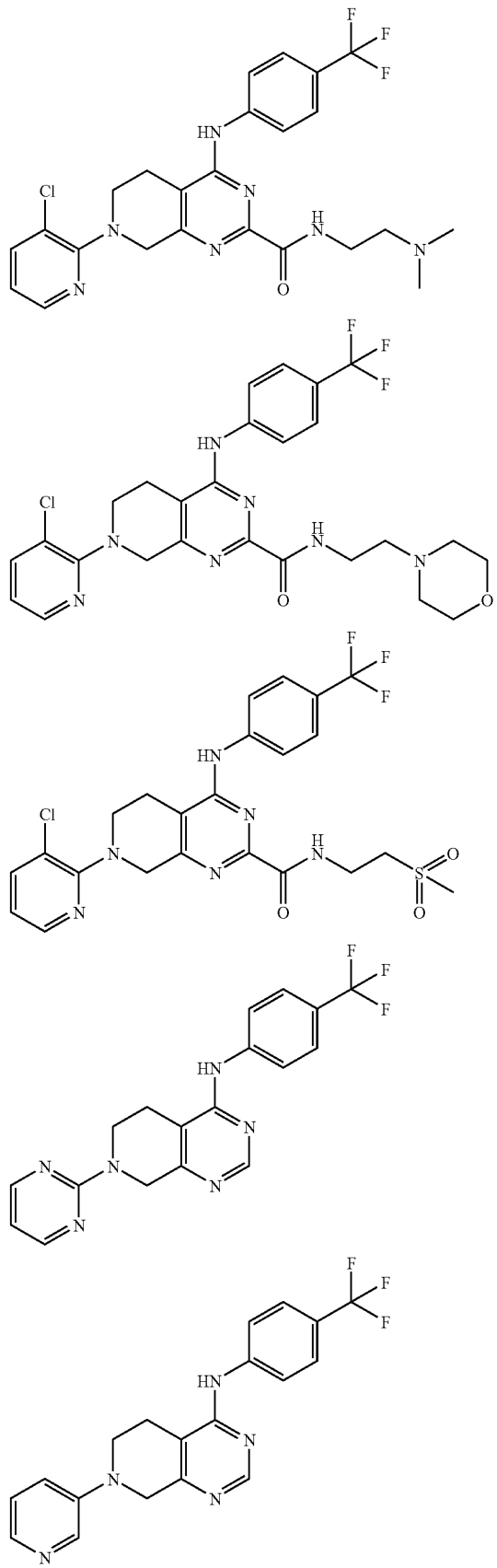

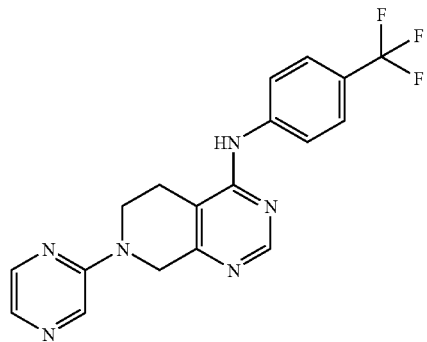
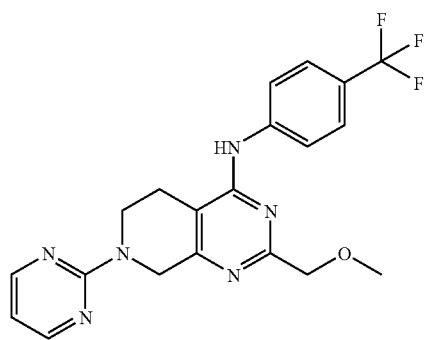
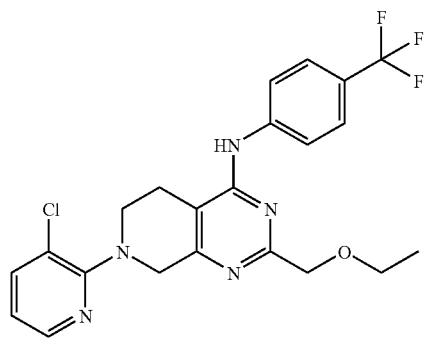
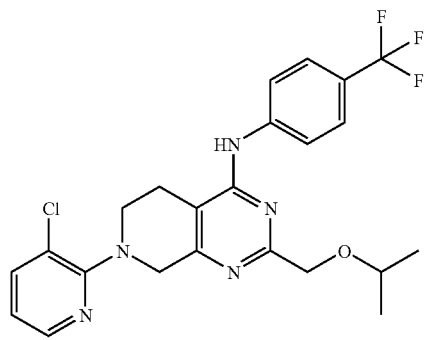
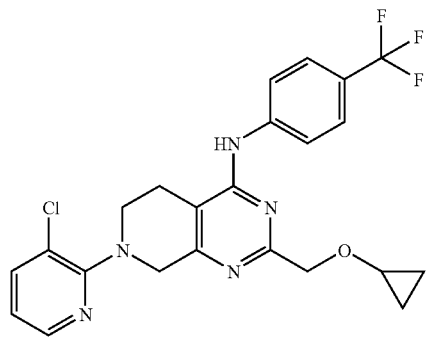
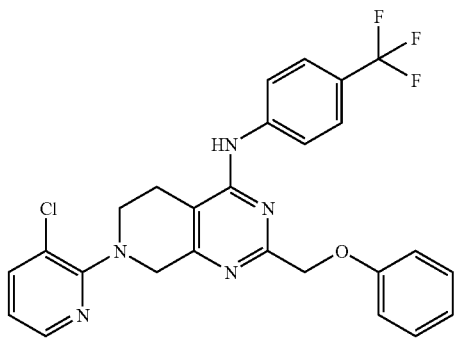
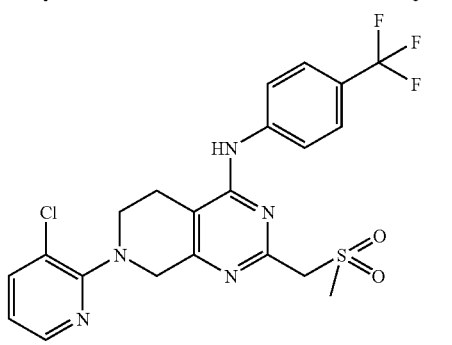
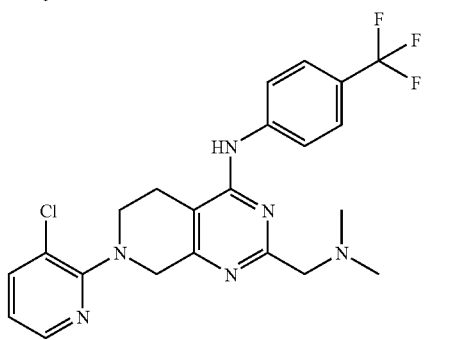
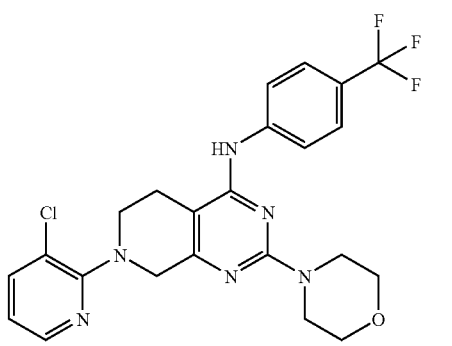
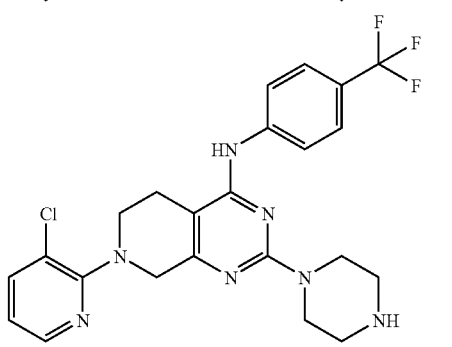

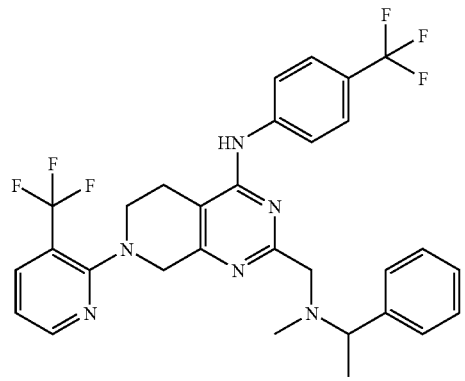
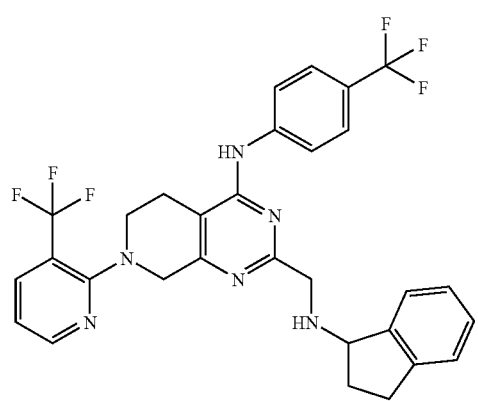
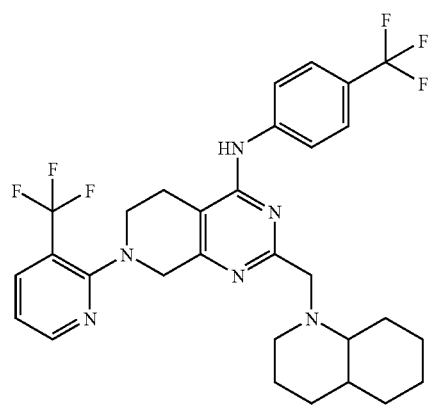
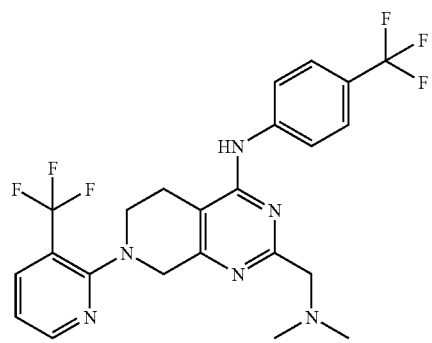
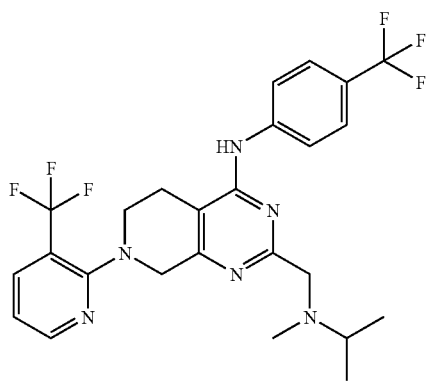
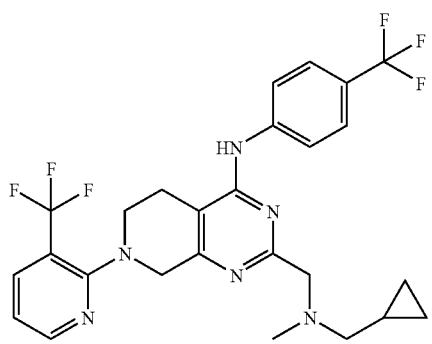
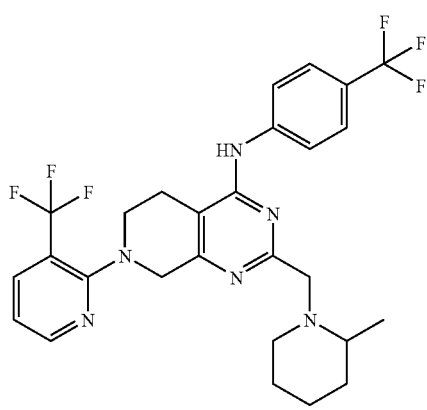
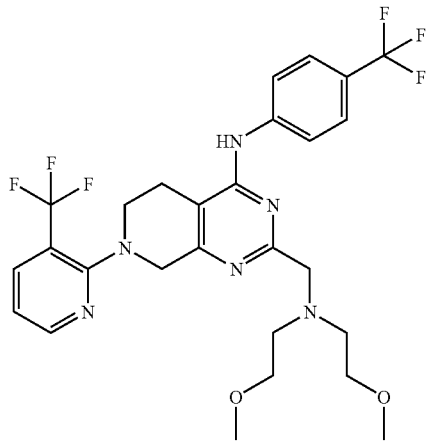

-continued
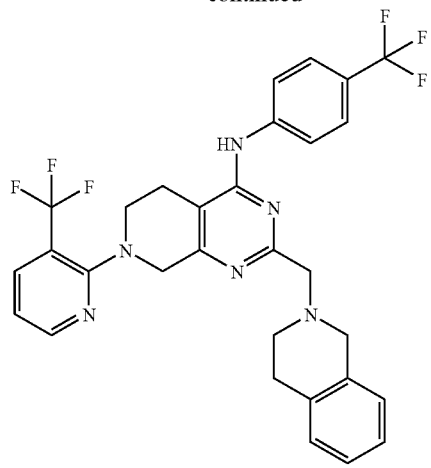
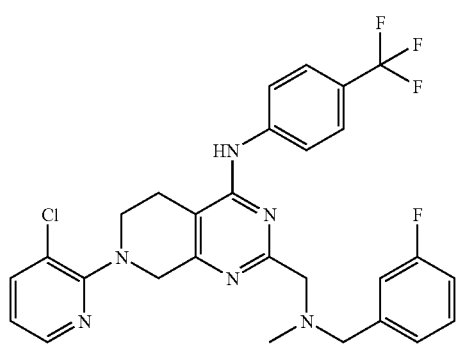
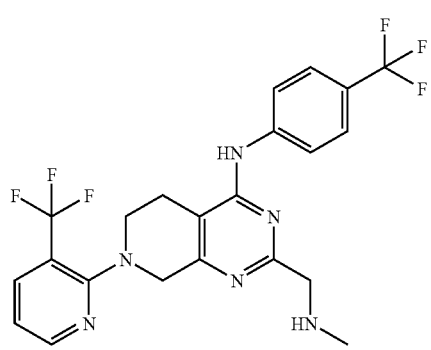
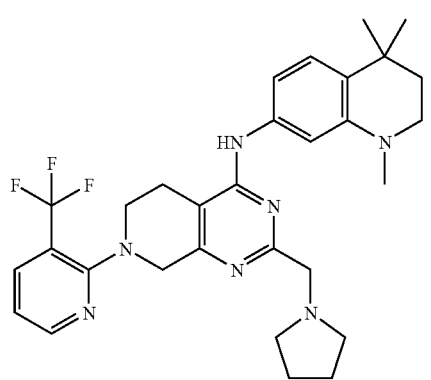
-continued
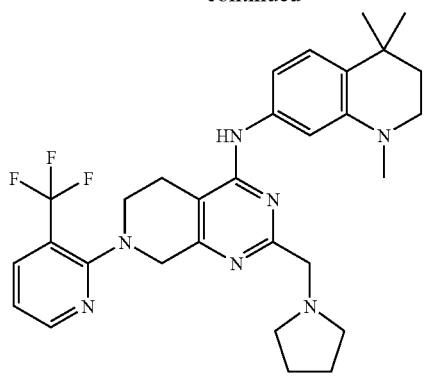
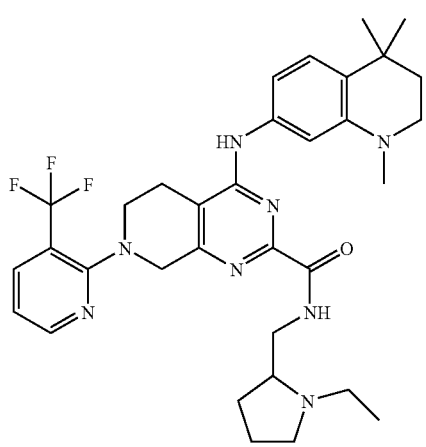
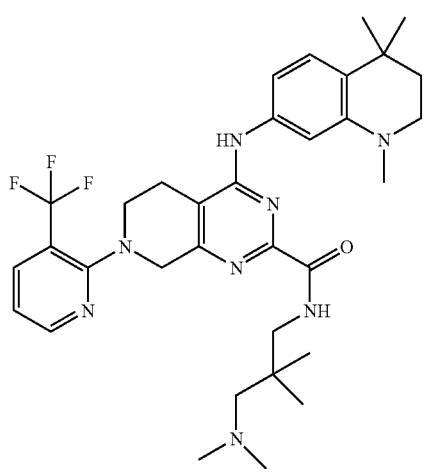
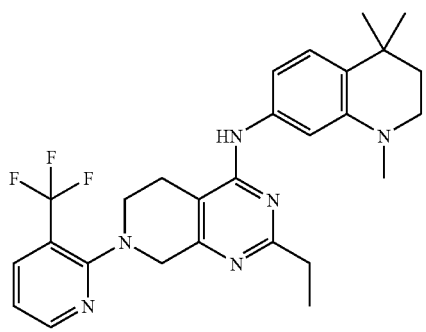

-continued
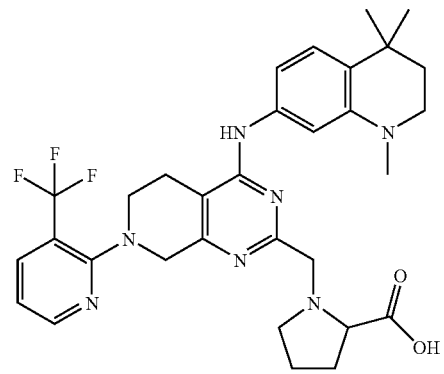
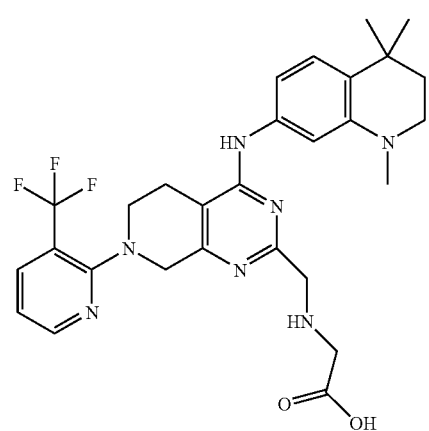
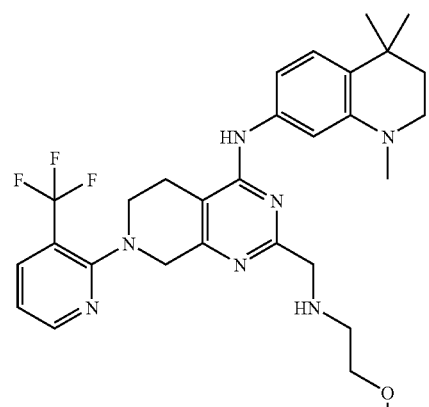
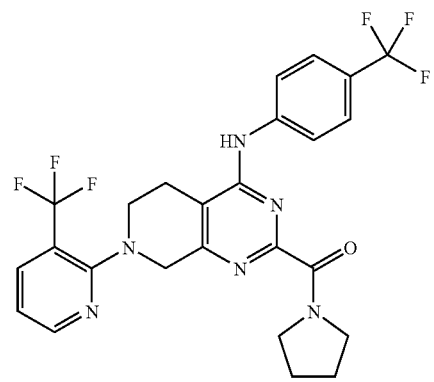
-continued
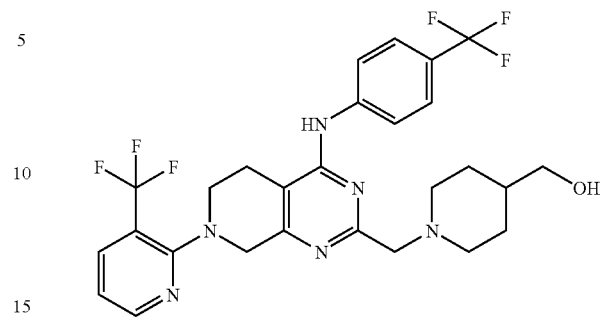
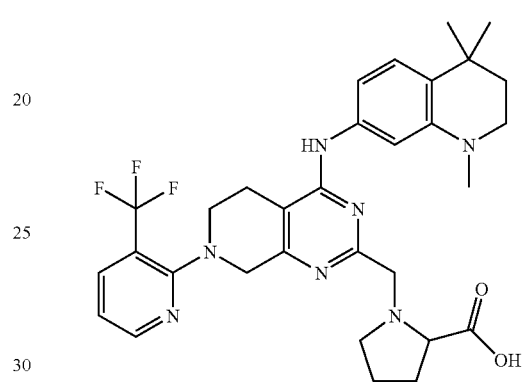
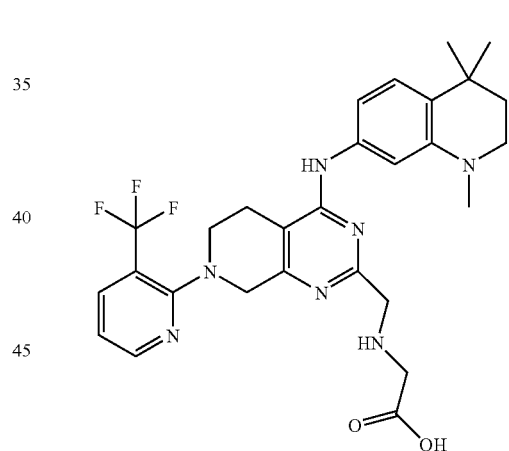
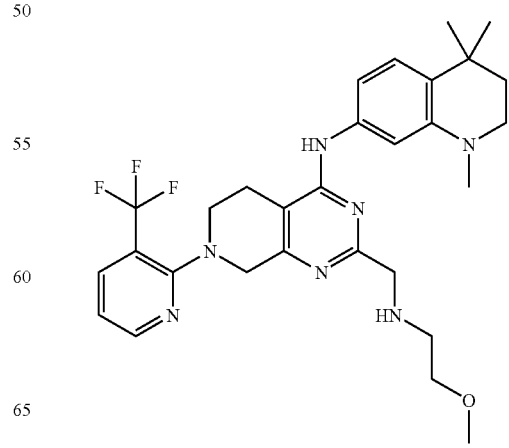

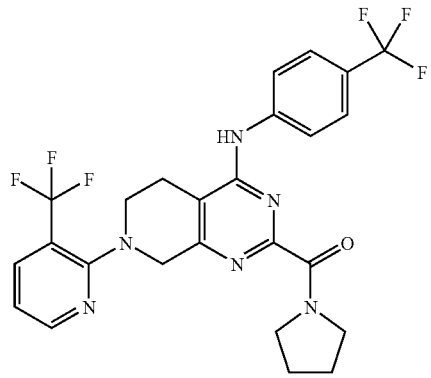
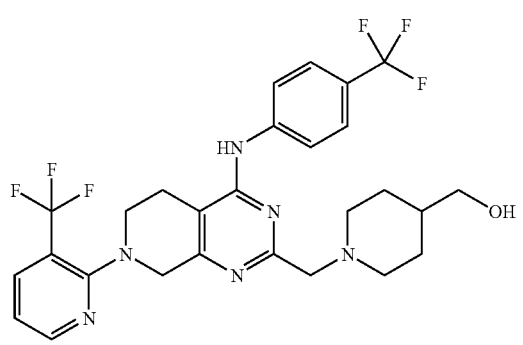
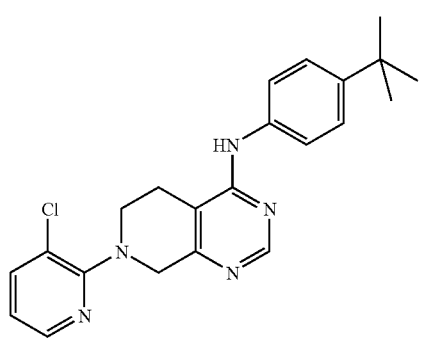
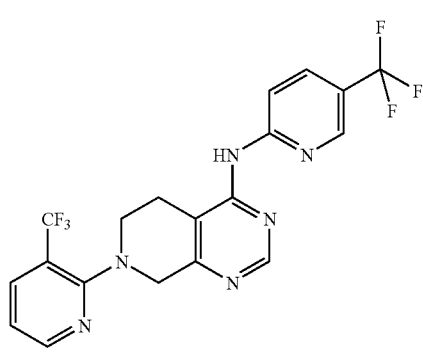
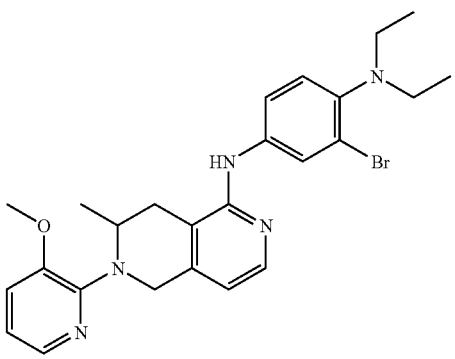
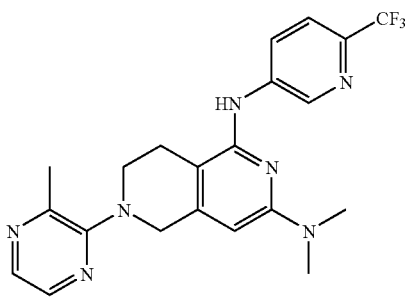
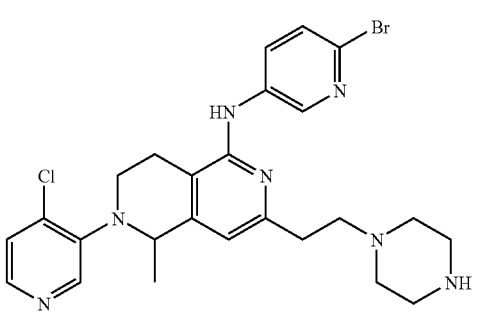
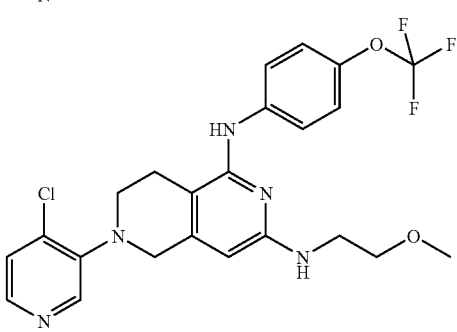
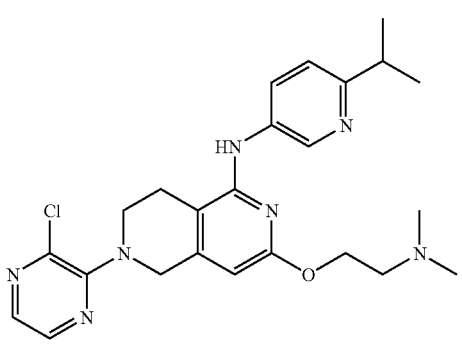

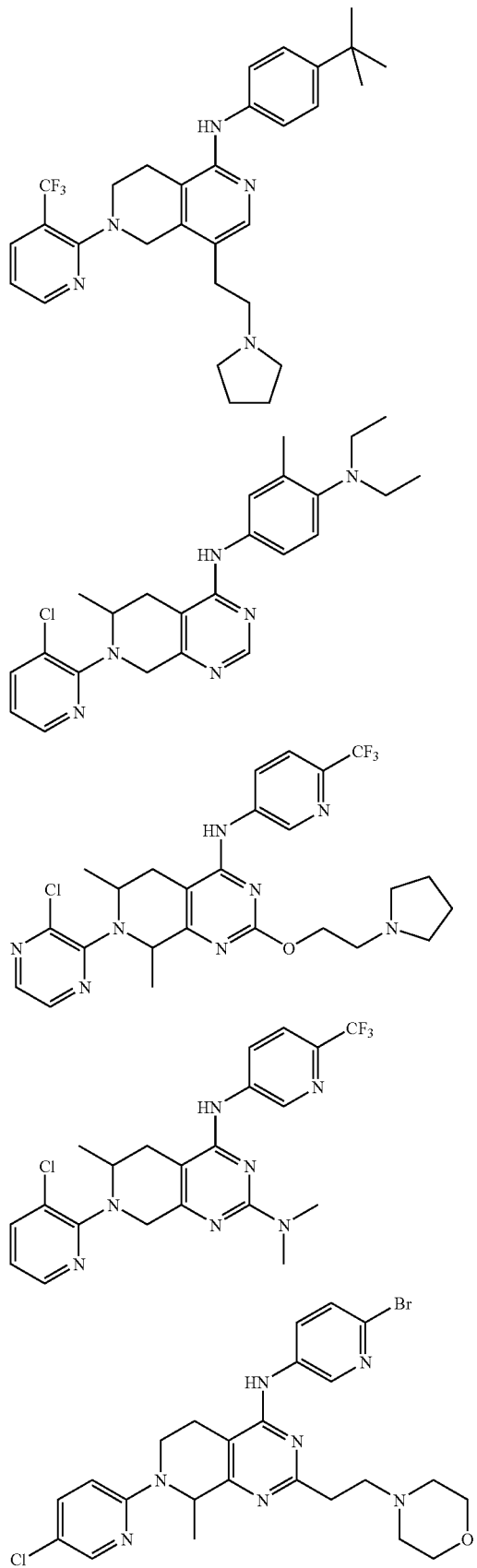
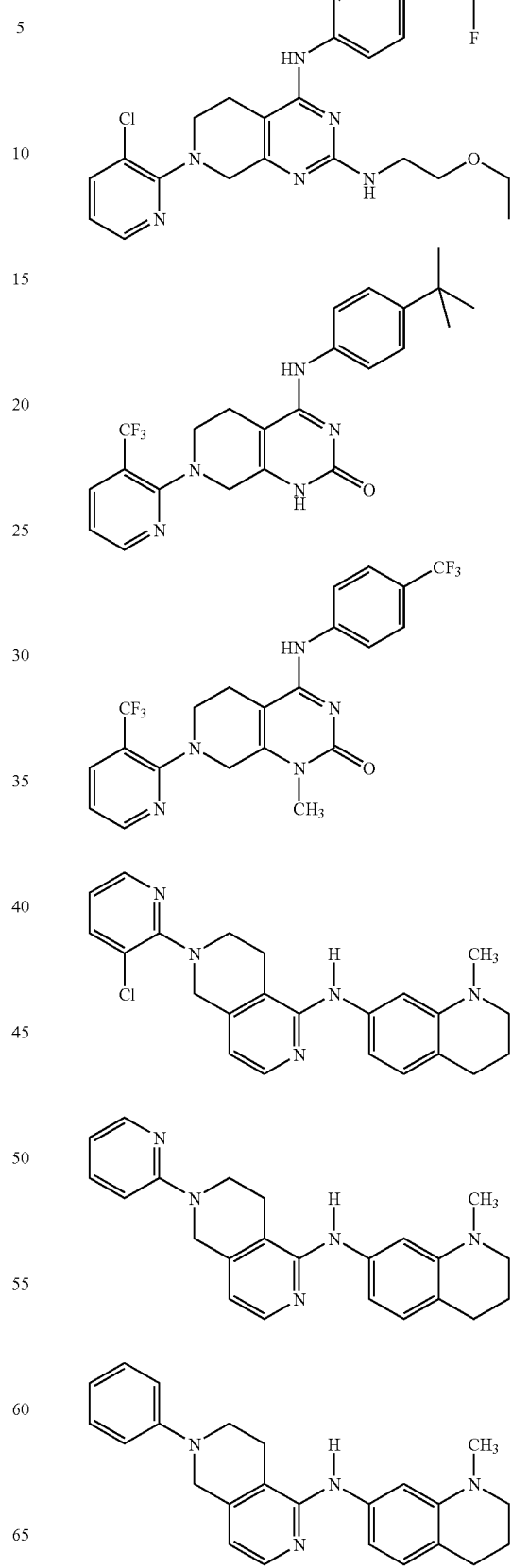

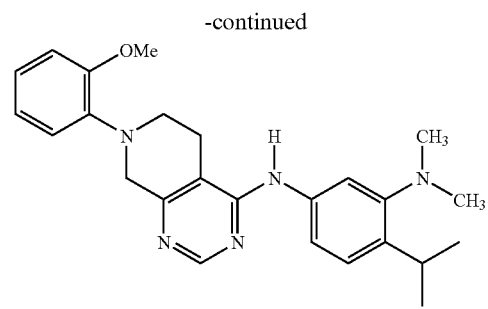
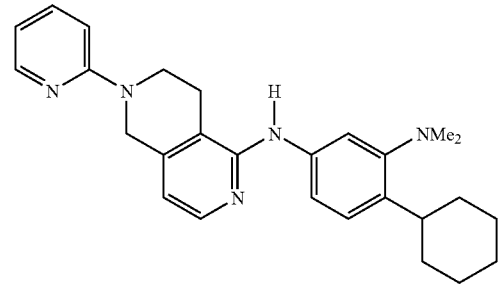
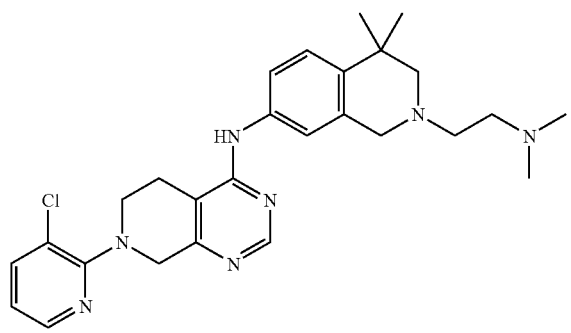
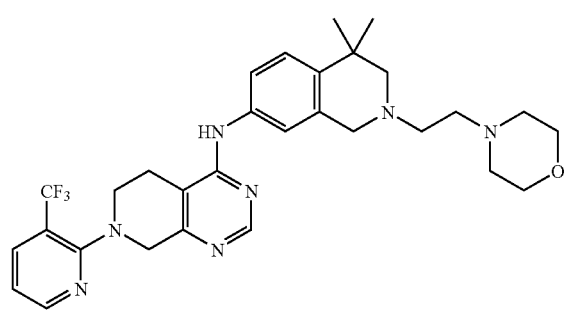
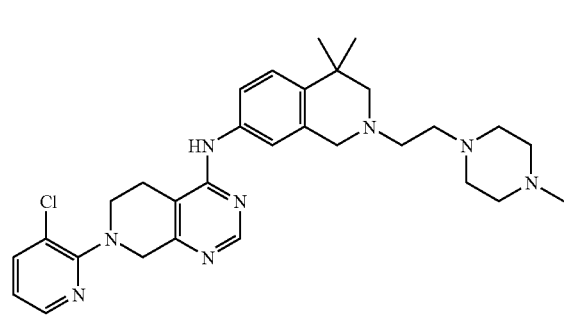
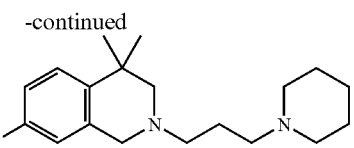
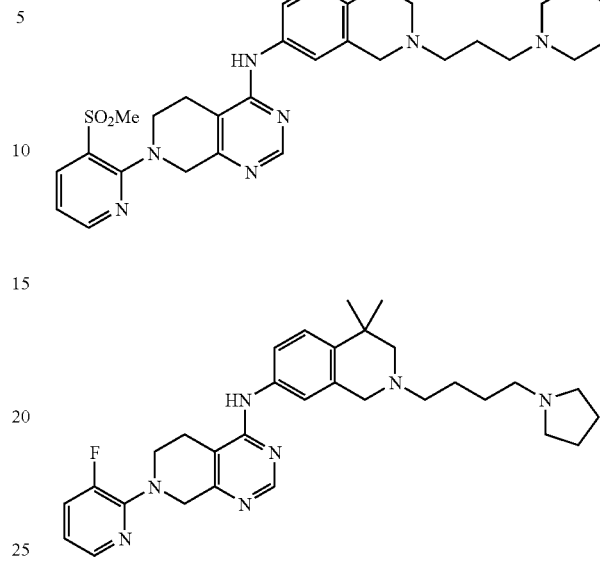
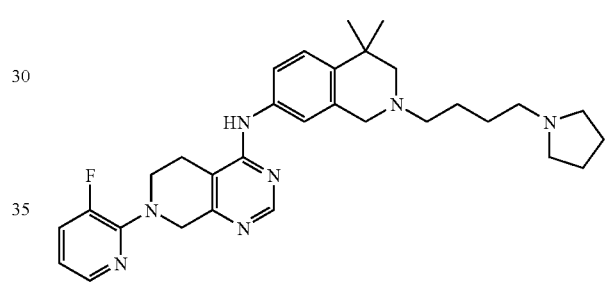
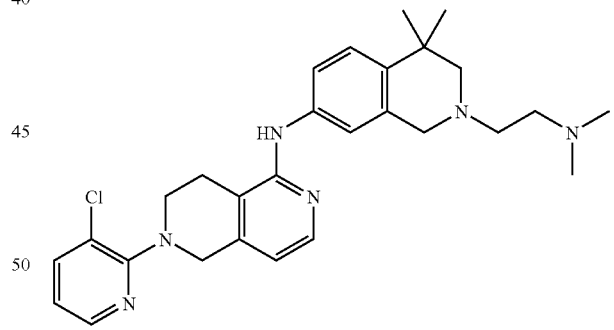
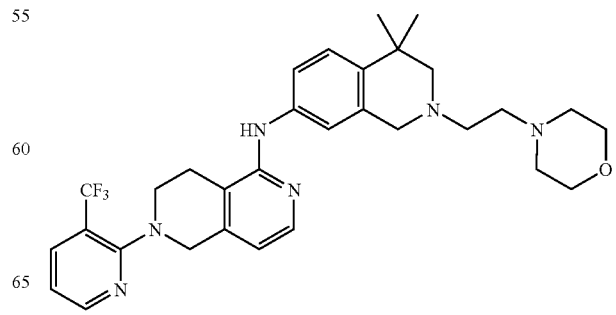

-continued
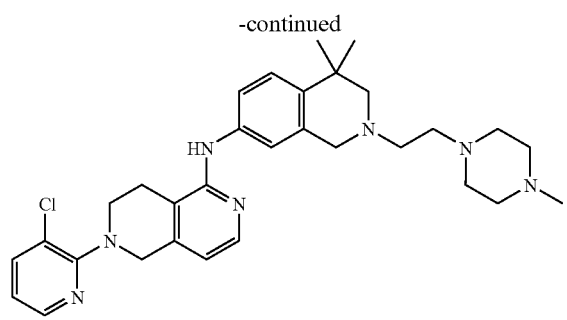
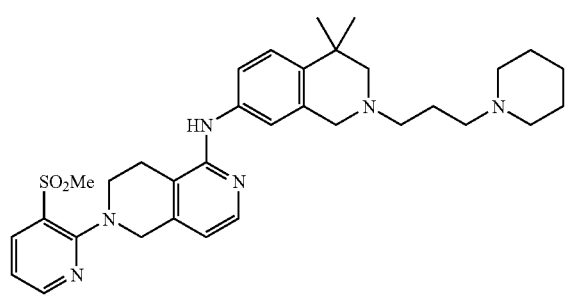
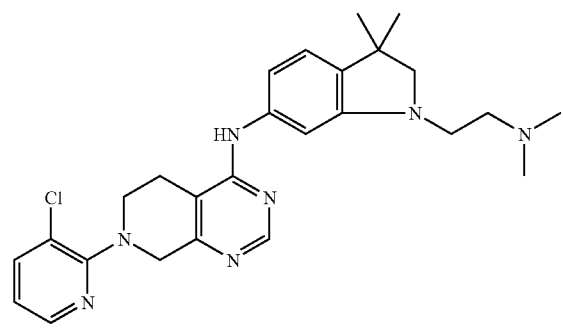
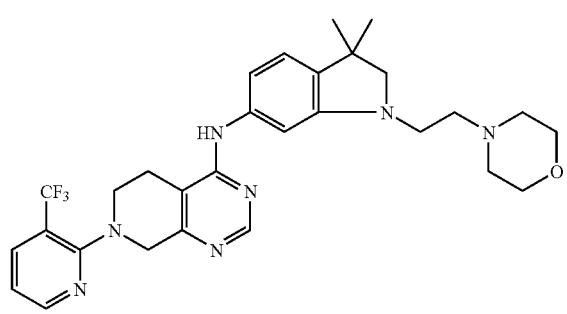
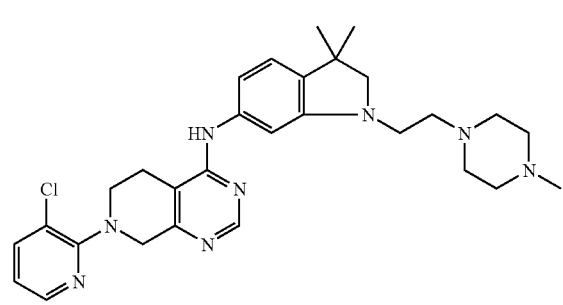
-continued
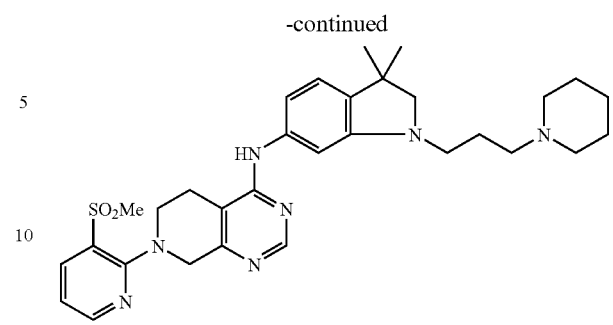
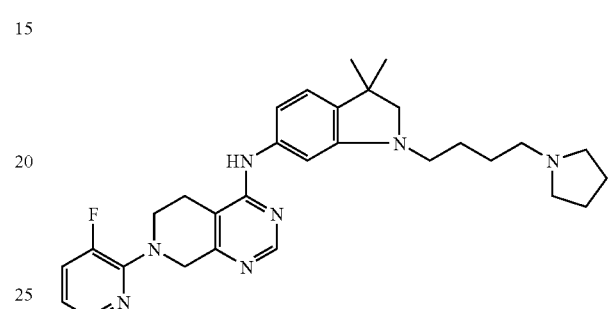
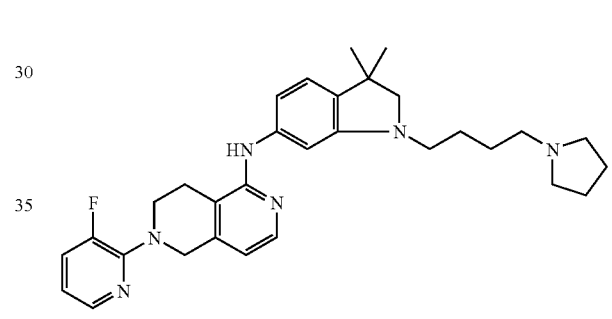
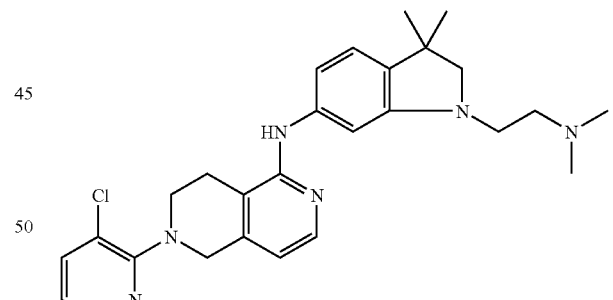
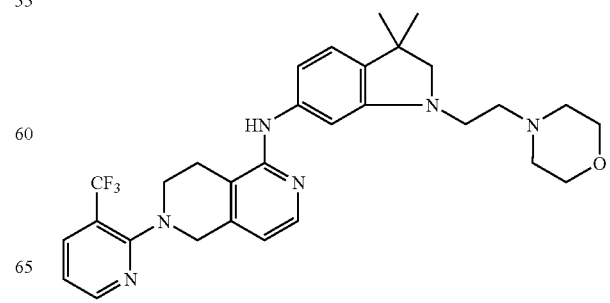

-continued
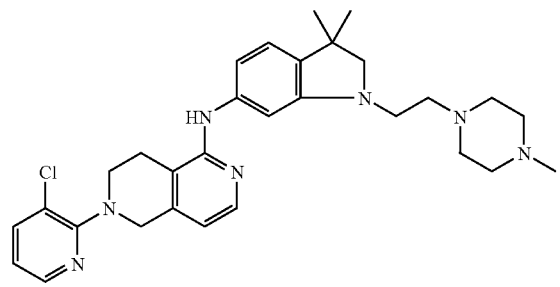
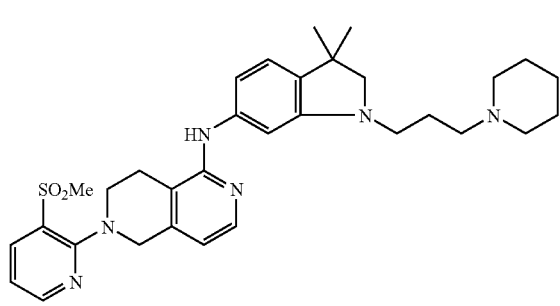
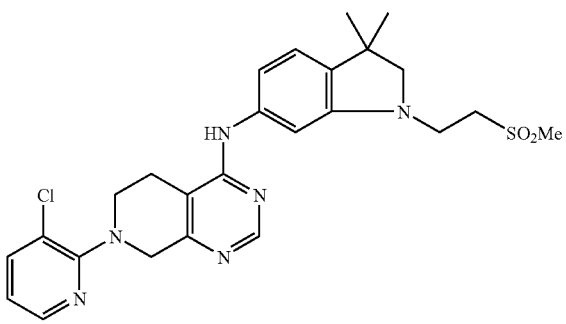
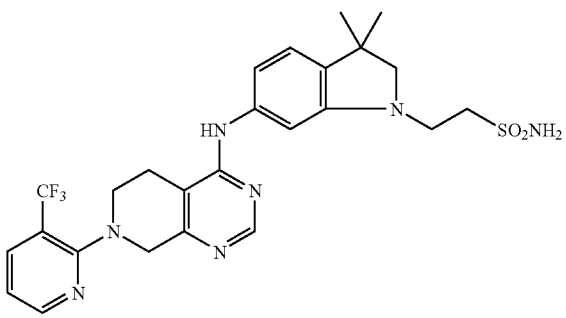
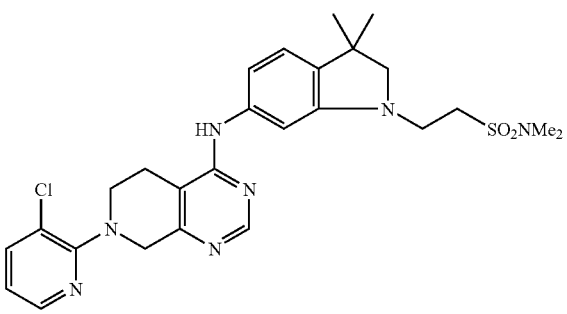
-continued
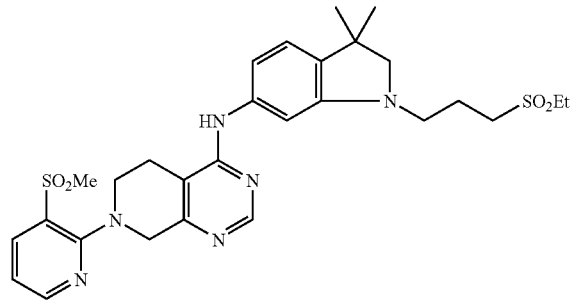
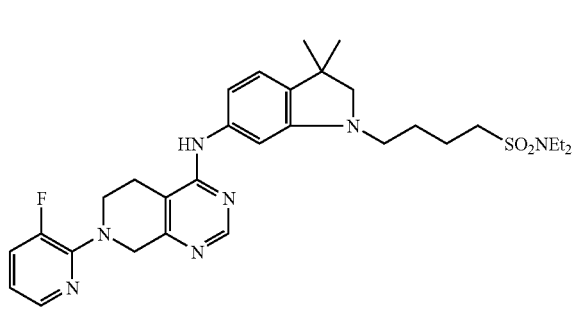
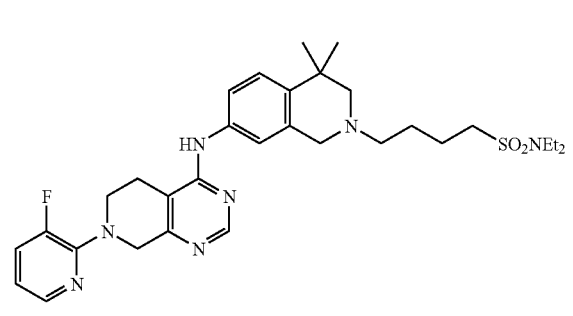
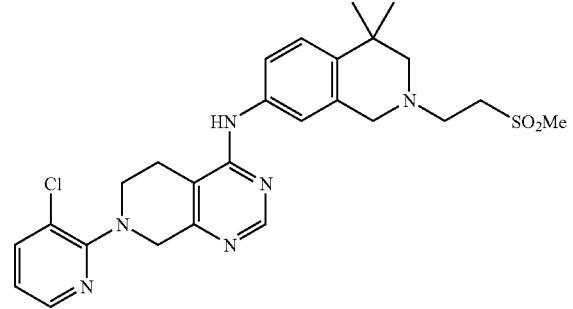
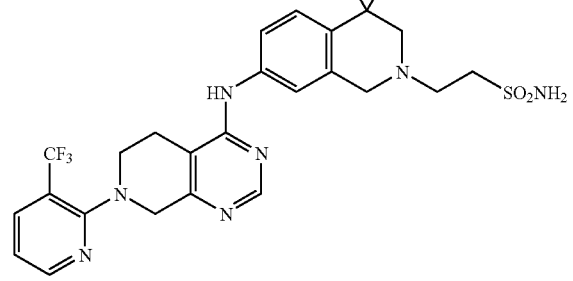

-continued
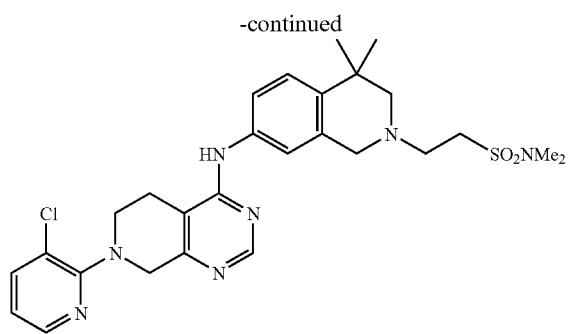
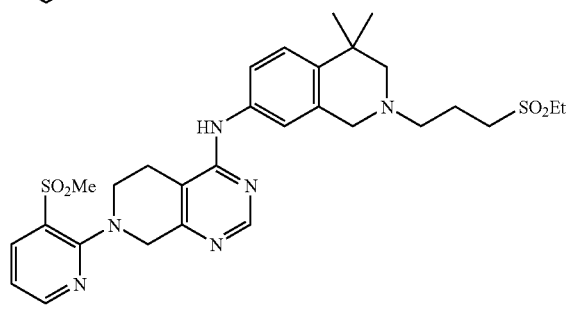
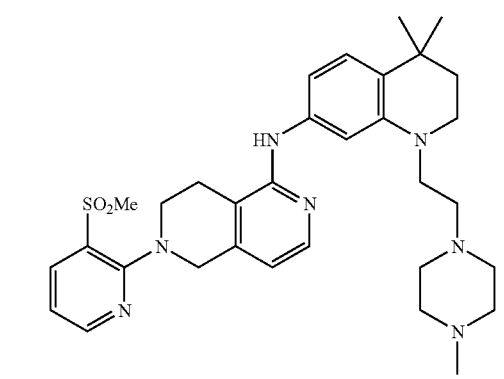
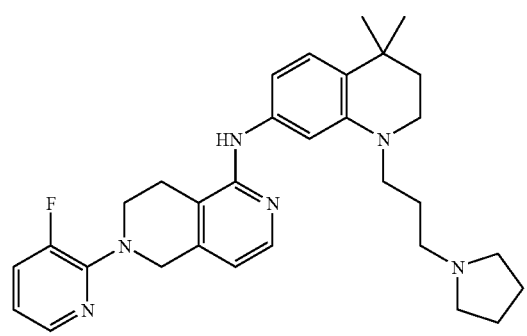
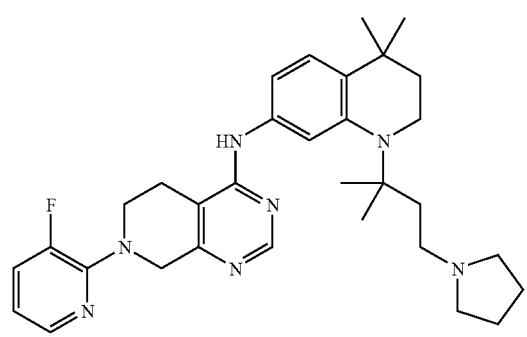
-continued
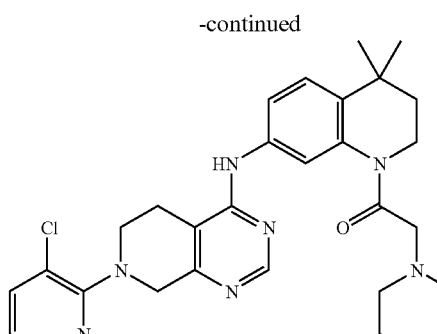
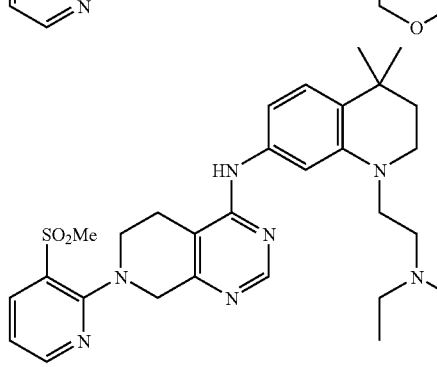
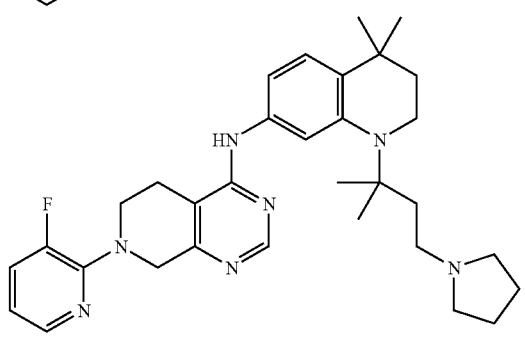
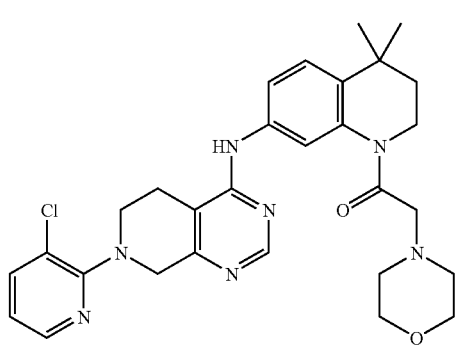
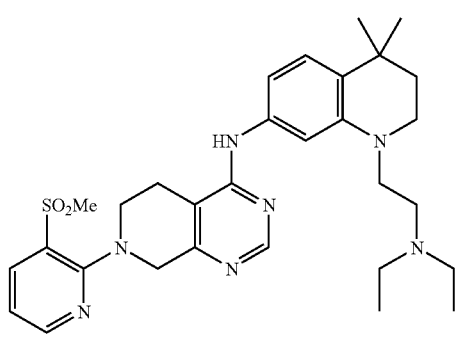

-continued
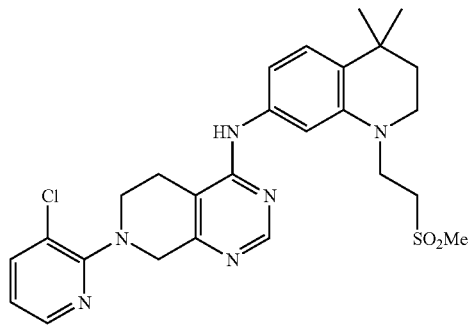
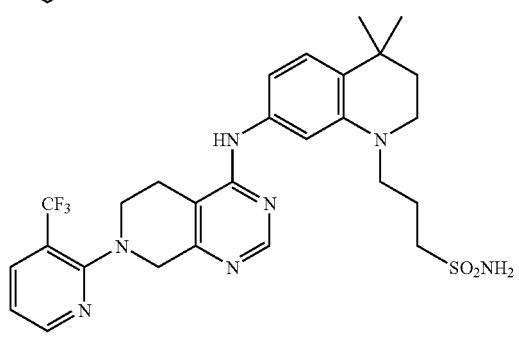
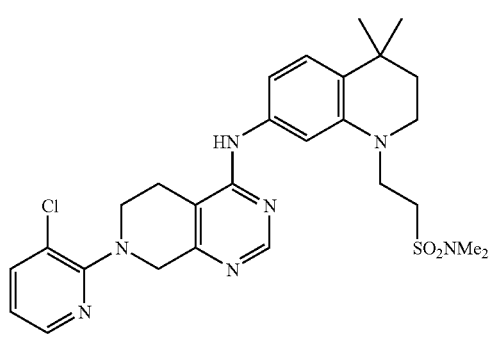
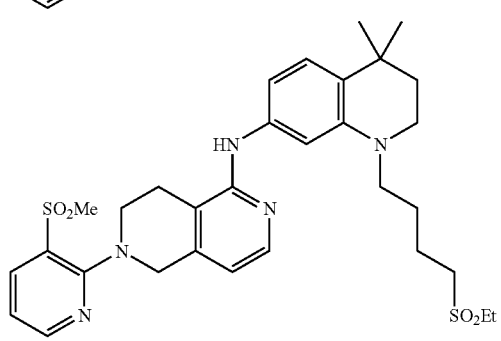
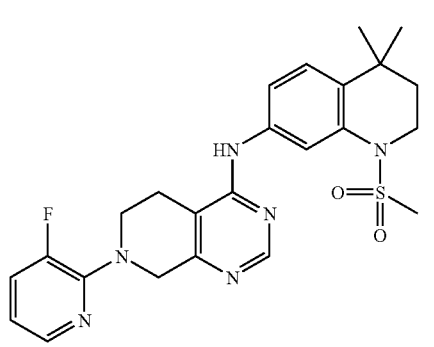
-continued
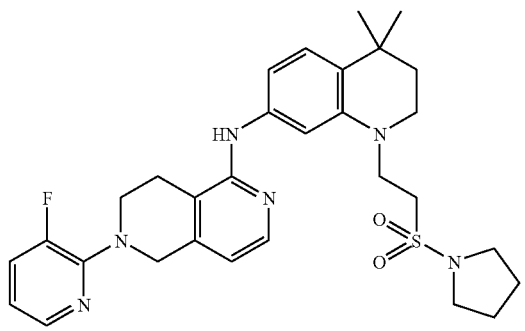
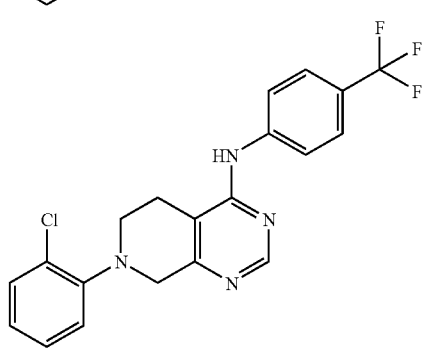
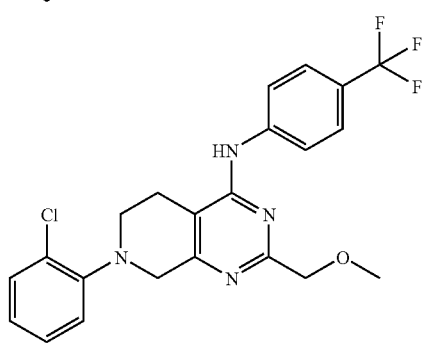
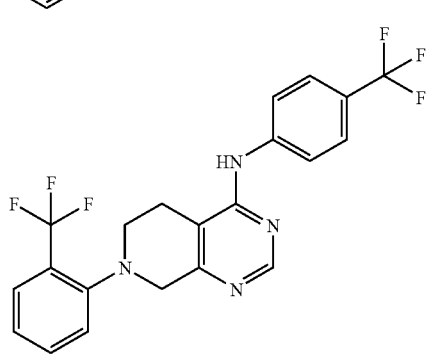
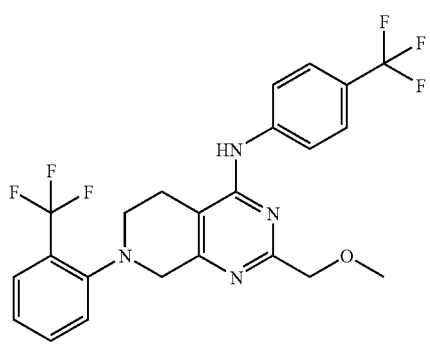

-continued
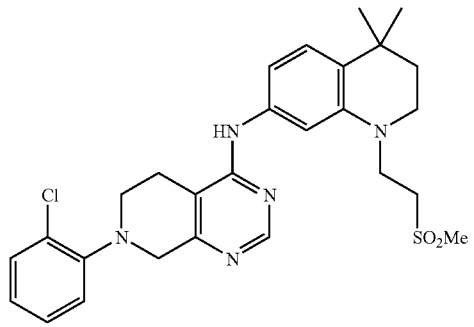
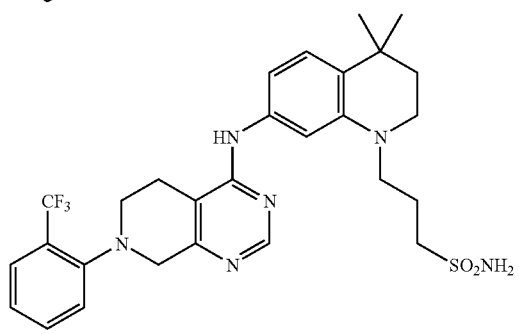
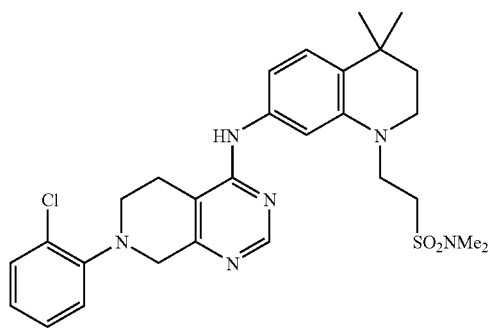
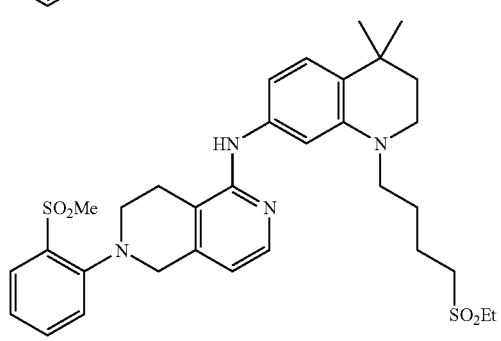
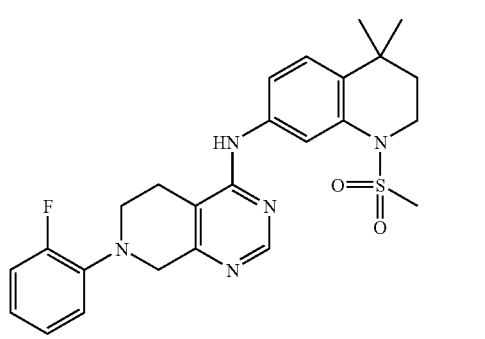
-continued
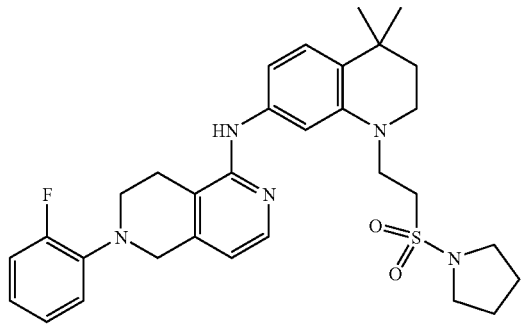
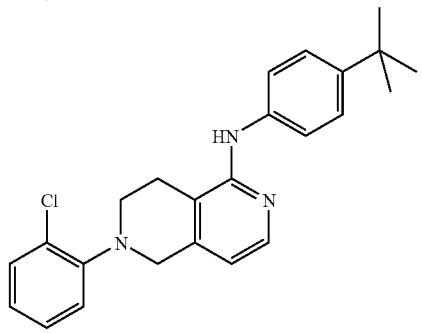
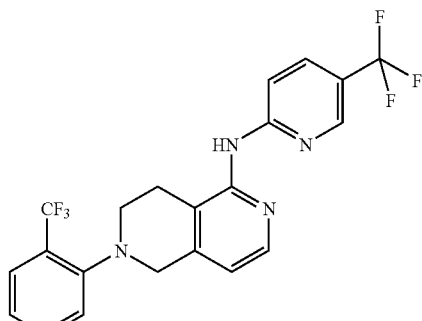
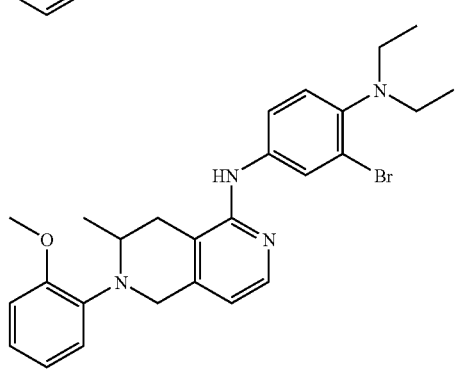
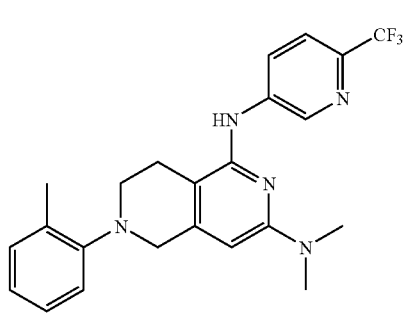

157 158
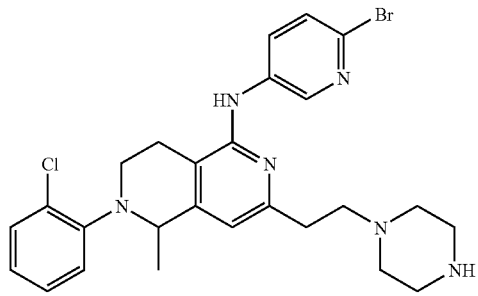
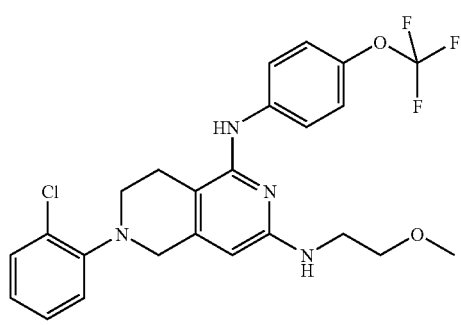
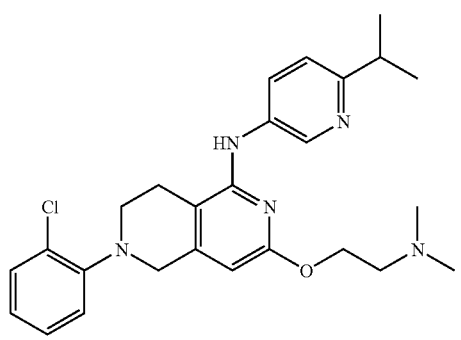
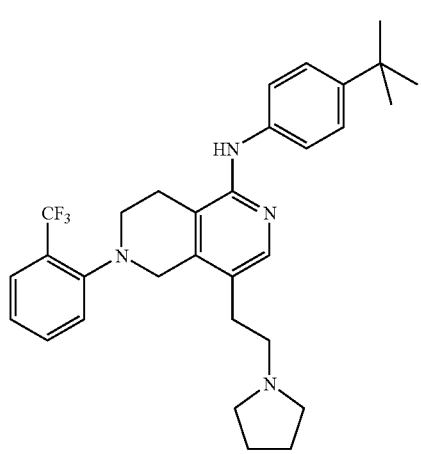
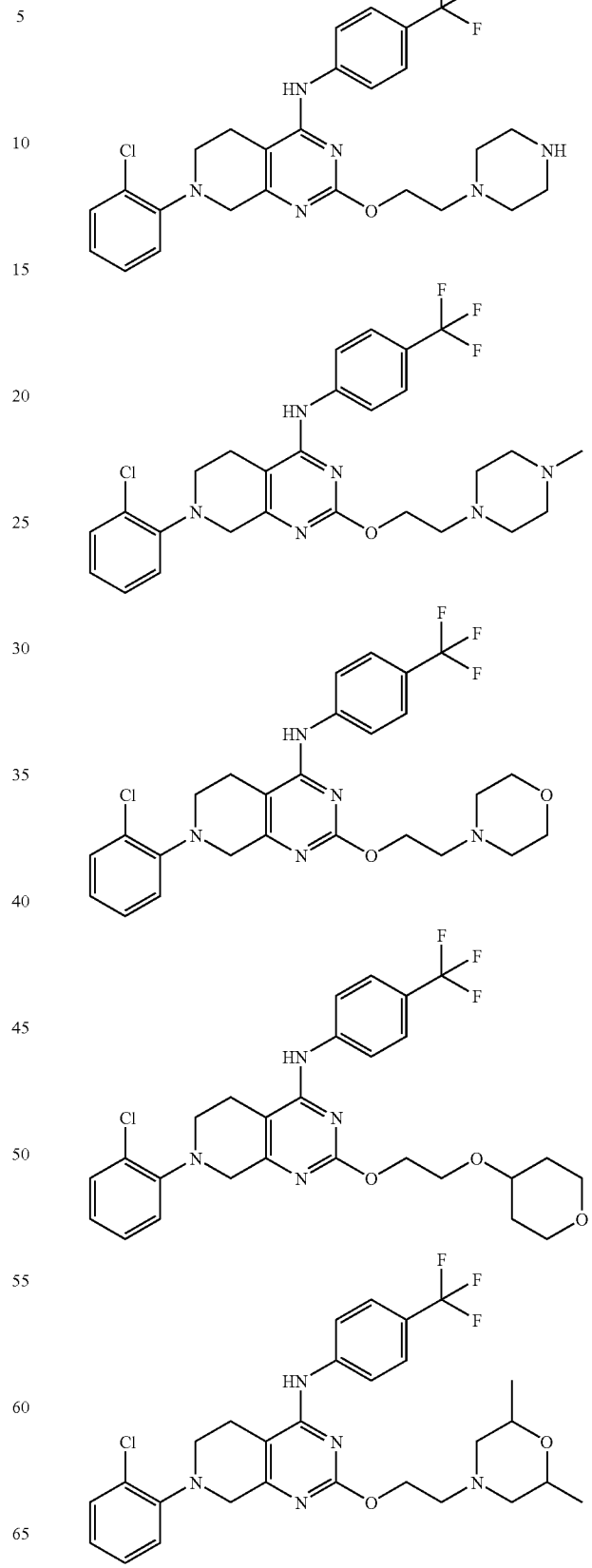

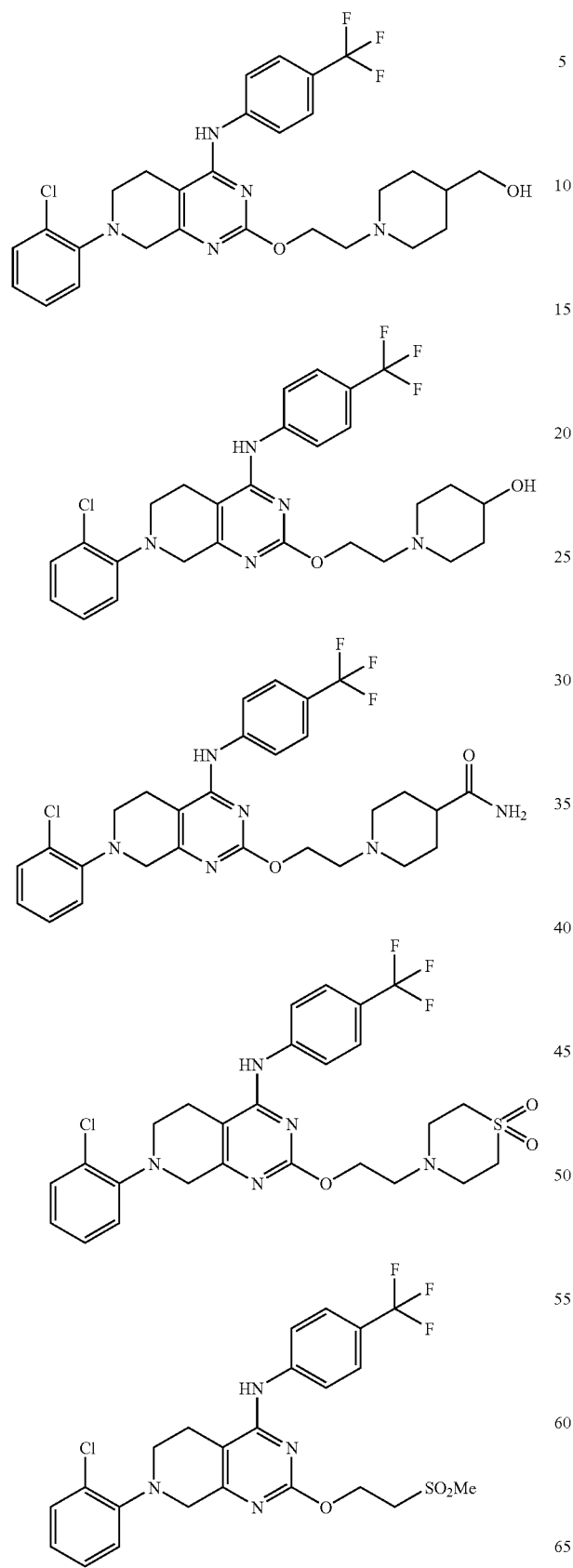
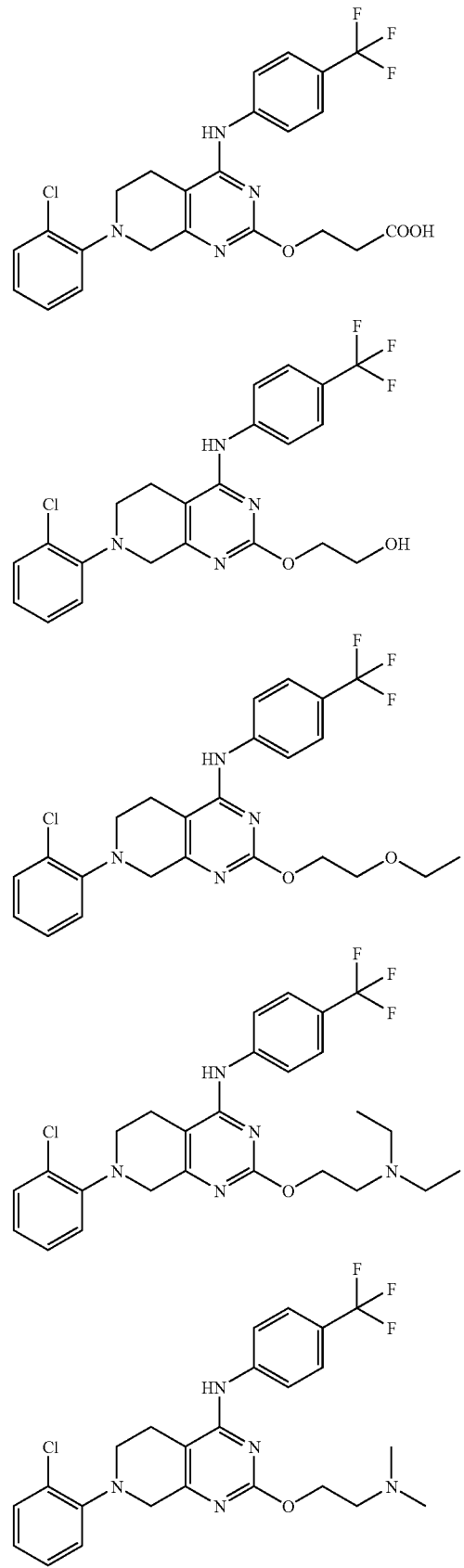

-continued

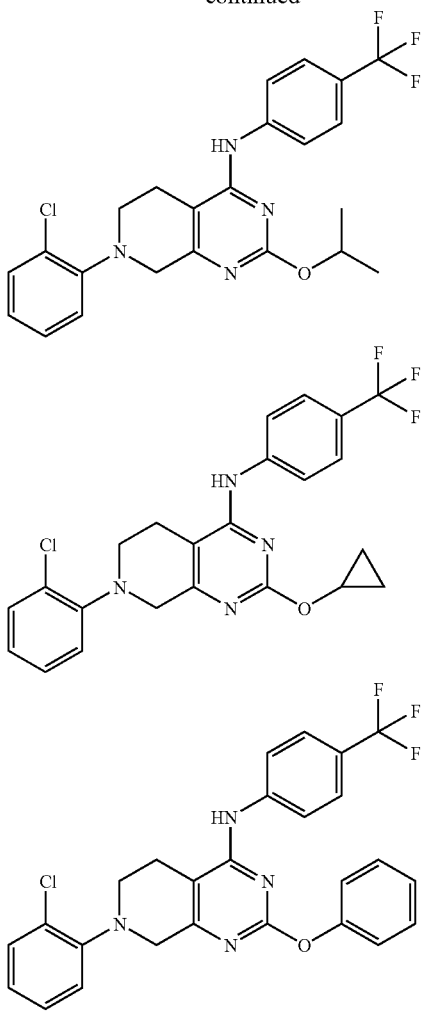

The following biological examples, Examples 80-84, are offered to illustrate the present invention and are not to be construed in any way as limiting its scope. In the examples below, all temperatures are in degrees Celsius (unless otherwise indicated).

Example 80

High Throughput Screening of VR1 Antagonists for Determination of In Vitro Efficacy Using a Calcium Imaging Assay VR1 protein is a heat-gated cation channel that exchanges about 10 calcium ions for every sodium ion resulting in neuronal membrane depolarization and elevated intracellular calcium ion levels. Therefore the functional activity of compounds at the VR1 receptor may be determined by measuring changes in intracellular calcium levels in 293 cells expressing capsaicin-insensitive VR1 receptor variants. A dual wavelength ratiometric dye, Fura2, was used as an indicator of relative levels of calcium ions in a 96 well format using a bench top scanning fluorometer with integrated fluidics and temperature control (Flex Station, Molecular Devices).

A dual wavelength ratiometric dye, Fura2, was used as an indicator of relative levels of [Ca2+] in a 96 well format using a bench top scanning fluorometer with integrated fluidics and temperature control (Flex Station, Molecular Devices).

HEK 293 cells expressing hVR1 were grown on PDL coated 96-well black-walled plates, in the presence of a DMEM medium containing 5% Penstrep, 5% Glutamax, 200 ug/mL Hygromycin, 5 µg/mL Blasticide and 10% heat inactivated FBS. Prior to assay, the cells were loaded with 5 µg/mL Fura2 in normal saline solution at 37° C. for 40 minutes. Cells were then washed with normal saline to remove the dye.

The assay consists of two stages; a pre-treatment phase followed by a treatment phase. In the pretreatment phase, 50 µl of a compound solution was added to the cells. Immediately following, 50 µl of the test compound in the presence of agonist (a saline solution plus 10 mM citric acid bufferd to pH 5.7 with HCl) was added. Fura2 was excited at 340 and 380 nM to indicate relative calcium concentration. Changes in wavelength measurements were made throughout the course of the experiment in 4 second intervals over a period of 3 minutes. The fluorescence ratio from the excitations at 340 nM and 380 nM was recorded for analysis. Responses were measured as peak fluorescence ratio after compound-agonist addition minus baseline fluorescence ratio prior to treatment and were calculated for each concentration tested using the SoftMaxPro software. Data was expressed as percentage inhibition calculated as follows:

$$\text{Percentage Inhibition} = \left[1 - \frac{(\text{Response of Compound with Agonist}) - (\text{Response of saline Control})}{(\text{Response of Agonist} - \text{Response of saline Control})}\right] \times 100$$

To establish the $IC_{50}$ of each compound, compounds were tested at concentrations ranging from 10 nM to 3.3 µM. A dose response curve was then determined, from which the $ID_{50}$ of each compound was calculated.

The relative strengths of the percentage inhibition values and the corresponding $IC_{50}$s are set forth in Table 1, below.

TABLE 1

| ID | MW | % Inhibition @ 1 µM | $IC_{50}$ (nM) |
|---|---|---|---|
| 1 | 405.8 | ++++ | *** |
| 3 | 393.9 | ++++ | **** |
| 4 | 427.5 | ++++ | **** |
| 5 | 438.0 | ++++ | **** |
| 6 | 471.5 | ++++ | **** |
| 8 | 437.6 | ++++ | *** |
| 9 | 449.5 | ++++ | *** |
| 10 | 463.5 | +++ | *** |
| 11 | 389.4 | ++++ | *** |
| 12 | 439.4 | ++++ | *** |
| 13 | 493.1 | ++ | |
| 14 | 447.5 | + | |
| 15 | 403.8 | +++ | *** |
| 16 | 477.5 | | * |
| 17 | 420.8 | ++++ | |
| 18 | 337.8 | + | * |
| 19 | 355.8 | + | * |
| 20 | 406.8 | ++++ | *** |
| 21 | 450.4 | +++ | *** |
| 22 | 469.9 | ++++ | **** |
| 23 | 513.5 | ++++ | *** |
| 24 | 451.9 | | *** |
| 26 | 404.8 | + | |
| 27 | 435.8 | | *** |

TABLE 1-continued

| ID | MW | % Inhibition @ 1 μM | IC$_{50}$ (nM) |
|---|---|---|---|
| 28 | 440.0 | ++++ | **** |
| 29 | 423.9 | ++++ | **** |
| 33 | 534.0 | + | |
| 34 | 448.9 | + | *** |
| 35 | 449.9 | ++++ | |
| 36 | 374.4 | ++ | |
| 37 | 430.8 | ++++ | |
| 38 | 367.5 | | *** |
| 39 | 365.9 | ++++ | *** |
| 40 | 400.3 | +++ | * |
| 41 | 386.3 | ++ | *** |
| 42 | 406.7 | ++ | |
| 44 | 370.4 | + | * |
| 45 | 384.4 | ++++ | **** |
| 46 | 384.4 | + | * |
| 47 | 384.4 | ++ | ** |
| 48 | 449.9 | ++++ | *** |
| 49 | 394.9 | ++++ | |
| 50 | 433.9 | + | |
| 51 | 379.9 | + | |
| 52 | 381.9 | + | |
| 56 | 404.9 | ++++ | **** |
| 57 | 421.8 | + | * |
| 58 | 448.9 | | * |
| 59 | 420.9 | | *** |
| 60 | 435.0 | | **** |
| 61 | 463.0 | | * |
| 62 | 420.9 | | * |
| 63 | 495.5 | +++ | *** |
| 64 | 493.5 | +++ | ** |
| 65 | 408.8 | +++ | *** |
| 66 | 493.9 | ++++ | **** |
| 67 | 420.9 | | * |
| 68 | 448.9 | +++ | ** |
| 69 | 406.9 | ++++ | *** |
| 70 | 420.9 | ++++ | **** |
| 71 | 429.4 | + | * |
| 72 | 401.4 | + | * |
| 73 | 401.4 | + | * |
| 74 | 395.8 | ++ | * |
| 75 | 479.8 | + | * |
| 76 | 503.4 | ++++ | **** |
| 77 | 437.4 | ++++ | *** |
| 78 | 421.8 | ++++ | **** |
| 79 | 455.4 | ++++ | **** |

"+" compound exhibited 0-25% inhibition of calcium ion influx induced by proton stimulation.
"++" compound exhibited 26-50% inhibition of calcium ion influx induced by proton stimulation.
"+++" compound exhibited 51-75% inhibition of calcium ion influx induced by proton stimulation.
"++++" compound exhibited 76% or greater inhibition of calcium ion influx induced by proton stimulation.
"****" compound exhibited IC$_{50}$ values of <100 nM.
"***" compound exhibited IC$_{50}$ values of 101-500 nM.
"**" compound exhibited IC$_{50}$ values of 501-1000 nM.
"*" compound exhibited IC$_{50}$ values of >1000 nM.

For purpose of Table 1, the activity of each compound is expressed as follows:

Example 81

Two-electrode Voltage Clamp Recording Using the Opus Express (Axon Instruments/Molecular Devices Corporation)

Oocyte Preparation

Xenopus ovaries obtained from NASCO were isolated by enzymatic dissociation using collagenase (Worthington, 2 mg/ml). Oocytes were then individually injected with HsVR1 RNA (0.5 μg/μl). Injected oocytes are stored in standard oocyte incubation solution, ND96, containing 96 mM NaCl, 2 mM KCl, 1 mM MgCl$_2$, 0.3 mM CaCl$_2$ and 50 g/ml Gentamicin at 16° C. Capsaicin induced VR1 current is observed in oocytes 4-5 days after injection.

Eight oocytes are placed in the recording chambers. Each oocyte is impaled by 2 glass electrodes having resistances of 0.5 to 1 MOhm when filled with a 3 M KCl solution. Electrode advancement and oocyte impalement are under software control (OpusXpress 1.1, Axon Instruments).

VR1 expression in the oocytes is verified using 250 nM capsaicin. Test solution delivery to the oocytes during the experiment is also under software control. The solutions are prepared in 96 well plates and robotically pipetted into the oocyte recording chambers by an 8 channel pipetter.

Oocytes are exposed to several 250 μl applications of 250 nM capsaicin until a stable current amplitude is obtained with each application.

A set of 96 well plates containing the test solutions is prepared so that the sequence of solution application to the oocyte is as follows: 250 μls of 250 nM capsaicin is followed by a several minute wash with standard oocyte saline. 1 ml of the test compound is then added at a particular test concentration, followed immediately by 250 μl of the compound at the same concentration plus 250 nM capsaicin.

The capsaicin induced VR1 current is recorded in the presence and absence of test compound for each concentration. The standard test concentrations range from 0.3 to 2000 nM.

Quantitative measurement of VR1 current block was carried out by calculating the area under the curve described by the inward current. The resulting numbers for capsaicin induced currents in the presence of increasing compound concentration are normalized to the maximum current obtained. These points are then plotted on a logarithmic scale and fitted by a Hill function. The IC$_{50}$ values for each compound tested were then calculated from the resulting Hill fit.

All compounds that inhibited capsaicin induced current greater than 50% were considered positives. The data obtained for compounds tested in this assay are set forth in Table 2, below. The IC$_{50}$ dose response data for Compound 1 are also presented in FIG. 1.

TABLE 2

| Compound ID | MW | EPHYS IC$_{50}$, nM |
|---|---|---|
| 1 | 405.8 | *** |
| 3 | 393.9 | **** |
| 5 | 438.0 | **** |
| 8 | 437.6 | *** |
| 9 | 449.5 | *** |
| 10 | 463.5 | *** |
| 12 | 439.3 | **** |
| 20 | 406.8 | *** |
| 22 | 469.9 | **** |
| 23 | 513.5 | *** |
| 26 | 404.8 | * |
| 28 | 440.0 | **** |
| 29 | 424.0 | **** |
| 33 | 534.0 | ** |
| 34 | 448.9 | ** |
| 35 | 449.9 | *** |
| 37 | 430.8 | *** |
| 39 | 365.9 | * |
| 45 | 384.4 | **** |
| 46 | 384.4 | ** |

TABLE 2-continued

| Compound ID | MW | EPHYS IC$_{50}$, nM |
|---|---|---|
| 48 | 449.9 | **** |
| 64 | 493.5 | *** |

"****" compound exhibited IC$_{50}$ values of <100 nM.
"***" compound exhibited IC$_{50}$ values of 101-500 nM.
"**" compound exhibited IC$_{50}$ values of 501-1000 nM.
"*" compound exhibited IC$_{50}$ values of >1000 nM.

For purposes of Table 2, the activity of each compound is expressed as follows:

Example 82

Thermal Hyperalgesia

Sprague-Dawley male rats obtained from Charles River, San Diego, Calif. were purchased at 150-175 g, and held for at least one week before testing. Pain was induced by injecting 100 μl of 2% carrageenan in 0.9% saline sub-Q into the right ventral hindpaw while the animals were under isofluorane anesthesia. Animals were then dosed one hour after with a concentration of 30 mg/kg of Compound 1. Two hours later, after acclimatizing in testing chambers for 20-30 minutes, animals were tested on both hindpaws for latency of paw withdrawal using a thermal testing apparatus. 2-3 trials were conducted with 10 minutes between trials. As demonstrated in FIG. 2, a dose of Compound 1 at 30 mg/kg significantly increased latency of paw withdrawal demonstrating reversal of thermal hyperalagesia. The figure depicts the time in seconds until animals withdraw from thermal stimulation at baseline and two hours after administration of delivery vehicle, control compound, and the dose of 30 mg/kg of Compound 1.

Example 83

Pharmacokinetic Profile

The pharmacokinetic profile of Compound 1 was evaluated following intravenous and oral administration in rats. Sprague-Dawley male rats obtained from Charles River, San Diego, Calif. were acclimated for 24 hours.

Compounds of this invention were formulated at a concentration of 0.5 mg/mL for IV administration at a 1 mg/kg dose and 1 mg/mL for oral administration at a 5 mg/kg dose. All animals were weighed before dosing. The body weight was used to calculate the actual dose for each animal. The intravenous dose was administered through the jugular vein catheter in less than 1 minute. The oral dose volume was 1.5 mL for all PO rats administered through oral lavage.

For IV dosing, blood samples were collected using a pre-heparinized syringe via the carotid artery catheter before dosing and at t=2, 5, 15, 30, 60, 120, 180, 360, and 480 minutes post dosing. For PO dosing, blood samples were collected using a pre-heparinized syringe via the carotid artery catheter before dosing and at t=5, 15, 30, 60, 120, 180, 360, and 480 minutes post dosing. 250 uL of blood was obtained at each time point from each animal. Equal volumes of 0.9% normal saline were replaced to prevent dehydration. The whole blood samples were maintained on ice until centrifugation. Blood samples were centrifuged at 14,000 rpm for 10 minutes at 4° C., and the upper plasma layer was transferred into a clean vial and store at −80° C.

The plasma was analyzed. The rat PK properties are set forth in Table 3, below.

TABLE 3

| Compound ID | MW | Cmax (ng/mL) | Tmax (hr) | F (%) | Vd (L/Kg) | Cls (L/hrKg) | T/2 (hr) |
|---|---|---|---|---|---|---|---|
| 1 | 405.81 | 1379 | 1.01 | 37 | 1.28 | 0.34 | 2.52 |
| 9 | 449.46 | 156 | 1.67 | 47.9 | 13 | 1.99 | 4.37 |
| 37 | 430.82 | 49.43 | 3.33 | 17.9 | 12.4 | 4.02 | 2.15 |

Example 84

Analysis of Plasma Protein Binding

Membranes from Harvard/Amika with a molecular weight cutoff of 5,000 were rinsed with dH$_2$O then placed in pH 7.4 PBS supplied by Gibco. The membranes were allowed to soak for 1 hour. A stock of the test article was pooled with Warfarin, Atropine at 2 mM in DMSO. The test article was then dosed into human plasma in sodium citrate, Rat Plasma, and Mouse Plasma to a final 10 μM concentration (0.5% DMSO v/v).

The pre-soaked membranes were then placed into dialysis chambers. 500 μL of PBS was added to one side of the chamber, and 500 μL of the Matrix containing the test article was added to the other side of the chamber. The chambers were then placed into an enclosed, heated rocker, which was pre-warmed to 37° C. and allowed to reach equilibrium for at least 22 hours. After 22 hours both sides were sampled. 100 μL of the donor side was added to 500 μL of PBS. 100 μL of the PBS side was added to 20 μL of fresh matrix. Samples then were crashed with 1:1 Acetonitrile and centrifuged at 10,000 RPM for 10 minutes. 100 μL of supernatant was placed into LC/MS vials for analysis.

Standards were prepared in a 1:5 plasma:PBS mixture at 5, 1.5, 0.5, 0.15, 0.05, 0.015 and 0.005 μM concentrations. The samples and standards were placed into HPLC vials and assayed by LC/MS. Protein binding values were calculated as follows:

% Bound=[(Concentration in Donor−Concentration in Receiver)/(Concentration in Donor)]×100.

% Recovery=[(Concentration in donor+Concentration in Receiver)]/(Concentration in Normal Initial)]×100

From the above, Compound 1 demonstrated rat and human plasma protein binding of more than 99.9%.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

What is claimed is:

1. An amine compound of the formula 1:

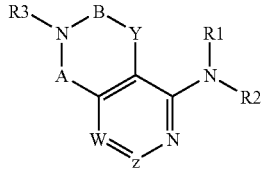

wherein

A, B and Y are $CR^{2'}R^{2'}$;

W is N; and Z is $CR^4$;

$R^1$ is selected from phenyl, unsubstituted or substituted with alkyl, substituted alkyl, acyl, substituted acyl, substituted or unsubstituted alkylamino, substituted or unsubstituted alkythio, substituted or unsubstituted alkoxy, alkoxycarbonyl, substituted alkoxycarbonyl, amino, substituted or unsubstituted sulfo, substituted or unsubstituted sulfonyl, substituted or unsubstituted sulfanyl, substituted or unsubstituted aminosulfonyl, substituted or unsubstituted dihydroxyphosphoryl, substituted or unsubstituted aminodihydroxyphosphoryl, azido, carboxy, cyano, substituted or unsubstituted cycloalkyl, substituted or unsubstituted cycloheteroalkyl, substituted or unsubstituted dialkylamino, halo, substituted or unsubstituted heteroalkyl, hydroxy, nitro, and thiol; or $R^1$ is selected from substituted or unsubstituted pyridyl, substituted or unsubstituted indolyl, substituted or unsubstituted benzimidazolyl, substituted or unsubstituted benzo(1,4)dioxinyl, substituted or unsubstituted indazolyl, substituted or unsubstituted tetrahydroquinoline, and substituted or unsubstituted tetrahydroisoquinoline;

$R^2$ is H; and each $R^{2'}$ is independently selected from hydrogen, substituted or unsubstituted $C_1$-$C_6$ alkyl;

$R^3$ is selected from substituted or unsubstituted phenyl;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, amino, substituted or unsubstituted sulfo, substituted or unsubstituted sulfonyl, substituted or unsubstituted sulfanyl, substituted or unsubstituted aminosulfonyl, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, substituted or unsubstituted heteroalkyl, hydroxy, nitro, and thiol;

however, provided that when A, B and Y all are $CH_2$s, W is N, Z is $CR^4$, then $R^4$ is other than alkylamino, dialkylamino or alkylarylamino;

or a pharmaceutically acceptable salt, or solvate or stereoisomers or tautomers thereof.

2. An amine compound of the formula 1:

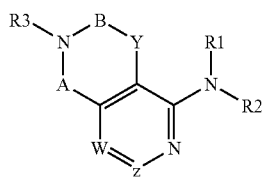

wherein

A, B and Y are $CR_2R^{2'}$;

W is N; and Z is $CR^4$;

$R^1$ is selected from phenyl, unsubstituted or substituted with alkyl, substituted alkyl, acyl, substituted acyl, substituted or unsubstituted alkylamino, substituted or unsubstituted alkythio, substituted or unsubstituted alkoxy, alkoxycarbonyl, substituted alkoxycarbonyl, amino, substituted or unsubstituted sulfo, substituted or unsubstituted sulfonyl, substituted or unsubstituted sulfanyl, substituted or unsubstituted aminosulfonyl, substituted or unsubstituted dihydroxyphosphoryl, substituted or unsubstituted aminodihydroxyphosphoryl, azido, carboxy, cyano, substituted or unsubstituted cycloalkyl, substituted or unsubstituted cycloheteroalkyl, substituted or unsubstituted dialkylamino, halo, substituted or unsubstituted heteroalkyl, hydroxy, nitro, and thiol; or $R^1$ is selected from substituted or unsubstituted pyridyl, substituted or unsubstituted indolyl, substituted or unsubstituted benzimidazolyl, substituted or unsubstituted benzo(1,4)dioxinyl, substituted or unsubstituted indazolyl, substituted or unsubstituted tetrahydroquinoline, and substituted or unsubstituted tetrahydroisoquinoline;

$R^2$ is H; and each $R^{2'}$ is independently selected from hydrogen, substituted or unsubstituted $C_1$-$C_6$ alkyl;

$R^3$ is 2-pyridyl unsubstituted or substituted with amido, alkyl, alkoxy, sulfonyl, or sulfonamidyl;

$R^4$ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, amino, substituted or unsubstituted sulfo, substituted or unsubstituted sulfonyl, substituted or unsubstituted sulfanyl, substituted or unsubstituted aminosulfonyl, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, substituted or unsubstituted heteroalkyl, hydroxy, nitro, and thiol;

however, provided that when A, B and Y all are $CH_2$s, W is N, Z is $CR^4$, and $R^4$ is other than alkylamino, dialkylamino or alkylarylamino;

or a pharmaceutically acceptable salt, or solvate or stereoisomers or tautomers thereof.

3. An amine compound of the formula 1:

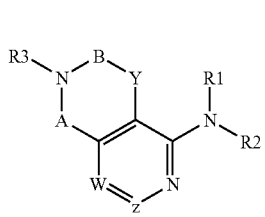

wherein

A, B and Y are $CR^{2'}R^{2'}$;

W is N; and Z is $CR^4$;

$R^1$ is selected from phenyl, unsubstituted or substituted with alkyl, substituted alkyl, acyl, substituted acyl, substituted or unsubstituted alkylamino, substituted or unsubstituted alkythio, substituted or unsubstituted alkoxy, alkoxycarbonyl, substituted alkoxycarbonyl, amino, substituted or unsubstituted sulfo, substituted or unsubstituted sulfonyl, substituted or unsubstituted sulfanyl, substituted or unsubstituted aminosulfonyl, substituted or unsubstituted dihydroxyphosphoryl, substituted or unsubstituted aminodihydroxyphosphoryl, azido, carboxy, cyano, substituted or unsubstituted cycloalkyl, substituted or unsubstituted cycloheteroalkyl, substituted or unsubstituted dialkylamino, halo, substituted or unsubstituted heteroalkyl, hydroxy, nitro, and thiol; or $R^1$ is selected from substituted or unsubstituted pyridyl, substituted or unsubstituted indolyl, substituted or unsubstituted benzimidazolyl, substituted or unsubstituted benzo(1,4)dioxinyl, substituted or unsubstituted indazolyl, substituted or unsubstituted tetrahydroquinoline, and substituted or unsubstituted tetrahydroisoquinoline;

$R^2$ is H; and each $R^{2'}$ is independently selected from hydrogen, substituted or unsubstituted $C_1$-$C_6$ alkyl;

$R^3$ is 2-pyridyl substituted with halo, or trifluoromethyl;

$R^4$ is selected from alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, amino, substituted or unsubstituted sulfo, substituted or unsubstituted sulfonyl, substituted or unsubstituted sulfanyl, substituted or unsubstituted aminosulfonyl, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, substituted or unsubstituted heteroalkyl, hydroxy, nitro, and thiol;

however, provided that when A, B and Y all are $CH_2s$, W is N, Z is $CR^4$, then $R^4$ is other than dialkylamino or alkylarylamino;

or a pharmaceutically acceptable salt, or solvate or stereoisomers or tautomers thereof.

4. A compound according to claim 3, wherein the compound is depicted by the formula

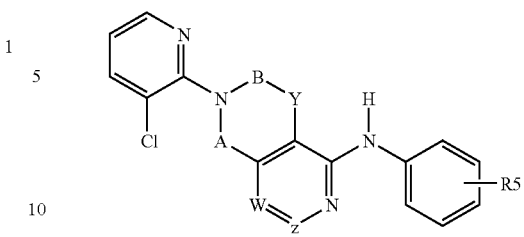

wherein each of A, B and Y is $CH_2$; W is N; Z is $CR^4$; $R^4$ selected from cyano, amido, and a group represented by $X—(CR^{2'}R^{2'})_n—R^{3''}$; wherein X is a bond, O, S, SO, $SO_2$, or $NR^{2'}$; each $R^{2'}$ is selected from hydrogen, and $C_1$-$C_6$ alkyl; $R^{3''}$ is selected from a hydrogen, a hetero substituent, phenyl, heteroalkyl, cycloalkyl, cycloheteroalkyl, pyridyl, imidazolyl, tetrazolyl, quinoline, isoquinoline, tetrahydroquinoline, and tetrahydroisoquinoline; and n is selected from 0-4; provided when X is other than a bond, $R^{3''}$ is hetero substituent then n is at least 2; and $R^5$ is selected from 4-t-Bu, 4-Cl, 4-F, $4\text{-}CF_3$, 4-iso-Pr, 4-OMe, $4\text{-}OCF_3$, $4\text{-}OCHF_2$, $4\text{-}SO_2CF_3$, $4\text{-}SO_2R^{2'}$, $4\text{-}SO_2NR^{2'}R^{2'}$, $4\text{-}C(Me)_2CN$, 3,4-diCl and $4\text{-}NR^{2'}R^{2'}$.

5. A compound according to claim 3, wherein the compound is depicted by the formula

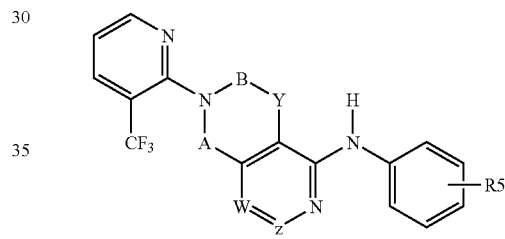

wherein each of A, B and Y is $CH_2$; W is N; Z is $CR^4$; $R^4$ selected from cyano, amido, and a group represented by $X—(CR^{2'}R^{2'})_n—R^{3''}$; wherein X is a bond, O, S, SO, $SO_2$, or $NR^{2'}$; each $R^{2'}$ is selected from hydrogen, and $C_1$-$C_6$ alkyl; $R^{3''}$ is selected from a hydrogen, a hetero substituent, phenyl, heteroalkyl, cycloalkyl, cycloheteroalkyl, pyridyl, imidazolyl, tetrazolyl, quinoline, isoquinoline, tetrahydroquinoline, and tetrahydroisoquinoline; and n is selected from 0-4; provided when X is other than a bond, $R^{3''}$ is hetero substituent then n is at least 2; and $R^5$ is selected from 4-t-Bu, 4-Cl, 4-F, $4\text{-}CF_3$, 4-iso-Pr, 4-OMe, $4\text{-}OCF_3$, $4\text{-}OCHF_2$, $4\text{-}SO_2CF_3$, $4\text{-}SO_2R^{2'}$, $4\text{-}SO_2NR^{2'}R^{2'}$, $4\text{-}C(Me)_2CN$, 3,4-diCl and $4\text{-}NR^{2'}R^{2'}$.

6. A compound according to claim 2, wherein the compound is depicted by the formula

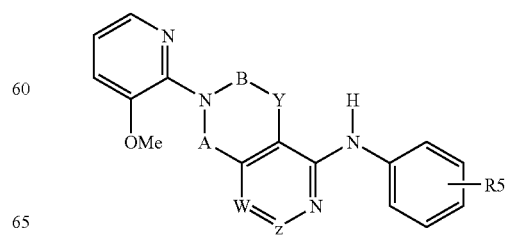

wherein each of A, B and Y is CH$_2$; W is N; Z is CR$^4$; R$^4$ selected from hydrogen, cyano, amido, and a group represented by X—(CR$^{2'}$R$^{2'}$)$_n$—R$^{3''}$; wherein X is a bond, O, S, SO, SO$_2$, or NR$^{2'}$; each R$^{2'}$ is selected from hydrogen, and C$_1$-C$_6$ alkyl; R$^{3''}$ is selected from a hydrogen, a hetero substituent, phenyl, heteroalkyl, cycloalkyl, cycloheteroalkyl, pyridyl, imidazolyl, tetrazolyl, quinoline, isoquinoline, tetrahydroquinoline, and tetrahydroisoquinoline; and n is selected from 0-4; provided when X is other than a bond, R$^{3''}$ is hetero substituent then n is at least 2; and R$^5$ is selected from 4-t-Bu, 4-Cl, 4-F, 4-CF$_3$, 4-iso-Pr, 4-OMe, 4-OCF$_3$, 4-OCHF$_2$, 4-SO$_2$CF$_3$, 4-SO$_2$R$^{2'}$, 4-SO$_2$NR$^{2'}$R$^{2'}$, 4-C(Me)$_2$CN, 3,4-diCl and 4-NR$^{2'}$R$^{2'}$.

7. A compound according to claim 3, wherein the compound is depicted by the formula

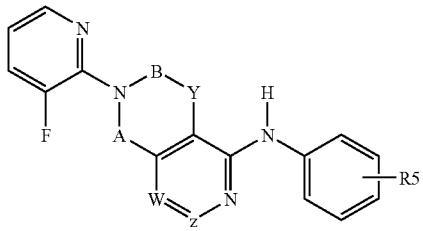

wherein each of A, B and Y is CH$_2$; W is N; Z is CR$^4$; R$^4$ selected from hydrogen, cyano, amido, and a group represented by X—(CR$^{2'}$R$^{2'}$)$_n$—R$^{3''}$; wherein X is a bond, O, S, SO, SO$_2$, or NR$^{2'}$; each R$^{2'}$ is selected from hydrogen, and C$_1$-C$_6$ alkyl; R$^{3''}$ is selected from a hydrogen, a hetero substituent, phenyl, heteroalkyl, cycloalkyl, cycloheteroalkyl, pyridyl, imidazolyl, tetrazolyl, quinoline, isoquinoline, tetrahydroquinoline, and tetrahydroisoquinoline; and n is selected from 0-4; provided when X is other than a bond, R$^{3''}$ is hetero substituent then n is at least 2; and R$^5$ is selected from 4-t-Bu, 4-Cl, 4-F, 4-CF$_3$, 4-iso-Pr, 4-OMe, 4-OCF$_3$, 4-OCHF$_2$, 4-SO$_2$CF$_3$, 4-SO$_2$R$^{2'}$, 4-SO$_2$NR$^{2'}$R$^{2'}$, 4-C(Me)$_2$CN, 3,4-diCl and 4-NR$^{2'}$R$^{2'}$.

8. A compound according to claim 2, wherein the compound is depicted by the formula

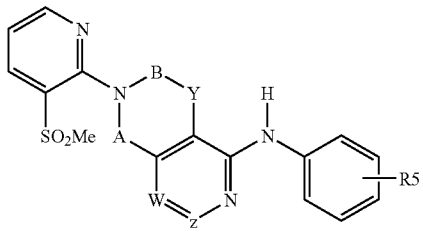

wherein each of A, B and Y is CH$_2$; W is N; Z is CR$^4$; R$^4$ selected from hydrogen, cyano, amido, and a group represented by X—(CR$^{2'}$R$^{2'}$)$_n$—R$^{3''}$; wherein X is a bond, O, S, SO, SO$_2$, or NR$^{2'}$; each R$^{2'}$ is selected from hydrogen, and C$_1$-C$_6$ alkyl; R$^{3''}$ is selected from a hydrogen, a hetero substituent, phenyl, heteroalkyl, cycloalkyl, cycloheteroalkyl, pyridyl, imidazolyl, tetrazolyl, quinoline, isoquinoline, tetrahydroquinoline, and tetrahydroisoquinoline; and n is selected from 0-4; provided when X is other than a bond, R$^{3''}$ is hetero substituent then n is at least 2; and R$^5$ is selected from 4-t-Bu, 4-Cl, 4-F, 4-CF$_3$, 4-iso-Pr, 4-OMe, 4-OCF$_3$, 4-OCHF$_2$, 4-SO$_2$CF$_3$, 4-SO$_2$R$^{2'}$, 4-SO$_2$NR$^{2'}$R$^{2'}$, 4-C(Me)$_2$CN, 3,4-diCl and 4-NR$^{2'}$R$^{2'}$.

9. A compound according to claim 2, wherein the compound is depicted by the formula

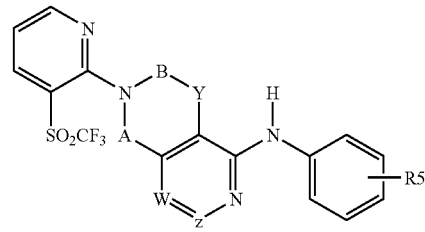

wherein each of A, B and Y is CH$_2$; W is N; Z is CR$^4$; R$^4$ selected from hydrogen, cyano, amido, and a group represented by X—(CR$^{2'}$R$^{2'}$)$_n$—R$^{3''}$; wherein X is a bond, O, S, SO, SO$_2$, or NR$^{2'}$; each R$^{2'}$ is selected from hydrogen, and C$_1$-C$_6$ alkyl; R$^{3''}$ is selected from a hydrogen, a hetero substituent, phenyl, heteroalkyl, cycloalkyl, cycloheteroalkyl, pyridyl, imidazolyl, tetrazolyl, quinoline, isoquinoline, tetrahydroquinoline, and tetrahydroisoquinoline; and n is selected from 0-4; provided when X is other than a bond, R$^{3''}$ is hetero substituent then n is at least 2; and R$^5$ is selected from 4-t-Bu, 4-Cl, 4-F, 4-CF$_3$, 4-iso-Pr, 4-OMe, 4-OCF$_3$, 4-OCHF$_2$, 4-SO$_2$CF$_3$, 4-SO$_2$R$^{2'}$, 4-SO$_2$NR$^{2'}$R$^{2'}$, 4-C(Me)$_2$CN, 3,4-diCl and 4-NR$^{2'}$R$^{2'}$.

10. An amine compound of the formula:

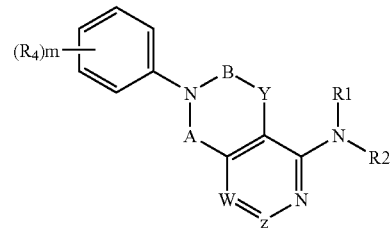

wherein

A, B and Y are CR$_2$R$^{2'}$;

W is N;

Z is CR$^4$;

R$^1$ is selected from phenyl, unsubstituted or substituted with alkyl, substituted alkyl, acyl, substituted acyl, substituted or unsubstituted alkylamino, substituted or unsubstituted alkythio, substituted or unsubstituted alkoxy, alkoxycarbonyl, substituted alkoxycarbonyl, amino, substituted or unsubstituted sulfo, substituted or unsubstituted sulfonyl, substituted or unsubstituted sulfanyl, substituted or unsubstituted aminosulfonyl, substituted or unsubstituted dihydroxyphosphoryl, substituted or unsubstituted aminodihydroxyphosphoryl, azido, carboxy, cyano, substituted or unsubstituted cycloalkyl, substituted or unsubstituted cycloheteroalkyl, substituted or unsubstituted dialkylamino, halo, substituted or unsubstituted heteroalkyl, hydroxy, nitro, and thiol; or R$^1$ is selected from substituted or unsubstituted pyridyl, substituted or unsubstituted indolyl, substituted or unsubstituted benzimidazolyl, substituted or unsubstituted benzo(1,4)dioxinyl, substituted or unsubstituted indazolyl, substituted or unsubstituted tetrahydroquinoline, and substituted or unsubstituted tetrahydroisoquinoline;

R² is hydrogen;

each of R²' is independently hydrogen;

R⁴ is selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, amino, substituted or unsubstituted sulfo, substituted or unsubstituted sulfonyl, substituted or unsubstituted sulfanyl, substituted or unsubstituted aminosulfonyl, substituted or unsubstituted dihydroxyphosphoryl, substituted or unsubstituted aminodihydroxyphosphoryl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, substituted or unsubstituted heteroalkyl, hydroxy, nitro, and thiol; and m is selected from 0-4;

or a pharmaceutically acceptable salt, or solvate or stereoisomers or tautomers thereof.

11. A compound according to claim 10, wherein the compound is depicted by the formula

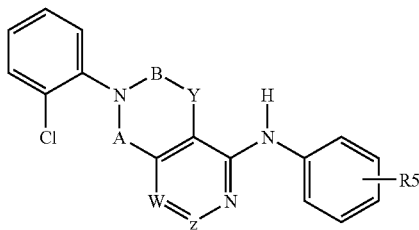

wherein each of A, B and Y is CH₂; W is N; Z is CR⁴; R⁴ selected from hydrogen, cyano, amido, and a group represented by X—(CR²'R²')ₙ—R³'''; wherein X is a bond, O, S, SO, SO₂, or NR²'; each R²' is selected from hydrogen, and C₁-C₆ alkyl; R³''' is selected from a hydrogen, a hetero substituent, phenyl, heteroalkyl, cycloalkyl, cycloheteroalkyl, pyridyl, imidazolyl, tetrazolyl, quinoline, isoquinoline, tetrahydroquinoline, and tetrahydroisoquinoline; and n is selected from 0-4; provided when X is other than a bond, R³''' is hetero substituent then n is at least 2; and R⁵ is selected from 4-t-Bu, 4-Cl, 4-F, 4-CF₃, 4-iso-Pr, 4-OMe, 4-OCF₃, 4-OCHF₂, 4-SO₂CF₃, 4-SO₂R²', 4-SO₂NR²'R²', 4-C(Me)₂CN, 3,4-diCl and 4-NR²'R²'.

12. A compound according to claim 10, wherein the compound is depicted by the formula

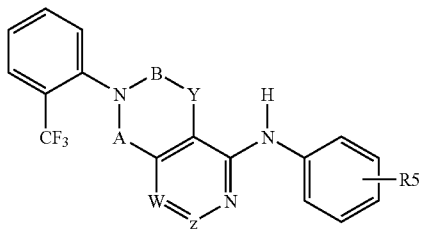

wherein each of A, B and Y is CH₂; W is N; Z is CR⁴; R⁴ selected from hydrogen, cyano, amido, and a group represented by X—(CR²'R²')ₙ—R³'''; wherein X is a bond, O, S, SO, SO₂, or NR²'; each R²' is selected from hydrogen, and C₁-C₆ alkyl; R³''' is selected from a hydrogen, a hetero substituent, phenyl, heteroalkyl, cycloalkyl, cycloheteroalkyl, pyridyl, imidazolyl, tetrazolyl, quinoline, isoquinoline, tetrahydroquinoline, and tetrahydroisoquinoline; and n is selected from 0-4; provided when X is other than a bond, R³''' is hetero substituent then n is at least 2; and R⁵ is selected from 4-t-Bu, 4-Cl, 4-F, 4-CF₃, 4-iso-Pr, 4-OMe, 4-OCF₃, 4-OCHF₂, 4-SO₂CF₃, 4-SO₂R²', 4-SO₂NR²'R²', 4-C(Me)₂CN, 3,4-diCl and 4-NR²'R²'.

13. A compound according to claim 10, wherein the compound is depicted by the formula

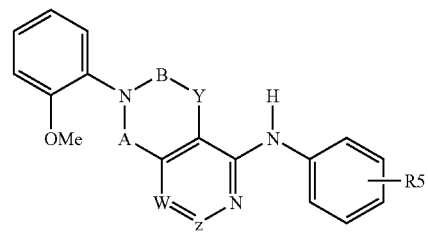

wherein each of A, B and Y is CH₂; W is N; Z is CR⁴; R⁴ selected from hydrogen, cyano, amido, and a group represented by X—(CR²'R²')ₙ—R³'''; wherein X is a bond, O, S, SO, SO₂, or NR²'; each R²' is selected from hydrogen, and C₁-C₆ alkyl; R³''' is selected from a hydrogen, a hetero substituent, phenyl, heteroalkyl, cycloalkyl, cycloheteroalkyl, pyridyl, imidazolyl, tetrazolyl, quinoline, isoquinoline, tetrahydroquinoline, and tetrahydroisoquinoline; and n is selected from 0-4; provided when X is other than a bond, R³''' is hetero substituent then n is at least 2; and R⁵ is selected from 4-t-Bu, 4-Cl, 4-F, 4-CF₃, 4-iso-Pr, 4-OMe, 4-OCF₃, 4-OCHF₂, 4-SO₂CF₃, 4-SO₂R²', 4-SO₂NR²'R²', 4-C(Me)₂CN, 3,4-diCl and 4-NR²'R²'.

14. A compound according to claim 10, wherein the compound is depicted by the formula wherein each of A, B and Y is CH₂; W is N; Z is CR⁴; R⁴ selected from hydrogen, cyano, amido, and a group represented by X—(CR²'R²')ₙ—R³'''; wherein X is a bond, O, S, SO, SO₂, or NR²'; each R²' is selected from hydrogen, and C₁-C₆ alkyl; R³''' is selected from a hydrogen, a hetero substituent, phenyl, heteroalkyl, cycloalkyl, cycloheteroalkyl, pyridyl, imidazolyl, tetrazolyl, quinoline, isoquinoline, tetrahydroquinoline, and tetrahydroisoquinoline; and n is selected from 0-4; provided when X is other than a bond, R³''' is hetero substituent then n is at least 2; and R⁵ is selected from 4-t-Bu, 4-Cl, 4-F, 4-CF₃, 4-iso-Pr, 4-OMe, 4-OCF₃, 4-OCHF₂, 4-SO₂CF₃, 4-SO₂R²', 4-SO₂NR²'R²', 4-C(Me)₂CN, 3,4-diCl and 4-NR²'R²'.

15. A compound according to claim 10, wherein the compound is depicted by the formula

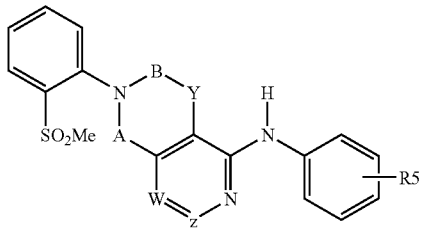

wherein each of A, B and Y is CH$_2$; W is N; Z is CR$^4$; R$^4$ selected from hydrogen, cyano, amido, and a group represented by X—(CR$^{2'}$R$^{2'}$)$_n$—R$^{3"}$; wherein X is a bond, O, S, SO, SO$_2$, or NR$^{2'}$; each R$^{2'}$ is selected from hydrogen, and C$_1$-C$_6$ alkyl; R$^{3"}$ is selected from a hydrogen, a hetero substituent, phenyl, heteroalkyl, cycloalkyl, cycloheteroalkyl, pyridyl, imidazolyl, tetrazolyl, quinoline, isoquinoline, tetrahydroquinoline, and tetrahydroisoquinoline; and n is selected from 0-4; provided when X is other than a bond, R$^{3"}$ is hetero substituent then n is at least 2; and R$^5$ is selected from 4-t-Bu, 4-Cl, 4-F, 4-CF$_3$, 4-iso-Pr, 4-OMe, 4-OCF$_3$, 4-OCHF$_2$, 4-SO$_2$CF$_3$, 4-SO$_2$R$^{2'}$, 4-SO$_2$NR$^{2'}$R$^{2'}$, 4-C(Me)$_2$CN, 3,4-diCl and 4-NR$^{2'}$R$^{2'}$.

16. A compound according to claim 10, wherein the compound is depicted by the formula

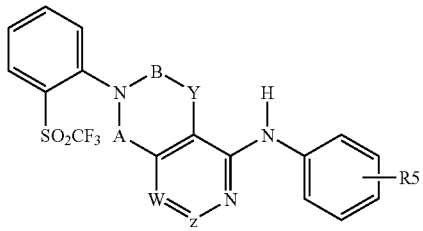

wherein each of A, B and Y is CH$_2$; W is N; Z is CR$^4$; R$^4$ selected from hydrogen, cyano, amido, and a group represented by X—(CR$^{2'}$R$^{2'}$)$_n$—R$^{3"}$; wherein X is a bond, O, S, SO, SO$_2$, or NR$^{2'}$; each R$^{2'}$ is selected from hydrogen, and C$_1$-C$_6$ alkyl; R$^{3"}$ is selected from a hydrogen, a hetero substituent, phenyl, heteroalkyl, cycloalkyl, cycloheteroalkyl, pyridyl, imidazolyl, tetrazolyl, quinoline, isoquinoline, tetrahydroquinoline, and tetrahydroisoquinoline; and n is selected from 0-4; provided when X is other than a bond, R$^{3"}$ is hetero substituent then n is at least 2; and R$^5$ is selected from 4-t-Bu, 4-Cl, 4-F, 4-CF$_3$, 4-iso-Pr, 4-OMe, 4-OCF$_3$, 4-OCHF$_2$, 4-SO$_2$CF$_3$, 4-SO$_2$R$^{2'}$, 4-SO$_2$NR$^{2'}$R$^{2'}$, 4-C(Me)$_2$CN, 3,4-diCl and 4-NR$^{2'}$R$^{2'}$.

17. A compound according to any one of claims 6 and 8-16, wherein R$^4$ is H.

18. A compound according to any one of claims 4-16, wherein R$^4$ is X—(CR$^{2'}$R$^{2'}$)$_n$—R$^{3"}$.

19. A compound according to claim 18, wherein X is a bond, each R$^{2'}$ is H; and n is 0-4.

20. A compound according to claim 18, wherein X is O, S, SO or SO$_2$; each R$^{2'}$ is H; and n is 2-4.

21. A compound according to claim 20, wherein R$^{3"}$ is substituted or unsubstituted cycloalkyl, cycloheteroalkyl, phenyl, pyridyl, imidazolyl, tetrazolyl, quinoline, isoquinoline, tetrahydroquinoline, or tetrahydroisoquinoline.

22. A compound according to claim 20, wherein R$^{3"}$ is a hetero substituent.

23. A compound according to claim 22, wherein R$^{3"}$ is selected from COOH, SO$_2$Me, SMe, OH, OEt, OMe, NEt$_2$, NHSO$_2$Me, CONH$_2$, CONMe$_2$ and SO$_2$NMe$_2$.

24. A compound according to any one of claims 4-16, wherein R$^4$ represents CH$_2$OMe, OMe, OEt, SMe or OCH$_2$CH$_2$CO$_2$Me.

25. A compound according to either of claims 2 or 3, wherein R$^1$ is unsubstituted pyridyl.

26. A compound according to either of claims 2 or 3, wherein R$^1$ is substituted pyridyl.

27. A compound according to claim 26, wherein the substitution is selected from t-Bu, Cl, F, iso-Pr, CF$_3$, OMe, OCF$_3$, OCHF$_2$, SO$_2$CF$_3$, SO$_2$R$^{2'}$, SO$_2$NR$^{2'}$R$^{2'}$, CN, C(Me)$_2$CN, and NR$^1$R$^2$.

28. A compound according to any one of claims 1-3 and 10, wherein R$^1$ is selected from substituted or unsubstituted indolyl, benzimidazolyl, indazolyl, tetrahydroquinoline, and tetrahydroisoquinoline.

29. A compound according to any one of claims 1-3 and 10, wherein R$^1$ is

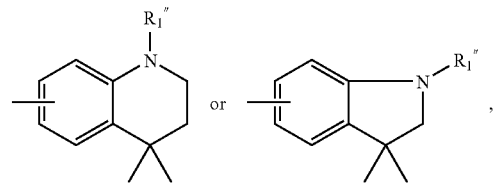

and wherein R$^{1"'}$ is selected from H and alkyl.

30. A compound according to claim 29, wherein R$^4$ is selected from CH$_2$OMe, OMe, OEt, SMe and OCH$_2$CH$_2$CO$_2$Me.

31. A compound of any one of claims 1-3 and 10, wherein A, B and Y are all CH$_2$s; R$^1$ is

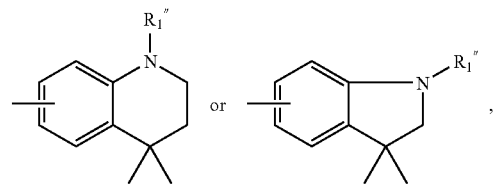

and R$^{1"'}$ is selected from H and alkyl.

32. A compound of any one of claims 1-3 and 10, wherein A and B are independently selected from CH$_2$ and CHCH$_3$, and Y is CH$_2$; R$^1$ is

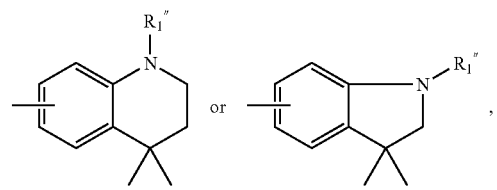

and R$^{1"'}$ is selected from H and alkyl.

33. A compound selected from the group consisting of:
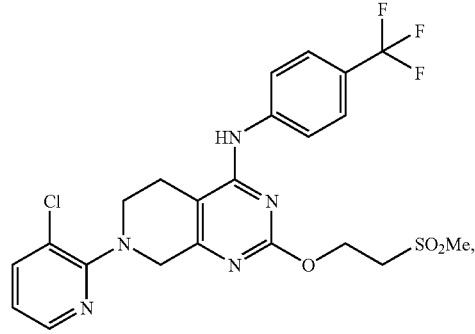
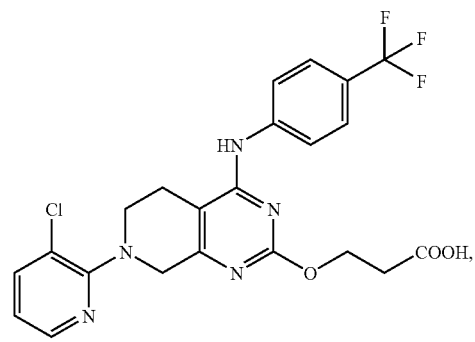
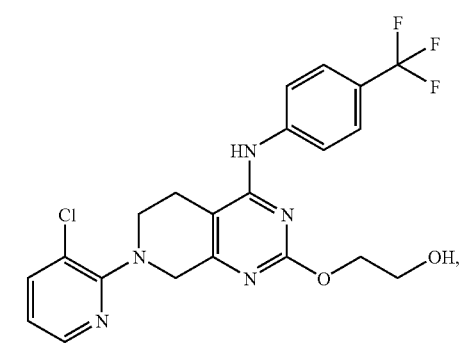
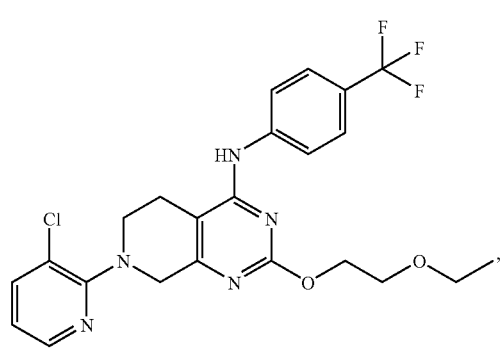
-continued
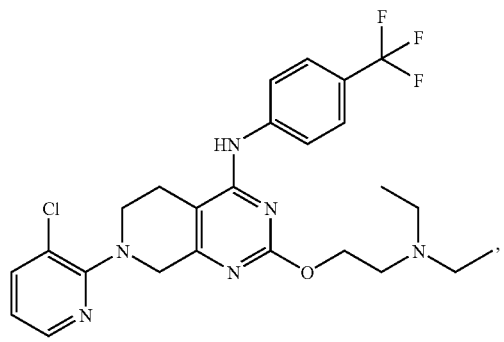
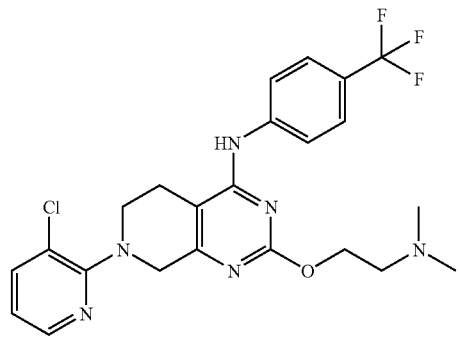
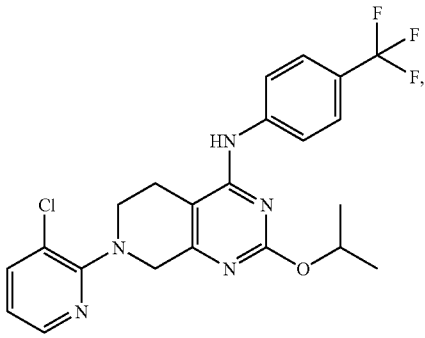
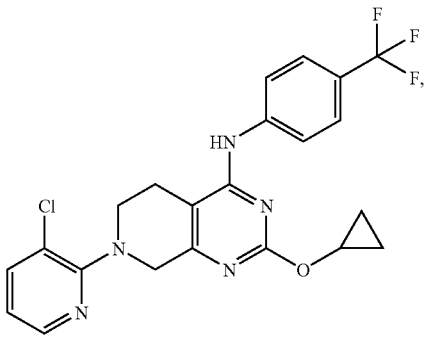
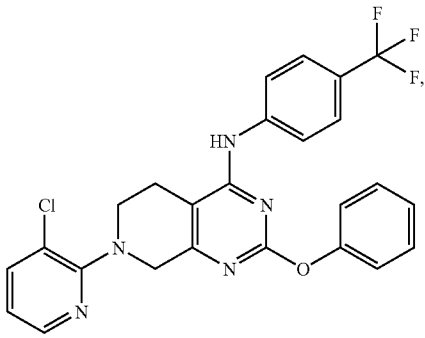

-continued
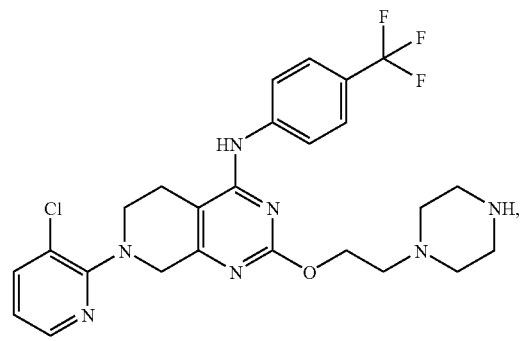
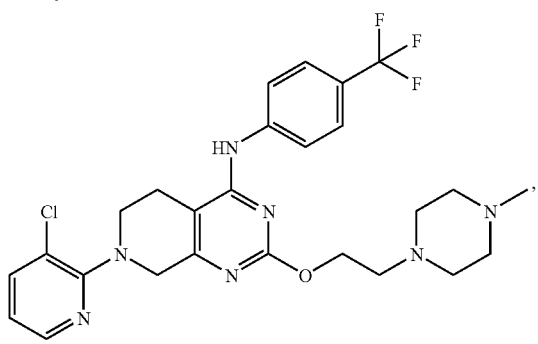
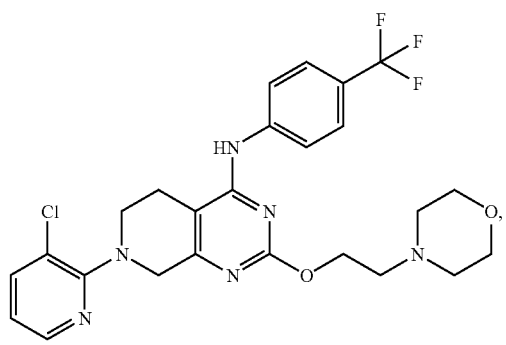
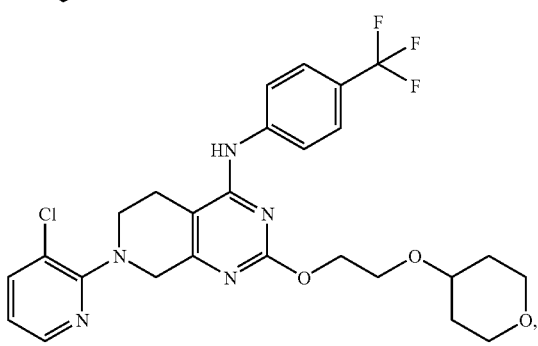
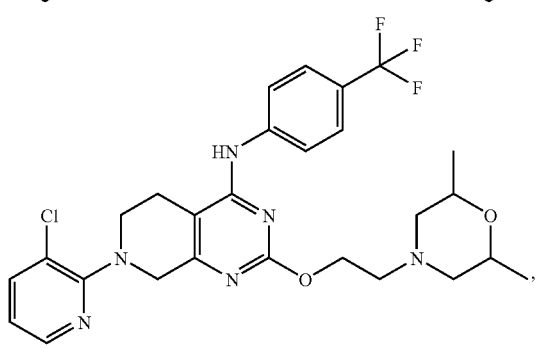
-continued
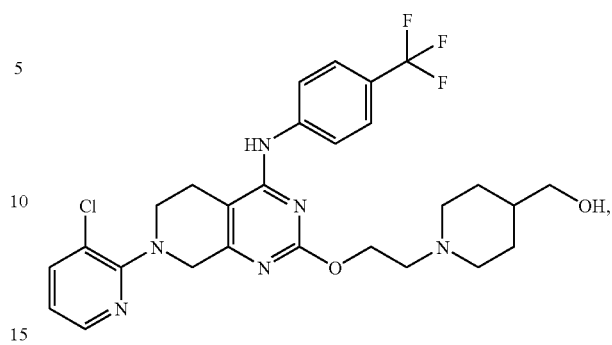
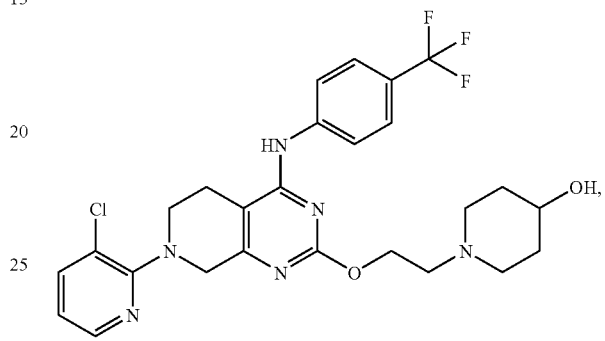
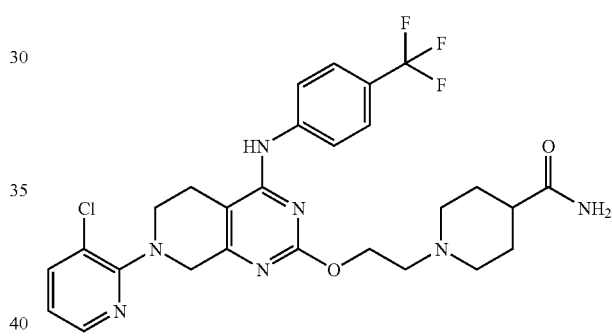
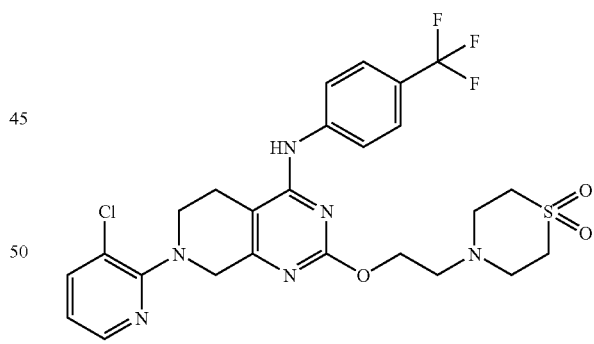
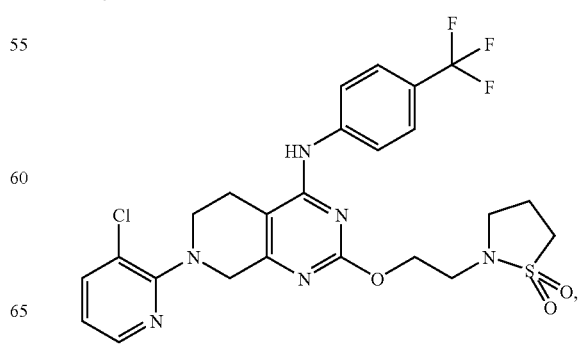

-continued
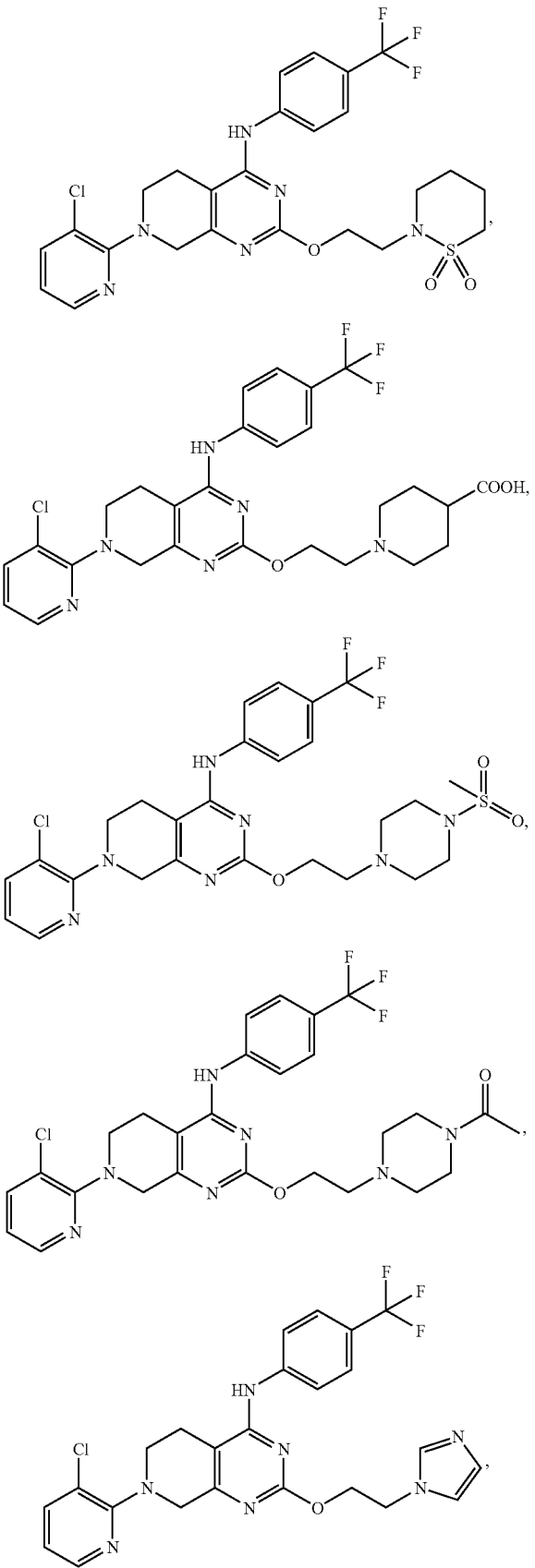
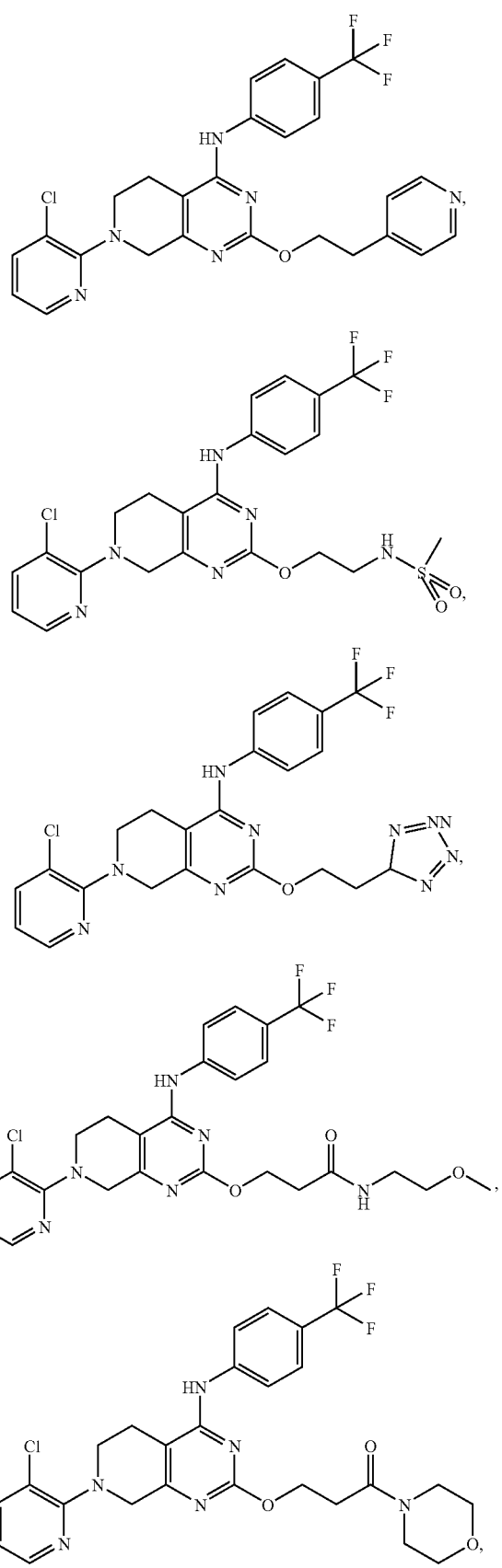

-continued
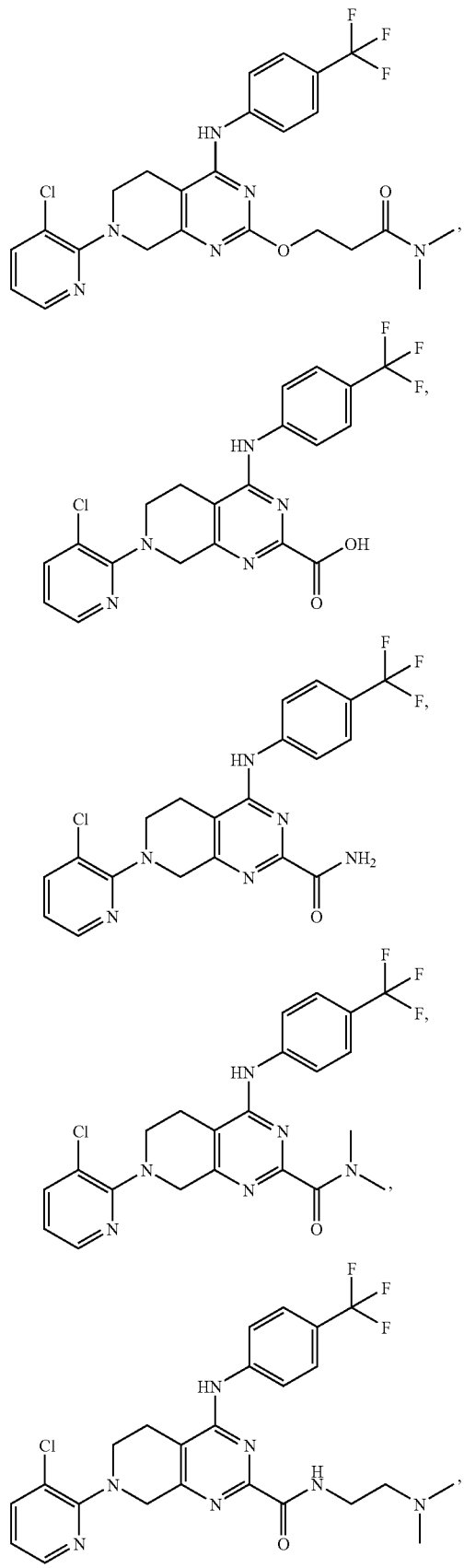
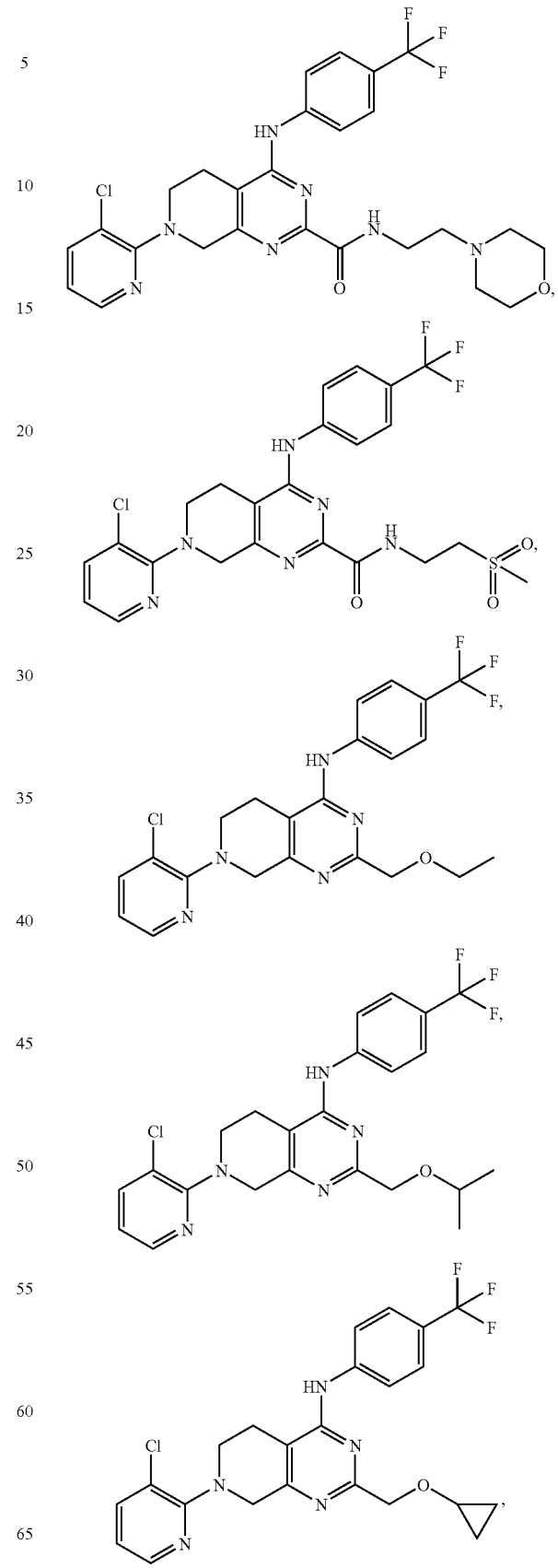

-continued
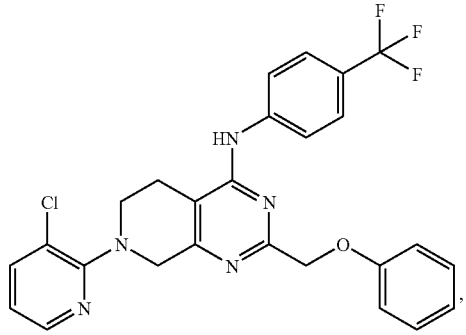
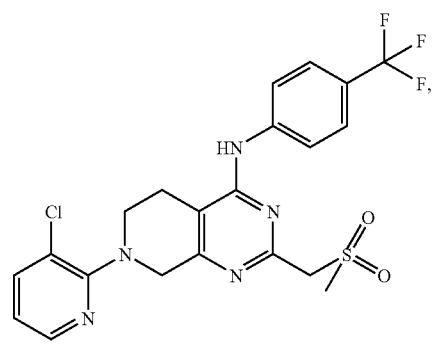
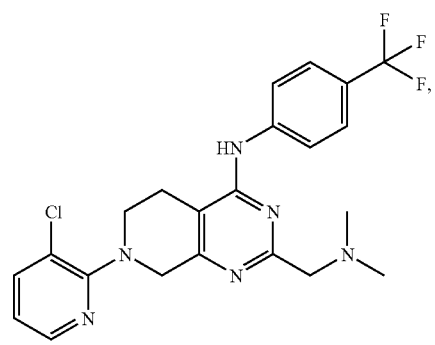
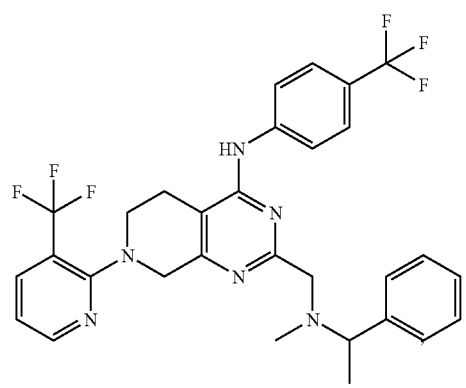
-continued
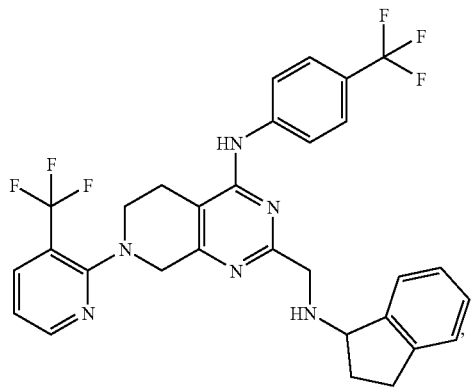
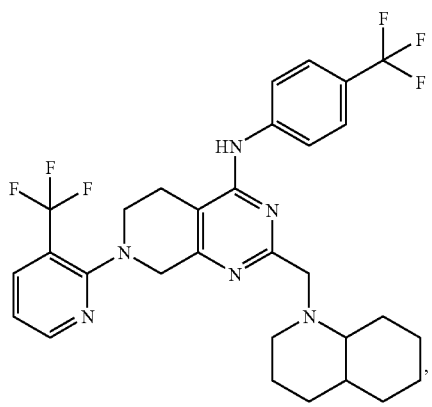
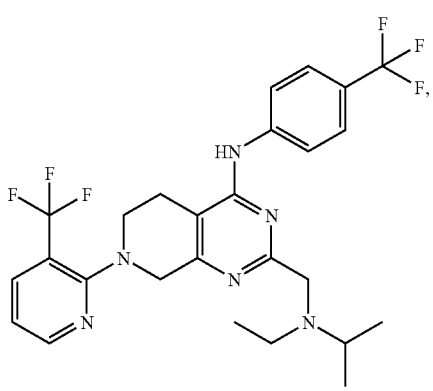
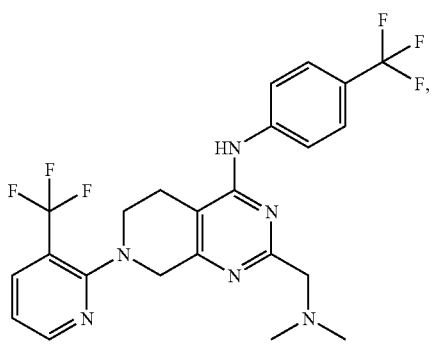

-continued
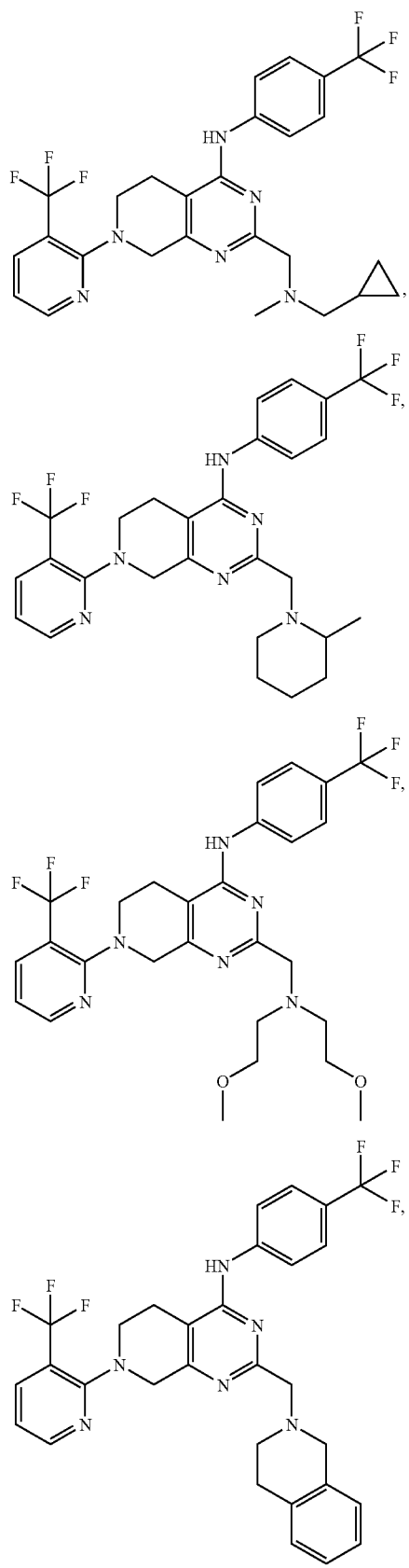
-continued
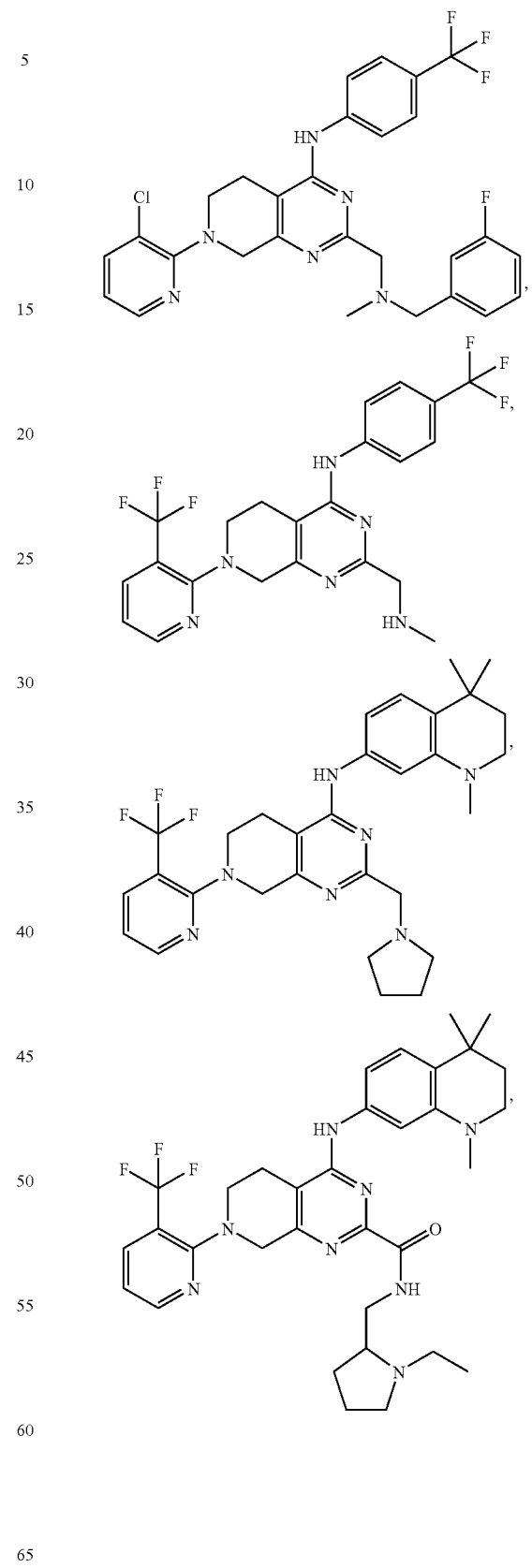

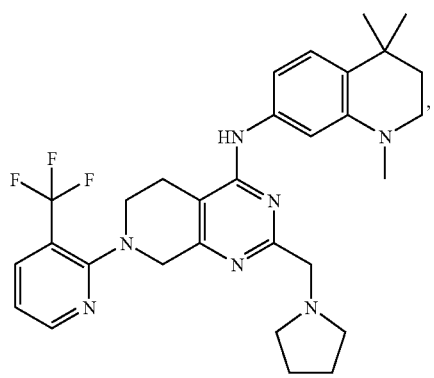
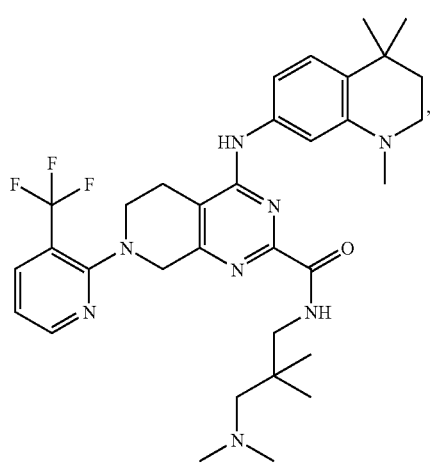
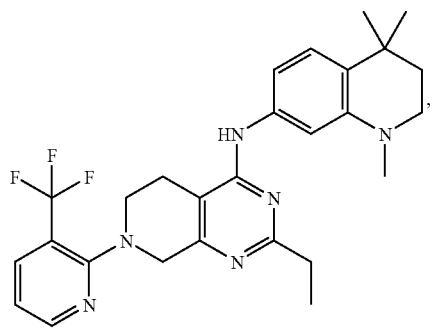
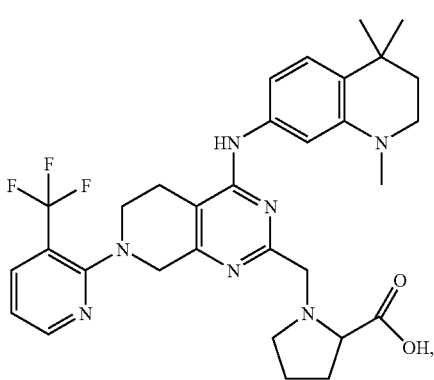
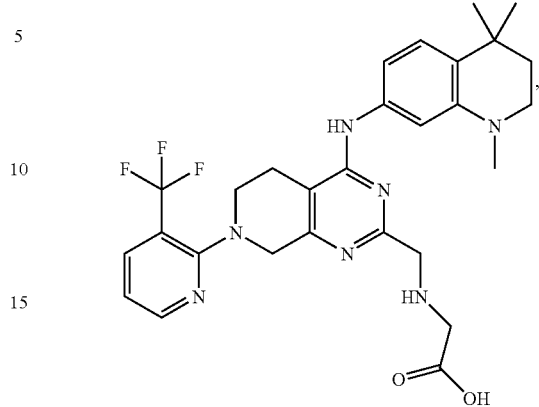
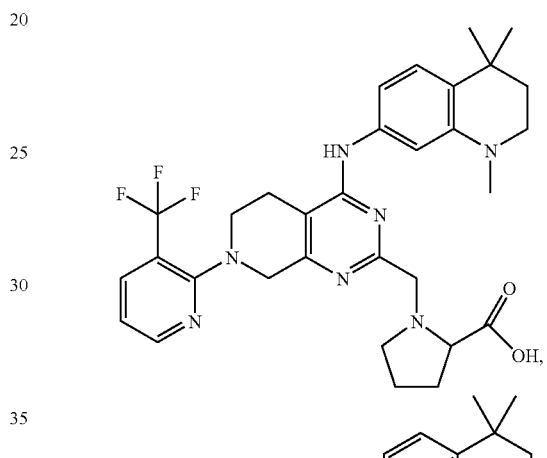
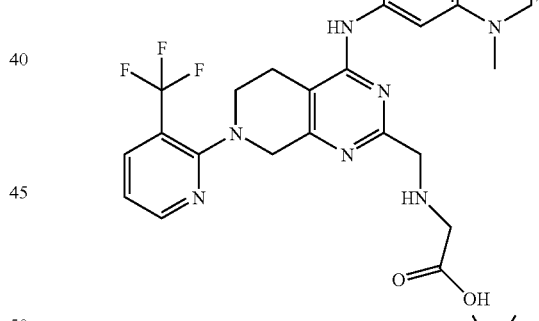
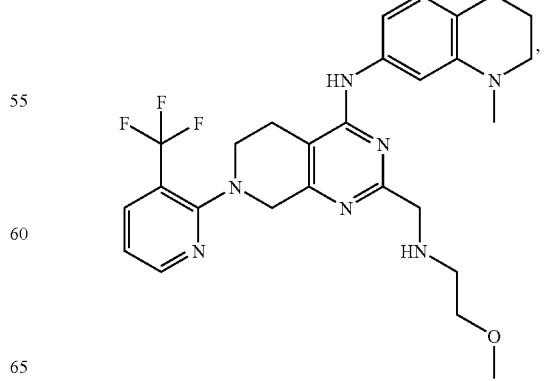

191
-continued
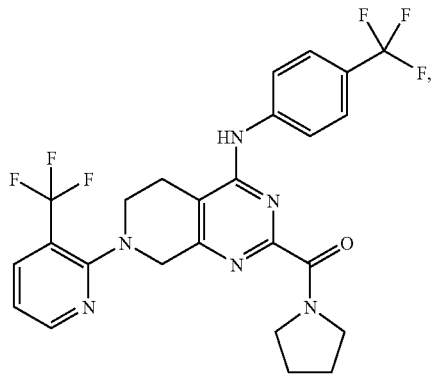
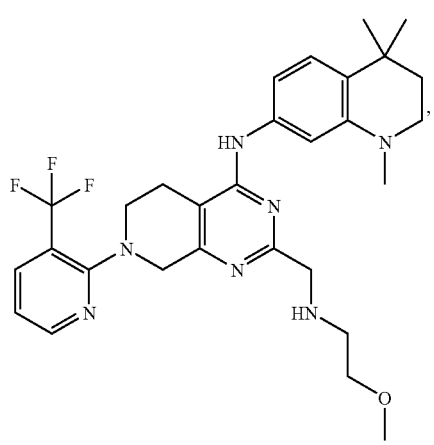
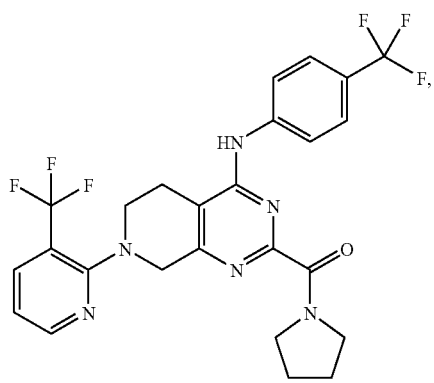
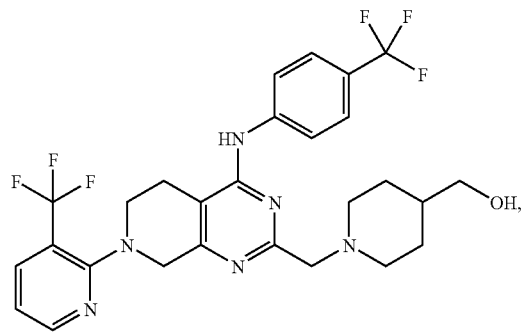
192
-continued
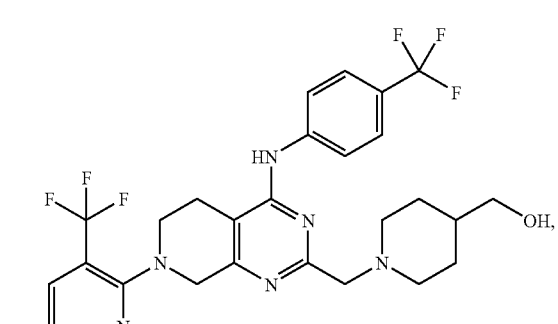
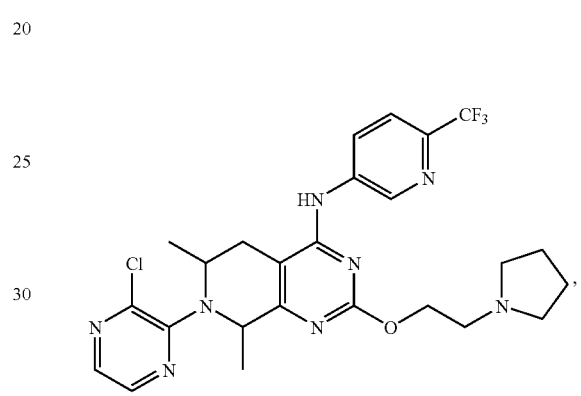
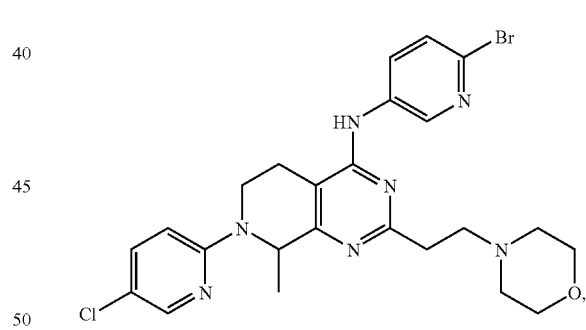
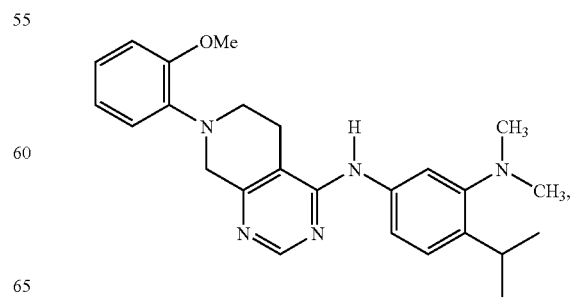

-continued

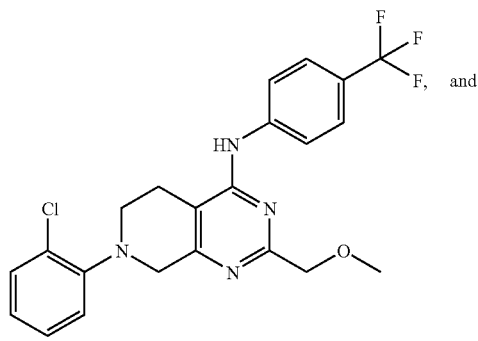, and

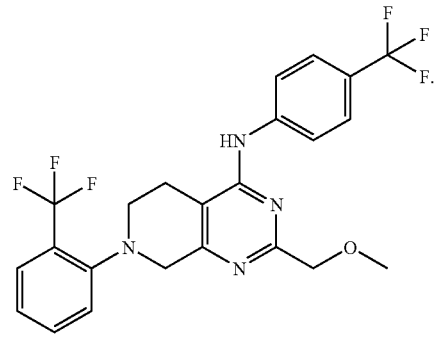

34. A compound selected from the group consisting of:

| STRUCTURE | NAME |
|---|---|
| 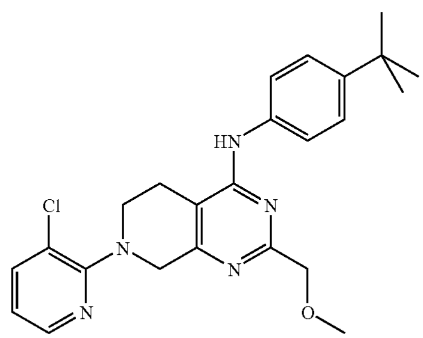 | N-(4-tert-Butyl-phenyl)-[7-(3-chloro-pyridin-2-yl)-2-methoxymethyl-5,6,7,8-tetrahydro-pyrido[3,4-d]pyrimidin-4-yl]-amine; |
| 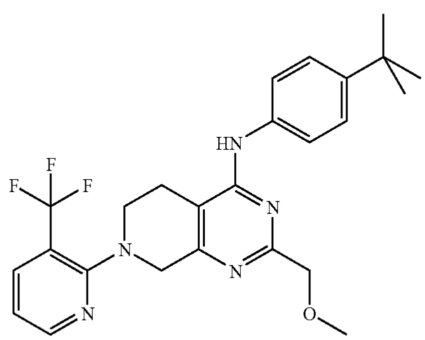 | N-(4-tert-Butyl-phenyl)-[2-methoxymethyl-7-(3-trifluoromethyl-pyridin-2-yl)-5,6,7,8-tetrahydro-pyrido[3,4-d]pyrimidin-4-yl]-amine; |
| 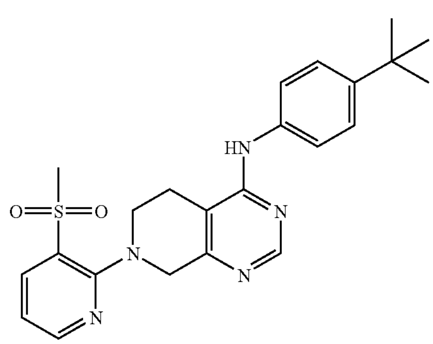 | N-(4-tert-Butyl-phenyl)-[7-(3-methanesulfonyl-pyridin-2-yl)-5,6,7,8-tetrahydro-pyrido[3,4-d]pyrimidin-4-yl]-amine; |

-continued

| STRUCTURE | NAME |
|---|---|
| 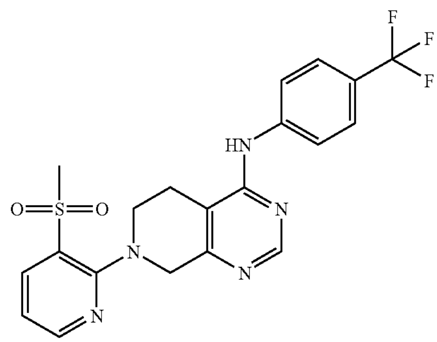 | [7-(3-Methanesulfonyl-pyridin-2-yl)-5,6,7,8-tetrahydro-pyrido[3,4-d]pyrimidin-4-yl]-(4-trifluoromethyl-phenyl)-amine; |
| 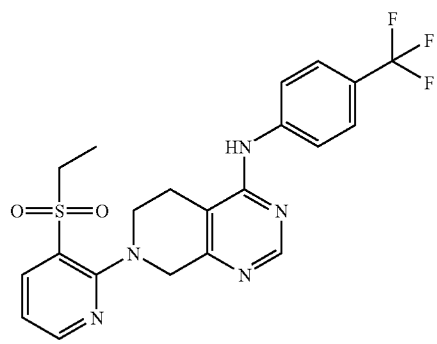 | 7-(3-(Ethylsulfonyl)pyridin-2-yl)-N-(4-(trifluoromethyl)phenyl)-5,6,7,8-tetrahydropyrido-[3,4-d]pyrimidin-4-amine; |
| 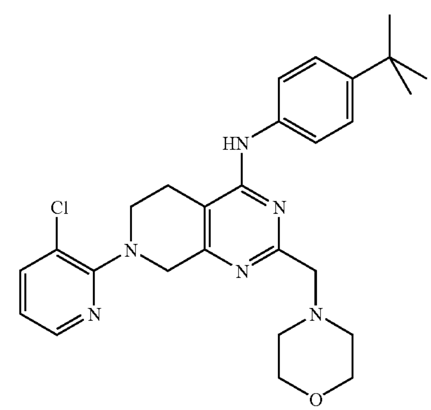 | N-(4-tert-Butylphenyl)-7-(3-chloropyridin-2-yl)-5,6,7,8-tetrahydro-2-(morpholinomethyl)pyrido[3,4-d]pyrimidin-4-amine; |
| 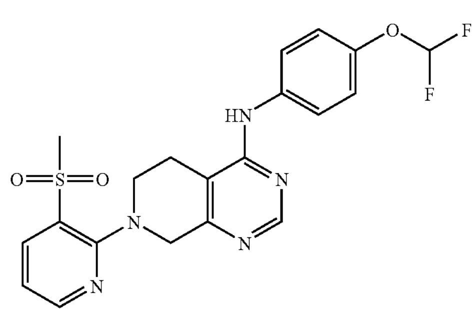 | N-(4-(difluoromethoxy)phenyl)-5,6,7,8-tetrahydro-7-(3-(methylsulfonyl)pyridin-2-yl)pyrido[3,4-d]pyrimidin-4-amine; |

| STRUCTURE | NAME |
|---|---|
| 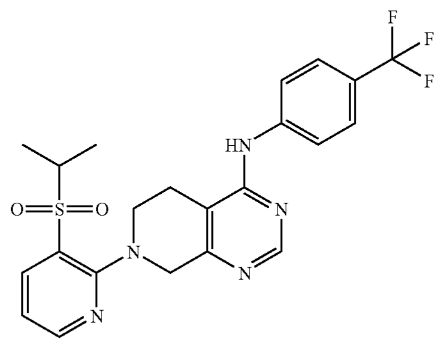 | N-(4-(trifluoromethyl)phenyl)-5,6,7,8-tetrahydro-7-(3-(isopropylsulfonyl)pyridin-2-yl)pyrido[3,4-d]pyrimidin-4-amine; |
| 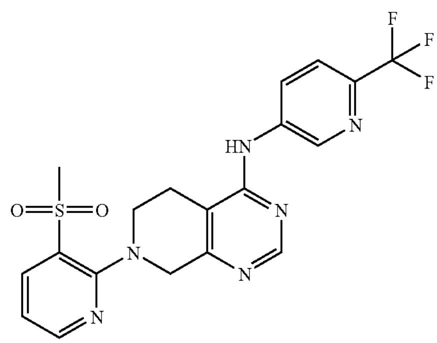 | N-(6-(trifluoromethyl)pyridin-3-yl)-5,6,7,8-tetrahydro-7-(3-(methylsulfonyl)pyridin-2-yl)pyrido[3,4-d]pyrimidin-4-amine; |
| 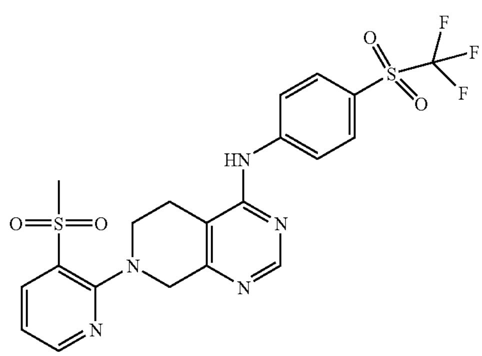 | 5,6,7,8-tetrahydro-7-(3-(methylsulfonyl)pyridin-2-yl)-N-(4-(trifluoromethylsulfonyl)phenyl)pyrido[3,4-d]pyrimidin-4-amine; |
| 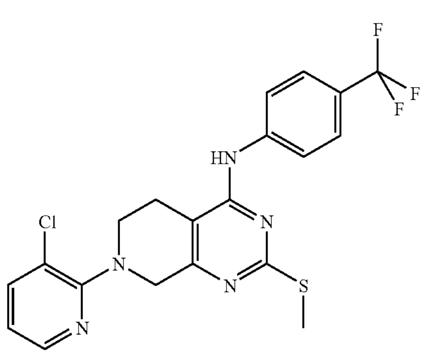 | 7-(3-Chloropyridin-2-yl)-N-(4-(trifluoromethyl)phenyl)-5,6,7,8-tetrahydro-2-(methylthio)pyrido[3,4-d]pyrimidin-4-amine; |

-continued

| STRUCTURE | NAME |
|---|---|
| 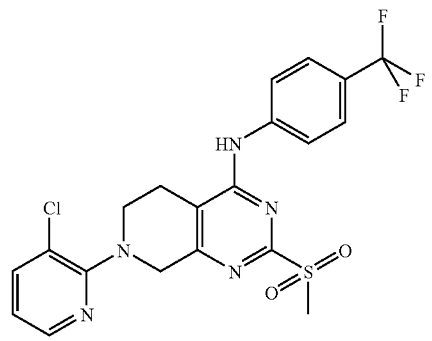 | [7-(3-Chloro-pyridin-2-yl)-2-methanesulfonyl-5,6,7,8-tetrahydro-pyrido[3,4-d]pyrimidin-4-yl]-(4-trifluoromethyl-phenyl)-amine; |
| 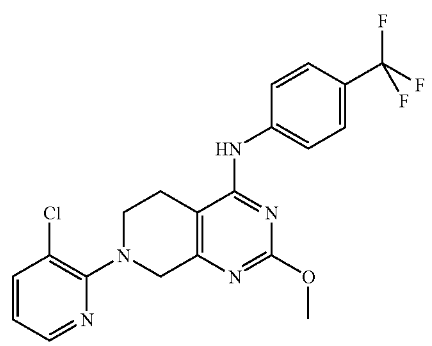 | 7-(3-Chloropyridin-2-yl)-N-(4-(trifluoromethyl)phenyl)-5,6,7,8-tetrahydro-2-methoxypyrido[3,4-d]pyrimidin-4-amine; |
| 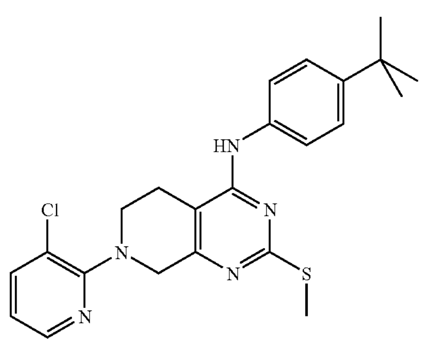 | N-(4-tert-Butylphenyl)-7-(3-chloropyridin-2-yl)-5,6,7,8-tetrahydro-2-(methylthio)pyrido[3,4-d]pyrimidin-4-amine; |
| | N-(4-tert-Butylphenyl)-7-(3-chloropyridin-2-yl)-5,6,7,8-tetrahydro-2-methoxypyrido[3,4-d]-pyrimidin-4-amine; |

-continued

| STRUCTURE | NAME |
| --- | --- |
| 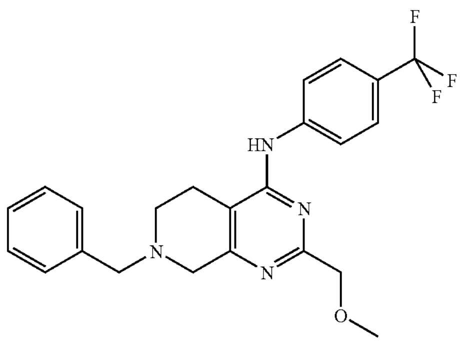 | 7-Benzyl-N-(4-(trifluoromethyl)phenyl)-5,6,7,8-tetrahydro-2-(methoxymethyl)pyrido[3,4-d]pyrimidin-4-amine; |
| 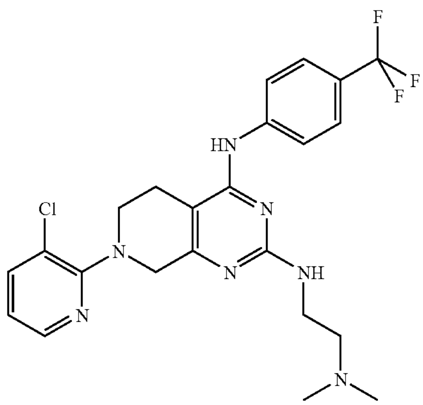 | 7-(3-Chloropyridin-2-yl)-N2-(2-(dimethylamino)ethyl)-N4-(4-(trifluoromethyl)-phenyl)-5,6,7,8-tetrahydropyrido[3,4-d]pyrimidine-2,4-diamine; |
| 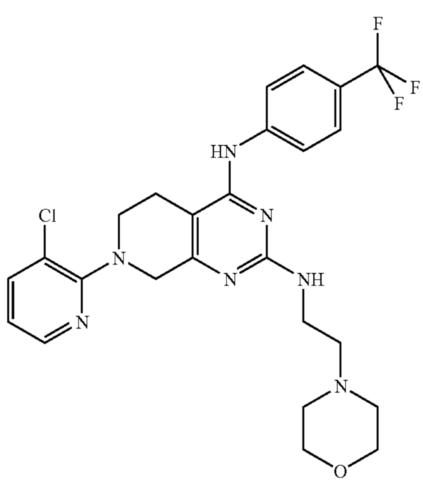 | 7-(3-Chloropyridin-2-yl)-N4-(4-(trifluoromethyl)phenyl)-5,6,7,8-tetrahydro-N2-(2-morpholinoethyl)pyrido[3,4-d]pyrimidine-2,4-diamine; |
| 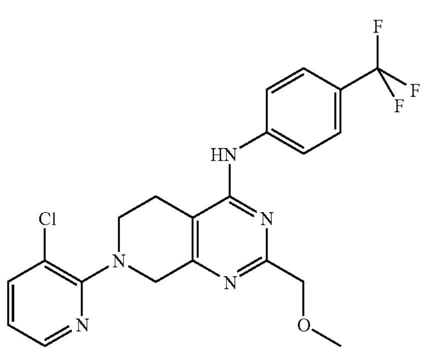 | 7-(3-Chloropyridin-2-yl)-N-(4-(trifluoromethyl)phenyl)-5,6,7,8-tetrahydro-2-(methoxymethyl)pyrido[3,4-d]pyrimidin-4-amine; |

| STRUCTURE | NAME |
|---|---|
| 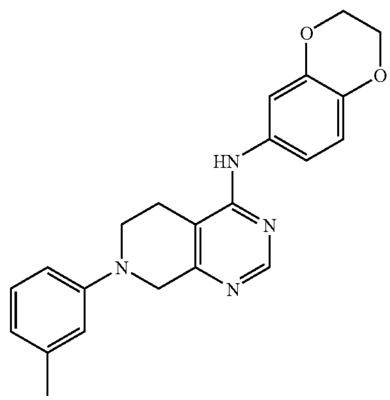 | 5,6,7,8-tetrahydro-N-(2,3-dihydrobenzo[b][1,4]dioxin-6-yl)-7-m-tolylpyrido[3,4-d]pyrimidin-4-amine; |
| 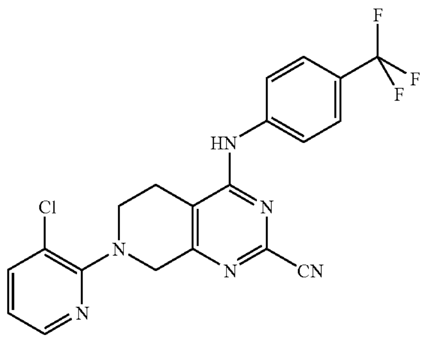 | 4-(4-(Trifluoromethyl)phenylamino)-7-(3-chloropyridin-2-yl)-5,6,7,8-tetrahydropyrido[3,4-d]pyrimidine-2-carbonitrile; |
| 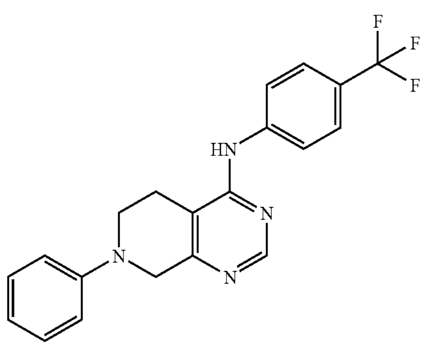 | N-(4-(trifluoromethyl)phenyl)-5,6,7,8-tetrahydro-7-phenylpyrido[3,4-d]pyrimidin-4-amine; |
| 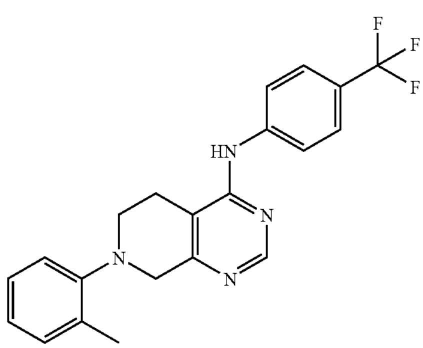 | N-(4-(trifluoromethyl)phenyl)-5,6,7,8-tetrahydro-7-o-tolylpyrido[3,4-d]pyrimidin-4-amine; |

-continued

| STRUCTURE | NAME |
|---|---|
| 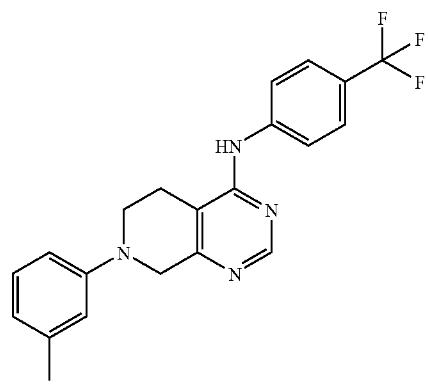 | N-(4-(trifluoromethyl)phenyl)-5,6,7,8-tetrahydro-7-m-tolylpyrido[3,4-d]pyrimidin-4-amine; |
| 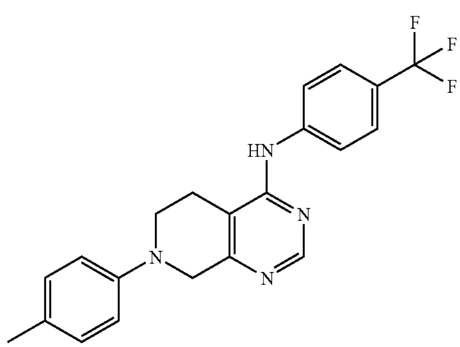 | N-(4-(trifluoromethyl)phenyl)-5,6,7,8-tetrahydro-7-p-tolylpyrido[3,4-d]pyrimidin-4-amine; |
| 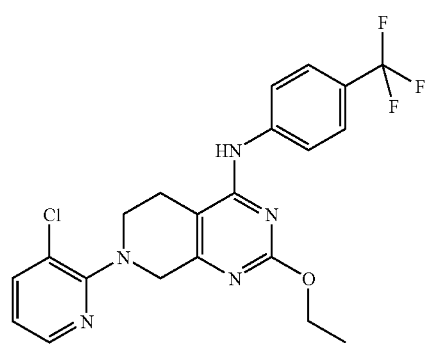 | 7-(3-Chloropyridin-2-yl)-2-ethoxy-N-(4-(trifluoromethyl)phenyl)-5,6,7,8-tetrahydropyrido[3,4-d]pyrimidin-4-amine; |
| 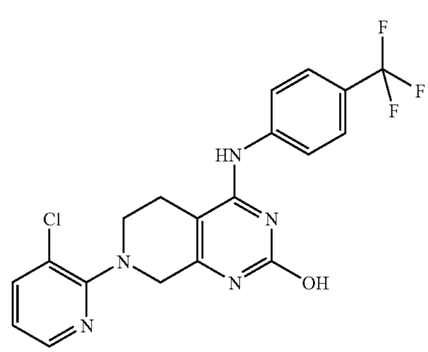 | 4-(4-(Trifluoromethyl)phenylamino)-7-(3-chloropyridin-2-yl)-5,6,7,8-tetrahydropyrido[3,4-d]pyrimidin-2-ol; |

| STRUCTURE | NAME |
|---|---|
| (structure) | N-(4-(Trifluoromethyl)phenyl)-5,6,7,8-tetrahydro-7-(3-(methylsulfonyl)pyridin-2-yl)-2-(methylthio)pyrido[3,4-d]pyrimidin-4-amine; |
| (structure) | 2-Ethoxy-N-(4-(trifluoromethyl)phenyl)-5,6,7,8-tetrahydro-7-(3-(methylsulfonyl)pyridin-2-yl)pyrido[3,4-d]pyrimidin-4-amine; |
| (structure) | Methyl 2-(4-(4-(trifluoromethyl)phenylamino)-7-(3-chloropyridin-2-yl)-5,6,7,8-tetrahydropyrido[3,4-d]pyrimidin-2-yloxy)acetate; and |
| (structure) | 2-(4-(4-(Trifluoromethyl)phenylamino)-7-(3-chloropyridin-2-yl)-5,6,7,8-tetrahydropyrido[3,4-d]pyrimidin-2-yloxy)acetic acid. |

35. A pharmaceutical composition comprising a pharmaceutically acceptable carrier and a pharmaceutically effective amount of a compound of any one of claims 1-3, 10, 33 and 34.

36. The pharmaceutical composition of claim 35, wherein the carrier is a parenteral carrier.

37. The pharmaceutical composition of claim 35, wherein the carrier is an oral carrier.

38. The pharmaceutical composition of claim 35, wherein the carrier is a topical carrier.

* * * * *